United States Patent
Woller et al.

(10) Patent No.: US 8,859,584 B2
(45) Date of Patent: Oct. 14, 2014

(54) TRPV1 ANTAGONISTS

(71) Applicant: AbbVie Inc., North Chicago, IL (US)

(72) Inventors: Kevin R. Woller, Antioch, IL (US);
Gregory A. Gfesser, Lindenhurst, IL (US); Huaqing Liu, Buffalo Grove, IL (US); Jerome F. Daanen, Racine, WI (US); Eric A. Voight, Pleasant Prairie, WI (US); Irene I. Drizin, Wadsworth, IL (US); Anurupa Shrestha, Gurnee, IL (US); Kathleen H. Mortell, Chicago, IL (US); Philip R. Kym, Libertyville, IL (US); Michael E. Kort, Lake Bluff, IL (US); Arthur Gomtsyan, Vernon Hills, IL (US)

(73) Assignee: AbbVie, Inc., North Chicago, IL (US)

( * ) Notice: Subject to any disclaimer, the term of this patent is extended or adjusted under 35 U.S.C. 154(b) by 0 days.

(21) Appl. No.: 13/716,837

(22) Filed: Dec. 17, 2012

(65) Prior Publication Data

US 2013/0158067 A1    Jun. 20, 2013

Related U.S. Application Data

(60) Provisional application No. 61/577,360, filed on Dec. 19, 2011, provisional application No. 61/704,787, filed on Sep. 24, 2012.

(51) Int. Cl.
| | | |
|---|---|---|
| *A61K 31/44* | (2006.01) | |
| *A61K 31/35* | (2006.01) | |
| *A61K 31/47* | (2006.01) | |
| *A61K 31/17* | (2006.01) | |
| *C07D 215/46* | (2006.01) | |
| *C07D 498/02* | (2006.01) | |
| *C07D 311/68* | (2006.01) | |
| *A61K 45/06* | (2006.01) | |
| *C07D 311/96* | (2006.01) | |
| *C07D 311/04* | (2006.01) | |
| *C07C 275/30* | (2006.01) | |
| *A61K 31/192* | (2006.01) | |
| *C07D 311/70* | (2006.01) | |
| *A61K 31/353* | (2006.01) | |
| *C07D 491/052* | (2006.01) | |
| *A61K 31/436* | (2006.01) | |
| *C07D 215/42* | (2006.01) | |
| *C07C 275/32* | (2006.01) | |

(52) U.S. Cl.
CPC .......... *C07D 311/04* (2013.01); *C07D 215/46* (2013.01); *C07D 311/68* (2013.01); *A61K 45/06* (2013.01); *C07D 311/96* (2013.01); *C07C 275/30* (2013.01); *A61K 31/192* (2013.01); *C07D 311/70* (2013.01); *A61K 31/353* (2013.01); *C07D 491/052* (2013.01); *A61K 31/436* (2013.01); *C07D 215/42* (2013.01); *A61K 31/17* (2013.01); *A61K 31/47* (2013.01); *C07C 275/32* (2013.01)

USPC .......................................................... 514/300

(58) Field of Classification Search
USPC ................... 514/300, 456, 596; 546/162, 115
See application file for complete search history.

(56) References Cited

U.S. PATENT DOCUMENTS

| | | | |
|---|---|---|---|
| 6,353,011 B1 * | 3/2002 | Pershadsingh et al. ....... | 514/369 |
| 6,993,311 B2 | 1/2006 | Li et al. | |
| 7,015,233 B2 | 3/2006 | Gomtsyan et al. | |
| 7,375,126 B2 | 5/2008 | Gomtsyan et al. | |
| 7,504,520 B2 | 3/2009 | Gomtsyan et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,622,493 B2 | 11/2009 | Brown et al. | |
| 7,875,627 B2 | 1/2011 | Turner et al. | |

(Continued)

FOREIGN PATENT DOCUMENTS

| | | |
|---|---|---|
| EP | 2128157 A1 | 7/2008 |
| JP | 2011201777 | 10/2011 |

(Continued)

OTHER PUBLICATIONS

Apostolidis, A. et al., "Capsaicin Receptor TRPV1 in Urothelium of Neurogenic Human Bladders and Effect of Intravesical Resiniferatoxin," Urology, 65(2): 400-405 (2005).

(Continued)

*Primary Examiner* — Jeffrey H Murray
*Assistant Examiner* — Oluwafemi Masha

(57) ABSTRACT

Disclosed herein are compounds of formula (I):

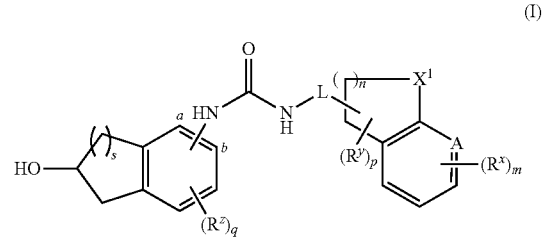

or pharmaceutically acceptable salts thereof, wherein $X^1$, L, $R^x$, $R^y$, $R^z$, A, m, n, p, q, s, and positions a and b are as defined in the specification. Compositions comprising such compounds and methods for treating conditions and disorders using such compounds and compositions are also disclosed.

20 Claims, No Drawings

(56) References Cited

U.S. PATENT DOCUMENTS

| | | | |
|---|---|---|---|
| 7,910,751 | B2 | 3/2011 | Uchida et al. |
| 7,998,982 | B2 | 8/2011 | Vasudevan et al. |
| 8,026,256 | B2 | 9/2011 | Gomtsyan et al. |
| 8,084,616 | B2 | 12/2011 | Gomtsyan et al. |
| 2003/0109700 | A1 | 6/2003 | Ksander |
| 2006/0128689 | A1 | 6/2006 | Gomtsyan et al. |
| 2007/0099954 | A1 | 5/2007 | Gomtsyan et al. |
| 2008/0153871 | A1 | 6/2008 | Bayburt et al. |
| 2008/0287676 | A1 | 11/2008 | Gomtsyan et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2012/0245163 | A1 | 9/2012 | Gomtsyan et al. |
| 2013/0172334 | A1 | 7/2013 | Dart et al. |

FOREIGN PATENT DOCUMENTS

| | | | |
|---|---|---|---|
| WO | 9507271 | A1 | 3/1995 |
| WO | 9710223 | A1 | 3/1997 |
| WO | 03097586 | A1 | 11/2003 |
| WO | 2005040100 | A1 | 5/2005 |
| WO | 2005099353 | A2 | 10/2005 |
| WO | 2006008754 | A1 | 1/2006 |
| WO | 2006065484 | A2 | 6/2006 |
| WO | 2007010383 | A1 | 1/2007 |
| WO | 2007042906 | A1 | 4/2007 |
| WO | 2007121299 | A2 | 10/2007 |
| WO | 2008040360 | A2 | 4/2008 |
| WO | 2008040361 | A2 | 4/2008 |
| WO | 2008059339 | A2 | 5/2008 |
| WO | 2008079683 | A2 | 7/2008 |
| WO | 2008091021 | A1 | 7/2008 |
| WO | 2008110863 | A1 | 9/2008 |
| WO | 2010010935 | A1 | 1/2010 |
| WO | 2010045401 | A1 | 4/2010 |
| WO | 2010045402 | A1 | 4/2010 |

OTHER PUBLICATIONS

Barone, F. C. et al., "Brain Cooling During Transient Focal Ischemia Provides Complete Neuroprotection," Neurosci. Biobehav. Rev., 21(1): 31-44 (1997).

Bernard, S. A. et al., "Treatment of Comatose Survivors of Out-of-Hospital Cardiac Arrest With Induced Hypothermia," N. Engl. J. Med., 346(8): 557-563 (2002).

Beylot, M. et al., "In vivo Studies of Intrahepatic Metabolic Pathways," Diabetes & Metabolism (Paris), 23: 251-257 (1997).

Blagojevic, N. et al., "Role of Heavy Water in Boron Neutron Capture Therapy," Dosimetry & Treatment Planning for Neutron Capture Therapy, Editors R. Zamenhof, G. Solares and O. Harling, Advanced Medical Publishing, Madison, WI. pp. 125-134 (1994).

Blake, M. I. et al., "Studies With Deuterated Drugs," J. Pharm. Sci. 64(3): 367-391 (1975).

Brickner, S. J. et al., "Synthesis and Antibacterial Activity of U-100592 and U-100766, Two Oxazolidinone Antibacterial Agents for the Potential Treatment of Multidrug-Resistant Gram-Positive Bacterial Infections," J Med Chem, 39(3): 673-679 (1996).

Burgard, A. et al., "Asymmetric synthesis of 4-amino-3,4-dihydro-2,2-dimethyl-2H-1-benzopyrans," Tetrahedron, 55(24): 7555-7562 (1999).

Caterina, M. J. et al., "The Vanilloid Receptor: A Molecular Gateway to the Pain Pathway," Annu. Rev. Neurosci., 24: 487-517 (2001).

Caterina, M. J. et al., "Impaired Nociception and Pain Sensation in Mice Lacking the Capsaicin Receptor," Science, 288(5464): 306-313 (2000).

Caterina, M. J. et al., "The Capsaicin Receptor: A Heat-Activated Ion Channel in the Pain Pathway," Nature, 389(6653): 816-824 (1997).

Coimbra, C. et al., "Moderate Hypothermia Mitigates Neuronal Damage in the Rat Brain When Initiated Several Hours Following Transient Cerebral Ischemia," Acta Neuropathol. 87(4): 325-331 (1994).

Colbourne, F. et al., "Prolonged but Delayed Postischemic Hypothermia: A Long-term Outcome Study in the Rat Middle Cerebral Artery Occlusion Model," J. Cereb. Blood Flow Metab., 20(1-2): 1702-1708 (2000).

Corey, E. J. et al., "An Efficient and Catalytically Enantioselective Route to (S)-(-)-Phenyloxirane" J. Org. Chem., 53(12): 2861-2863 (1988).

Cross, L. C. et al., "IUPAC 1974 Recommendations for Section E, Fundamental Stereochemistry," Pure Appl. Chem., 45: 13-30 (1976).

Czajka, D. M. et al., "Effect of Deuterium Oxide on the Reproductive Potential of Mice," Ann. N.Y. Acad. Sci., 84: 770-779 (1960).

Czajka, D. M. et al., "Physiological Effects of Deuterium on Dogs," Am. J. Physiol., 201(2): 357-362 (1961).

Davis, J. et al., "Vanilloid Receptor-1 is Essential for Inflammatory Thermal Hyperalgesia," Nature, 405: 183-187 (2000).

Fernihough, J. et al. "Regulation of Calcitonin Gene-Related Peptide and TRPV1 in a Rat Model of Osteoarthritis," Neurosci. Lett., 388(2): 75-80 (2005).

Foster, Allan B. "Deuterium Isotope Effects in the Metabolism of Drugs and Xenobiotics: Implications of Drug Design," Advances in Drug Research, vol. 14, pp. 2-36 (Bernard Testa, Editor), Academic press, London, 1985.

Garami, A. et al., "Contributions of Different Modes of TRPV1 Activation to TRPV1 Antagonist-Induced Hyperthermia" J. Neurosci., 30(4): 1435-1440 (2010).

Garrett, C. E. et al., "The Enantioselective Reduction of 2'-Fluoroacetophenone Utilizing a Simplified CBS-Reduction Procedure," Tetrahedron Asymmetry, 13(13): 1347-1349 (2002).

Gavva, N. R. et al., "Pharmacological Blockade of the Vanilloid Receptor TRPV1 Elicits Marked Hyperthermia in Humans" Pain, 136(1-2): 202-210 (2008).

Gavva, N. R. et al., "Repeated Administration of Vanilloid Receptor TRPV1 Antagonists Attenuates Hyperthermia Elicited by TRPV1 Blockade" J. Pharmacol. Exp. Ther., 323(1): 128-137 (2007).

Gavva, N. R. et al., "The Vanilloid Receptor TRPV1 is Tonically Activated in vivo and Involved in Body Temperature Regulation" J. Neurosci., 27(13): 3366-3374 (2007).

Geppetti, P. et al., "The Transient Receptor Potential Vanilloid 1: Role in Airway Inflammation and Disease," Eur. J. Pharmacol., 533(1-3): 207-214 (2006).

Gilchrist, H. D. et al., "Enhanced Withdrawal Responses to Heat and Mechanical Stimuli Following Intraplantar Injection of Capsaicin in Rats," Pain, 67(1): 179-188 (1996).

Gololobov, Yu. G. et al. "Sixty Years of Staudinger Reaction," Tetrahedron, 37(3): 437-72 (1981).

Greene, T. et al., Editor, Protective Groups in Organic Synthesis (3rd ed.), John Wiley & Sons, NY (1999), (20 pages, Table of Contents).

Grennan, D. M. et al., "Rheumatoid Arthritis," Textbook of Pain, 3$^{rd}$ Ed., Patrick Wall et al. Editors, Churchill Livingstone, pp. 397-407 (1994).

Hayes, P. et al. "Cloning and functional expression of a human orthologue of rat vanilloid receptor-1," Pain, 88(2): 205-215 (2000).

Higuchi T. et al., "Pro-drugs as Novel Delivery Systems," vol. 14 of the A.C.S. Symposium Series; American Chemical Society, Washington, DC, 1975. (13 pages, Table of Contents).

Holzer, M. et al., "Mild Therapeutic Hypothermia to Improve the Neurologic Outcome After Cardiac Arrest," N. Engl. J. Med., 346(8): 549-556 (2002).

Honore, P. et al., "A-425619 [1-isoquinolin-5-y1-3-(4-trifluoromethyl-benzyl)-urea], A Novel Transient Receptor Potential Type V1 Receptor Antagonist, Relieves Pathophysiological Pain Associated With Inflammation and Tissue Injury in Rats," J. Pharmacol. Exp. Ther., 314(1): 410-421 (2005).

Houge, J. H. et al., "Pathophysiology and First-Line Treatment of Osteoarthritis," Ann. Pharmacother., 36(4): 679-686 (2002).

Iida, T. et al., "Attenuated Fever Response in Mice Lacking TRPV1" Neurosci. Lett., 378(1): 28-33 (2005).

(56) References Cited

OTHER PUBLICATIONS

International Search Report and Written Opinion issued in Application No. PCT/US2012/070151 on Feb. 7, 2013 (11 pages).
Jia, Y. et al., "Anandamide Induces Cough in Conscious Guinea-Pigs Through VR1 Receptors," Br. J. Pharmacol., 137(6): 831-836 (2002).
Kato, S. et al., "Synthesis of Deuterated Mosapride Citrate," J. Labeled Comp. Radiopharmaceut., 36(10): 927-932 (1995).
Kawai, N. et al., "Effects of delayed intraischemic and postischemic hypothermia on a focal model of transient cerebral ischemia in rats," Stroke, 31: 1982-89; discussion 1989 (2000).
Kawanami, S. et al., "Practical Enantioselective Reduction of Ketones Using Oxazaborolidine Catalyst Generated in Situ From Chiral Lactam Alcohol and Borane," Tetrahedron, 59(42): 8411-8414 (2003).
Kort, M. E. et al., "2 TRPV1 Antagonists: Clinical Setbacks and Prospects for Future Development," Progress in Medicinal Chemistry, vol. 51, pp. 57-70, G. Lawton and D.R. Witty Editors, Elsevier B.V., (2012).
Kushner, D. J. et al., "Pharmacological Uses and Perspectives of Heavy Water and Deuterated Compounds," Can. J. Physiol. Pharmacol., 77(2): 79-88 (1999).
Lehto, S. G. et al., "Antihyperalgesic effects of (R,E)-N-(2-hydroxy-2,3-dihydro-1H-inden-4-yl)-3-(2-(piperidin-1-yl)-4-(trifluoromethyl)phenyl)-acrylamide (AMG8562), A Novel Transient Receptor Potential Vanilloid Type 1 Modulator That Does Not Cause Hyperthermia in Rats" J. Pharmacol. Exp. Ther., 326(1): 218-229 (2008).
Levine, J. et al., "Inflammatory Pain," Textbook of Pain, $3^{rd}$ Ed., Patrick Wall et al. Editors, Churchill Livingstone, pp. 45-56 (1994).
Lizondo, J et al., "Linezolid—Oxazolidinone Antibacterial" Drugs Future, 21(11): 1116-1123 (1996).
Maier, C. M. et al., "Delayed Induction and Long-Term Effects of Mild Hypothermia in A Focal Model of Transient Cerebral Ischemia: Neurological Outcome and Infarct Size," J. Neurosurg., 94(1): 90-96 (2001).
Maier, C. M. et al., "Optimal Depth and Duration of Mild Hypothermia in A Focal Model of Transient Cerebral Ischemia: Effects on Neurologic Outcome, Infarct Size, Apoptosis, and Inflammation," Stroke, 29: 2171-2180 (1998).
Mallesham, B et al., "Highly Efficient CuI-Catalyzed Coupling of Aryl Bromides With Oxazolidinones Using Buchwald's Protocol: A Short Route to Linezolid and Toloxatone," Org Lett, 5(7): 963-965 (2003).
Marsch, R. et al., "Reduced Anxiety, Conditioned Fear, and Hippocampal Long-Term Potentiation in Transient Receptor Potential Vanilloid Type 1 Receptor-Deficient Mice," J. Neurosci., 27(4): 832-839 (2007).
McCarthy, C. et al., "Osteoarthritis," Textbook of Pain, $3^{rd}$ Ed., Patrick Wall et al. Editors, Churchill Livingstone, pp. 387-395 (1994).
Meyer, R. A. et al., "Peripheral Neural Mechanisms of Nociception," Textbook of Pain, $3^{rd}$ Ed., Patrick Wall et al. Editors, Churchill Livingstone, pp. 13-44 (1994).
Millan, Mark J. "The Induction of Pain: An Integrative Review," Prog. Neurobiol., 57: 1-164 (1999). (Uploaded in 2 parts due to size).
Murata, Y. et al., "Peripheral and Central Distribution of TRPV1, Substance P and CGRP of Rat Corneal Neurons," Brain Res., 1085(1): 87-94 (2006).
Nolano, M. et al., "Topical Capsaicin in Humans: Parallel Loss of Epidermal Nerve Fibers and Pain Sensation," Pain, 81(1-2): 135-145 (1999).
Onesti, S. T. et al., "Transient Hypothermia Reduces Focal Ischemic Brain Injury in the Rat," Neurosurgery, 29(3): 369-373 (1991).
Ooboshi, H. et al., "Hypothermia Inhibits Ischemia-Induced Efflux of Amino Acids and Neuronal Damage in the Hippocampus of Aged Rats," Brain Res., 884(1): 23-30 (2000).
Prescott, David M., Editor, Methods in Cell Biology, vol. XIV, Academic Press, New York, N. Y., (1976), (12 pages, Table of Contents).
Reilly, R. M. et al., "Pharmacology of Modality-Specific Transient Receptor Potential Vanilloid-1 Antagonists That Do Not Alter Body Temperature," Journal of Pharmacology and Experimental Therapeutics, 342(2): 416-428 (2012).
Roche, Edward B., Editor, Bioreversible Carriers in Drug Design, American Pharmaceutical Association and Pergamon Press (1987), (4 pages, Table of Contents).
Sappington, R. M. et al., "TRPV1: Contribution to Retinal Ganglion Cell Apoptosis and Increased Intracellular Ca2+ With Exposure to Hydrostatic Pressure," Invest. Ophthalmol. Vis. Sci., 50(2): 717-728 (2009).
Steiner, A. A. et al., "Nonthermal Activation of Transient Receptor Potential Vanilloid-1 Channels in Abdominal Viscera Tonically Inhibits Autonomic Cold-Defense Effectors" J. Neurosci., 27(28): 7459-7468 (2007).
Suri, A. et al., "The Emerging Role of TRPV1 in Diabetes and Obesity," Trends Pharmacol. Sci., 29(1): 29-36 (2008).
Swanson, D. M. et al., "Identification and Biological Evaluation of 4-(3-trifluoromethylpyridin-2-yl)piperazine-1-carboxylic acid (5-trifluoromethylpyridin-2-yl)amide, a High Affinity TRPV1 (VR1) Vanilloid Receptor Antagonist" J. Med. Chem., 48(6): 1857-1872 (2005).
Szallasi, A. et al., "The Vanilloid Receptor TRPV1: 10 Years From Channel Cloning to Antagonist Proof-of-Concept" Nature Rev., 6: 357-373 (2007).
Tamayo, N. et al., "Design and Synthesis of Peripherally Restricted Transient Receptor Potential Vanilloid 1 (TRPV1) Antagonists" J. Med. Chem., 51(9): 2744-2757 (2008).
Tanuwidjaja, J. et al. "One-Pot Asymmetric Synthesis of Either Diastereomer of Tert-Butanesulfinyl-Protected Amines From Ketones," J. Org. Chem., 72(2): 626-629 (2007).
Thomson J. F., "Physiological Effects of D20 in Mammals," Ann. NY Acad. Sci., 84: 736-744 (1960).
Tzavara, E. et al., "Endocannabinoids Activate Transient Receptor Potential Vanilloid 1 Receptors to Reduce Hyperdopaminergia-Related Hyperactivity: Therapeutic Implications," Biol. Psych., 59: 508-515 (2006).
Voight, E. A. et al., "Transient receptor potential vanilloid-1 antagonists: a survey of recent patent literature," Expert Opinion Ther. Patents, 20(9): 1107-1122 (2010).
Watanabe N. et al , "Immunohistochemical Localization of Vanilloid Receptor Subtype 1 (TRPV1) in the Guinea Pig Respiratory System," Pulmonary Pharmacol. Ther., 18(3): 187-197 (2005).
Woolf, C. J. et al., "Neuronal Plasticity: Increasing the Gain in Pain," Science, 288(5472): 1765-1768 (2000).
Woolf, C. J. et al., "Implications of Recent Advances in The Understanding of Pain Pathophysiology for the Assessment of Pain in Patients," Pain Supp., 82(6): S141-S147 (1999).
Woolf, C. J. et al. "Neuropathic Pain: Aetiology, Symptoms, Mechanisms, and Management," Lancet, 353(9168): 1959-1964 (1999).
Yamashita, K. et al., "Mild Hypothermia Ameliorates Ubiquitin Synthesis and Prevents Delayed Neuronal Death in the Gerbil Hippocampus," Stroke, 22(12): 1574-1581 (1991).
Zhang, Y. et al., "The Effect of Intraischemic Mild Hypothermia on Focal Cerebral Ischemia/Reperfusion Injury," Acta Anaesthesiol. Sin., 39(2): 65-69 (2001).
Zhang, F. et al., "Transient Receptor Potential Vanilloid 1 Activation Induces Inflammatory Cytokine Release in Corneal Epithelium Through MAPK Signaling," J. Cell. Physiol., 213(3): 730-739 (2007).

* cited by examiner

TRPV1 ANTAGONISTS

CROSS REFERENCE TO RELATED APPLICATIONS

This application claims priority to U.S. Provisional Application No. 61/577,360 filed Dec. 19, 2011, and U.S. Provisional Application No. 61/704,787 filed Sep. 24, 2012, which are incorporated herein by reference in their entirety.

TECHNICAL FIELD

Described herein are ureas which are useful for treating pain, cough, bladder overactivity, urinary incontinence, or conditions and disorders modulated by the TRPV1 channel. Pharmaceutical compositions comprising said compounds and methods for treating pain, diabetic neuropathy, cough, asthma, bladder overactivity, urinary incontinence, anxiety, or conditions and disorders modulated by the TRPV1 channel are also included.

BACKGROUND

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as the transient receptor potential vanilloid-1 (TRPV1). TRPV1 is also known as vanilloid receptor-1 (VR1). The intradermal administration of capsaicin is characterized by an initial burning or hot sensation followed by a prolonged period of analgesia. The analgesic component of the TRPV1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist, can reduce inflammation-induced hyperalgesia in animal models. TRPV1 receptors are also localized on sensory afferents, which innervate the bladder. Capsaicin or resiniferatoxin have been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids, and thus is classified as a ligand-gated ion channel. The TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

In the course of characterizing analgesic properties of structurally distinct TRPV1 antagonists, multiple investigators have observed core body temperature elevating ("hyperthermic") attributes of these compounds in rodent behavioral models of pain (Swanson, D. M. et al., *J. Med. Chem.*, 2005, 48, 1857; Gavva, N. R. et al., *J. Pharmacol. Exp. Ther.*, 2007, 323, 128; Steiner, A. A. et al., *J. Neurosci.*, 2007, 27, 7459; Tamayo, N. et al., *J. Med. Chem.*, 2008, 51, 2744; Gavva, N. R. et al., *J. Neurosci.*, 2007, 27, 3366). Often modest (0.5° C.), the associated temperature elevation can be considerably more robust (1-2° C.), and also has been reported preclinically in dogs and monkeys (Gavva, N. R. et al., *J. Pharmacol. Exp. Ther.*, 2007, 323, 128; Gavva, N. R. et al., *J. Neurosci.*, 2007, 27, 3366) and in human subjects in the course of clinical trials (Gavva, N. R. et al., *Pain*, 2008, 136, 202). These effects have the potential to be self-limiting; they are generally transient and attenuate with repeat dosing (Gavva, N. R. et al., *J. Pharmacol. Exp. Ther.*, 2007, 323, 128). The temperature effects are considered to be mechanism based (Lida, T. et al., *Neurosci. Lett.*, 2005, 378, 28) since TRPV1 null mice show no deficits in thermoregulation, even when dosed with antagonists that elevate temperature in wild-type mice (Steiner, A. A. et al., *J. Neurosci.*, 2007, 27, 7459; Garami, A. et al., *J. Neurosci.*, 2010, 30, 1435).

Efforts to understand and separate the nociceptive and thermoregulatory functions of TRPV1 have led to directed research to identify antagonists that afford analgesic benefit without affecting core body temperature (Lehto, S. G. et al., *J. Pharmacol. Exp. Ther.*, 2008, 326, 218) or imparting insensitivity to noxious heat, as observed in TRPV1 null mice (Caterina, M. J. et al., *Science*, 2000, 288, 306).

Certain chromane and indane derivatives that are TRPV1 modulators are discussed in the following publications: WO 2005/040100, WO 2007/042906, WO 2008/059339, US 2006/0128689, WO 2007/121299, US 2008/0153871, WO 2008/110863, WO 2008/091021, WO 2007/010383, WO 2010/010935, WO 2010/045401, WO 2010/045402, U.S. Pat. No. 7,375,126, U.S. Pat. No. 7,015,233, U.S. Pat. No. 8,026,256, US 2008/0287676, and US 2007/0099954.

We describe herein certain TRPV1 antagonists that have little or no significant effects on the sensation of noxious heat.

SUMMARY OF THE INVENTION

One aspect is directed towards compounds of formula (I) or pharmaceutical salts, solvates, prodrugs, or combinations thereof,

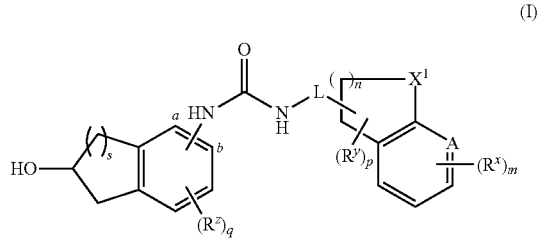

wherein

L is a bond or $CH_2$, and is bound to any one of the carbon atom of the monocyclic ring containing $X^1$;

$X^1$ is $CH_2$, O, or $N(R^w)$ wherein $R^w$ is hydrogen, alkyl, or haloalkyl;

n is 1, 2, or 3;

A is CH or N;

m is 0, 1, 2, 3, or 4;

$R^x$, at each occurrence, represents optional substituent on any substitutable carbon atom of the ring containing A and each $R^x$ is independently alkyl, halogen, haloalkyl, OH, O(alkyl), O(haloalkyl), $NH_2$, N(H)(alkyl), or $N(alkyl)_2$;

p is 0, 1, 2, 3, 4, 5, or 6;

$R^y$, at each occurrence, represents optional substituent on any substitutable carbon atom of the ring containing $X^1$ and each $R^y$ is independently alkyl, haloalkyl, —($C_1$-$C_6$ alkylenyl)-O(alkyl), $G^1$, and —($C_1$-$C_6$ alkylenyl)-$G^1$; wherein $G^1$, at each occurrence, is independently an aryl, optionally substituted with 1, 2, 3, or 4 substituents independently selected from the group consisting of alkyl, halogen, haloalkyl, O(alkyl), and O(haloalkyl);

two $R^y$ groups that are attached to the same carbon atom, together with said carbon atom to which they are attached, optionally form a $C_3$-$C_6$ monocyclic cycloalkyl ring, wherein the monocyclic cycloalkyl ring is optionally substituted with 1, 2, or 3 substituents independently selected from the group consisting of alkyl, oxo, halogen, and haloalkyl;

s is 0 or 1;

The alphabets a and b on the bicyclic ring independently represent the positions at which the —NH— of the urea moiety and a carbon atom of the ring are bound to each other, provided that when s is 1, the binding position for —NH— is at position a; and when s is 0, the binding position for —NH— is at position b;

$R^z$, at each occurrence, represents optional substituent on any substitutable position of the bicyclic ring and is independently halogen, haloalkyl, or alkyl; and q is 0, 1, 2, or 3.

Another aspect is related to methods for treating or preventing ischemia such as acute cerebral ischemia, cerebrovascular ischemia; pain such as acute pain, chronic pain, neuropathic pain, nociceptive pain, allodynia, inflammatory pain, inflammatory hyperalgesia, neuropathies, neuralgia, diabetic neuropathy, HIV-related neuropathy, nerve injury, rheumatoid arthritic pain, osteoarthritic pain, burns, back pain, eye pain, visceral pain, cancer pain (e.g. bone cancer pain), dental pain, headache, migraine, carpal tunnel syndrome, fibromyalgia, neuritis, sciatica, pelvic hypersensitivity, pelvic pain, post herpetic neuralgia, post operative pain, post stroke pain, and menstrual pain; bladder disease such as incontinence, bladder overactivity, micturition disorder, renal colic and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and bronchi constriction; gastrointestinal disease such as gastro esophageal reflux disease (GERD), dysphagia, ulcer, irritable bowel syndrome (IBS), inflammatory bowel disease (IBD), colitis and Crohn's disease; emesis such as cancer chemotherapy-induced emesis, or obesity, said method comprising the step of administering a therapeutically effective amount of a compound described herein, or a pharmaceutically acceptable salt, prodrug, solvate, salt of a solvate, or solvate of a salt thereof, to a subject in need thereof, alone or in combination with an analgesic (e.g. acetaminophen, opioids such as, but not limited to, morphine), or a nonsteroidal anti-inflammatory drug (NSAID), or a combination thereof, and with or without a pharmaceutically acceptable carrier.

Another aspect relates to pharmaceutical compositions comprising therapeutically effective amount of a compound described herein or pharmaceutically acceptable salt, prodrug, solvate, salt of a solvate, or solvate of a salt thereof, in combination with a pharmaceutically acceptable carrier. Such compositions can be administered in accordance with methods described herein, typically as part of a therapeutic regimen for treatment or prevention of conditions and disorders related to TRPV1 activity. For example, the methods are useful for treating or preventing conditions described above. In one embodiment, the methods are useful for treating or preventing pain such as those delineated above. In one embodiment, the pain state is osteoarthritic pain.

Further, included herein are uses of present compounds or pharmaceutically acceptable salts, prodrugs, solvates, salts of solvates, or solvates of salts thereof, in the manufacture of medicaments for the treatment or prevention of the diseases or conditions described above, with or without a pharmaceutically acceptable carrier, and alone, or in combination with an analgesic (e.g. acetaminophen, opioids), or with a nonsteroidal anti-inflammatory drug (NSAID), or combinations thereof.

These and other objectives are described in the following paragraphs. These objectives should not be deemed to narrow the scope of the invention.

DETAILED DESCRIPTION OF THE INVENTION

Disclosed herein are compounds of formula (I)

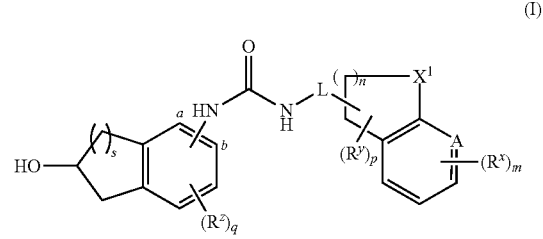

wherein $X^1$, L, $R^x$, $R^y$, $R^z$, A, m, n, p, q, s, and positions a and b are as defined above in the Summary of the Invention and below in the Detailed Description. Compositions comprising such compounds and methods for treating conditions and disorders using such compounds and compositions are also disclosed.

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated from a reaction mixture.

A. DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkyl" as used herein, means a saturated, straight or branched hydrocarbon chain containing from 1 to 10 carbon atoms. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylenyl" means a divalent group derived from a straight or branched, saturated hydrocarbon chain of 1 to 10 carbon atoms, for example, of 1 to 6 carbon atoms. The term "$C_1$-$C_6$ alkylenyl" means a divalent group derived from a straight or branched, saturated hydrocarbon chain of 1 to 6 carbon atoms. Examples of alkylene include, but are not limited to, —$CH_2$—, —C(H)($CH_3$)—, —$CH_2CH_2$—, —$CH_2CH_2CH_2$—, —$CH_2CH_2CH_2CH_2$—, and —$CH_2CH(CH_3)CH_2$—.

The term "aryl" as used herein, means phenyl or a bicyclic aryl. The bicyclic aryl is naphthyl, or a phenyl fused to a $C_3$-$C_6$ monocyclic cycloalkyl. Non-limiting examples of the aryl groups include dihydroindenyl(indanyl), naphthyl, and tetrahydronaphthalenyl. The bicyclic aryls are attached to the parent molecular moiety through any carbon atom contained within the bicyclic ring systems and can be unsubstituted or substituted.

The term "$C_3$-$C_6$ monocyclic cycloalkyl" means an optionally substituted monocyclic ring selected from the group consisting of cyclopropyl, cyclobutyl, cyclopentyl, and cyclohexyl, each of which is optionally substituted.

The term "haloalkyl" as used herein, means an alkyl group, as defined herein, in which one, two, three, four, five, six, or seven hydrogen atoms are replaced by halogen. The term "lower haloalkyl" means a $C_1$-$C_6$ alkyl group in which one, two, three, four, five, six, or seven hydrogen atoms are replaced by halogen. Representative examples of haloalkyl and lower haloalkyl include, but are not limited to, chloromethyl, fluoromethyl, 2-fluoroethyl, 2,2-difluoroethyl, trifluoromethyl, 2,2,2-trifluoroethyl, difluoromethyl, pentafluoroethyl, 2-chloro-3-fluoropentyl, and 2-iodoethyl.

The term "halogen" as used herein, means F, Cl, Br, or I.

The term "oxo" as used herein, means =O.

The terms "treat", "treating", and "treatment" refer to a method of alleviating or abrogating a disease or a condition and/or its attendant symptoms.

The terms "prevent", "preventing", and "prevention" refer to a method of preventing the onset of a disease and/or its attendant symptoms or barring a subject from acquiring a disease or condition. As used herein, "prevent", "preventing" and "prevention" also include delaying the onset of a disease or a condition and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

B. COMPOUNDS

TRPV1 antagonists have formula (I) as described above.

Particular values of variable groups in compounds of formula (I) are as follows. Such values can be used where appropriate with any of the other values, definitions, claims or embodiments defined hereinbefore or hereinafter.

In certain compounds of formula (I), s is 1 and the —NH— of the urea moiety and a carbon atom of the bicyclic ring are bound to each other at position a, such as those exemplified in formula (I-a)

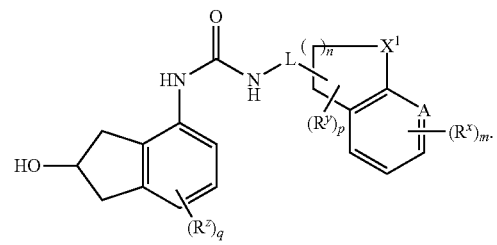

(I-a)

In certain compounds of formula (I), s is 0 and the —NH— of the urea moiety and a carbon atom of the bicyclic ring are bound to each other at position b, such as those exemplified in formula (I-b)

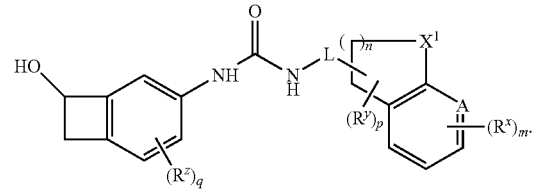

(I-b)

The variables $X^1$, L, $R^x$, $R^y$, $R^z$, A, m, n, p, and q of formula (I-a) and (I-b) are as disclosed in the Summary and embodiments described herein below.

In compounds of formula (I), (I-a), and (I-b), $X^1$, n, and L are as defined in the Summary. For example, in certain embodiments of compounds of formula (I) and (I-a), $X^1$ is $CH_2$, n is 1, and L is a bond. In the embodiments that $X^1$ is $CH_2$, n is 1, and L is a bond, the NH group of the urea moiety can be attached to the ring containing $X^1$ at a variety of positions, for example, the NH group can be attached to the second carbon atom relative to $X^1$, such compounds can be exemplified by, but not limited to, those of formula (I-c) and (I-a-i)

(I-c)

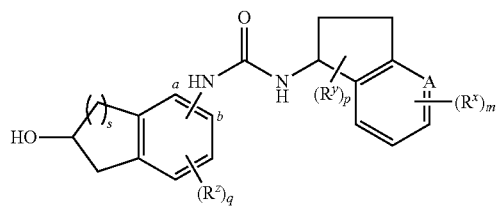

(I-a-i)

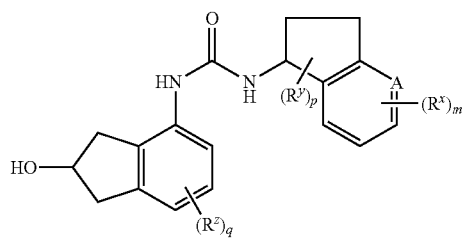

wherein the variables $R^x$, $R^y$, $R^z$, A, m, p, q, s, and positions a and b are as defined above in the Summary and embodiments herein.

In other embodiments of compounds of formula (I), (I-a), and (I-b), $X^1$ is O or $N(R^w)$ and n is 2. In the embodiments wherein $X^1$ is O or $N(R^w)$ and n is 2, the variable L can be attached to the ring containing $X^1$ at a variety of positions, for example, the L group can be attached to the $1^{st}$, $2^{nd}$, or $3^{rd}$ carbon atom relative to $X^1$, such compounds can be exemplified by, but not limited to, those of formula (I-d), (I-e), (I-f), (I-a-ii), (I-a-iii), (I-a-iv), and (I-b-i)

(I-d)

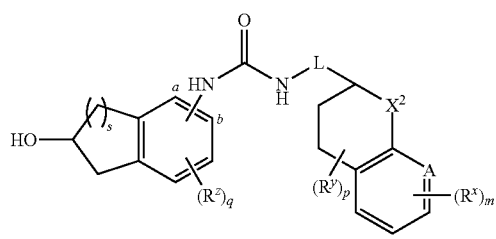

(I-e)

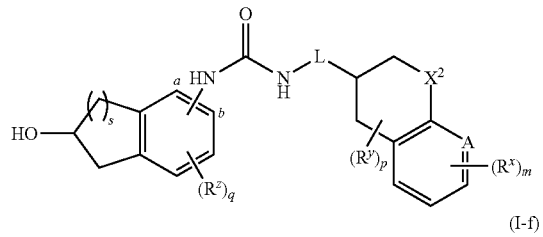

(I-f)

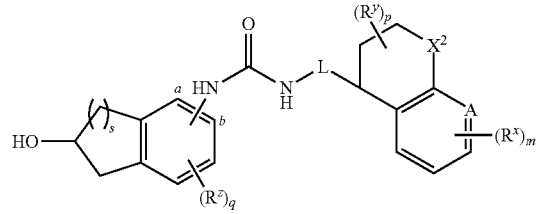

(I-a-ii)

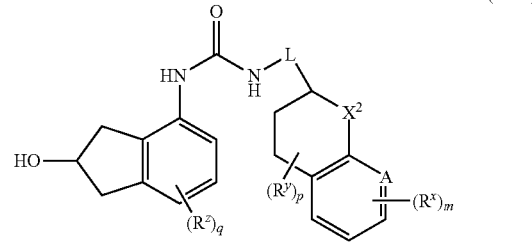

(I-a-iii)

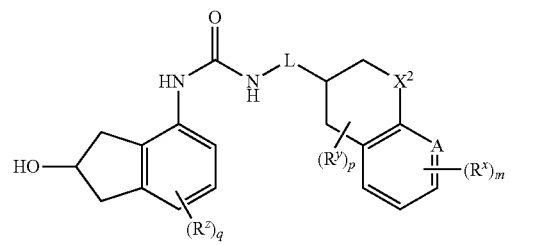

(I-a-iv)

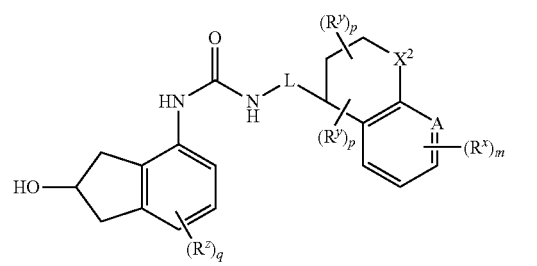

(I-b-i)

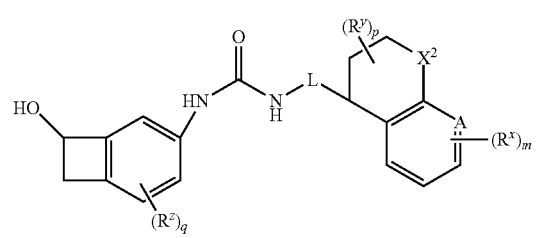

wherein $X^2$ is O or $N(R^w)$, and the variables L, $R^x$, $R^y$, $R^z$, A, m, p, q, s, and positions a and b are as defined above in the Summary and embodiments herein above and below. For example, in certain embodiments of compounds of formula (I), (I-a), (I-d), (I-e), (I-a-ii), and (I-a-iii), L is $CH_2$. In certain embodiments of compounds of formula (I-e) and (I-a-iii), L is $CH_2$ or a bond. In certain embodiments of formula (I), (I-a), (I-b), (I-e), (I-f), (I-a-iii), (I-a-iv), and (I-b-i), L is a bond.

In certain embodiments of compounds of formula (I), (I-a), and (I-b), $X^1$ is O and n is 2.

In other embodiments of compounds of formula (I) and (I-a), $X^1$ is $N(R^w)$ and n is 2.

In certain embodiments of compounds of formula (I-f) and (I-a-iv), $X^2$ is $N(R^w)$.

In certain embodiments of compounds of formula (I-d), (I-e), (I-f), (I-a-ii), (I-a-iii), (I-a-iv), and (I-b-i), $X^2$ is O.

$R^w$ is as defined in the Summary, for example, in certain embodiments, $R^w$ is alkyl (e.g. $C_1$-$C_6$ alkyl such as, but not limited to, methyl).

In compounds of formula (I), (I-a), (I-b), (I-c), (I-d), (I-e), (I-f), (I-a-i), (I-a-ii), (I-a-iii), (I-a-iv), and (I-b-i), the variable A is CH or N. In certain embodiments, the variable A is CH. In yet other embodiments, the variable A is N.

In compounds of formula (I), (I-a), (I-b), (I-c), (I-d), (I-e), (I-f), (I-a-i), (I-a-ii), (I-a-iii), (I-a-iv), and (I-b-i), the variable m has meaning as defined in the Summary and embodiments herein. For example, in certain embodiments, m is 0, 1, or 2.

In compounds of formula (I), (I-a), (I-b), (I-c), (I-d), (I-e), (I-f), (I-a-i), (I-a-ii), (I-a-iii), (I-a-iv), and (I-b-i), the optional substituents (IV) on any substitutable carbon atom of the ring containing A, if present, are as disclosed in the Summary and embodiments herein. For example, each $R^x$, if present, is independently alkyl (e.g. $C_1$-$C_6$ alkyl such as, but not limited to, methyl, tert-butyl), halogen (e.g. F, Cl, Br), haloalkyl (e.g. trifluoromethyl, difluoromethyl, fluoromethyl), O(alkyl) (e.g. O(methyl)), or O(haloalkyl) (e.g. O(trifluoromethyl)). In certain embodiments, each $R^x$, if present, is independently halogen (e.g. F, Cl, Br), haloalkyl (e.g. trifluoromethyl), or O(haloalkyl) (e.g. O(trifluoromethyl)).

In compounds of formula (I), (I-a), (I-b), (I-c), (I-d), (I-e), (I-f), (I-a-i), (I-a-ii), (I-a-iii), (I-a-iv), and (I-b-i), the variable p has meaning as defined in the Summary and embodiments herein. For example, in certain embodiments, p is 0, 1, or 2. In certain embodiments, p is 0. In certain embodiments, p is 1. In certain embodiments, p is 2.

In compounds of formula (I), (I-a), (I-b), (I-d), (I-e), (I-f), (I-a-ii), (I-a-iii), (I-a-iv), and (I-b-i) wherein $X^1$ and $X^2$ are O and p is 2, it is preferred that the two substituents ($R^y$) are on the carbon atom adjacent to $X^1$ and $X^2$.

In compounds of formula (I), (I-a), (I-b), (I-c), (I-d), (I-e), (I-f), (I-a-i), (I-a-ii), (I-a-iii), (I-a-iv), and (I-b-i), the optional substituents ($R^y$) on any substitutable carbon atom of the ring containing $X^1$, if present, are as disclosed in the Summary and embodiments herein. For example, each $R^y$, if present, is independently alkyl (e.g. $C_1$-$C_6$ alkyl such as, but not limited to, methyl, ethyl, n-propyl), haloalkyl (e.g. fluoromethyl, difluoromethyl), —($C_1$-$C_6$ alkylenyl)-O(alkyl) (e.g. —$CH_2$—O(methyl)), $G^1$ (e.g. optionally substituted phenyl), or —($C_1$-$C_6$ alkylenyl)-$G^1$ (e.g. —$CH_2$—$G^1$ wherein $G^1$ is, for example, optionally substituted phenyl). In certain embodiments, each $R^y$, if present, is independently alkyl (e.g. $C_1$-$C_6$ alkyl such as, but not limited to, methyl) or haloalkyl (e.g. fluoromethyl, difluoromethyl).

In certain embodiments, two $R^y$ groups that are attached to the same carbon atom, together with said carbon atom, form a $C_3$-$C_6$ monocyclic cycloalkyl ring as described in the Summary and embodiments herein. In certain embodiments, the monocyclic cycloalkyl ring is cyclobutyl, cyclopentyl, or cyclohexyl, each of which is optionally substituted as described in the Summary and embodiments herein. For example, in certain embodiments, the monocyclic cycloalkyl ring (e.g. cyclobutyl, cyclopentyl, or cyclohexyl) is unsubstituted. In certain embodiments, the monocyclic cycloalkyl is unsubstituted cyclobutyl.

The variable, q, of compounds of formula (I), (I-a), (I-b), (I-c), (I-d), (I-e), (I-f), (I-a-i), (I-a-ii), (I-a-iii), (I-a-iv), and (I-b-i) are as disclosed in the Summary and embodiments herein. In certain embodiments, q, for example, is 0 or 1. In certain embodiments, q is 0. In certain embodiments, q is 1.

The optional substituents ($R^z$) are as defined in the Summary and embodiments herein. For example, in certain embodiments, $R^z$, if present, is halogen. In certain embodiments, $R^z$, if present, is F.

It is appreciated that compounds of formula (I), (I-a), (I-b), (I-c), (I-d), (I-e), (I-f), (I-a-i), (I-a-ii), (I-a-iii), (I-a-iv), and (I-b-i) with combinations of the above embodiments, including particular, more particular and preferred embodiments are contemplated.

Accordingly, one aspect is directed to a group of compounds of formula (I) and (I-a) wherein A is CH, $X^1$ is $CH_2$, and n is 1.

Another aspect is directed to a group of compounds of formula (I) and (I-a) wherein A is CH, $X^1$ is $CH_2$, n is 1, and L is a bond.

Another aspect is directed to a group of compounds of formula (I), (I-a), and (I-b) wherein A is CH, $X^1$ is O or $N(R^w)$, and n is 2. $R^w$ is as defined in the Summary and embodiments herein above. For example, in certain embodiments, $R^w$ is alkyl. In certain embodiments, $R^w$ is methyl.

Another aspect is directed to a group of compounds of formula (I), (I-a), and (I-b) wherein A is CH, $X^1$ is O or $N(R^w)$, n is 2, and L is a bond. $R^w$ is as defined in the Summary and embodiments herein above. For example, in certain embodiments, $R^w$ is alkyl. In certain embodiments, $R^w$ is methyl.

Another aspect is directed to a group of compounds of formula (I) and (I-a), wherein A is CH, $X^1$ is O or $N(R^w)$, n is 2, and L is $CH_2$. $R^w$ is as defined in the Summary and embodiments herein above. For example, in certain embodiments, $R^w$ is alkyl. In certain embodiments, $R^w$ is methyl.

Another aspect is directed to a group of compounds of formula (I), (I-a), and (I-b) wherein A is CH, $X^1$ is O, and n is 2.

Another aspect is directed to a group of compounds of formula (I), (I-a), and (I-b) wherein A is CH, $X^1$ is O, n is 2, and L is a bond.

Another aspect is directed to a group of compounds of formula (I) and (I-a), wherein A is CH, $X^1$ is O, n is 2, and L is $CH_2$.

Another aspect is directed to a group of compounds of formula (I) and (I-a) wherein A is CH, $X^1$ is $N(R^w)$, and n is 2. $R^w$ is as defined in the Summary and embodiments herein above. For example, in certain embodiments, $R^w$ is alkyl. In certain embodiments, $R^w$ is methyl.

Another aspect is directed to a group of compounds of formula (I) and (I-a) wherein A is CH, $X^1$ is $N(R^w)$, n is 2, and L is a bond. $R^w$ is as defined in the Summary and embodiments herein above. For example, in certain embodiments, $R^w$ is alkyl. In certain embodiments, $R^w$ is methyl.

Another aspect is directed to a group of compounds of formula (I-d), (I-e), (I-f), (I-a-ii), (I-a-iii), (I-a-iv), and (I-b-i) wherein A is CH and $X^2$ is O or $N(R^w)$. $R^w$ is as defined in the Summary and embodiments herein above. For example, in certain embodiments, $R^w$ is alkyl. In certain embodiments, $R^w$ is methyl.

Another aspect is directed to a group of compounds of formula (I-f) and (I-a-iv) wherein A is CH and $X^2$ is $N(R^w)$. $R^w$ is as defined in the Summary and embodiments herein above. For example, in certain embodiments, $R^w$ is alkyl. In certain embodiments, $R^w$ is methyl.

Another aspect is directed to a group of compounds of formula (I-f) and (I-a-iv) wherein A is CH, $X^2$ is N($R^w$), and L is a bond. $R^w$ is as defined in the Summary and embodiments herein above. For example, in certain embodiments, $R^w$ is alkyl. In certain embodiments, $R^w$ is methyl.

Another aspect is directed to a group of compounds of formula (I-d), (I-e), (I-f), (I-a-ii), (I-a-iii), (I-a-iv), and (I-b-i) wherein A is CH and $X^2$ is O.

Another aspect is directed to a group of compounds of formula (I-e), (I-f), (I-a-iii), (I-a-iv), and (I-b-i) wherein A is CH, $X^2$ is O, and L is a bond.

Another aspect is directed to a group of compounds of formula (I-d), (I-e), (I-a-ii), and (I-a-iii) wherein A is CH, $X^2$ is O, and L is $CH_2$.

Another aspect is directed to a group of compounds of formula (I) wherein A is N, $X^1$ is O, and L is a bond.

Another aspect is directed to a group of compounds of formula (I-a), (I-f), and (I-a-iv), wherein A is N, $X^2$ is O, and L is a bond.

Within each group of compounds described $R^x$, $R^y$, $R^z$, m, p, and q have values as described in the Summary and embodiments herein above.

Exemplary compounds include, but are not limited to,
1-[(4R)-6,8-difluoro-2,2-bis(fluoromethyl)-3,4-dihydro-2H-chromen-4-yl]-3-[(2R)-2-hydroxy-2,3-dihydro-1H-inden-4-yl]urea;
1-[(4R)-8-chloro-2,2-bis(fluoromethyl)-3,4-dihydro-2H-chromen-4-yl]-3-[(2R)-2-hydroxy-2,3-dihydro-1H-inden-4-yl]urea;
1-[(4R)-2,2-dimethyl-7-(trifluoromethyl)-3,4-dihydro-2H-chromen-4-yl]-3-[(2R)-2-hydroxy-2,3-dihydro-1H-inden-4-yl]urea;
1-[(4R)-7-chloro-2,2-bis(fluoromethyl)-3,4-dihydro-2H-chromen-4-yl]-3-[(2R)-2-hydroxy-2,3-dihydro-1H-inden-4-yl]urea;
1-[(4R)-7-fluoro-2,2-dimethyl-3,4-dihydro-2H-chromen-4-yl]-3-[(2R)-2-hydroxy-2,3-dihydro-1H-inden-4-yl]urea;
1-[(2R)-2-hydroxy-2,3-dihydro-1H-inden-4-yl]-3-[(4R)-8-(trifluoromethoxy)-3,4-dihydro-2H-chromen-4-yl]urea;
1-[(4R)-2,2-bis(fluoromethyl)-7-(trifluoromethyl)-3,4-dihydro-2H-chromen-4-yl]-3-[(2R)-2-hydroxy-2,3-dihydro-1H-inden-4-yl]urea;
1-[(4R)-6-fluoro-3,4-dihydrospiro[chromene-2,1'-cyclobutan]-4-yl]-3-[(2R)-2-hydroxy-2,3-dihydro-1H-inden-4-yl]urea;
1-[(4R)-7,8-difluoro-2,2-dimethyl-3,4-dihydro-2H-chromen-4-yl]-3-[(2R)-2-hydroxy-2,3-dihydro-1H-inden-4-yl]urea;
1-[(4R)-7-chloro-8-fluoro-2,2-dimethyl-3,4-dihydro-2H-chromen-4-yl]-3-[(2R)-2-hydroxy-2,3-dihydro-1H-inden-4-yl]urea;
1-[(4R)-7-chloro-8-fluoro-2,2-bis(fluoromethyl)-3,4-dihydro-2H-chromen-4-yl]-3-[(2R)-2-hydroxy-2,3-dihydro-1H-inden-4-yl]urea;
1-[(4R)-8-chloro-7-fluoro-2,2-dimethyl-3,4-dihydro-2H-chromen-4-yl]-3-[(2R)-2-hydroxy-2,3-dihydro-1H-inden-4-yl]urea;
1-[(4R)-7-chloro-2,2-dimethyl-3,4-dihydro-2H-chromen-4-yl]-3-[(2R)-2-hydroxy-2,3-dihydro-1H-inden-4-yl]urea;
1-[(2R)-2-hydroxy-2,3-dihydro-1H-inden-4-yl]-3-[(4R)-7-(trifluoromethoxy)-3,4-dihydro-2H-chromen-4-yl]urea;
1-[(2R,4R)-7-chloro-2-(fluoromethyl)-2-methyl-3,4-dihydro-2H-chromen-4-yl]-3-[(2R)-2-hydroxy-2,3-dihydro-1H-inden-4-yl]urea;
1-[(2S,4R)-7-chloro-2-(fluoromethyl)-2-methyl-3,4-dihydro-2H-chromen-4-yl]-3-[(2R)-2-hydroxy-2,3-dihydro-1H-inden-4-yl]urea;
1-[(4R)-2,2-dimethyl-3,4-dihydro-2H-chromen-4-yl]-3-[(2R)-2-hydroxy-2,3-dihydro-1H-inden-4-yl]urea;
1-[(2R)-2-hydroxy-2,3-dihydro-1H-inden-4-yl]-3-[(4R)-8-(trifluoromethyl)-3,4-dihydro-2H-chromen-4-yl]urea;
1-[(4R)-2,2-dimethyl-8-(trifluoromethoxy)-3,4-dihydro-2H-chromen-4-yl]-3-[(2R)-2-hydroxy-2,3-dihydro-1H-inden-4-yl]urea;
1-[(2S,4R)-7-chloro-2-(difluoromethyl)-2-methyl-3,4-dihydro-2H-chromen-4-yl]-3-[(2R)-2-hydroxy-2,3-dihydro-1H-inden-4-yl]urea;
1-[(2R)-2-hydroxy-2,3-dihydro-1H-inden-4-yl]-3-[(4R)-7-(trifluoromethyl)-3,4-dihydro-2H-chromen-4-yl]urea;
1-[(4R)-3,4-dihydrospiro[chromene-2,1'-cyclobutan]-4-yl]-3-[(2R)-2-hydroxy-2,3-dihydro-1H-inden-4-yl]urea;
1-[(2R)-2-hydroxy-2,3-dihydro-1H-inden-4-yl]-3-[(4R)-1-methyl-7-(trifluoromethyl)-1,2,3,4-tetrahydroquinolin-4-yl]urea;
1-[(4R)-7-chloro-2,2-bis(fluoromethyl)-3,4-dihydro-2H-chromen-4-yl]-3-[(2S)-2-hydroxy-2,3-dihydro-1H-inden-4-yl]urea;
1-[(2R,4R)-7-chloro-2-(fluoromethyl)-2-methyl-3,4-dihydro-2H-chromen-4-yl]-3-(5-fluoro-2-hydroxy-2,3-dihydro-1H-inden-4-yl)urea;
1-[(2R)-2-hydroxy-2,3-dihydro-1H-inden-4-yl]-3-{[6-(trifluoromethyl)-3,4-dihydro-2H-chromen-2-yl]methyl}urea;
1-[(3S)-6-chloro-3,4-dihydro-2H-chromen-3-yl]-3-[(2R)-2-hydroxy-2,3-dihydro-1H-inden-4-yl]urea;
1-[(6-fluoro-3,4-dihydro-2H-chromen-3-yl)methyl]-3-[(2R)-2-hydroxy-2,3-dihydro-1H-inden-4-yl]urea;
1-[(4R)-2,2-dimethyl-8-(trifluoromethyl)-3,4-dihydro-2H-chromen-4-yl]-3-[(2R)-2-hydroxy-2,3-dihydro-1H-inden-4-yl]urea;
1-[(4R)-2,2-dimethyl-7-(trifluoromethoxy)-3,4-dihydro-2H-chromen-4-yl]-3-[(2R)-2-hydroxy-2,3-dihydro-1H-inden-4-yl]urea;
1-[(4R)-2,2-bis(fluoromethyl)-7-(trifluoromethoxy)-3,4-dihydro-2H-chromen-4-yl]-3-[(2R)-2-hydroxy-2,3-dihydro-1H-inden-4-yl]urea;
1-[(4R)-7-fluoro-2,2-dimethyl-3,4-dihydro-2H-chromen-4-yl]-3-[(2S)-2-hydroxy-2,3-dihydro-1H-inden-4-yl]urea;
1-[(2R,4R)-7-chloro-2-(difluoromethyl)-2-methyl-3,4-dihydro-2H-chromen-4-yl]-3-[(2R)-2-hydroxy-2,3-dihydro-1H-inden-4-yl]urea;
1-[(4R)-2,2-dimethyl-8-(trifluoromethyl)-3,4-dihydro-2H-chromen-4-yl]-3-[(2S)-2-hydroxy-2,3-dihydro-1H-inden-4-yl]urea;
1-[(4R)-7-chloro-8-fluoro-2,2-dimethyl-3,4-dihydro-2H-chromen-4-yl]-3-[(2S)-2-hydroxy-2,3-dihydro-1H-inden-4-yl]urea;
1-[(4R)-8-chloro-7-fluoro-2,2-dimethyl-3,4-dihydro-2H-chromen-4-yl]-3-[(2S)-2-hydroxy-2,3-dihydro-1H-inden-4-yl]urea;
1-[(2S)-2-hydroxy-2,3-dihydro-1H-inden-4-yl]-3-[(4R)-7-(trifluoromethoxy)-3,4-dihydro-2H-chromen-4-yl]urea;
1-[(4R)-7,8-difluoro-2,2-dimethyl-3,4-dihydro-2H-chromen-4-yl]-3-[(2S)-2-hydroxy-2,3-dihydro-1H-inden-4-yl]urea;
1-[(1R)-5-chloro-2,3-dihydro-1H-inden-1-yl]-3-[(2R)-2-hydroxy-2,3-dihydro-1H-inden-4-yl]urea;
1-[(2R)-2-hydroxy-2,3-dihydro-1H-inden-4-yl]-3-[(1R)-5-(trifluoromethyl)-2,3-dihydro-1H-inden-1-yl]urea;
1-[(2R)-2-hydroxy-2,3-dihydro-1H-inden-4-yl]-3-[(1R)-4-(trifluoromethyl)-2,3-dihydro-1H-inden-1-yl]urea;

1-[(2R)-2-hydroxy-2,3-dihydro-1H-inden-4-yl]-3-[(4R)-7-(trifluoromethyl)-3,4-dihydrospiro[chromene-2,1'-cyclobutan]-4-yl]urea;

1-[(2R,4R)-2-(fluoromethyl)-2-methyl-7-(trifluoromethyl)-3,4-dihydro-2H-chromen-4-yl]-3-[(2R)-2-hydroxy-2,3-dihydro-1H-inden-4-yl]urea;

1-[(2S,4R)-2-(fluoromethyl)-2-methyl-7-(trifluoromethyl)-3,4-dihydro-2H-chromen-4-yl]-3-[(2R)-2-hydroxy-2,3-dihydro-1H-inden-4-yl]urea;

1-[(4R)-7-bromo-2,2-bis(fluoromethyl)-3,4-dihydro-2H-chromen-4-yl]-3-[(2R)-2-hydroxy-2,3-dihydro-1H-inden-4-yl]urea;

1-[(4R)-8-fluoro-2,2-dimethyl-3,4-dihydro-2H-chromen-4-yl]-3-[(2R)-2-hydroxy-2,3-dihydro-1H-inden-4-yl]urea;

1-[(4R)-3,4-dihydro-2H-chromen-4-yl]-3-[(2R)-2-hydroxy-2,3-dihydro-1H-inden-4-yl]urea;

1-[(4R)-2,2-diethyl-8-fluoro-3,4-dihydro-2H-chromen-4-yl]-3-[(2R)-2-hydroxy-2,3-dihydro-1H-inden-4-yl]urea;

1-[(4R)-2,2-diethyl-3,4-dihydro-2H-chromen-4-yl]-3-[(2R)-2-hydroxy-2,3-dihydro-1H-inden-4-yl]urea;

1-[(1R)-5-tert-butyl-2,3-dihydro-1H-inden-1-yl]-3-[(2R)-2-hydroxy-2,3-dihydro-1H-inden-4-yl]urea;

1-[(4R)-8-tert-butyl-3,4-dihydro-2H-chromen-4-yl]-3-[(2R)-2-hydroxy-2,3-dihydro-1H-inden-4-yl]urea;

1-[(4R)-2,2-diethyl-7-fluoro-3,4-dihydro-2H-chromen-4-yl]-3-[(2R)-2-hydroxy-2,3-dihydro-1H-inden-4-yl]urea;

1-[(4R)-2,2-diethyl-7-(trifluoromethyl)-3,4-dihydro-2H-chromen-4-yl]-3-[(2R)-2-hydroxy-2,3-dihydro-1H-inden-4-yl]urea;

1-[(4R)-7-chloro-2,2-diethyl-3,4-dihydro-2H-chromen-4-yl]-3-[(2R)-2-hydroxy-2,3-dihydro-1H-inden-4-yl]urea;

1-[(4R)-7,8-dichloro-2,2-diethyl-3,4-dihydro-2H-chromen-4-yl]-3-[(2R)-2-hydroxy-2,3-dihydro-1H-inden-4-yl]urea;

1-[(4R)-6-fluoro-2,2-dipropyl-3,4-dihydro-2H-chromen-4-yl]-3-[(2R)-2-hydroxy-2,3-dihydro-1H-inden-4-yl]urea;

1-[(4R)-6-fluoro-2,2-bis(fluoromethyl)-3,4-dihydro-2H-chromen-4-yl]-3-[(2R)-2-hydroxy-2,3-dihydro-1H-inden-4-yl]urea;

1-[(4R)-2,2-diethyl-6-fluoro-3,4-dihydro-2H-chromen-4-yl]-3-[(2R)-2-hydroxy-2,3-dihydro-1H-inden-4-yl]urea;

1-[(4R)-8-fluoro-2,2-dipropyl-3,4-dihydro-2H-chromen-4-yl]-3-[(2R)-2-hydroxy-2,3-dihydro-1H-inden-4-yl]urea;

1-[(4R)-2,2-diethyl-7-(trifluoromethoxy)-3,4-dihydro-2H-chromen-4-yl]-3-[(2R)-2-hydroxy-2,3-dihydro-1H-inden-4-yl]urea;

1-[(4R)-6-chloro-2-(difluoromethyl)-2-methyl-3,4-dihydro-2H-chromen-4-yl]-3-[(2R)-2-hydroxy-2,3-dihydro-1H-inden-4-yl]urea;

1-[(4R)-7-fluoro-2,2,8-trimethyl-3,4-dihydro-2H-chromen-4-yl]-3-[(2R)-2-hydroxy-2,3-dihydro-1H-inden-4-yl]urea;

1-[(1R)-3,3-dimethyl-2,3-dihydro-1H-inden-1-yl]-3-[(2R)-2-hydroxy-2,3-dihydro-1H-inden-4-yl]urea;

1-[(4R)-6,8-difluoro-3,4-dihydro-2H-chromen-4-yl]-3-[(2R)-2-hydroxy-2,3-dihydro-1H-inden-4-yl]urea;

1-[(4R)-7-fluoro-3,4-dihydro-2H-chromen-4-yl]-3-[(2R)-2-hydroxy-2,3-dihydro-1H-inden-4-yl]urea;

1-[(2R,4R)-8-fluoro-2-(fluoromethyl)-2-methyl-3,4-dihydro-2H-chromen-4-yl]-3-[(2R)-2-hydroxy-2,3-dihydro-1H-inden-4-yl]urea;

1-[(4R)-7-chloro-2-(fluoromethyl)-2-methyl-3,4-dihydro-2H-chromen-4-yl]-3-[(2R)-2-hydroxy-2,3-dihydro-1H-inden-4-yl]urea;

1-[(4R)-6-fluoro-2,2-bis(methoxymethyl)-3,4-dihydro-2H-chromen-4-yl]-3-[(2R)-2-hydroxy-2,3-dihydro-1H-inden-4-yl]urea;

1-[(4R)-2,2-bis(fluoromethyl)-3,4-dihydro-2H-chromen-4-yl]-3-[(2R)-2-hydroxy-2,3-dihydro-1H-inden-4-yl]urea;

1-[(4R)-8-fluoro-2,2-bis(fluoromethyl)-3,4-dihydro-2H-chromen-4-yl]-3-[(2R)-2-hydroxy-2,3-dihydro-1H-inden-4-yl]urea;

1-[(4R)-8-fluoro-2,2-dimethyl-3,4-dihydro-2H-chromen-4-yl]-3-[(2S)-2-hydroxy-2,3-dihydro-1H-inden-4-yl]urea;

1-[(4R)-2,2-dimethyl-7-(trifluoromethoxy)-3,4-dihydro-2H-chromen-4-yl]-3-[(2S)-2-hydroxy-2,3-dihydro-1H-inden-4-yl]urea;

1-[(2S)-2-hydroxy-2,3-dihydro-1H-inden-4-yl]-3-[(4R)-8-(trifluoromethoxy)-3,4-dihydro-2H-chromen-4-yl]urea;

1-[(4R)-2,2-bis(fluoromethyl)-7-(trifluoromethyl)-3,4-dihydro-2H-chromen-4-yl]-3-[(2S)-2-hydroxy-2,3-dihydro-1H-inden-4-yl]urea;

1-[(4R)-8-chloro-2,2-bis(fluoromethyl)-3,4-dihydro-2H-chromen-4-yl]-3-[(2S)-2-hydroxy-2,3-dihydro-1H-inden-4-yl]urea;

1-[(4R)-2,2-bis(fluoromethyl)-7-(trifluoromethoxy)-3,4-dihydro-2H-chromen-4-yl]-3-[(2S)-2-hydroxy-2,3-dihydro-1H-inden-4-yl]urea;

1-[(4R)-2,2-dimethyl-7-(trifluoromethyl)-3,4-dihydro-2H-chromen-4-yl]-3-[(2S)-2-hydroxy-2,3-dihydro-1H-inden-4-yl]urea;

1-[(4R)-6-fluoro-2,2-bis(fluoromethyl)-3,4-dihydro-2H-chromen-4-yl]-3-[(2S)-2-hydroxy-2,3-dihydro-1H-inden-4-yl]urea;

1-[(4R)-6,8-difluoro-2,2-bis(fluoromethyl)-3,4-dihydro-2H-chromen-4-yl]-3-[(2S)-2-hydroxy-2,3-dihydro-1H-inden-4-yl]urea;

1-[(4R)-6-fluoro-3,4-dihydrospiro[chromene-2,1'-cyclobutan]-4-yl]-3-[(2S)-2-hydroxy-2,3-dihydro-1H-inden-4-yl]urea;

1-[(4R)-7-chloro-8-fluoro-2,2-bis(fluoromethyl)-3,4-dihydro-2H-chromen-4-yl]-3-[(2S)-2-hydroxy-2,3-dihydro-1H-inden-4-yl]urea;

1-[(4R)-2,2-dimethyl-3,4-dihydro-2H-chromen-4-yl]-3-[(2S)-2-hydroxy-2,3-dihydro-1H-inden-4-yl]urea;

1-[(4R)-6-fluoro-2,2-dimethyl-3,4-dihydro-2H-chromen-4-yl]-3-[(2S)-2-hydroxy-2,3-dihydro-1H-inden-4-yl]urea;

1-[(2S)-2-hydroxy-2,3-dihydro-1H-inden-4-yl]-3-[(4R)-1-methyl-7-(trifluoromethyl)-1,2,3,4-tetrahydroquinolin-4-yl]urea;

1-[(4R)-7-chloro-2,2-dimethyl-3,4-dihydro-2H-chromen-4-yl]-3-[(2S)-2-hydroxy-2,3-dihydro-1H-inden-4-yl]urea;

1-[(4R)-2,2-bis(fluoromethyl)-3,4-dihydro-2H-chromen-4-yl]-3-[(2S)-2-hydroxy-2,3-dihydro-1H-inden-4-yl]urea;

1-[(4R)-8-fluoro-2,2-bis(fluoromethyl)-3,4-dihydro-2H-chromen-4-yl]-3-[(2S)-2-hydroxy-2,3-dihydro-1H-inden-4-yl]urea;

1-[(4R)-2,2-dimethyl-8-(trifluoromethoxy)-3,4-dihydro-2H-chromen-4-yl]-3-[(2S)-2-hydroxy-2,3-dihydro-1H-inden-4-yl]urea;

1-[(3R)-6-chloro-3,4-dihydro-2H-chromen-3-yl]-3-[(2R)-2-hydroxy-2,3-dihydro-1H-inden-4-yl]urea;

1-[(2S,4R)-7-chloro-8-fluoro-2-(fluoromethyl)-2-methyl-3,4-dihydro-2H-chromen-4-yl]-3-[(2R)-2-hydroxy-2,3-dihydro-1H-inden-4-yl]urea;

1-(6-fluoro-2,2-dimethyl-3,4-dihydro-2H-chromen-3-yl)-3-[(2R)-2-hydroxy-2,3-dihydro-1H-inden-4-yl]urea;

1-[(1R)-5-fluoro-2,3-dihydro-1H-inden-1-yl]-3-[(2R)-2-hydroxy-2,3-dihydro-1H-inden-4-yl]urea;

1-[(2R)-2-hydroxy-2,3-dihydro-1H-inden-4-yl]-3-[(4S)-7-(trifluoromethoxy)-3,4-dihydro-2H-chromen-4-yl]urea;

1-[(2S)-2-hydroxy-2,3-dihydro-1H-inden-4-yl]-3-[(4S)-7-(trifluoromethoxy)-3,4-dihydro-2H-chromen-4-yl]urea;

1-[(4R)-2,2-bis(fluoromethyl)-7-(trifluoromethyl)-3,4-dihydro-2H-chromen-4-yl]-3-[(2S)-5-fluoro-2-hydroxy-2,3-dihydro-1H-inden-4-yl]urea;

1-[(4R)-2,2-bis(fluoromethyl)-7-(trifluoromethyl)-3,4-dihydro-2H-chromen-4-yl]-3-[(2R)-5-fluoro-2-hydroxy-2,3-dihydro-1H-inden-4-yl]urea;

1-[(4S)-7-chloro-2,2-bis(fluoromethyl)-3,4-dihydro-2H-chromen-4-yl]-3-[(2R)-2-hydroxy-2,3-dihydro-1H-inden-4-yl]urea;

1-[(4S)-7-chloro-2,2-bis(fluoromethyl)-3,4-dihydro-2H-chromen-4-yl]-3-[(2S)-2-hydroxy-2,3-dihydro-1H-inden-4-yl]urea;

1-(7-chloro-3,4-dihydro-2H-chromen-3-yl)-3-[(2R)-2-hydroxy-2,3-dihydro-1H-inden-4-yl]urea;

1-[(2R,4R)-7-chloro-2-(fluoromethyl)-2-methyl-3,4-dihydro-2H-chromen-4-yl]-3-[(2S)-5-fluoro-2-hydroxy-2,3-dihydro-1H-inden-4-yl]urea;

1-[(4S)-6-fluoro-3,4-dihydrospiro[chromene-2,1'-cyclobutan]-4-yl]-3-[(2R)-2-hydroxy-2,3-dihydro-1H-inden-4-yl]urea;

1-[(4S)-6-fluoro-3,4-dihydrospiro[chromene-2,1'-cyclobutan]-4-yl]-3-[(2S)-2-hydroxy-2,3-dihydro-1H-inden-4-yl]urea;

1-[(4S)-6-fluoro-2,2-dimethyl-3,4-dihydro-2H-chromen-4-yl]-3-[(2S)-2-hydroxy-2,3-dihydro-1H-inden-4-yl]urea;

1-[(4S)-6-fluoro-2,2-dimethyl-3,4-dihydro-2H-chromen-4-yl]-3-[(2R)-2-hydroxy-2,3-dihydro-1H-inden-4-yl]urea;

1-[(4R)-2,2-dimethyl-7-(trifluoromethyl)-3,4-dihydro-2H-pyrano[2,3-b]pyridin-4-yl]-3-[(2R)-2-hydroxy-2,3-dihydro-1H-inden-4-yl]urea;

1-[(2R)-2-hydroxy-2,3-dihydro-1H-inden-4-yl]-3-[(1R)-5-(trifluoromethoxy)-2,3-dihydro-1H-inden-1-yl]urea;

1-(2-hydroxy-2,3-dihydro-1H-inden-4-yl)-3-(7-methoxy-3,4-dihydro-2H-chromen-4-yl)urea;

1-(2-hydroxy-2,3-dihydro-1H-inden-4-yl)-3-(3-phenyl-3,4-dihydro-2H-chromen-4-yl)urea;

1-[3-(3,4-dimethoxybenzyl)-3,4-dihydro-2H-chromen-4-yl]-3-(2-hydroxy-2,3-dihydro-1H-inden-4-yl)urea;

1-[2-(3-chlorophenyl)-3,4-dihydro-2H-chromen-4-yl]-3-(2-hydroxy-2,3-dihydro-1H-inden-4-yl)urea;

1-(3-benzyl-3,4-dihydro-2H-chromen-4-yl)-3-(2-hydroxy-2,3-dihydro-1H-inden-4-yl)urea;

1-[3-(3,4-dichlorobenzyl)-3,4-dihydro-2H-chromen-4-yl]-3-(2-hydroxy-2,3-dihydro-1H-inden-4-yl)urea;

1-[2-(3,4-dimethoxyphenyl)-3,4-dihydro-2H-chromen-4-yl]-3-(2-hydroxy-2,3-dihydro-1H-inden-4-yl)urea;

1-[3-(3,4-dichlorobenzyl)-7-methoxy-3,4-dihydro-2H-chromen-4-yl]-3-(2-hydroxy-2,3-dihydro-1H-inden-4-yl)urea;

1-[3-(4-chlorophenyl)-3,4-dihydro-2H-chromen-4-yl]-3-(2-hydroxy-2,3-dihydro-1H-inden-4-yl)urea;

1-(2-hydroxy-2,3-dihydro-1H-inden-4-yl)-3-[3-(4-methoxyphenyl)-3,4-dihydro-2H-chromen-4-yl]urea;

1-[2-(4-chlorophenyl)-3,4-dihydro-2H-chromen-4-yl]-3-(2-hydroxy-2,3-dihydro-1H-inden-4-yl)urea;

1-(2-hydroxy-2,3-dihydro-1H-inden-4-yl)-3-(2-phenyl-3,4-dihydro-2H-chromen-4-yl)urea;

1-[2-(4-fluorophenyl)-3,4-dihydro-2H-chromen-4-yl]-3-(2-hydroxy-2,3-dihydro-1H-inden-4-yl)urea;

1-[2-(2-chlorophenyl)-3,4-dihydro-2H-chromen-4-yl]-3-(2-hydroxy-2,3-dihydro-1H-inden-4-yl)urea;

1-(2-hydroxy-2,3-dihydro-1H-inden-4-yl)-3-{2-[4-(trifluoromethyl)phenyl]-3,4-dihydro-2H-chromen-4-yl}urea;

1-[2-(4-chlorophenyl)-7-methoxy-3,4-dihydro-2H-chromen-4-yl]-3-(2-hydroxy-2,3-dihydro-1H-inden-4-yl)urea;

1-(3,4-dihydrospiro[chromene-2,1'-cyclohexan]-4-yl)-3-(2-hydroxy-2,3-dihydro-1H-inden-4-yl)urea;

1-[2-(3,4-dichlorobenzyl)-2,3-dihydro-1H-inden-1-yl]-3-(2-hydroxy-2,3-dihydro-1H-inden-4-yl)urea;

1-(2-benzyl-2,3-dihydro-1H-inden-1-yl)-3-(2-hydroxy-2,3-dihydro-1H-inden-4-yl)urea;

1-[(2S,4R)-2-(difluoromethyl)-2-methyl-3,4-dihydro-2H-chromen-4-yl]-3-[(2R)-2-hydroxy-2,3-dihydro-1H-inden-4-yl]urea;

1-[(2R,4R)-2-(difluoromethyl)-2-methyl-3,4-dihydro-2H-chromen-4-yl]-3-[(2R)-2-hydroxy-2,3-dihydro-1H-inden-4-yl]urea;

1-[(4R)-3,4-dihydrospiro[chromene-2,1'-cyclopentan]-4-yl]-3-[(2R)-2-hydroxy-2,3-dihydro-1H-inden-4-yl]urea;

1-[(4R)-7-fluoro-2,2-bis(fluoromethyl)-3,4-dihydro-2H-chromen-4-yl]-3-[(2R)-2-hydroxy-2,3-dihydro-1H-inden-4-yl]urea;

1-[(4R)-7-(difluoromethyl)-2,2-bis(fluoromethyl)-3,4-dihydro-2H-chromen-4-yl]-3-[(2R)-2-hydroxy-2,3-dihydro-1H-inden-4-yl]urea;

1-[(2R,4R)-7-chloro-2-(fluoromethyl)-2-methyl-3,4-dihydro-2H-chromen-4-yl]-3-(8-hydroxybicyclo[4.2.0]octa-1,3,5-trien-3-yl)urea;

1-[(2R,4R)-2-(fluoromethyl)-2-methyl-3,4-dihydro-2H-chromen-4-yl]-3-(8-hydroxybicyclo[4.2.0]octa-1,3,5-trien-3-yl)urea;

1-[(4R)-7-chloro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-7-chloro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-2,2-dimethyl-8-(trifluoromethyl)-3,4-dihydro-2H-chromen-4-yl]-3-[(2S)-7-fluoro-2-hydroxy-2,3-dihydro-1H-inden-4-yl]urea;

1-[(4R)-8-fluoro-2,2-dimethyl-3,4-dihydro-2H-chromen-4-yl]-3-[(2S)-7-fluoro-2-hydroxy-2,3-dihydro-1H-inden-4-yl]urea;

1-[(2S)-7-fluoro-2-hydroxy-2,3-dihydro-1H-inden-4-yl]-3-[(4R)-8-(trifluoromethoxy)-3,4-dihydro-2H-chromen-4-yl]urea;

1-[(4R)-7-fluoro-2,2-dimethyl-3,4-dihydro-2H-chromen-4-yl]-3-[(2S)-7-fluoro-2-hydroxy-2,3-dihydro-1H-inden-4-yl]urea;

1-[(4R)-2,2-bis(fluoromethyl)-7-(trifluoromethoxy)-3,4-dihydro-2H-chromen-4-yl]-3-[(2S)-7-fluoro-2-hydroxy-2,3-dihydro-1H-inden-4-yl]urea;

1-[(4R)-2,2-dimethyl-7-(trifluoromethyl)-3,4-dihydro-2H-chromen-4-yl]-3-[(2S)-7-fluoro-2-hydroxy-2,3-dihydro-1H-inden-4-yl]urea;

1-[(4R)-6-fluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-6,8-difluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-6-fluoro-3,4-dihydrospiro[chromene-2,1'-cyclobutan]-4-yl]-3-[(2S)-7-fluoro-2-hydroxy-2,3-dihydro-1H-inden-4-yl]urea;

1-[(4R)-7-chloro-8-fluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-2,2-dimethyl-3,4-dihydro-2H-chromen-4-yl]-3-[(2S)-7-fluoro-2-hydroxy-2,3-dihydro-1H-inden-4-yl]urea;

1-[(4R)-6-fluoro-2,2-dimethyl-3,4-dihydro-2H-chromen-4-yl]-3-[(2S)-7-fluoro-2-hydroxy-2,3-dihydro-1H-inden-4-yl]urea;

1-[(4R)-8-chloro-7-fluoro-2,2-dimethyl-3,4-dihydro-2H-chromen-4-yl]-3-[(2S)-7-fluoro-2-hydroxy-2,3-dihydro-1H-inden-4-yl]urea;

1-[(2S)-7-fluoro-2-hydroxy-2,3-dihydro-1H-inden-4-yl]-3-[(4R)-1-methyl-7-(trifluoromethyl)-1,2,3,4-tetrahydroquinolin-4-yl]urea;

1-[(4R)-7-chloro-2,2-dimethyl-3,4-dihydro-2H-chromen-4-yl]-3-[(2S)-7-fluoro-2-hydroxy-2,3-dihydro-1H-inden-4-yl]urea;

1-[(2S)-7-fluoro-2-hydroxy-2,3-dihydro-1H-inden-4-yl]-3-[(4R)-7-(trifluoromethoxy)-3,4-dihydro-2H-chromen-4-yl]urea;

1-[(4R)-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-8-fluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-7,8-difluoro-2,2-dimethyl-3,4-dihydro-2H-chromen-4-yl]-3-[(2S)-7-fluoro-2-hydroxy-2,3-dihydro-1H-inden-4-yl]urea;

1-[(4R)-2,2-dimethyl-8-(trifluoromethoxy)-3,4-dihydro-2H-chromen-4-yl]-3-[(2S)-7-fluoro-2-hydroxy-2,3-dihydro-1H-inden-4-yl]urea;

1-(7-fluoro-2-hydroxy-2,3-dihydro-1H-inden-4-yl)-3-[5-(trifluoromethyl)-2,3-dihydro-1H-inden-1-yl]urea;

1-[(4R)-2,2-dimethyl-8-(trifluoromethyl)-3,4-dihydro-2H-chromen-4-yl]-3-[(2R)-7-fluoro-2-hydroxy-2,3-dihydro-1H-inden-4-yl]urea;

1-[(4R)-8-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-7-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-2,2-bis(fluoromethyl)-7-(trifluoromethoxy)-3,4-dihydro-2H-chromen-4-yl]-3-[(2R)-7-fluoro-2-hydroxy-2,3-dihydro-1H-inden-4-yl]urea;

1-[(4R)-2,2-dimethyl-7-(trifluoromethyl)-3,4-dihydro-2H-chromen-4-yl]-3-[(2R)-7-fluoro-2-hydroxy-2,3-dihydro-1H-inden-4-yl]urea;

1-[(4R)-6-fluoro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-6,8-difluoro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-6-fluoro-3,4-dihydrospiro[chromene-2,1'-cyclobutan]-4-yl]-3-[(2R)-7-fluoro-2-hydroxy-2,3-dihydro-1H-inden-4-yl]urea;

1-[(4R)-2,2-dimethyl-3,4-dihydro-2H-chromen-4-yl]-3-[(2R)-7-fluoro-2-hydroxy-2,3-dihydro-1H-inden-4-yl]urea;

1-[(4R)-6-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-8-chloro-7-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-7-chloro-2,2-dimethyl-3,4-dihydro-2H-chromen-4-yl]-3-[(2R)-7-fluoro-2-hydroxy-2,3-dihydro-1H-inden-4-yl]urea;

1-[(2R)-7-fluoro-2-hydroxy-2,3-dihydro-1H-inden-4-yl]-3-[(4R)-7-(trifluoromethoxy)-3,4-dihydro-2H-chromen-4-yl]urea;

1-[(4R)-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-8-fluoro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-7,8-difluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-2,2-dimethyl-8-(trifluoromethoxy)-3,4-dihydro-2H-chromen-4-yl]-3-[(2R)-7-fluoro-2-hydroxy-2,3-dihydro-1H-inden-4-yl]urea;

1-[(2R)-7-fluoro-2-hydroxy-2,3-dihydro-1H-inden-4-yl]-3-[(4R)-8-(trifluoromethyl)-3,4-dihydro-2H-chromen-4-yl]urea;

1-(5-chloro-2,3-dihydro-1H-inden-1-yl)-3-(7-fluoro-2-hydroxy-2,3-dihydro-1H-inden-4-yl)urea;

1-[(4R)-7-chloro-2,2-bis(fluoromethyl)-3,4-dihydro-2H-chromen-4-yl]-3-[(2R)-5-fluoro-2-hydroxy-2,3-dihydro-1H-inden-4-yl]urea; and 1-[(4R)-7-chloro-2,2-bis(fluoromethyl)-3,4-dihydro-2H-chromen-4-yl]-3-[(2S)-5-fluoro-2-hydroxy-2,3-dihydro-1H-inden-4-yl]urea.

In one embodiment, the compound of Formula (I) when administered to a human subject produces an increase in average time for hand withdrawal from a temperature-controlled water bath that is less than about 30 seconds relative to a vehicle control. In another embodiment, the compound of Formula (I) when administered to a human subject produces an increase in average time for hand withdrawal from a temperature-controlled water bath that is less than about 10 seconds relative to a vehicle control. In another embodiment, the compound of Formula (I) when administered to a human subject produces an increase in average time for hand withdrawal from a temperature-controlled water bath that is less than about 5 seconds relative to a vehicle control. In still another embodiment, the compound of Formula (I) when administered to a human subject does not significantly change the average time for hand withdrawal from a temperature-controlled water bath relative to a vehicle control. In one embodiment, the water bath is maintained at a constant temperature in the range from about 46° C. to about 52° C. In still another embodiment, the water bath is maintained at a constant temperature of about 49° C.

In one embodiment, the compound of Formula (I), when tested in a rat tail immersion model of noxious thermosensation (such as the model described in the Biological Data section of this application), produces a percent increase in average response latency for tail withdrawal relative to a vehicle control that is less than about 20%. In another embodiment, the compound of Formula (I), when tested in a rat tail immersion model of noxious thermosensation, produces a percent increase in average response latency for tail withdrawal relative to a vehicle control that is less than about 10%. In still another embodiment, the compound of Formula (I), when tested in a rat tail immersion model of noxious thermosensation, produces no statistically significant increase in the average response latency for tail withdrawal relative to a vehicle control.

In one embodiment, the compound of Formula (I), when contacted in vitro at a concentration of about 10 μM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

In one embodiment, the compound of Formula (I), (a) when tested in a rat tail immersion model of noxious thermosensation (such as the model described in the Biological Data section of this application), produces a percent increase in average response latency for tail withdrawal relative to a vehicle control that is less than about 20%; and (b) when contacted in vitro at a concentration of about 10 μM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

In one embodiment, the compound of Formula (I), (a) when tested in a rat tail immersion model of noxious thermosensation (such as the model described in the Biological Data section of this application), produces a percent increase in average response latency for tail withdrawal relative to a vehicle control that is less than about 10%; and (b) when contacted in vitro at a concentration of about 10 μM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

In one embodiment, the compound of Formula (I), (a) when tested in a rat tail immersion model of noxious thermosensation (such as the model described in the Biological Data section of this application), produces no statistically significant increase in the average response latency for tail withdrawal relative to a vehicle control; and (b) when contacted in vitro at a concentration of about 10 μM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

Compounds described herein can exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It can be appreciated two or more asymmetric centers can be present in the present compounds, hence several diastereomers and enantiomers of the exemplified structures can often be possible, and that pure diastereomers and enantiomers represent preferred embodiments. It is intended that pure diastereomers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

For example, compounds of formula (I-f) wherein L is a bond can be isolated as any one of the diastereomers as shown below, or mixtures of two or more of diastereomers of various ratios:

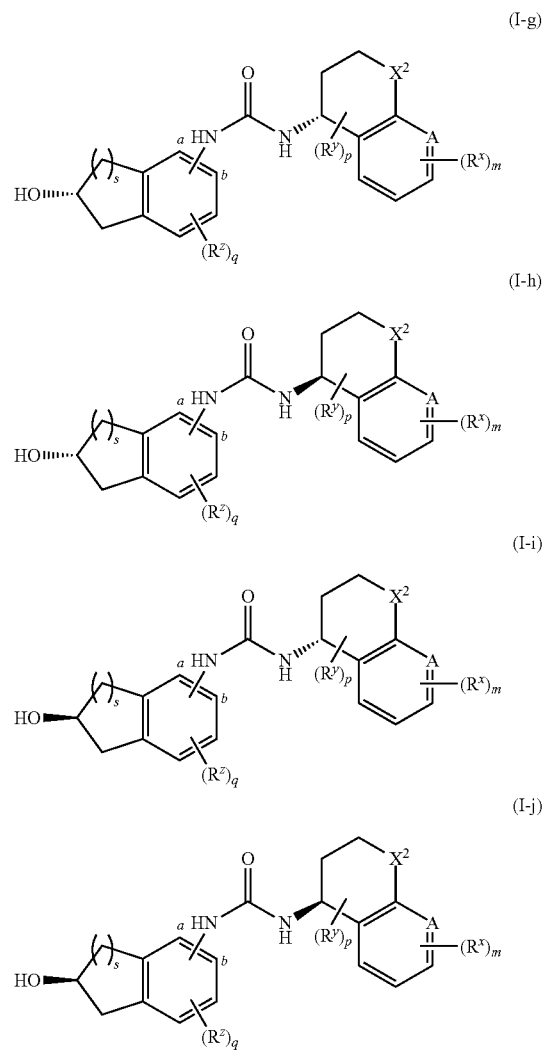

It is to be understood that the substituents and variables, and combinations thereof, in formula (I-g)-(I-j) have the same values as those discussed above.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein can exhibit the phenomenon of tautomerism.

Thus, the formula drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formula drawings.

Compounds of the invention can exist in isotope-labeled or isotope-enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of TRPV1 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labeled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to TRPV1 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D. M. and Finkel A. J, Ann. N.Y. Acad. Sci. 1960 84: 770; Thomson J. F., Ann. New York Acad. Sci. 1960 84: 736; Czakja D. M. et al., Am. J. Physiol. 1961 201: 357). Acute replacement of as high as 15%-23% in human fluids with deuterium was found not to cause toxicity (Blagojevic N. et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions, potentially altering the pharmacokinetic profile or efficacy relative to the non-isotopic compound.

C. GENERAL SYNTHESIS

This invention is intended to encompass compounds described herein when prepared by synthetic processes or by metabolic processes. Preparation of the compounds by metabolic processes includes those occurring in the human or animal body (in vivo) or processes occurring in vitro.

The compounds can be prepared by a variety of processes well known for the preparation of compounds of this class. For example, compounds disclosed herein wherein the groups $X^1$, $X^2$, L, $R^x$, $R^y$, $R^z$, A, m, n, p, q, s, and positions a and b have the meanings as set forth in the summary and detailed description sections unless otherwise noted, can be synthesized as shown in the accompanying Schemes 1-16.

As used in the descriptions of the schemes and the examples, certain abbreviations are intended to have the following meanings: $Ac_2O$ for acetic anhydride; AcOH for acetic acid; AcCl for acetyl chloride; AgOAc for silver acetate; BINAP for 2,2'-bis(diphenylphosphino)-1,1'-binaphthyl; Boc for tert-butoxycarbonyl; $(Boc)_2O$ for di-tert-butyl dicarbonate; n-BuLi for n-butyllithium; dba for dibenzylideneacetone; DABCO for 1,4-diazabicyclo[2.2.2]octane; DCE for dichloroethane; DMF for dimethylformamide; DMSO for dimethyl sulfoxide; DSC for N,N-disuccinimidyl carbonate; DME for dimethoxyethane; DPPA for diphenylphosphoryl azide; $Et_3N$ for triethylamine; EtOAc for ethyl acetate; $Et_2O$ for diethyl ether; IPA for isopropanol; EtOH for ethanol; KOt-Bu for potassium tert-butoxide; mCPBA for 3-chloroperoxybenzoic acid; MeOH for methanol; Me-THF for 2-methyl tetrahydrofuran; MOM for methoxymethyl; MTBE for methyl ten-butyl ether; $Ms_2O$ for methanesulfonic anhydride; NCS for N-chlorosuccinimide; i-PrOH for isopropanol; $PhCH_3$ for toluene; pyr for pyridine; Ra—Ni for Raney nickel; THF for tetrahydrofuran; $Ti(OEt)_4$ for titatium(IV) ethoxide; TsOH for p-toluenesulfonic acid; TfOH for triflic acid (trifluoromethansulfonic acid); and HPLC for high performance liquid chromatography.

Ureas of general formula (I-a) can be prepared as described in Scheme 1. Amines of formula (I) can be reacted first with disuccinyl carbonate in the presence of a base such as but not limited to pyridine, and in a solvent such as acetonitrile, and subsequently with amine nucleophiles of formula (2) in the presence of an amine base such as but not limited to diisopropylethylamine, to provide ureas of general formula (I).

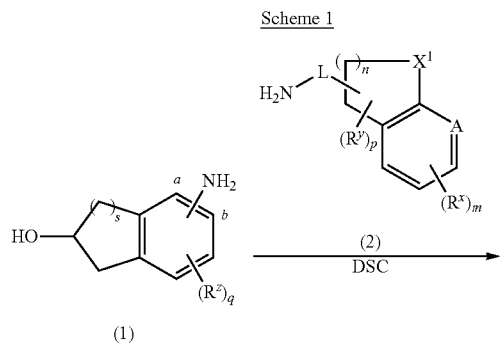

Alternatively, ureas can be prepared by direct formation of a carbon-nitrogen bond between a primary urea and halides of formula (4) as described in Scheme 2. Amines of general formula (2) can be reacted with phenyl carbamate in the presence of a non-nucleophilic amine base such as but not limited to diisopropyethylamine, at an elevated temperature (e.g. at about 50 to about 80° C.) in a solvent such as but not limited to THF to provide primary ureas of general formula (3). Primary ureas (3) can be reacted with halides of general formula (4) to give ureas of general formula (I). The reaction of (3) and (4), wherein X is Cl, Br, or I, to provide ureas (I) is generally performed in the presence of a palladium catalyst such as Pd2 dba3, a trivalent phosphine ligand such as, but not limited to, 5-(di-tert-butylphosphino)-1',3',5'-triphenyl-1'H-1,4'-bipyrazole (CAS #894086-00-1, Aldrich), a base such as potassium carbonate, at an elevated temperature and in the solvent of choice (for example, DME at about 40-60° C.).

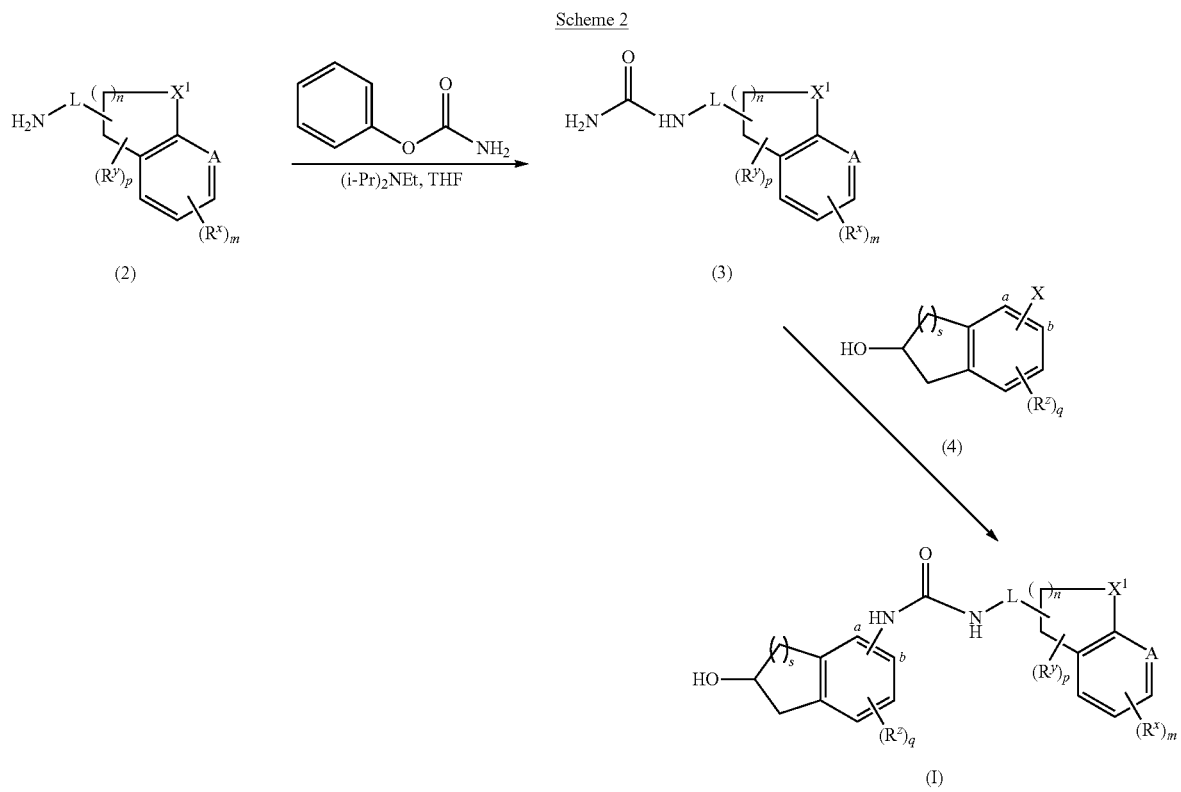

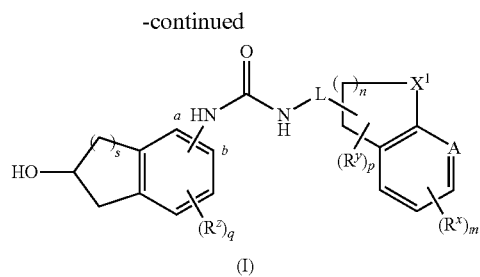

The requisite amines of general formula (2) can be prepared by any of several methods and synthetic intermediates selected by one of ordinary skill in the art as described in Schemes 3-5. As shown in Scheme 3, hydroxy benzoic acids of general formula (5) can be reacted with excess methyllithium in a solvent such as diethyl ether at reduced temperatures (less than about 20° C.) to provide methyl ketones of general formula (6). Methyl ketones (6) can be reacted with ketones of general formula (7) to provide chromanones of general formula (8). Non-limiting examples of ketones (7) include acetone and 3-pentanone. The reaction is generally performed in the presence of an amine base such as pyrrolidine, in a protic solvent such as but not limited to methanol.

Ketones of general formula (8) can be treated with a variety of chiral hydride sources known to those skilled in the art (Corey, E. J. et al., *J. Org. Chem.* 1988, 53, 2861; Kawanami, S. et al., *Tetrahedron* 2003, 59, 8411; Corey, E. J. et al., *Tetrahedron Asymm.* 2002, 13, 1347) to provide chiral alcohols of general formula (9). Alcohols (9) can be converted to azides of general formula (10) by activation with a sulfonylating agent such as but not limited to methanesulfonic anhydride, followed by displacement with a nucleophile azide source such as but not limited tetrabutylammonium azide (Burgard, A. et al. *Tetrahedron* 1999, 55, 7555). It is to be noted that the transformation of (9) to (10) proceeds with net overall inversion of absolute stereochemistry. Finally, amines of general formula (11) can be obtained by reduction of azides (10) by treatment with a phosphine agent such as triphenylphosphine under aqueous conditions with an appropriate water-miscible organic co-solvent such as but not limited to THF (Gololobov, Y. G. et al. *Tetrahedron* 1981, 37, 437). Alternatively, amines of general formula (11) can be obtained by reduction of azides (10) by treatment with hydrogen gas in the presence of a catalyst such as but not limited to Raney nickel (Ra—Ni) in a solvent such as but not limited to methanol. Chiral amines of formula (11) can be converted to compounds of formula (I) using synthetic methods as outlined in Schemes 1-2.

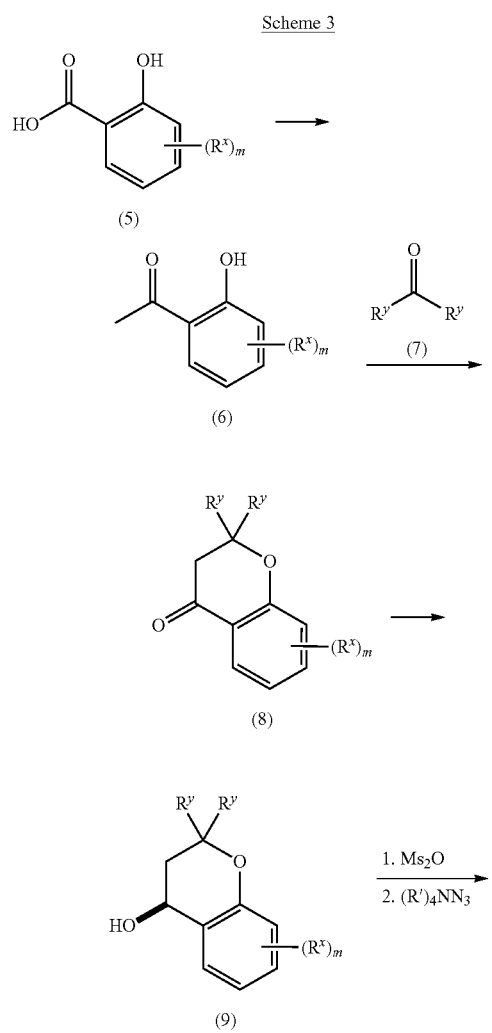

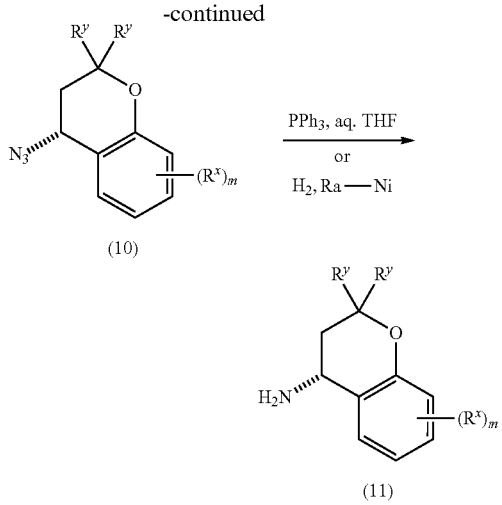

Racemic amines of general formula (2) wherein L is a bond can be prepared from the corresponding ketones (12) as shown in Scheme 4. Ketones (12) can be treated with hydroxylamines or alkoxyamines such as methoxyamine to provide oximes of general formula (13). The oxime group of (13) can be reduced using methodologies known by one skilled in the art, for example, by hydrogenolysis in the presence of a catalyst such as palladium on carbon to provide the amines of general formula (14).

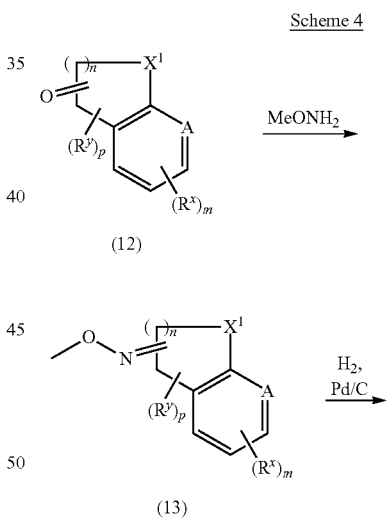

As shown in Scheme 5, amines of general formula (16) can be prepared according to the general procedure described by Ellman and co-workers (Tanuwidjaja, J.; Ellman, J. A. et al., *J. Org. Chem.* 2007, 72, 626). Ketones of general formula (12) can be condensed with a chiral sulfinamide such as tert-butanesulfinamide in the presence of a Lewis acid such as Ti(OEt)$_4$ to provide N-sulfinyl imine intermediates that can undergo a subsequent in situ reduction with reagents such as sodium borohydride to provide sulfinamides of general formula (15). Treatment of sulfinamides of general formula (15) with acetyl chloride and methanol in a solvent such as but not limited to methyl tert-butyl ether provides amine hydrochloride salts of general formula (16).

Scheme 5

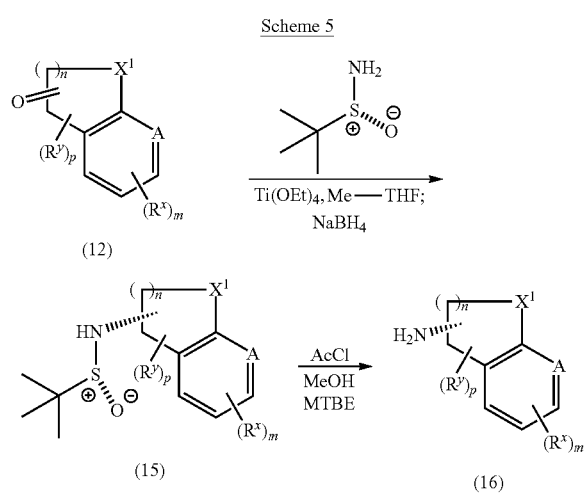

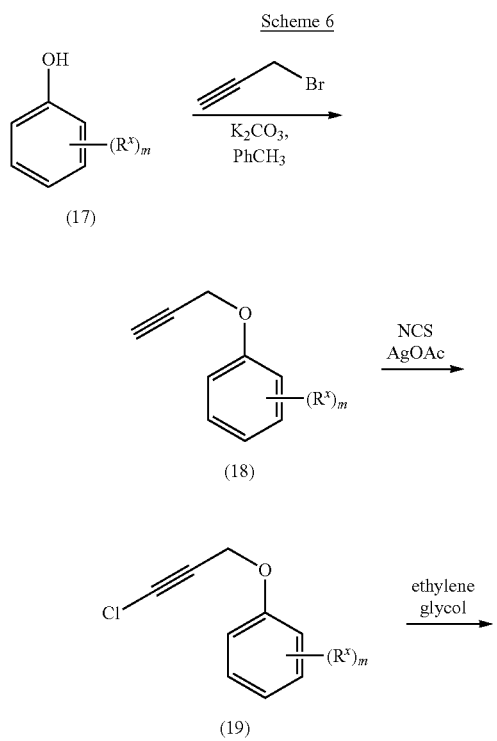

The requisite ketones of general formula (12) wherein A is CH, $X^1$ is O, p is 0, and n is 2 can also be prepared by any of several methods and synthetic intermediates selected by one of ordinary skill in the art as described in Schemes 6-7. As shown in Scheme 6, phenols of general formula (17) can be treated with a propargyl bromide and a base such as but not limited to potassium carbonate in a nonpolar solvent such as but not limited to toluene to provide aryl ethers of general formula (18). Reaction of (18) with NCS in the presence of silver acetate in a solvent such as but not limited to acetone affords chloro alkyne derivatives of general formula (19). Upon heating of chloro alkynes of general formula (19) in a solvent such as but not limited to ethylene glycol, cyclization occurs to give chromanones of general formula (12a).

In a related approach shown in Scheme 7, phenols of general formula (17) can be treated with 3-chloropropanoyl chloride in the presence of strong acid activators such as but not limited to TFA and triflic acid to afford directly chromanones of general formula (12a).

Scheme 7

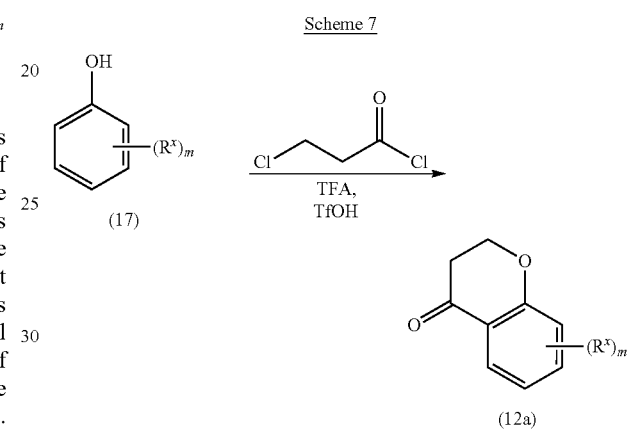

Certain chromanyl amine intermediates can be further functionalized using the sequence described in Scheme 8. Fluorinated chromanyl amines of general formula (20) wherein m' is 0, 1 or 2 can be protected as the corresponding tert-butoxy carbamates of general formula (21) using tert-butoxycarbonyl anhydride and an amine base such as but not limited to triethylamine. Reaction of (21) with a strong base or combination of strong bases such as but not limited to, n-BuLi, potassium tert-butoxide, and/or sec-butyllithium, in a solvent such as but not limited to THF effects deprotonation adjacent to the fluorine. It can be appreciated by those skilled in the art that these organometallic intermediates can be reacted with a wide variety of electrophilic reagents ($R^{41}X$) wherein $R^{41}$ is alkyl or haloalkyl and X is Cl, Br, or I. Non limiting examples of $R^{41}X$ include hexachloroethane and methyl iodide. Subsequent removal of the Boc protecting group with a strong acid, such as but not limited to, TFA provides amines of general formula (22).

Scheme 8

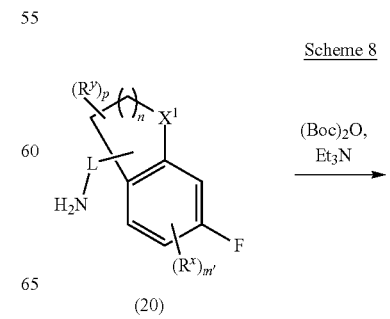

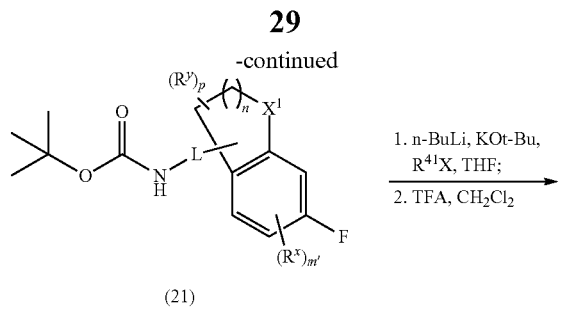

(21)

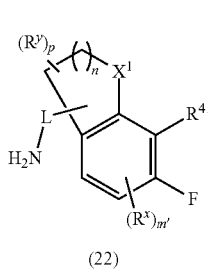

(22)

The requisite substituted methyl ketones (6) shown in Scheme 3 can be prepared by the methods described in Schemes 9 and 10. For example, phenols of general formula (17) can be protected and subsequently subjected to direct ortho-metalation as shown in Scheme 9. Treatment of (17) with methoxymethyl chloride in the presence of a non-nucleophilic amine base such as diisopropylethylamine in an aprotic solvent such as dichloromethane provides protected phenols of general formula (23). Other examples of suitable phenol oxygen protecting groups are known in the art. Reaction of (23) with an organolithium base such as n-butyllithium in a solvent at reduced temperature (such as THF at −78° C.) followed by quenching with carbon dioxide and subsequent exposure to mineral acid provides hydroxy benzoic acids of general formula (24). Hydroxy benzoic acids (24) can be transformed to methyl ketones (6) using the chemistry described in Scheme 3.

Scheme 9

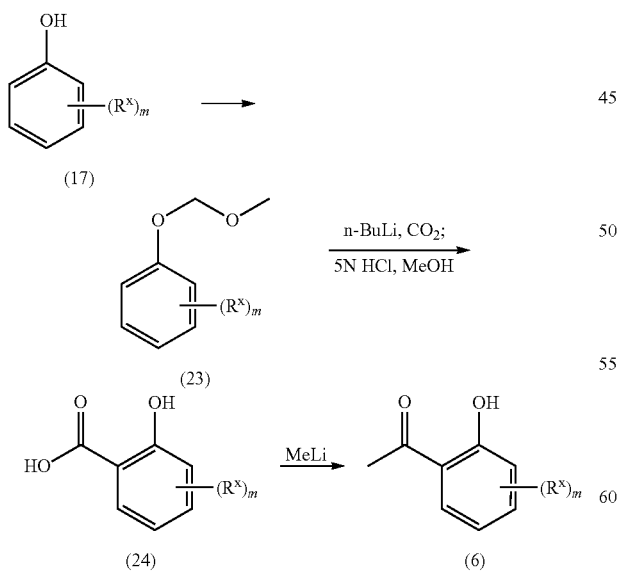

Substituted methyl ketones (6) also can be prepared according to Scheme 10. Phenols of general formula (17) can be treated with an acetylating agent, such as but not limited to, acetyl chloride in the presence of a base, such as but not limited to, pyridine to generate esters of general formula (25). Subjection to a Lewis acid such as but not limited to aluminum trichloride in a solvent such as but not limited to dichloroethane provides methyl ketones of general formula (6).

Scheme 10

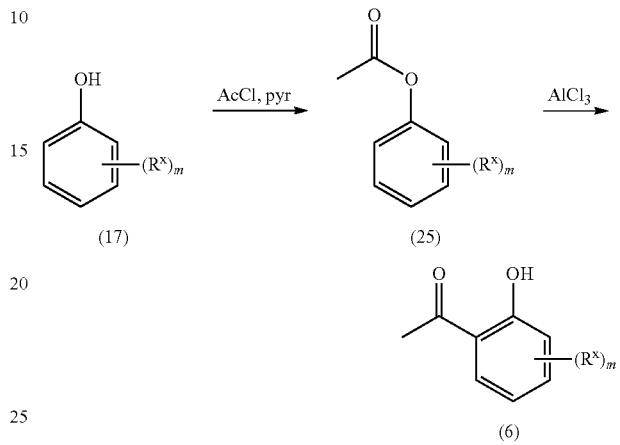

Scheme 11 describes a general approach to the preparation of chiral indanol building blocks. Acylated indanols of general formula (26) can be prepared according to the procedure outlined in US2003/109700. Treatment with potassium carbonate in the presence of a solvent such as but not limited to methanol provides racemic indanols of general formula (1). Single enantiomers (27) and (28) can be separated from racemic alcohol (1) by chiral HPLC using a chiral column such as, but not limited to, a Chiralpak IC or Chiralcel AD-H column (Chiral Technologies Inc., West Chester, Pa.) and solvent mixtures containing, for example, methanol, hexane, and isopropanol.

Scheme 11

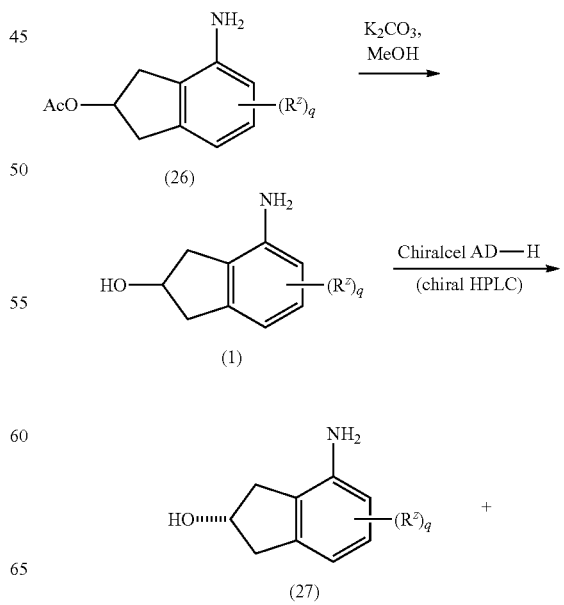

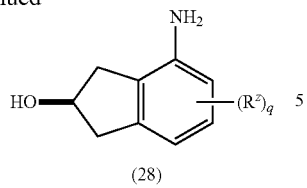

(28)

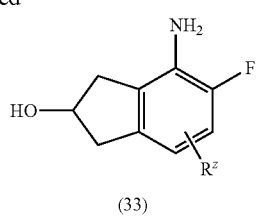

(33)

Fluorinated indanols can be prepared according to the sequence shown in Scheme 12. Fluoroindanones of general formula (29) can be treated with a mixture of bromine and a Lewis acid such as but not limited to aluminum trichloride in a nonpolar solvent such as but not limited to dichloromethane to provide brominated products of general formula (30). Ketones of general formula (30) can be treated with a reducing agent such as but not limited to sodium borohydride to provide the corresponding hydroxy derivative which upon exposure to a protic acid such as but not limited to TsOH undergo elimination to provide indenes of general formula (31). Exposure to an oxidizing agent such as but not limited to mCPBA in a nonpolar solvent such as, but not limited to, dichloromethane, provides epoxide intermediates which can undergo regioselective ring opening with a reducing agent such as but not limited to lithium aluminum hydride in an ethereal solvent such as but not limited to diethyl ether provides indanols of general formula (32). Indanols of general formula (32) can then be reacted with benzophenone imine and a palladium catalyst such as but not limited to Pd2(dba)3 and a phosphine ligand such as but not limited to BINAP. Acid hydrolysis of the intermediate imine provides indanols of general formula (33).

The regiochemistry of attachment of the amino or methylamino substituent on the chroman ring can be varied as described in Schemes 13-15. Scheme 13 describes the preparation of 3-amino substituted chromans. Hydroxy aldehydes of general formula (34), upon heading with acrylonitrile and DABCO, provide chromans of general formula (35). Exposure to aqueous sodium hydroxides affords carboxylic acids of general formula (36). Treatment of (36) with DPPA in the presence of an amine base such as but not limited to triethylamine and heating, followed by exposure to hydrochloric acid provides chromanones of general formula (37). Reaction of (37) with O-methylhydroxylamine in the presence of a base such as but not limited to pyridine provides compounds of general formula (38) which upon treatment with hydrogen gas in the presence of a catalyst such as but not limited to Raney nickel provides amines of general formula (39) Amines (39) can be coupled with indanols of general formula (I) using the conditions described in Schemes 1 or 2 to provide regioisomeric chromanyl ureas of general formula (40).

Scheme 12

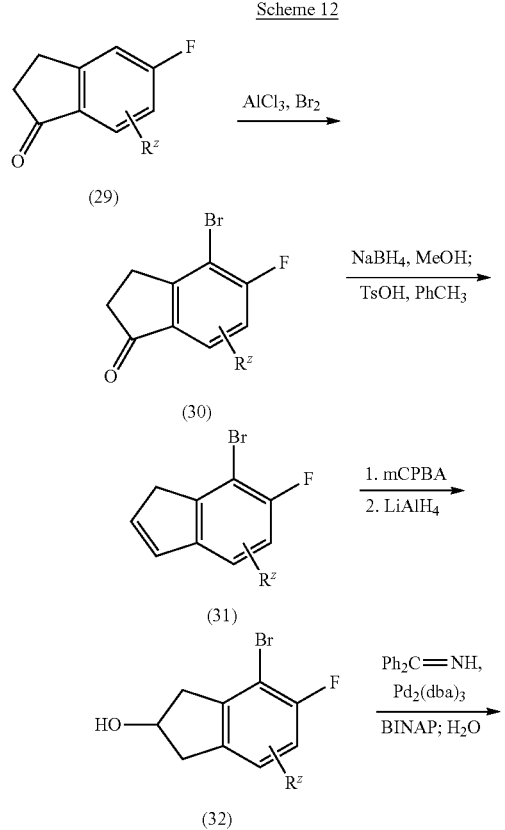

Scheme 13

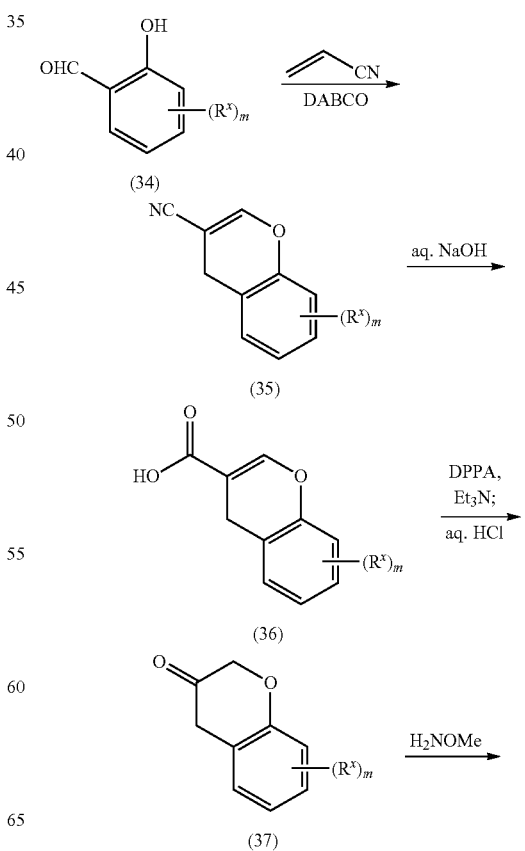

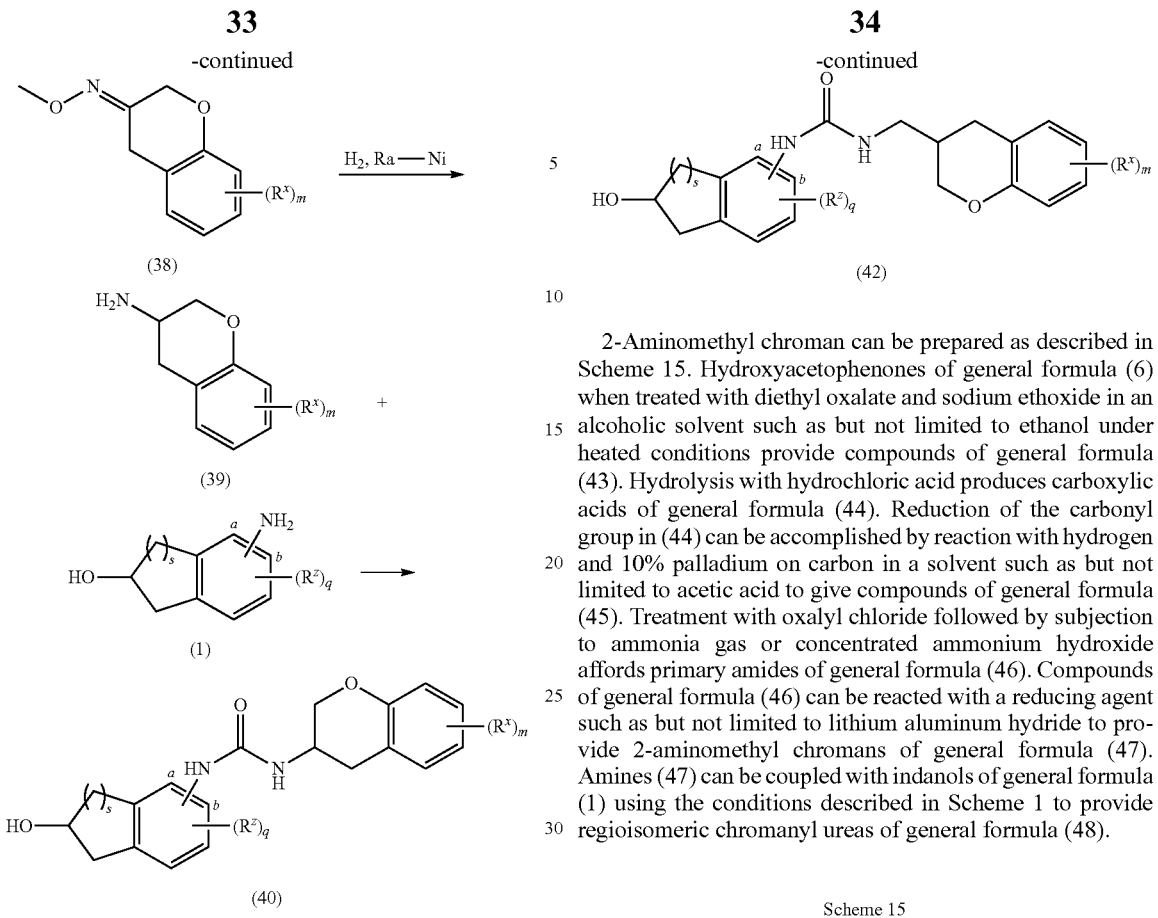

As shown in Scheme 14, 3-aminomethyl chromans can be prepared via the intermediacy of the nitriles (35) described in Scheme 13. Compounds of general formula (35) upon treatment with hydrogen gas in the presence of a catalyst such as but not limited to Raney nickel provides amines of general formula (41) Amines (41) can be coupled with indanols of general formula (1) using the conditions described in Schemes 1 and 2 to provide regioisomeric chromanyl ureas of general formula (42).

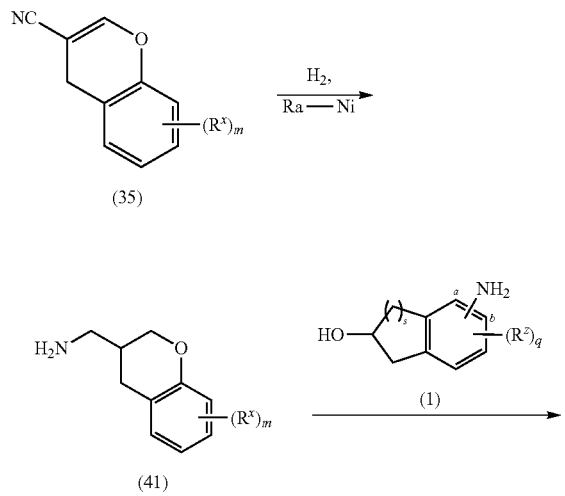

2-Aminomethyl chroman can be prepared as described in Scheme 15. Hydroxyacetophenones of general formula (6) when treated with diethyl oxalate and sodium ethoxide in an alcoholic solvent such as but not limited to ethanol under heated conditions provide compounds of general formula (43). Hydrolysis with hydrochloric acid produces carboxylic acids of general formula (44). Reduction of the carbonyl group in (44) can be accomplished by reaction with hydrogen and 10% palladium on carbon in a solvent such as but not limited to acetic acid to give compounds of general formula (45). Treatment with oxalyl chloride followed by subjection to ammonia gas or concentrated ammonium hydroxide affords primary amides of general formula (46). Compounds of general formula (46) can be reacted with a reducing agent such as but not limited to lithium aluminum hydride to provide 2-aminomethyl chromans of general formula (47). Amines (47) can be coupled with indanols of general formula (1) using the conditions described in Scheme 1 to provide regioisomeric chromanyl ureas of general formula (48).

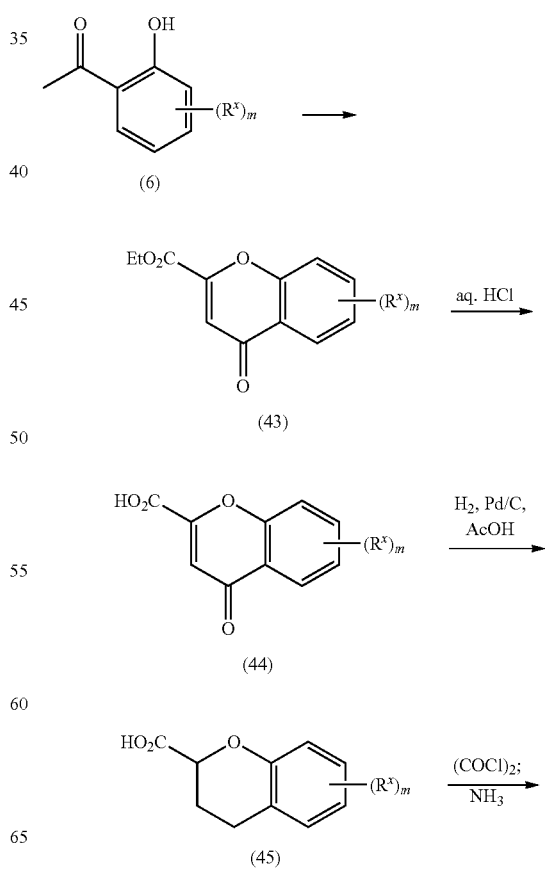

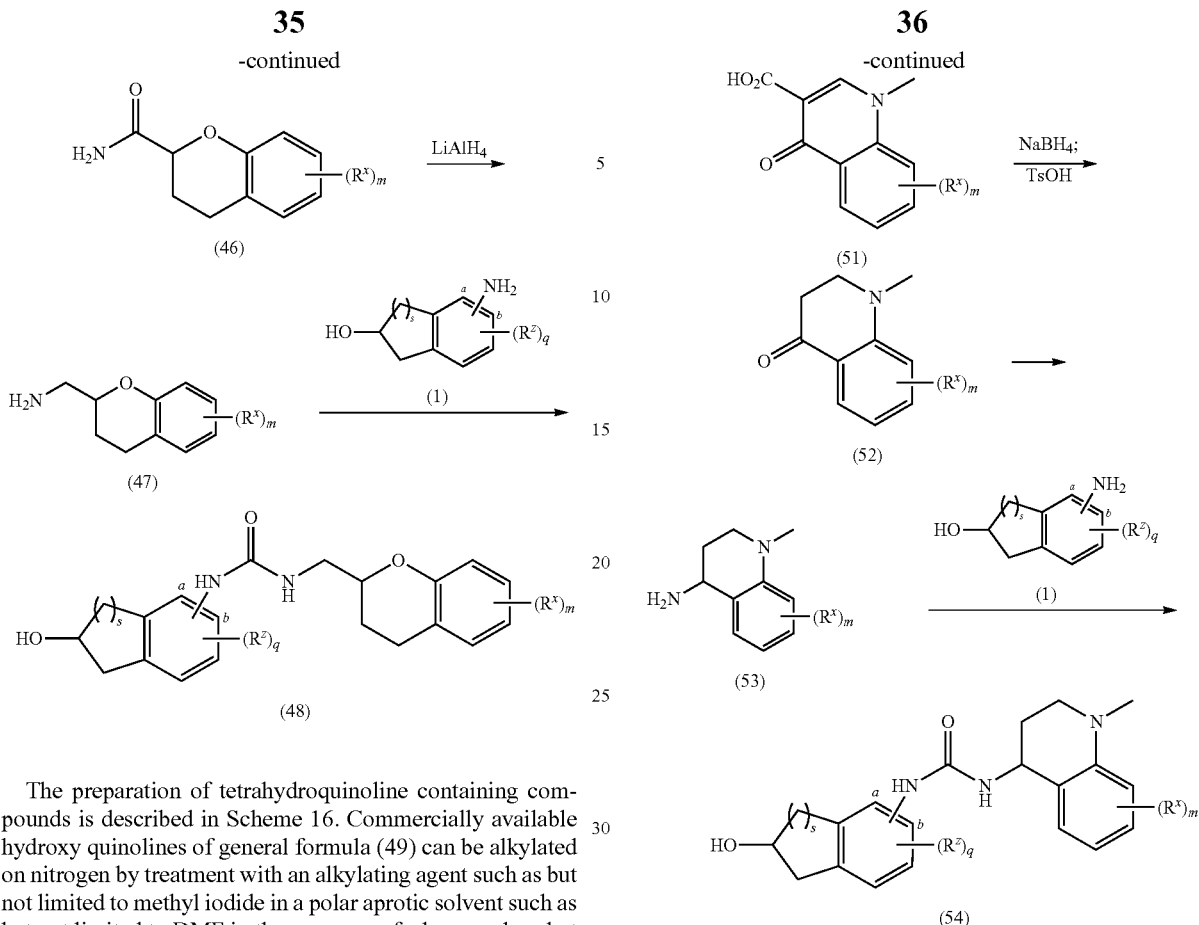

The preparation of tetrahydroquinoline containing compounds is described in Scheme 16. Commercially available hydroxy quinolines of general formula (49) can be alkylated on nitrogen by treatment with an alkylating agent such as but not limited to methyl iodide in a polar aprotic solvent such as but not limited to DMF in the presence of a base such as but not limited to potassium carbonate to afford compounds of general formula (50). Saponification with sodium hydroxide provides carboxylic acids of general formula (51), which can be treated with a reducing agent such as but not limited to sodium borohydride then decarboxylated with a protic acid such as but not limited to TsOH to afford quinolinones of general formula (52). Carbonyl derivatives of general formula (52) can be converted to amines of general formula (53) using the procedures of Scheme 5, which can be subsequently reacted with indanols of general formula (1) using the conditions described in Scheme 1 to provide tetrahydroquinolines of general formula (54).

Scheme 16

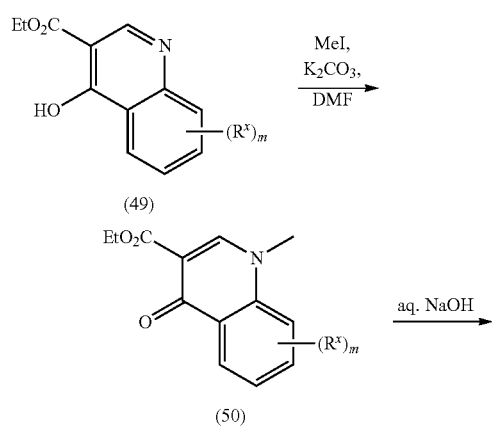

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Following Examples can be used for illustrative purposes and should not be deemed to narrow the scope of the invention.

D. EXAMPLES

Example 1

1-[(4R)-6,8-difluoro-2,2-bis(fluoromethyl)-3,4-dihydro-2H-chromen-4-yl]-3-[(2R)-2-hydroxy-2,3-dihydro-1H-inden-4-yl]urea

Example 1A 6,8-difluoro-2,2-bis(fluoromethyl)chroman-4-one

A solution of 1-(3,5-difluoro-2-hydroxyphenyl)ethanone (4.98 g, 28.9 mmol), MeOH (50 mL), 1,3-difluoroacetone (5.44 g, 57.9 mmol), and pyrrolidine (4.79 mL, 57.9 mmol) was heated at 60° C. for 20 hours. The dark solution was cooled, concentrated, chased with toluene, and then passed through a silica gel plug, washing with toluene (200 mL) and MTBE (200 mL). The filtrate was washed with 2N NaOH (50 mL×2), dried (Na$_2$SO$_4$), filtered, and concentrated to afford the title compound (5.80 g, 23.37 mmol, 81%), which was used without further purification in the next step. MS (DCI) m/z 299 (M+51)$^+$.

Example 1B

A solution of Example 1A (5.80 g, 23.37 mmol), (R)-(+)-2-methyl-2-propanesulfinamide (4.25 g, 35.1 mmol), 2-methyltetrahydrofuran (100 mL), and titanium(IV) ethoxide (19.60 mL, 93 mmol) was heated at 70° C. for 200 minutes. After cooling to −40° C., sodium borohydride (1.77 g, 46.7 mmol) was added to the reaction mixture. The slurry was slowly warmed to 10° C. and stirred overnight, then 10% aqueous citric acid (100 mL) was added carefully and the mixture was stirred vigorously for 1 hour at ambient temperature. The mixture was diluted with MTBE (200 mL), and the layers separated. The organic layer was washed with water (100 mL) and brine (50 mL), dried (Na$_2$SO$_4$), filtered, and concentrated, giving 7.90 g crude product. The crude solid was dissolved in MTBE (5 vol, 40 mL), then hexanes (10 vol, 80 mL) was added slowly and the slurry was cooled to <5° C. The white slurry was filtered and washed with cold 2:1 hexanes/MTBE. The solid was dried in a vacuum oven at 45° C. to afford the title compound (4.58 g, 13.0 mmol, 55%). MS (DCI) m/z 354 (M+H)$^+$.

Example 1C (4R)-6,8-difluoro-2,2-bis(fluoromethyl)chroman-4-amine, hydrochloride salt A light brown slurry of Example 1B (4.58 g, 13.0 mmol) in MTBE (130 mL) was stirred at ambient temperature and MeOH/HCl [formed by adding acetyl chloride (1.84 mL, 25.9 mmol) to methanol (4.72 mL, 117 mmol) at <25° C.] was added. The mixture was stirred at ambient temperature for 1 hour, at 35° C. for 1 hour, and at 45° C. for 1 hour. After cooling to ambient temperature the white slurry was filtered and washed with MTBE (50 mL). The white solid was dried in a vacuum oven at 60° C. to afford the title compound (3.52 g, 12.34 mmol, 95%). MS (DCI) m/z 250 (M+NH$_4$—H$_2$O)$^+$.

Example 1D 4-amino-2,3-dihydro-1H-inden-2-ol

A slurry of 4-amino-2,3-dihydro-1H-inden-2-yl acetate (12.6 g, 65.9 mmol; prepared according to US2003109700), MeOH (63 mL), and potassium carbonate (13.7 g, 99.0 mmol) was stirred at ambient temperature for 15 minutes. The reaction mixture was diluted with IPA (630 mL), passed through a plug of silica gel, washed with IPA (100 mL), and concentrated to give the title compound (9.70 g, 65.0 mmol, 99%). MS (DCI) m/z 267 (M+NH$_4$)$^+$.

Example 1E (R)-4-amino-2,3-dihydro-1H-inden-2-ol

Example 1D (9.70 g, 65.0 mmol) was dissolved in MeOH (120 mL), then IPA (120 mL) and hexanes (240 mL) were added. This solution was passed through an Chiralpak AD-H semi-prep column (2 cm×25 cm), 15% IPA/hexanes isochratic mobile phase, 10 mL/min, 5 mL/injection, giving the title compound, (R)-4-amino-2,3-dihydro-1H-inden-2-ol (4.89 g, 50%), and (S)-4-amino-2,3-dihydro-1H-inden-2-ol (4.56 g, 47%). Analytical chiral HPLC showed no minor enantiomer. MS (DCI) m/z 267 (M+NH$_4$)$^+$.

Example 1F

1-[(4R)-6,8-difluoro-2,2-bis(fluoromethyl)-3,4-dihydro-2H-chromen-4-yl]-3-[(2R)-2-hydroxy-2,3-dihydro-1H-inden-4-yl]urea A solution of N,N-disuccinimidyl carbonate (558 mg, 2.18 mmol), acetonitrile (4 mL), pyridine (0.176 mL, 2.18 mmol), and Example 1E (325 mg, 2.18 mmol) was stirred at ambient temperature. After 30 minutes, N,N-diisopropylethylamine (1.13 mL, 6.54 mmol) and Example 1C (622 mg, 2.18 mmol) were added. After 10 minutes, 2N HCl (100 mL) and EtOAc (200 mL) were added, the layers were separated, and the organic layer was washed with brine (50 mL), dried (Na$_2$SO$_4$), filtered, and concentrated. The residue was purified by silica gel chromatography (gradient elution, 25-100% EtOAc/hexanes) to afford the title compound (732 mg, 1.72 mmol, 79%). $^1$H NMR (300 MHz, DMSO-$d_6$) δ 7.86 (s, 1H), 7.74 (d, J=8.1 Hz, 1H), 7.26 (ddd, J=11.2, 8.5, 2.9 Hz, 1H), 7.05 (t, J=7.8 Hz, 1H), 6.99-6.90 (m, 2H), 6.84 (d, J=7.4 Hz, 1H), 5.06-4.96 (m, 1H), 4.86 (d, J=4.1 Hz, 1H), 4.82-4.55 (m, 4H), 4.55-4.47 (m, 1H), 3.05 (dd, J=16.3, 6.3 Hz, 1H), 2.99 (dd, J=16.3, 6.3 Hz, 1H), 2.74 (dd, J=16.0, 3.6 Hz, 1H), 2.66 (dd, J=16.1, 3.4 Hz, 1H), 2.36 (dd, J=13.8, 6.0 Hz, 1H), 1.99 (ddd, J=13.7, 10.6, 2.8 Hz, 1H); MS (ESI$^+$) m/z 425 (M+H)$^+$, 442 (M+NH$_4$)$^+$; [α]$^{23}_D$=+0.27° (c 1.12, CH$_3$OH).

Example 2

1-[(4R)-8-chloro-2,2-bis(fluoromethyl)-3,4-dihydro-2H-chromen-4-yl]-3-[(2R)-2-hydroxy-2,3-dihydro-1H-inden-4-yl]urea

Example 2A 8-chloro-2,2-bis(fluoromethyl)chroman-4-one

The title compound was prepared according to the procedure of Example 1A, substituting 1-(3-chloro-2-hydroxyphenyl)ethanone for 1-(3,5-difluoro-2-hydroxyphenyl)ethanone. MS (DCI/NH$_3$) m/z 264 (M+NH$_4$)$^+$.

Example 2B (S)-8-chloro-2,2-bis(fluoromethyl)chroman-4-ol

A solution of MTBE (10 mL), (R)-diphenyl(pyrrolidin-2-yl)methanol (0.402 g, 1.585 mmol), and borane-N,N-diethylaniline complex (6.77 mL, 38.0 mmol) was heated to 45° C. and Example 2A (7.82 g, 31.7 mmol) in MTBE (68 mL) was added over 60 minutes via addition funnel. After 20 minutes, the solution was cooled to 25° C. and MeOH (40 mL) was added, keeping the temperature between 20 and 25° C. (H$_2$ evolution). After stirring for 10 minutes at ambient temperature, 2N HCl (80 mL) was added, the solution was stirred for 10 minutes, and MTBE (160 mL) was added. The layers were separated and the organic layer was washed with 2 N HCl (80 mL). The aqueous layer was back-extracted with MTBE (40 mL). The combined organic layers were washed with brine (40 mL), dried (Na$_2$SO$_4$), and concentrated to give the title compound (7.75 g, 31.2 mmol, 98%). This material was used without further purification in the next step.

Example 2C (R)-4-azido-8-chloro-2,2-bis(fluoromethyl)chroman

A solution of Example 2B (7.75 g, 31.2 mmol) and THF (116 mL) was cooled to <5° C. and 1,8-diazabicyclo[5.4.0]undec-7-ene (7.91 mL, 53.0 mmol) and diphenylphosphoryl azide (10.09 mL, 46.8 mmol) were added. The yellow slurry was warmed slowly to ambient temperature, becoming a brown solution. After 14 hours, the mixture was concentrated, diluted with MTBE (200 mL), and washed with 2N NaOH (50 mL×2), brine (50 mL), 2N HCl (50 mL×2), and brine (50 mL). The organic layer was dried (Na$_2$SO$_4$), filtered, and concentrated to give the title compound. This material was used without further purification in the next step.

Example 2D (R)-8-chloro-2,2-bis(fluoromethyl)chroman-4-amine

Example 2C (31.2 mmol) in methanol (78 mL) was added to Ra—Ni, water-wet (4.27 g, 72.7 mmol) in a 250 mL pressure bottle, and the mixture was shaken under 30 psi of hydrogen at ambient temperature for 2 hours with periodic venting of N$_2$. The mixture was filtered through a nylon membrane and concentrated, giving the title compound. This material was used without further purification in the next step.

Example 2E (4R)-8-chloro-2,2-bis(fluoromethyl)chroman-4-amine, D-(−) tartaric acid salt A slurry of Example 2D (7.73 g, 31.2 mmol), IPA (77 mL) and D-(−)-tartaric acid (4.68 g, 31.2 mmol) was heated to 70° C. At this temperature, the slurry became viscous, then thinned again. The slurry was cooled to ambient temperature over 30 minutes and filtered. The solid was washed with IPA (20 mL) and dried in a vacuum oven at 60° C. to give the title compound (6.41 g, 16.12 mmol, 52% overall yield). Chiral HPLC showed the amine to be >95% ee. MS (DCI/NH$_3$) m/z 248 (M+NH$_4$—H$_2$O)$^+$.

Example 2F

1-[(4R)-8-chloro-2,2-bis(fluoromethyl)-3,4-dihydro-2H-chromen-4-yl]-3-[(2R)-2-hydroxy-2,3-dihydro-1H-inden-4-yl]urea The title compound was prepared according to the procedure of Example 1F, substituting Example 2E for Example 1C. $^1$H NMR (300 MHz, DMSO-$d_6$) δ 7.83 (s, 1H), 7.77 (d, J=8.1 Hz, 1H), 7.37 (ddd, J=7.9, 1.5, 0.6 Hz, 1H), 7.27 (ddd, J=7.8, 1.6, 1.0 Hz, 1H), 7.04 (t, J=7.8 Hz, 1H), 6.99 (t, J=7.8 Hz, 1H), 6.93 (d, J=8.1 Hz, 1H), 6.83 (d, J=7.4 Hz, 1H), 4.98-5.08 (m, 1H), 4.85 (d, J=4.1 Hz, 1H), 4.81-4.55 (m, 4H), 4.55-4.47 (m, 1H), 3.05 (dd, J=16.0, 6.1 Hz, 1H), 2.96 (dd, J=16.0, 6.1 Hz, 1H), 2.74 (dd, J=16.0, 3.6 Hz, 1H), 2.65 (dd, J=16.0, 3.3 Hz, 1H), 2.34 (dd, J=13.8, 5.9 Hz, 1H), 1.98 (ddd, J=13.4, 10.9, 2.7 Hz, 1H); MS (ESI+) m/z 423 (M+H)$^+$, 440 (M+NH$_4$)$^+$; [α]$^{23}_D$=+5.39° (c 0.76, CH$_3$OH).

Example 3

1-[(4R)-2,2-dimethyl-7-(trifluoromethyl)-3,4-dihydro-2H-chromen-4-yl]-3-[(2R)-2-hydroxy-2,3-dihydro-1H-inden-4-yl]urea

Example 3A 1-(2-hydroxy-4-(trifluoromethyl)phenyl)ethanone

A solution of 2-hydroxy-4-(trifluoromethyl)benzoic acid (10.0 g, 48.5 mmol) and THF (100 mL) was cooled to <5° C. and methyllithium (95 mL, 1.6M solution in diethyl ether, 152 mmol) was slowly added, keeping the internal temperature <20° C. The resulting solution was warmed to ambient temperature and stirred for 1 hour. The solution was then cooled to 10° C. and treated carefully with EtOAc (100 mL) and 2N HCl (100 mL). The reaction mixture was further diluted with EtOAc (100 mL) then washed with water (100 mL) and brine (20 mL). The organic portion was dried (Na$_2$SO$_4$), filtered, and concentrated to give the title compound (10.3 g). This material was used without further purification in the next step.

Example 3B 2,2-dimethyl-7-(trifluoromethyl)chroman-4-one

Acetone (3.56 mL, 48.5 mmol) and pyrrolidine (8.02 mL, 97.0 mmol) were added to a solution of Example 3A in methanol (100 mL). The reaction mixture was stirred at ambient temperature for 14 hours concentrated, diluted with EtOAc (300 mL), then washed with water (100 mL), 2N HCl (2×100 mL), water (50 mL), 2N NaOH (2×100 mL), water (50 mL), and brine (20 mL). The organic layer was dried ($Na_2SO_4$), filtered, and concentrated. The residue was purified by silica gel chromatography (gradient elution, 0-20% EtOAc/hexanes) to give the title compound (8.93 g, 36.6 mmol, 75%) as a white solid. MS (ESI) m/z 245 (M+H)$^+$.

Example 3C

A solution of Example 3B (5.45 g, 22.3 mmol), (R)-2-methylpropane-2-sulfinamide (4.06 g, 33.5 mmol), 2-methyltetrahydrofuran (60 mL), and tetraethoxytitanium (18.7 mL, 89.0 mmol) was heated at 70° C. overnight. The reaction mixture was cooled to −10° C. and sodium borohydride (1.69 g, 44.6 mmol) was added. The slurry was warmed to ambient temperature over 2 hours, then cooled to <5° C. and 10% aqueous citric acid (50 mL) was added carefully. The white slurry was stirred vigorously for 2 hours, diluted with MTBE, and the layers separated. The organic layer was washed with water (100 mL) and brine (50 mL), dried ($Na_2SO_4$), filtered, and concentrated. The residue was purified by silica gel chromatography (gradient elution, 20-100% EtOAc/hexanes) to afford the title compound (6.50 g, 18.6 mmol, 83%). (DCI/$NH_3$) m/z 350 (M+H)$^+$.

Example 3D (R)-2,2-dimethyl-7-(trifluoromethyl)chroman-4-aminium chloride

The title compound was prepared according to the procedure of Example 1C, substituting Example 3C for Example 1B. The wet cake was used in the next step without drying.

Example 3E (4R)-2,2-dimethyl-7-(trifluoromethyl)chroman-4-amine, D-(−) tartaric acid salt A slurry of Example 3D (18.6 mmol) in MTBE (200 mL) was washed with 30% aqueous $K_3PO_4$ (200 mL) and brine (50 mL). The organic layer was dried ($Na_2SO_4$), filtered, concentrated, and diluted with IPA (33 mL). In a separate flask, D-(−)-tartaric acid (2.93 g, 19.5 mmol) and IPA (33 mL) were heated to 70° C. The amine solution was added slowly to the tartaric acid solution, keeping the temperature >70° C. After 10 minutes, the white slurry was cooled slowly to ambient temperature, filtered, washed with IPA (10 mL), and dried in a vacuum oven at 60° C. to give the title compound (4.72 g, 11.9 mmol, 64%). Chiral HPLC showed >99% ee. (DCI/$NH_3$) m/z 229 (M−$NH_4$)$^+$.

Example 3F

1-[(4R)-2,2-dimethyl-7-(trifluoromethyl)-3,4-dihydro-2H-chromen-4-yl]-3-[(2R)-2-hydroxy-2,3-dihydro-1H-inden-4-yl]urea The title compound was prepared according to the procedure of Example 1F, substituting Example 3E for Example 1C. $^1$H NMR (300 MHz, DMSO-$d_6$) δ 7.82 (s, 1H), 7.79 (d, J=7.7 Hz, 1H), 7.49 (d, J=8.1 Hz, 1H), 7.24 (dd, J=8.1, 1.9 Hz, 1H), 7.06 (d, J=6.6 Hz, 1H), 7.04 (d, J=7.7 Hz, 1H), 6.91 (d, J=8.4 Hz, 1H), 6.83 (d, J=7.4 Hz, 1H), 4.97-5.07 (m, 1H), 4.85 (d, J=4.0 Hz, 1H), 4.56-4.48 (m, 1H), 3.05 (dd, J=16.0, 6.1 Hz, 1H), 2.96 (dd, J=16.2, 6.1 Hz, 1H), 2.74 (dd, J=15.8, 3.9 Hz, 1H), 2.65 (dd, J=16.1, 3.3 Hz, 1H), 2.20 (dd, J=13.3, 6.1 Hz, 1H), 1.78 (dd, J=13.1, 11.3 Hz, 1H), 1.43 (s, 3H), 1.31 (s, 3H); MS (DCI+) m/z 438 (M+$NH_4$)$^+$; [α]$^{23}_D$=+1.0° (c 0.39, $CH_3OH$).

Example 4

1-[(4R)-7-chloro-2,2-bis(fluoromethyl)-3,4-dihydro-2H-chromen-4-yl]-3-[(2R)-2-hydroxy-2,3-dihydro-1H-inden-4-yl]urea Example 4A 7-chloro-2,2-bis(fluoromethyl)chroman-4-one The title compound was prepared according to the procedure of Example 1A, substituting 1-(4-chloro-2-hydroxyphenyl)ethanone for 1-(3,5-difluoro-2-hydroxyphenyl)ethanone. MS (DCI/$NH_3$) m/z 264 (M+$NH_4$)$^+$.

Example 4B (4R)-7-chloro-2,2-bis(fluoromethyl)chroman-4-amine, D-(−) tartaric acid salt The title compound was prepared from Example 4A according to the methods described in Example 3C, Example 1C, and Example 3E. MS (DCI/$NH_3$) m/z 248 (M+$NH_4$—$H_2O$)$^+$.

Example 4C

1-[(4R)-7-chloro-2,2-bis(fluoromethyl)-3,4-dihydro-2H-chromen-4-yl]-3-[(2R)-2-hydroxy-2,3-dihydro-1H-inden-4-yl]urea The title compound was prepared according to the procedure of Example 1F, substituting Example 4B for Example 1C. $^1$H NMR (300 MHz, DMSO-$d_6$) δ 7.81 (s, 1H), 7.77 (d, J=8.1 Hz, 1H), 7.31 (dd, J=8.2, 0.9 Hz, 1H), 7.05 (dd, J=8.3, 2.1 Hz, 1H), 7.04 (t, J=7.8 Hz, 1H), 6.98 (d, J=2.1 Hz, 1H), 6.91 (d, J=8.0 Hz, 1H), 6.82 (d, J=7.3 Hz, 1H), 5.02-4.93 (m, 1H), 4.86 (d, J=4.0 Hz, 1H), 4.77-4.67 (m, 2H), 4.61-4.49 (m, 3H), 3.05 (dd, J=16.1, 6.1 Hz, 1H), 2.96 (dd, J=16.1, 6.1 Hz, 1H), 2.74 (dd, J=16.1, 3.4 Hz, 1H), 2.65 (dd, J=15.8, 3.3 Hz, 1H), 2.31 (dd, J=13.8, 6.1 Hz, 1H), 1.93 (ddd, J=13.4, 10.6, 2.6 Hz, 1H); MS (ESI+) m/z 423 (M+H)$^+$, 440 (M+$NH_4$)$^+$.

Example 5

1-[(4R)-7-fluoro-2,2-dimethyl-3,4-dihydro-2H-chromen-4-yl]-3-[(2R)-2-hydroxy-2,3-dihydro-1H-inden-4-yl]urea Example 5A (4R)-2,2-dimethyl-7-fluoro-chroman-4-amine, D-(−) tartaric acid salt The title compound was prepared from 1-(4-fluoro-2-hydroxy-phenyl)ethanone according to the methods described in Example 3B, Example 2B, Example 2C, Example 2D, and Example 2E (using MeOH instead of IPA for final salt isolation). Chiral HPLC showed >99% ee. MS (DCI/NH3) m/z 196 (M+NH4—H2O)+.

Example 5B

1-[(4R)-7-fluoro-2,2-dimethyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 5A for Example 1C. $^1$H NMR (300 MHz, DMSO-d$_6$) δ 7.80 (d, J=8.1 Hz, 1H), 7.77 (s, 1H), 7.29 (ddd, J=8.5, 6.8, 0.8 Hz, 1H), 7.04 (t, J=7.7 Hz, 1H), 6.84 (d, J=6.7 Hz, 1H), 6.81 (d, J=6.7 Hz, 1H), 6.74 (td, J=8.6, 2.7 Hz, 1H), 6.59 (dd, J=10.6, 2.6 Hz, 1H), 4.97-4.87 (m, 1H), 4.85 (d, J=4.1 Hz, 1H), 4.56-4.47 (m, 1H), 3.05 (dd, J=16.0, 6.1 Hz, 1H), 2.95 (dd, J=16.1, 6.0 Hz, 1H), 2.74 (dd, J=16.0, 3.5 Hz, 1H), 2.64 (dd, J=16.0, 3.5 Hz, 1H), 2.16 (dd, J=13.3, 6.1 Hz, 1H), 1.71 (dd, J=13.3, 10.7 Hz, 1H), 1.40 (s, 3H), 1.29 (s, 3H); MS (ESI+) m/z 371 (M+H)$^+$; [α]$^{23}_D$=−1.48° (c 1.08, CH$_3$OH).

Example 6

1-[(2R)-2-hydroxy-2,3-dihydro-1H-inden-4-yl]-3-[(4R)-8-(trifluoromethoxy)-3,4-dihydro-2H-chromen-4-yl]urea

Example 6A 1-(prop-2-ynyloxy)-2-(trifluoromethoxy)benzene

To a solution of 2-trifluoromethoxyphenol (10.0 g, 56.1 mmol) in acetonitrile (120 mL) was added potassium carbonate (9.31 g, 67.4 mmol) and propargyl bromide (80% in toluene, 10.0 g, 7.70 mL, 67.4 mmol). The reaction mixture was stirred at ambient temperature for seven days, then diluted with water (150 mL) and extracted with diethyl ether (300 mL). The organic layer was separated and concentrated to obtain the title compound (13.05 g) which was used without further purification in the next step.

Example 6B 1-(3-chloroprop-2-ynyloxy)-2-(trifluoromethoxy)benzene

To a solution of the product of Example 6A (13.0 g, 56.1 mmol) in acetone (200 mL) was added N-chlorosuccinimide (8.99 g, 67.3 mmol) and silver acetate (0.936 g, 5.61 mmol). The reaction mixture was heated at reflux for 16 hours, cooled to ambient temperature, and the solvent removed under reduced pressure. The residue was taken up in a mixture of diethyl ether and water, and filtered to remove the silver salts. The filtrate was extracted with diethyl ether (300 mL). The combined organic layers were washed with saturated sodium bicarbonate (75 mL) and concentrated to give the title compound (12.9 g) which was used without further purification in the next step. MS (DCI) m/z 268 (M+NH$_4$)$^+$.

Example 6C 8-(trifluoromethoxy)chroman-4-one

A solution of the product of Example 6B (12.8 g, 51.2 mmol) in ethylene glycol (200 mL) was heated at reflux for 6 hours, cooled to ambient temperature, stirred for 16 hours at ambient temperature, then heated at reflux for an additional 3 hours. After cooling, the reaction mixture was poured into water (100 mL) and extracted with diethyl ether (250 mL). The mixture was partitioned and the organic portion was concentrated. The resulting residue was purified by silica gel chromatography (gradient elution, 0%-20% EtOAc/hexanes) to obtain the title compound (3.62 g, 28% for three steps). $^1$H NMR (300 MHz, CDCl$_3$) δ 7.86 (dd, J=8.1, 1.7 Hz, 1H), 7.44 (d, J=7.8 Hz, 1H), 7.05-6.98 (m, 1H), 4.66-4.60 (m, 2H), 2.90-2.84 (m, 2H).

Example 6D (4R)-8-(trifluoromethoxy)chroman-4-amine, D-(−) tartaric acid salt The title compound was prepared from the product of Example 6C according to the methods described in Example 2B, Example 2C, Example 2D, and Example 2E (using MeOH instead of IPA for final salt isolation). MS (DCI/NH$_3$) m/z 234 (M+H)$^+$.

Example 6E

1-[(2R)-2-hydroxy-2,3-dihydro-1H-inden-4-yl]-3-[(4R)-8-(trifluoromethoxy)-3,4-dihydro-2H-chromen-4-yl]urea The title compound was prepared according to the procedure of Example 1F, substituting Example 6D for Example 1C. $^1$H NMR (300 MHz, DMSO-d$_6$) δ 7.81 (d, J=8.1 Hz, 1H), 7.65 (s, 1H), 7.34-7.30 (m, 1H), 7.24-7.30 (m, 1H), 7.05 (d, J=7.9 Hz, 1H), 7.03 (d, J=8.3 Hz, 1H), 6.98 (t, J=8.0 Hz, 1H), 6.81 (d, J=7.3 Hz, 1H), 4.96-4.89 (m, 1H), 4.84 (d, J=4.0 Hz, 1H), 4.54-4.46 (m, 1H), 4.45-4.37 (m, 1H), 4.21 (ddd, J=11.4, 8.8, 2.8 Hz, 1H), 3.04 (dd, J=16.0, 6.1 Hz, 1H), 2.92 (dd, J=16.1, 6.1 Hz, 1H), 2.73 (dd, J=16.1, 3.5 Hz, 1H), 2.61 (dd, J=16.0, 3.3 Hz, 1H), 2.22-1.93 (m, 2H); MS (LCMS) m/z 409 (M+H)$^+$.

Example 7

1-[(4R)-2,2-bis(fluoromethyl)-7-(trifluoromethyl)-3,4-dihydro-2H-chromen-4-yl]-3-[(2R)-2-hydroxy-2,3-dihydro-1H-inden-4-yl]urea

Example 7A (4R)-2,2-bis(fluoromethyl)-7-(trifluoromethyl)chroman-4-amine, D-(−) tartaric acid salt The title compound was prepared from 2-hydroxy-4-(trifluoromethyl)benzoic acid according to the methods described in Example 3A, Example 1A, Example 2B, Example 2C, Example 2D, and Example 2E (using MeOH/diethylether instead of IPA for final salt isolation). MS (DCI/NH$_3$) m/z 282 (M+H)$^+$.

Example 7B

1-[(4R)-2,2-bis(fluoromethyl)-7-(trifluoromethyl)-3,4-dihydro-2H-chromen-4-yl]-3-[(2R)-2-hydroxy-2,3-dihydro-1H-inden-4-yl]urea The title compound was prepared according to the procedure of Example 1F, substituting Example 7A for Example 1C. $^1$H NMR (300 MHz, DMSO-d$_6$) δ 7.86 (s, 1H), 7.77 (d, J=8.1 Hz, 1H), 7.52 (d, J=8.1 Hz, 1H), 7.34 (dd, J=8.1, 1.8 Hz, 1H), 7.21 (d, J=1.8 Hz, 1H), 7.05 (t, J=7.7 Hz, 1H), 6.98 (d, J=8.1 Hz, 1H), 6.83 (d, J=7.4 Hz, 1H), 5.02-5.11 (m, 1H), 4.87 (d, J=4.0 Hz, 1H), 4.82-4.55 (m, 4H), 4.55-4.48 (m, 1H), 3.05 (dd, J=16.0, 6.1 Hz, 1H), 2.97 (dd, J=16.1, 6.1 Hz, 1H), 2.74 (dd, J=15.8, 3.5 Hz, 1H), 2.66 (dd, J=16.1, 3.3 Hz, 1H), 2.36 (dd, J=13.6, 6.0 Hz, 1H), 1.93-2.04 (m, 1H); MS (ESI+) m/z 457 (M+H)$^+$; [α]$^{23}_D$=+0.58° (c 0.685, CH$_3$OH).

Example 8

1-[(4R)-6-fluoro-3,4-dihydrospiro[chromene-2,1'-cyclobutan]-4-yl]-3-[(2R)-2-hydroxy-2,3-dihydro-1H-inden-4-yl]urea Example 8A 6-fluorospiro[chroman-2,1'-cyclobutan]-4-one The title compound was prepared according to the procedure of Example 1A, using 1-(5-fluoro-2-hydroxyphenyl)ethanone and substituting cyclobutanone for 1,3-difluoroacetone. MS (DCI/NH$_3$) m/z 207 (M+H)$^+$.

Example 8B (E)-6-fluorospiro[chroman-2,1'-cyclobutan]-4-one O-methyl oxime

In a 500 mL round-bottomed flask was added Example 8A (19.4 g, 94.9 mmol) and O-methylhydroxylamine hydrochloride (8.53 mL, 112 mmol) in pyridine (150 mL) to give a yellow solution. The reaction mixture was stirred for 54 hours at ambient temperature, concentrated, diluted with EtOAc (1 L), and washed with water (400 mL). The organic portion was dried (Na$_2$SO$_4$), filtered, and concentrated. The resulting yellow residue was purified by silica gel chromatography (gradient elution, 0-30% EtOAc/hexanes) to provide the title compound (21.8 g, 94.0 mmol, 99%) as a pale yellow solid. MS (DCI/NH$_3$) m/z 224 (M+NH$_4$)$^+$.

Example 8C 6-fluorospiro[chroman-2,1'-cyclobutan]-4-amine

Example 8B (21.8 g, 94.0 mmol) and Raney nickel (5.49 g, water wet) were stirred in EtOH containing 7 M ammonia (150 mL). The reactor mixture was sealed and sparged with hydrogen. The reaction mixture was stirred for 3 hours at 32° C., cooled, diluted with EtOAc (250 mL) and filtered through a pad of Celite (50 g). The resulting solution was filtered through a plug of silica gel (50 g) and the filtrate evaporated to give the title compound (10.8 g, 52.1 mmol, 56%) as a pale oil. MS (DCI/NH$_3$) m/z 208 (M+H)$^+$.

Example 8D (R)-6-fluorospiro[chroman-2,1'-cyclobutan]-4-amine

Example 8C was resolved by semi-preparative chiral HPLC (Chiralcel OD 5×50 cm, 5% isopropanol/hexane+0.1% diethylamine, 23° C., 100 mL/min). The later of the two eluting peaks (retention time=26.0 min) was collected and the solvent evaporated to afford the title compound as an off-white solid in 99% ee versus a racemic reference (prepared as described above using sodium borohydride as the reducing agent). MS (DCI/NH$_3$) m/z 208 (M+H)$^+$.

Example 8E

1-[(4R)-6-fluoro-3,4-dihydrospiro[chromene-2,1'-cyclobutan]-4-yl]-3-[(2R)-2-hydroxy-2,3-dihydro-1H-inden-4-yl]urea The title compound was prepared according to the procedure of Example 1F, substituting Example 8D for Example 1C. $^1$H NMR (300 MHz, DMSO-d$_6$) δ 7.81 (s, 1H), 7.80 (d, J=7.4 Hz, 1H), 7.05 (t, J=7.6 Hz, 1H), 6.96-7.03 (m, 2H), 6.92 (d, J=8.2 Hz, 1H), 6.85-6.78 (m, 2H), 4.99-4.87 (m, 1H), 4.85 (d, J=4.1 Hz, 1H), 4.57-4.48 (m, 1H), 3.05 (dd, J=16.1, 6.1 Hz, 1H), 2.97 (dd, J=16.1, 6.2 Hz, 1H), 2.74 (dd, J=15.9, 3.5 Hz, 1H), 2.65 (dd, J=16.0, 3.3 Hz, 1H), 2.38 (dd, J=13.3, 5.9 Hz, 1H), 2.32-2.03 (m, 4H), 1.92-1.64 (m, 3H); MS (ESI+) m/z 383 (M+H)$^+$; [α]$^{23}_D$=+11.8° (c 1.06, CH$_3$OH).

Example 9

1-[(4R)-7,8-difluoro-2,2-dimethyl-3,4-dihydro-2H-chromen-4-yl]-3-[(2R)-2-hydroxy-2,3-dihydro-1H-inden-4-yl]urea Example 9A 2,3-difluorophenyl acetate To a solution of 2,3-difluorophenol (30.0 g, 231 mmol) and pyridine (18.6 mL, 231 mmol) in dichloromethane (230 mL) at 0° C. was carefully added acetyl chloride (16.4 mL, 231 mmol). The reaction was allowed to warm to ambient temperature and stirred for 16 hours. The reaction mixture was then diluted with dichloromethane (100 mL), washed with 1N aqueous hydrochloric acid (2×50 mL) and brine (75 mL), and concentrated to produce 41.0 g (100%) of the title compound. MS (DCI/NH$_3$) m/z 190 (M+NH$_4$)$^+$.

Example 9B 1-(3,4-difluoro-2-hydroxyphenyl)ethanone

To a slurry of aluminum trichloride (30.8 g, 231 mmol) in dichloroethane (25 mL) at 0° C. was added drop wise a solution of Example 9A (41.0 g, 231 mmol) in dichloroethane (25 mL). After addition was complete, the reaction was heated at reflux for 16 hours. The reaction mixture was then cooled to 0° C. and quenched by the addition of water. The resulting mixture was extracted with dichloromethane (2×75 mL). The organic layer was washed with water (40 mL) and brine (60 mL), and concentrated to produce 35.8 g (90%) of the title compound. MS (DCI/NH$_3$) m/z 190 (M+NH$_4$)$^+$.

Example 9C 7,8-difluoro-2,2-dimethylchroman-4-one

The title compound was prepared according to the procedure of Example 3B, substituting Example 9B for Example 3A. MS (DCI/NH$_3$) m/z 230 (M+NH$_4$)$^+$.

Example 9D (4R)-7,8-difluoro-2,2-dimethylchroman-4-amine, D-(−) tartaric acid salt The title compound was prepared from Example 9C according to the methods described in Example 3C, Example 1C, and Example 3E. MS (DCI/NH$_3$) m/z 214 (M+H)$^+$.

Example 9E

1-[(4R)-7,8-difluoro-2,2-dimethyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 9D for Example 1C. $^1$H NMR (300 MHz, DMSO-d$_6$) δ 7.82 (s, 1H), 7.78 (d, J=8.0 Hz, 1H), 7.14-7.06 (m, 1H), 7.05 (t, J=7.8 Hz, 1H), 6.98-6.89 (m, 1H), 6.88 (d, J=8.3 Hz, 1H), 6.82 (d, J=7.3 Hz, 1H), 5.02-4.89 (m, 1H), 4.86 (d, J=4.1 Hz, 1H), 4.54-4.47 (m, 1H), 3.05 (dd, J=16.0, 5.9 Hz, 1H), 2.95 (dd, J=16.1, 6.1 Hz, 1H), 2.74 (dd, J=16.1, 3.4 Hz, 1H), 2.65 (dd, J=16.0, 3.1 Hz, 1H), 2.19 (dd, J=13.4, 6.1 Hz, 1H), 1.77 (dd, J=13.3, 11.0 Hz, 1H), 1.46 (s, 3H), 1.33 (s, 3H); MS (ESI+) m/z 389 (M+H)$^+$; [α]$^{23}_D$=−1.0° (c 0.975, CH$_3$OH).

Example 10

1-[(4R)-7-chloro-8-fluoro-2,2-dimethyl-3,4-dihydro-2H-chromen-4-yl]-3-[(2R)-2-hydroxy-2,3-dihydro-1H-inden-4-yl]urea

Example 10A 1-(4-chloro-3-fluoro-2-hydroxyphenyl)ethanone

The title compound was prepared according to the procedures of Examples 9A and 9B, substituting 3-chloro-2-fluorophenol for 2,3-difluorophenol. MS (DCI/NH$_3$) m/z 211 (M+23)$^+$.

Example 10B (4R)-7-chloro-8-fluoro-2,2-dimethylchroman-4-amine, D-(−) tartaric acid salt The title compound was prepared from Example 10A according to the methods described in Example 3B, Example 3C, Example 1C, and Example 3E. MS (DCI/NH$_3$) m/z 231 (M+H)$^+$.

Example 10C

1-[(4R)-7-chloro-8-fluoro-2,2-dimethyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 10B for Example 1C. $^1$H NMR (300 MHz, DMSO-d$_6$) δ 7.83 (s, 1H), 7.78 (d, J=8.1 Hz, 1H), 7.01-7.14 (m, 3H), 6.89 (d, J=8.4 Hz, 1H), 6.82 (d, J=7.4 Hz, 1H), 5.02-4.92 (m, 1H), 4.85 (d, J=4.0 Hz, 1H), 4.56-4.47 (m, 1H), 3.05 (dd, J=15.9, 6.2 Hz, 1H), 2.96 (dd, J=16.2, 6.2 Hz, 1H), 2.74 (dd, J=16.1, 3.4 Hz, 1H), 2.65 (dd, J=15.9, 3.3 Hz, 1H), 2.20 (dd, J=13.3, 6.1 Hz, 1H), 1.79 (dd, J=13.3, 11.1 Hz, 1H), 1.46 (s, 3H), 1.33 (s, 3H); MS (ESI+) m/z 405 (M+H)$^+$.

Example 11

1-[(4R)-7-chloro-8-fluoro-2,2-bis(fluoromethyl)-3,4-dihydro-2H-chromen-4-yl]-3-[(2R)-2-hydroxy-2,3-dihydro-1H-inden-4-yl]urea

Example 11A (4R)-7-chloro-8-fluoro-2,2-bis(fluoromethyl)chroman-4-amine, D-(−) tartaric acid salt The title compound was prepared from Example 10A according to the procedures of Examples 1A, 3C, 1C, and 3E. MS (LCMS) m/z 249 (M−NH$_2$)$^+$.

Example 11B

1-[(4R)-7-chloro-8-fluoro-2,2-bis(fluoromethyl)-3,4-dihydro-2H-chromen-4-yl]-3-[(2R)-2-hydroxy-2,3-dihydro-1H-inden-4-yl]urea The title compound was prepared according to the procedure of Example 1F, substituting Example 11A for Example 1C. $^1$H NMR (300 MHz, DMSO-d$_6$) δ 7.86 (s, 1H), 7.74 (d, J=8.1 Hz, 1H), 7.26 (ddd, J=11.2, 8.5, 2.9 Hz, 1H), 7.05 (t, J=7.8 Hz, 1H), 6.90-6.99 (m, 2H), 6.84 (d, J=7.4 Hz, 1H), 4.96-5.06 (m, 1H), 4.86 (d, J=4.1 Hz, 1H), 4.55-4.82 (m, 4H), 4.55-4.47 (m, 1H), 3.05 (dd, J=16.3, 6.3 Hz, 1H), 2.99 (dd, J=16.3, 6.3 Hz, 1H), 2.74 (dd, J=16.0, 3.6 Hz, 1H), 2.66 (dd, J=16.1, 3.4 Hz, 1H), 2.36 (dd, J=13.8, 6.0 Hz, 1H), 1.99 (ddd, J=13.7, 10.6, 2.8 Hz, 1H); MS (ESI+) m/z 425 (M+H)$^+$, 442 (M+NH$_4$)$^+$; [α]$^{23}_D$=+0.27° (c 1.12, CH$_3$OH).

Example 12

1-[(4R)-8-chloro-7-fluoro-2,2-dimethyl-3,4-dihydro-2H-chromen-4-yl]-3-[(2R)-2-hydroxy-2,3-dihydro-1H-inden-4-yl]urea

Example 12A (R)-tert-butyl 7-fluoro-2,2-dimethylchroman-4-ylcarbamate

Example 5A (8.02 g, 14.84 mmol), THF (80 mL) and triethylamine (4.14 mL, 29.7 mmol) were stirred at ambient temperature and di-tert-butyl dicarbonate (6.89 mL, 29.7 mmol) was added. The resulting white slurry was heated to 50° C. After 110 minutes, the reaction mixture was cooled and concentrated and MTBE (160 mL) was added. The reaction mixture was partitioned, and the organic portion was washed with water (40 mL), 2N HCl (40 mL), and brine (20 mL). The organic portion was dried (Na$_2$SO$_4$), filtered, and concentrated, to give the title compound (8.47 g, 28.7 mmol, 97%). MS (ESI+) m/z 295 (M$^+$).

Example 12B (4R)-8-chloro-7-fluoro-2,2-dimethylchroman-4-amine

A solution of Example 12A (4.00 g, 13.5 mmol) in THF (40 mL) was cooled to −70° C. and n-butyllithium (2.5 M in hexanes, 11.38 mL, 28.4 mmol) added at ≤−50° C. The mixture was cooled back to −70° C. and potassium tert-butoxide (14.9 mL, 14.9 mmol) was added at <−65° C. After 90 min, additional n-butyllithium (0.5 equiv, 2.7 mL) and potassium tert-butoxide (0.5 equiv, 6.8 mL) were added along with THF (20 mL) to facilitate stirring of the gelatinous slurry. After 1 hour, hexachloroethane (3.07 mL, 27.1 mmol) was added (internal temperature at −45° C.); LCMS showed complete clean conversion to product. The reaction was quenched by addition of 2N HCl (60 mL), diluted with methyl tert-butyl ether (40 mL), and partitioned. The organic layer was washed with brine (20 mL), dried ($Na_2SO_4$), filtered, and concentrated. The crude product was used without further purification.

The crude (R)-tert-butyl 8-chloro-7-fluoro-2,2-dimethyl-chroman-4-ylcarbamate (4.47 g, 13.5 mmol), MeOH (36 mL), and concentrated HCl (4 mL) were heated to 50° C. After 2 hours, complete deprotection was observed by LCMS. The reaction mixture was cooled, stirred for 8 hours, and then diluted with MTBE (60 mL) and water (40 mL). The mixture was partitioned and the organic layer was extracted with water (50 mL). The aqueous layer was basified with 2N NaOH (40 mL) and extracted with dichloromethane (2×40 mL). The organic extracts were dried ($Na_2SO_4$), filtered, and concentrated to give the title compound (2.87 g, 12.50 mmol, 92%). MS ($ESI^+$) m/z 230 $(M+H)^+$.

Example 12C

1-[(4R)-8-chloro-7-fluoro-2,2-dimethyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 12B for Example 1C. $^1$H NMR (300 MHz, DMSO-$d_6$) δ 7.84 (s, 1H), 7.78 (d, J=8.1 Hz, 1H), 7.27 (ddd, J=8.7, 6.4, 1.0 Hz, 1H), 7.04 (t, J=7.7 Hz, 1H), 6.95 (t, J=8.8 Hz, 1H), 6.87 (d, J=8.3 Hz, 1H), 6.82 (d, J=7.4 Hz, 1H), 5.02-4.92 (m, 1H), 4.86 (d, J=4.0 Hz, 1H), 4.54-4.47 (m, 1H), 3.05 (dd, J=16.1, 6.1 Hz, 1H), 2.96 (dd, J=16.0, 6.1 Hz, 1H), 2.74 (dd, J=16.0, 3.5 Hz, 1H), 2.65 (dd, J=16.0, 3.3 Hz, 1H), 2.20 (dd, J=13.3, 6.1 Hz, 1H), 1.78 (dd, J=13.3, 11.0 Hz, 1H), 1.47 (s, 3H), 1.32 (s, 3H); MS (ESI+) m/z 405 $(M+H)^+$, 422 $(M+NH_4)^+$.

Example 13

1-[(4R)-7-chloro-2,2-dimethyl-3,4-dihydro-2H-chromen-4-yl]-3-[(2R)-2-hydroxy-2,3-dihydro-1H-inden-4-yl]urea Example 13A (4R)-2,2-dimethyl-7-chloro-chroman-4-amine, D-(−) tartaric acid salt The title compound was prepared from 1-(4-chloro-2-hydroxy-phenyl)ethanone according to the methods described in Example 3B, Example 2B, Example 2C, Example 2D, and Example 2E. MS ($DCI/NH_3$) m/z 195 $(M-NH_2)^+$.

Example 13B

1-[(4R)-7-chloro-2,2-dimethyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 13A for Example 1C. $^1$H NMR (300 MHz, DMSO-$d_6$) δ 7.79 (s, 1H), 7.79 (d, J=8.0 Hz, 1H), 7.28 (dd, J=8.3, 1.0 Hz, 1H), 7.04 (t, J=7.8 Hz, 1H), 6.95 (dd, J=8.3, 2.2 Hz, 1H), 6.85 (d, J=8.5 Hz, 1H), 6.84-6.79 (m, 2H), 4.98-4.88 (m, 1H), 4.86 (d, J=4.0 Hz, 1H), 4.56-4.47 (m, 1H), 3.05 (dd, J=16.0, 6.1 Hz, 1H), 2.96 (dd, J=16.0, 6.1 Hz, 1H), 2.74 (dd, J=16.0, 3.6 Hz, 1H), 2.65 (dd, J=16.0, 3.2 Hz, 1H), 2.16 (dd, J=13.3, 6.1 Hz, 1H), 1.71 (dd, J=13.2, 11.2 Hz, 1H), 1.40 (s, 3H), 1.28 (s, 3H); MS ($ESI^+$) m/z 387 $(M+H)^+$, 404 $(M+NH_4)^+$.

Example 14

1-[(2R)-2-hydroxy-2,3-dihydro-1H-inden-4-yl]-3-[(4R)-7-(trifluoromethoxy)-3,4-dihydro-2H-chromen-4-yl]urea Example 14A 7-(trifluoromethoxy)chroman-4-one A solution of 3-(trifluoromethoxy)phenol (7.13 mL, 55.0 mmol) and 3-chloropropanoyl chloride (5.5 mL, 57.6 mmol) in trifluoroacetic acid (25 mL) was stirred 15 minutes at ambient temperature, and then heated at 50° C. for 90 minutes. After stirring at ambient temperature overnight, the solution was added over 5 minutes to preheated triflic acid (20 mL) at 50° C. After 20 minutes, the mixture was removed from the oil bath, then cooled in an ice water bath. Crushed ice was added, slowly at first, keeping the temperature of the orange solution below 25° C. Eventually a solid precipitate formed, and the suspension was diluted with MTBE (200 mL). The mixture was cooled in an ice water bath. It was washed with brine and then four times with water, partially dried ($Na_2SO_4$), filtered, and concentrated. After standing overnight, the yellow mixture was dissolved in ethanol (180 mL) and added slowly over 22 minutes to 1.5 M aqueous $Na_2CO_3$ (180 mL) cooled with a water ice bath (internal temp did not exceed 15° C.). The suspension was permitted to come to ambient temperature overnight, and was then diluted with 2:1 EtOAc/hexanes (300 mL) and filtered. The solids were rinsed with more 2:1 solution (105 mL), and the aqueous phase of the filtrate was separated and extracted with 1:1 EtOAc/hexanes (3×100 mL). The combined organic phases were washed once with water (200 mL), and the aqueous phase was back-extracted once with 1:1 solution (40 mL). The organic phases were combined and washed with brine (30 mL), dried ($Na_2SO_4$), filtered, and concentrated, chromatographed on silica (gradient elution, 5-20% $Et_2O$/hexanes) to give the title compound (4.95 g, 21.3 mmol, 39% yield). $^1$H NMR (300 MHz, DMSO-$d_6$) δ 7.90-7.85 (m, 1H), 7.08-7.01 (m, 2H), 4.61 (dd, 2H), 2.83 (dd, 2H).

Example 14B (4R)-7-(trifluoromethoxy)chroman-4-amine, hydrochloride salt

The title compound was prepared from Example 14A according to the methods described in Example 3C and Example 1C. MS (ESI) m/z 217 $(M-NH_2)^+$.

Example 14C

1-[(2R)-2-hydroxy-2,3-dihydro-1H-inden-4-yl]-3-[(4R)-7-(trifluoromethoxy)-3,4-dihydro-2H-chromen-4-yl]urea The title compound was prepared according to the procedure of Example 1F, substituting Example 14B for Example 1C. ¹H NMR (300 MHz, DMSO-d₆) δ 7.81 (d, J=8.1 Hz, 1H), 7.65 (s, 1H), 7.40 (d, J=8.5 Hz, 1H), 7.05 (d, J=7.3 Hz, 1H), 7.02 (d, J=7.9 Hz, 1H), 6.91 (ddd, J=8.5, 2.5, 1.3 Hz, 1H), 6.82-6.78 (m, 2H), 4.92-4.85 (m, 1H), 4.85 (d, J=4.1 Hz, 1H), 4.54-4.46 (m, 1H), 4.37-4.30 (m, 1H), 4.17 (ddd, J=11.5, 8.7, 2.8 Hz, 1H), 3.04 (dd, J=16.1, 6.2 Hz, 1H), 2.92 (dd, J=16.1, 6.1 Hz, 1H), 2.73 (dd, J=16.0, 3.5 Hz, 1H), 2.61 (dd, J=16.0, 3.5 Hz, 1H), 2.18-2.06 (m, 1H), 2.04-1.93 (m, 1H); MS (ESI+) m/z 409 (M+H)⁺, 426 (M+NH₄)⁺.

Example 15

1-[(2R,4R)-7-chloro-2-(fluoromethyl)-2-methyl-3,4-dihydro-2H-chromen-4-yl]-3-[(2R)-2-hydroxy-2,3-dihydro-1H-inden-4-yl]urea

Example 15A 7-chloro-2-(fluoromethyl)-2-methylchroman-4-one

The title compound was prepared according to the procedure of Example 1A, substituting 1-(4-chloro-2-hydroxyphenyl)ethanone for 1-(3,5-difluoro-2-hydroxyphenyl)ethanone and substituting fluoroacetone for 1,3-difluoroacetone. MS (DCI/NH₃) m/z 246 (M+NH₄)⁺.

Example 15B (4S)-7-chloro-2-(fluoromethyl)-2-methylchroman-4-ol

The title compound was prepared according to the procedure of Example 2B substituting Example 15A for Example 2A. MS (LCMS) m/z 213 (M−OH)⁺.

Example 15C (2R,4S)-7-chloro-2-(fluoromethyl)-2-methylchroman-4-ol

Example 15B (12.6 g, 54.6 mmol) and THF (150 mL) were cooled to <5° C. and potassium tert-butoxide (1M in THF, 82 mL, 82 mmol) was added slowly. After stirring overnight at ambient temperature, the reaction was diluted with MTBE (150 mL), washed with saturated aqueous NH₄Cl (2×50 mL), dried (Na₂SO₄), filtered, and concentrated. Purification of the resulting residue by silica gel chromatography (gradient elution, 0-50% EtOAc/hexanes) gave the title compound (4.35 g, 18.9 mmol, 35%). MS (DCI/NH₃) m/z 248 (M+NH₄)⁺.

Example 15D (2R,4R)-7-chloro-2-(fluoromethyl)-2-methylchroman-4-amine, D-tartaric acid salt The title compound was prepared from Example 15C according to the methods described in Example 2C, Example 2D, and Example 2E. MS (DCI/NH₃) m/z 230 (M+H)⁺.

Example 15E

1-[(2R,4R)-7-chloro-2-(fluoromethyl)-2-methyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 15D for Example 1C. ¹H NMR (300 MHz, CDCl₃) δ 7.23-7.30 (m, 2H), 7.20 (t, J=7.8 Hz, 1H), 7.14-7.08 (m, 1H), 6.92-6.86 (m, 1H), 6.83 (d, J=2.1 Hz, 1H), 6.19-5.85 (br s, 1H), 5.35-5.21 (m, 1H), 4.82-4.69 (m, 2H), 4.40 (dd, J=47.9, 9.7 Hz, 1H), 4.31 (dd, J=47.0, 9.7 Hz, 1H), 3.25 (dd, J=16.7, 5.8 Hz, 1H), 3.14 (dd, J=16.4, 5.8 Hz, 1H), 2.95 (dd, J=17.1, 2.5 Hz, 1H), 2.89 (dd, J=16.2, 2.1 Hz, 1H), 2.21 (dd, J=13.2, 6.1 Hz, 1H), 1.86 (dd, J=12.7, 11.0 Hz, 1H), 1.33 (d, J=2.2 Hz, 3H).

Example 16

1-[(2S,4R)-7-chloro-2-(fluoromethyl)-2-methyl-3,4-dihydro-2H-chromen-4-yl]-3-[(2R)-2-hydroxy-2,3-dihydro-1H-inden-4-yl]urea

Example 16A (4R)-7-chloro-2-(fluoromethyl)-2-methylchroman-4-amine

The title compound was prepared from Example 15A, according to the methods described in Example 3C, Example 1C, and Example 3E (stopping at the free base amine without tartaric acid salt formation). MS (DCI/NH₃) m/z 230 (M+H)⁺.

Example 16B (2S,4R)-7-chloro-2-(fluoromethyl)-2-methylchroman-4-amine

A solution of (4R)-7-chloro-2-(fluoromethyl)-2-methylchroman-4-amine (2.21 g, 9.62 mmol) in THF (10 ml) was cooled to 0° C. Lithium bis(trimethylsilyl)amide (1M in THF, 20.2 mL, 20.2 mmol) was added slowly and the reaction was warmed to room temperature. After 4 hours, the reaction mixture was diluted with EtOAc (200 mL) and washed with 2N NaOH (50 mL) and brine (50 mL). The organic layer was dried (Na₂SO₄), filtered, and concentrated. The crude product was purified on SiO₂ (3% MeOH/EtOAc) to give the title compound (715 mg, 32%). MS (ESI+) M/Z 230 (M+H)⁺

Example 16C

1-[(2S,4R)-7-chloro-2-(fluoromethyl)-2-methyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 16B for Example 1C. ¹H NMR (300 MHz, DMSO-d₆) δ 7.80-7.77 (m, 2H), 7.29 (dd, J=8.3, 0.8 Hz, 1H), 7.04 (t, J=7.8 Hz, 1H), 6.99 (dd, J=8.3, 2.2 Hz, 1H), 6.90 (d, J=2.2 Hz, 1H), 6.87 (d, J=8.1 Hz, 1H), 6.82 (d, J=7.3 Hz, 1H), 4.98-4.88 (m, 1H), 4.86 (d, J=4.1 Hz, 1H), 4.60-4.36 (m, 3H), 3.05 (dd, J=16.1, 6.0 Hz, 1H), 2.95 (dd, J=16.1, 6.0 Hz, 1H), 2.74 (dd, J=16.0, 3.5 Hz, 1H), 2.64 (dd, J=16.0, 3.3 Hz, 1H), 2.33 (dd, J=13.8, 6.1 Hz, 1H), 1.85 (ddd, J=13.8, 10.1, 2.7 Hz, 1H), 1.38 (d, J=2.0 Hz, 3H); MS (ESI+) m/z 405 (M+H)⁺, 422 (M+NH₄)⁺; [α]²³_D=+1.74° (c 0.86, CH₃OH).

Example 17

1-[(4R)-2,2-dimethyl-3,4-dihydro-2H-chromen-4-yl]-3-[(2R)-2-hydroxy-2,3-dihydro-1H-inden-4-yl]urea

Example 17A (S)-2,2-dimethylchroman-4-ol

The title compound was prepared from 2,2-dimethylchroman-4-one according to the method described in Example 2B. MS (LCMS) m/z 236 (M+H$_2$O+CH$_3$CN)$^+$.

Example 17B (R)-2,2-dimethylchroman-4-amine

Example 17A (11.8 g, 66.4 mmol) and THF (240 mL) were cooled to −30° C. and methanesulfonic anhydride (14.46 ml, 113 mmol) was added. N,N-Diisopropylethylamine (18.56 mL, 106 mmol) was added at ≤−30° C. and the solution was warmed to −20° C. After 2 hours of stirring, more base (0.3 equiv) and methanesulfonic anhydride (0.2 equiv) were added. The mixture was stirred for 10 minutes at 0° C., then cooled to −30° C. and tetra-N-butylammonium azide (41.6 g, 146 mmol) was added. The slurry was allowed to slowly warm to room temperature overnight. After 14 hours, MeOH (60 mL) and 2N NaOH (60 mL) were added, and the mixture was stirred for 30 minutes, and diluted with MTBE (240 mL) and water (120 mL). The layers were separated and the organic layer was washed with water (60 mL), 2N HCl (2×60 mL), water (60 mL), and brine (24 mL). The aqueous portion was back-extracted with MTBE (200 mL). The organic layers were combined, dried (Na$_2$SO$_4$), filtered, and concentrated. The residue was dissolved in THF (216 mL) and water (24 mL), triphenylphosphine (19.2 g, 73.0 mmol) was added and the yellow solution was heated at 60° C. for 3 hours. The reaction was cooled, concentrated and dichloromethane (120 mL), water (120 mL), and 2N HCl (60 mL) were added. The layers were separated, and the aqueous layer was washed with dichloromethane (60 mL). To the aqueous layer, 2N NaOH (75 mL) was added. The basified aqueous suspension was extracted with dichloromethane (5×60 mL), dried (Na$_2$SO$_4$), filtered, and concentrated, giving the title compound (6.99 g, 39.4 mmol, 59%). Chiral HPLC (21% IPA/hexanes, ChiralPak OJ, 0.5 mL/min, major=10.9 min, minor=10.1 min) showed 70% ee. MS (LCMS) m/z 178 (M+H)+.

Example 17C (4R)-2,2-dimethylchroman-4-amine, (R)-(−)-mandelic acid salt

A solution of Example 17B (6.99 g, 39.4 mmol) and IPA (70 mL) was heated to 50° C. and (R)-(−)-mandelic acid (6.00 g, 39.4 mmol) was added. The thick white slurry was aged at 50° C. for 10 minutes, then hexanes (70 mL) were added over 45 minutes at 50° C. After the addition, the white slurry was cooled to room temperature over 60 minutes, filtered, and washed with 1:1 IPA/hexanes. The solid was dried in a vacuum oven at 45° C., giving the title compound (8.48 g, 25.7 mmol, 65%). The solid was >99% ee by chiral HPLC (method in Example 17B). MS (DCI/NH$_3$) m/z 178 (M+H)$^+$.

Example 17D

1-[(4R)-2,2-dimethyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 17C for Example 1C. $^1$H NMR (300 MHz, DMSO-d$_6$) δ 7.81 (d, J=8.1 Hz, 1H), 7.76 (s, 1H), 7.31-7.24 (m, 1H), 7.18-7.10 (m, 1H), 7.04 (t, J=7.7 Hz, 1H), 6.89 (td, J=7.4, 1.2 Hz, 1H), 6.84 (d, J=8.0 Hz, 1H), 6.81 (d, J=7.7 Hz, 1H), 6.74 (dd, J=8.1, 1.2 Hz, 1H), 5.01-4.91 (m, 1H), 4.85 (d, J=4.1 Hz, 1H), 4.56-4.47 (m, 1H), 3.05 (dd, J=15.9, 6.1 Hz, 1H), 2.96 (dd, J=16.1, 6.1 Hz, 1H), 2.74 (dd, J=16.1, 3.3 Hz, 1H), 2.64 (dd, J=15.9, 3.4 Hz, 1H), 2.16 (dd, J=13.2, 6.2 Hz, 1H), 1.70 (dd, J=13.2, 10.6 Hz, 1H), 1.39 (s, 3H), 1.28 (s, 3H); MS (ESI+) m/z 353 (M+H)$^+$; [α]$^{23}_D$=−8.49 (c 1.06, CH$_3$OH).

Example 18

1-[(2R)-2-hydroxy-2,3-dihydro-1H-inden-4-yl]-3-[(4R)-8-(trifluoromethyl)-3,4-dihydro-2H-chromen-4-yl]urea

Example 18A 1-(3-chloroprop-2-ynyloxy)-2-(trifluoromethyl)benzene

The title compound was prepared from 2-trifluoromethylphenol, according to the methods described in Example 6A and Example 6B. MS (DCI/NH$_3$) m/z 114 (M−121)+.

Example 18B 8-(trifluoromethyl)chroman-4-one

A solution of Example 18A (24.1 g, 103 mmol) and sulfuric acid (12 mL, 225 mmol) in trifluoroacetic acid (200 mL) was stirred at room temperature for 3 days. The reaction mixture was poured into ice-water and extracted with dichloromethane (2×200 mL). The organic layers were combined, washed with a saturated aqueous NaHCO$_3$ solution (200 mL), dried (MgSO$_4$), filtered, and concentrated. Silica gel chromatography (15% EtOAc/hexanes) gave the title compound (7.21 g, 33.4 mmol, 32%). MS (DCI/NH$_3$) m/z 216 (M+NH$_4$—H$_2$O)$^+$.

Example 18C (4R)-8-(trifluoromethyl)chroman-4-amine, D-(−) tartaric acid salt The title compound was prepared from Example 18B, according to the methods described in Example 17B and Example 2E (using 1:1 MeOH/MTBE in place of IPA for salt isolation). MS (DCI/NH$_3$) m/z 218 (M+H)$^+$.

Example 18D

1-[(2R)-2-hydroxy-2,3-dihydro-1H-inden-4-yl]-3-[(4R)-8-(trifluoromethyl)-3,4-dihydro-2H-chromen-4-yl]urea The title compound was prepared according to the procedure of Example 1F, substituting Example 18C for Example 1C. $^1$H NMR (300 MHz, DMSO-d$_6$) δ 7.81 (d, J=8.1 Hz, 1H), 7.65 (s, 1H), 7.57 (d, J=7.7 Hz, 1H), 7.54 (d, J=7.8 Hz, 1H), 7.09-7.01 (m, 3H), 6.81 (d, J=7.4 Hz, 1H), 4.97-4.91 (m, 1H), 4.84 (d, J=4.0 Hz, 1H), 4.55-4.38 (m, 2H), 4.26 (ddd, J=11.4, 8.8, 2.8 Hz, 1H), 3.04 (dd, J=16.1, 6.2 Hz, 1H), 2.92 (dd, J=16.1, 6.1 Hz, 1H), 2.73 (dd, J=16.0, 3.3 Hz, 1H), 2.61 (dd, J=16.0, 3.4 Hz, 1H), 2.23-1.95 (m, 2H); MS (DCI/NH$_3$) m/z 410 (M+NH$_4$)$^+$.

Example 19

1-[(4R)-2,2-dimethyl-8-(trifluoromethoxy)-3,4-dihydro-2H-chromen-4-yl]-3-[(2R)-2-hydroxy-2,3-dihydro-1H-inden-4-yl]urea

Example 19A 1-(methoxymethoxy)-2-(trifluoromethoxy)benzene

A solution of 2-(trifluoromethyloxy)phenol (12.0 g, 67.4 mmol) in dichloromethane (45 mL) was cooled to 5° C., and N,N-diisopropylethylamine (23.5 mL, 135 mmol) and methoxymethyl chloride (7.68 mL, 135 mmol) were added drop wise, keeping the internal temperature≤15° C. The reaction mixture was warmed to ambient temperature, stirred for 15 minutes at ambient temperature, then diluted with MTBE (250 mL) and washed with 2N HCl (2×50 mL), water (50 mL), 2N NaOH (2×30 mL), water (30 mL), and brine (30 mL). The organic portion was dried (Na$_2$SO$_4$), filtered, and concentrated to give the title compound (13.9 g, 62.6 mmol, 93%) which was used without further purification. MS (DCI/NH$_3$) m/z 222 (M+H)$^+$.

Example 19B 2-hydroxy-3-(trifluoromethoxy)benzoic acid

A solution of Example 19A (13.4 g, 60.3 mmol) in diethyl ether (135 mL) was cooled to −20° C. and n-butyllithium (26.5 mL of a 2.5 M solution in hexanes, 66.3 mmol) was added slowly, keeping the temperature at 0° C. The reaction mixture was warmed to ambient temperature and the resulting yellow slurry was stirred for 15 min. The reaction was cooled to −25° C. and CO$_2$ gas was bubbled through the reaction mixture for 10 minutes, keeping the temperature ≤−20° C. After 10 minutes, the reaction mixture was warmed to ambient temperature and quenched by addition of water (220 mL). The mixture was acidified with 5N HCl (pH 2) and stirred vigorously for 15 minutes. The resulting white solid was collected by filtration, washed with water, and dried in a vacuum oven for 12 hours.

The dried product from the reaction above was dissolved in methanol (65 mL) and 5N HCl (26 mL) was added. The reaction mixture was stirred for 20 minutes then concentrated to a volume of approximately 30 mL. The layers were partitioned and the aqueous portion was extracted with diethyl ether (25 mL). The combined organic portions were treated with 2N NaOH (100 mL) and stirred vigorously at ambient temperature for 15 minutes. The reaction mixture was then acidified (pH 2) by addition of 2N HCl (120 mL) and extracted with dichloromethane (2×120 mL). The combined organic portions were dried (Na$_2$SO$_4$), filtered, and concentrated to give the title compound (10.3 g, 46.4 mmol, 77%) as an oil. MS (DCI/NH$_3$) m/z 223 (M+H)$^+$.

Example 19C 1-(2-hydroxy-3-(trifluoromethoxy)phenyl)ethanone

A solution of Example 19B (10.3 g, 46.4 mmol) in THF (100 mL) was cooled to −10° C. and methyllithium (90 mL of a 1.6M solution in diethyl ether, 144 mmol) was added, keeping the temperature ≤0° C. (slow addition, methane generation). After 90 minutes of stirring at 0° C., LCMS analysis indicated complete reaction. The reaction was cooled to −5° C. and treated with EtOAc (140 mL) followed by 2N HCl (100 mL) keeping the temperature ≤10° C. The reaction mixture was diluted with EtOAc (100 mL) and portioned. The organic portion was washed with water (50 mL) and brine (30 mL), dried (Na$_2$SO$_4$), filtered, and concentrated, to give the title compound (6.85 g, 31.1 mmol, 67%). MS (DCI/NH$_3$) m/z 238 (M+NH$_4$)$^+$.

Example 19D (4R)-2,2-dimethyl-8-(trifluoromethoxy)chroman-4-amine, hydrochloride salt The title compound was prepared from Example 19C, according to the methods described in Example 3B, Example 3C, and Example 1C. MS (DCI/NH$_3$) m/z 262 (M+NH$_4$—H$_2$O)$^+$.

Example 19E

1-[(4R)-2,2-dimethyl-8-(trifluoromethoxy)-3,4-dihydro-2H-chromen-4-yl]-3-[(2R)-2-hydroxy-2,3-dihydro-1H-inden-4-yl]urea The title compound was prepared according to the procedure of Example 1F, substituting Example 19D for Example 1C. $^1$H NMR (300 MHz, DMSO-d$_6$) δ 7.79 (d, J=7.7 Hz, 1H), 7.79 (s, 1H), 7.29-7.34 (m, 1H), 7.26-7.21 (m, 1H), 7.05 (t, J=7.8 Hz, 1H), 6.96 (t, J=7.9 Hz, 1H), 6.93 (d, J=8.0 Hz, 1H), 6.82 (d, J=7.4 Hz, 1H), 5.04-4.95 (m, 1H), 4.86 (d, J=4.0 Hz, 1H), 4.54-4.48 (m, 1H), 3.05 (dd, J=16.1, 6.2 Hz, 1H), 2.96 (dd, J=15.8, 5.9 Hz, 1H), 2.74 (dd, J=15.7, 3.3 Hz, 1H), 2.64 (dd, J=16.0, 3.2 Hz, 1H), 2.21 (dd, J=13.3, 6.2 Hz, 1H), 1.78 (dd, J=13.3, 10.8 Hz, 1H), 1.43 (s, 3H), 1.30 (s, 3H); MS (ESI+) m/z 437 (M+H)$^+$, 454 (M+NH$_4$)$^+$.

Example 20

1-[(2S,4R)-7-chloro-2-(difluoromethyl)-2-methyl-3,4-dihydro-2H-chromen-4-yl]-3-[(2R)-2-hydroxy-2,3-dihydro-1H-inden-4-yl]urea

Example 20A 7-chloro-2-(difluoromethyl)-2-methylchroman-4-one 1-(4-Chloro-2-hydroxyphenyl)ethanone (8.07 g, 47.3 mmol), MeOH (81 mL), 1,1-difluoroacetone (4.89 g, 52.0 mmol), and pyrrolidine (4.30 ml, 52.0 mmol) were stirred at ambient temperature for 45 hours, at 35° C. for 7 hours, then at 50° C. for 3 hours. The reaction mixture was concentrated, diluted with MTBE (75 mL), then washed with water (40 mL), 2N HCl (2×25 mL), brine (20 mL), 2N NaOH (2×20 mL), and brine (2×20 mL). The organic portion was dried (Na$_2$SO$_4$), filtered, and concentrated to give the title compound (9.78 g, 39.7 mmol, 84%) as a brown oil. MS (DCI/NH$_3$) m/z 264 (M+NH$_4$)$^+$.

Example 20B

A solution of Example 20A (9.78 g, 39.7 mmol), (R)-2-methylpropane-2-sulfinamide (7.21 g, 59.5 mmol), 2-methyltetrahydrofuran (100 mL), and tetraethoxytitanium (433 mL, 159 mmol) was heated to 75° C. After 7 hours at 70° C., the reaction was cooled to −30° C. and sodium borohydride (3.00 g, 79.0 mmol) was added. The reaction flask was wrapped with aluminum foil and allowed to warm gradually to ambient temperature with continued stirring over a period of 12 hours. The reaction was cooled to <5° C. and 10% aqueous citric acid (200 mL) was added; the reaction mixture was stirred vigorously for 2 hours, then diluted with MTBE (300 mL). The layers were partitioned and the organic portion was washed with water (75 mL). The aqueous layer was back-extracted with MTBE (75 mL) and the combined organic portions were washed with brine (75 mL). The organic portion was dried ($Na_2SO_4$), filtered, and concentrated to give the title compound, a mixture of diastereomers, that was used without further purification. MS ($DCI/NH_3$) m/z 352 $(M+H)^+$.

Example 20C

(4R)-7-chloro-2-(difluoromethyl)-2-methylchroman-4-amine, D-tartaric acid salt A yellow slurry of Example 20B (13.97 g, 39.70 mmol) in MTBE (140 mL) was stirred at ambient temperature and HCl in methanol [formed from addition of acetyl chloride (5.65 mL, 79.0 mmol) to methanol (14.5 mL, 357 mmol) at <5° C.] was added. After 10 min, the reaction mixture was filtered; the precipitate was collected and washed with 10% MeOH/MTBE (2×10 mL). The resulting off-white solid was dried in a vacuum oven at 60° C. and used without subsequent purification.

D-(−)-Tartaric acid (5.33 g, 35.5 mmol) and isopropanol (90 mL) were heated to 70° C., and a solution of crude (4R)-7-chloro-2-(difluoromethyl)-2-methylchroman-4-amine (8.80 g, 35.5 mmol) from above in isopropanol (45 mL) was added over 30 min.

The reaction mixture was cooled to ambient temperature and the precipitate collected by filtration, washed with isopropanol, and dried in a vacuum oven at 60° C. for 6 h to give the title compound (10.7 g, 26.9 mmol, 76%). MS ($DCI/NH_3$) m/z 248 $(M+NH_4-H_2O)^+$.

Example 20D

1-[(2S,4R)-7-chloro-2-(difluoromethyl)-2-methyl-3,4-dihydro-2H-chromen-4-yl]-3-[(2R)-2-hydroxy-2,3-dihydro-1H-inden-4-yl]urea The title compound was prepared according to the procedure of Example 1F, substituting Example 20C for Example 1C. The diastereomers were separated via semi-preparative chiral supercritical fluid chromatography on a (S,S)-Whelk-O®1 column (Regis Technologies Inc.), 21×250 mm, 5 μm, 100A Kromasil, using an outlet pressure of 100 bar, column temperature of 35° C., and mobile phase flow rate of 40 mL/min, gradient elution 10-30% $MeOH:CO_2$ over 25 min. $^1H$ NMR (300 MHz, DMSO-$d_6$) δ 7.82 (s, 1H), 7.78 (d, J=8.1 Hz, 1H), 7.30 (dd, J=8.2, 0.9 Hz, 1H), 7.09-7.00 (m, 2H), 6.96 (d, J=2.1 Hz, 1H), 6.88 (d, J=8.1 Hz, 1H), 6.82 (d, J=7.4 Hz, 1H), 6.20 (t, J=54.8 Hz, 1H), 4.94-5.02 (m, 1H), 4.85 (d, J=4.0 Hz, 1H), 4.56-4.47 (m, 1H), 3.05 (dd, J=16.1, 6.2 Hz, 1H), 2.96 (dd, J=16.1, 6.1 Hz, 1H), 2.74 (dd, J=16.1, 3.5 Hz, 1H), 2.65 (dd, J=16.1, 3.3 Hz, 1H), 2.41 (dd, J=14.1, 6.0 Hz, 1H), 1.92 (dd, J=14.1, 9.7 Hz, 1H), 1.42 (s, 3H); MS ($DCI/NH_3$) m/z 440 $(M+NH_4)^+$.

Example 21

1-[(2R)-2-hydroxy-2,3-dihydro-1H-inden-4-yl]-3-[(4R)-7-(trifluoromethyl)-3,4-dihydro-2H-chromen-4-yl]urea

Example 21A

7-(trifluoromethyl)chroman-4-one

The title compound was prepared from 3-trifluoromethylphenol according to EP1908753. MS ($DCI/NH_3$) m/z 234 $(M+NH_4)^+$.

Example 21B

(4R)-7-(trifluoromethyl)chroman-4-amine, hydrochloride salt

The title compound was prepared from Example 22A, according to the methods described in Example 20B and Example 1C. MS ($DCI/NH_3$) m/z 218 $(M+NH_4-H_2O)^+$.

Example 21C

1-[(2R)-2-hydroxy-2,3-dihydro-1H-inden-4-yl]-3-[(4R)-7-(trifluoromethyl)-3,4-dihydro-2H-chromen-4-yl]urea The title compound was prepared according to the procedure of Example 1F, substituting Example 21B for Example 1C. $^1H$ NMR (300 MHz, DMSO-$d_6$) δ 7.80 (d, J=8.1 Hz, 1H), 7.70 (s, 1H), 7.51 (d, J=8.0 Hz, 1H), 7.25 (dd, J=8.1, 1.9 Hz, 1H), 7.12 (d, J=1.8 Hz, 1H), 7.08-7.01 (m, 2H), 6.81 (d, J=7.4 Hz, 1H), 5.01-4.91 (m, 1H), 4.84 (d, J=4.0 Hz, 1H), 4.55-4.46 (m, 1H), 4.40-4.32 (m, 1H), 4.23 (ddd, J=11.3, 8.2, 3.1 Hz, 1H), 3.04 (dd, J=16.0, 6.2 Hz, 1H), 2.93 (dd, J=16.1, 6.2 Hz, 1H), 2.73 (dd, J=16.1, 3.6 Hz, 1H), 2.62 (dd, J=16.2, 3.4 Hz, 1H), 2.21-2.10 (m, 1H), 2.05-1.95 (m, 1H); MS (ESI+) m/z 393 $(M+H)^+$, 410 $(M+NH_4)^+$; $[\alpha]^{23}_D=+14.6°$ (c 1.03, $CH_3OH$).

Example 22

1-[(4R)-3,4-dihydrospiro[chromene-2,1'-cyclobutan]-4-yl]-3-[(2R)-2-hydroxy-2,3-dihydro-1H-inden-4-yl]urea

Example 22A

Spiro[chroman-2,1'-cyclobutan]-4-one

The title compound was prepared using method as described in Example 1A, substituting 2'-hydroxyacetophenone for 1-(3,5-difluoro-2-hydroxyphenyl)ethanone, and substituting cyclobutanone for 1,3-difluoroacetone.

Example 22B (4R)-spiro[chroman-2,1'-cyclobutan]-4-amine, (R)-(−) mandelic acid salt The title compound was prepared from Example 22A, according to the methods described in Examples 17A, 17B, and 17C. MS (DCI/NH$_3$) m/z 190 (M+H)$^+$.

Example 22C

1-[(4R)-3,4-dihydrospiro[chromene-2,1'-cyclobutan]-4-yl]-3-[(2R)-2-hydroxy-2,3-dihydro-1H-inden-4-yl]urea The title compound was prepared according to the procedure of Example 1F, substituting Example 22A for Example 1C. $^1$H NMR (300 MHz, DMSO-d$_6$) δ 7.82 (d, J=8.1 Hz, 1H), 7.77 (s, 1H), 7.27-7.21 (m, 1H), 7.19-7.12 (m, 1H), 7.05 (t, J=7.7 Hz, 1H), 6.90 (td, J=7.5, 1.3 Hz, 1H), 6.87 (d, J=8.3 Hz, 1H), 6.81 (d, J=7.3 Hz, 1H), 6.79 (dd, J=8.1, 1.1 Hz, 1H), 5.02-4.89 (m, 1H), 4.84 (d, J=4.2 Hz, 1H), 4.56-4.47 (m, 1H), 3.05 (dd, J=16.1, 6.1 Hz, 1H), 2.95 (dd, J=16.0, 6.1 Hz, 1H), 2.74 (dd, J=16.0, 3.6 Hz, 1H), 2.64 (dd, J=16.0, 3.4 Hz, 1H), 2.37 (dd, J=13.3, 5.8 Hz, 1H), 2.10-2.30 (m, 4H), 1.90-1.68 (m, 3H); MS (ESI+) m/z 365 (M+H)$^+$; [α]$^{23}_D$=+10.8° (c 0.65, CH$_3$OH).

Example 23

1-[(2R)-2-hydroxy-2,3-dihydro-1H-inden-4-yl]-3-[(4R)-1-methyl-7-(trifluoromethyl)-1,2,3,4-tetrahydroquinolin-4-yl]urea

Example 23A ethyl 1-methyl-4-oxo-7-(trifluoromethyl)-1,4-dihydroquinoline-3-carboxylate A slurry of ethyl 4-hydroxy-7-(trifluoromethyl)quinoline-3-carboxylate (10.0 g, 35.1 mmol), DMF (50 mL), potassium carbonate (12.11 g, 88.00 mmol), and methyl iodide (11.00 ml, 175.0 mmol) was heated to 90° C. After 20 minutes, the dark solution was cooled to room temperature and water (25 mL) was added slowly, keeping the temperature <40° C. The reaction mixture was cooled to ambient temperature, and the brown slurry was filtered and washed with 2:1 DMF/water (20 mL×2) and water (20 mL×2). The solids were partially dried on the frit giving the title compound (11.0 g, 36.8 mmol, 105% yield), which was used without further purification in the next step.

Example 23B 1-methyl-4-oxo-7-(trifluoromethyl)-1,4-dihydroquinoline-3-carboxylic acid A slurry of Example 23A (10.50 g, 35.1 mmol), and 2N sodium hydroxide (88 mL, 176 mmol) was heated to 90° C. After 30 minutes, the slurry was cooled to ambient temperature and acetic acid (44 mL) was added slowly, keeping the temperature <40° C. The mixture was cooled to ambient temperature and the brown slurry was filtered, and washed with 2:1 water/AcOH (20 mL×2) and water (20 mL×2). The light brown solid was dried in a vacuum oven at 45° C., giving the title compound (7.20 g, 26.5 mmol, 76%). MS (DCI/NH$_3$) m/z 272 (M+H)$^+$.

Example 23C 1-methyl-7-(trifluoromethyl)-2,3-dihydroquinolin-4(1H)-one

A slurry of Example 23B (7.00 g, 25.8 mmol) in MeOH (140 ml) was cooled in an ice bath to 10° C. and sodium borohydride (3.91 g, 103 mmol) was added portion wise at <40° C. After the addition, p-toluenesulfonic acid monohydrate (0.491 g, 2.58 mmol) was added and the dark solution was heated to 60° C. After 1 hour, the mixture was concentrated, diluted with EtOAc (200 mL), and washed with saturated aqueous NaHCO$_3$ (50 mL), water (50 mL), and brine (50 mL). The organic portions were dried (Na$_2$SO$_4$), filtered, and concentrated, giving the title compound (5.91 g, 25.8 mmol), which was used without further purification. MS (DCI/NH$_3$) m/z 247 (M+NH$_4$)$^+$.

Example 23D (4R)-1-methyl-7-(trifluoromethyl)-1,2,3,4-tetrahydroquinolin-4-amine dihydrochloride The title compound was prepared from Example 23C according to the methods described in Example 20B and Example 1C. MS (DCI/NH$_3$) m/z 231 (M+H)$^+$.

Example 23E

1-[(2R)-2-hydroxy-2,3-dihydro-1H-inden-4-yl]-3-[(4R)-1-methyl-7-(trifluoromethyl)-1,2,3,4-tetrahydroquinolin-4-yl]urea The title compound was prepared according to the procedure of Example 1F, substituting Example 23D for Example 1C. $^1$H NMR (300 MHz, DMSO-d$_6$) δ 7.82 (d, J=8.1 Hz, 1H), 7.65 (s, 1H), 7.30 (d, J=7.8 Hz, 1H), 7.03 (t, J=7.8 Hz, 1H), 6.89 (d, J=7.8 Hz, 1H), 6.88 (d, J=8.0 Hz, 1H), 6.82-6.77 (m, 2H), 4.83 (d, J=4.2 Hz, 1H), 4.88-4.79 (m, 1H), 4.55-4.45 (m, 1H), 3.41-3.21 (m, 2H), 3.03 (dd, J=16.1, 6.1 Hz, 1H), 2.95 (s, 3H), 2.92 (dd, J=16.2, 6.1 Hz, 1H), 2.72 (dd, J=16.0, 3.5 Hz, 1H), 2.61 (dd, J=15.8, 3.7 Hz, 1H), 1.88-2.07 (m, 2H); MS (ESI+) m/z 406 (M+H)$^+$.

Example 24

1-[(4R)-7-chloro-2,2-bis(fluoromethyl)-3,4-dihydro-2H-chromen-4-yl]-3-[(2S)-2-hydroxy-2,3-dihydro-1H-inden-4-yl]urea The title compound was prepared according to the procedure of Example 1F, substituting Example 4B for Example 1C and substituting (S)-4-amino-2,3-dihydro-1H-inden-2-ol (from chiral separation of Example 1D) for Example 1E. $^1$H NMR (300 MHz, DMSO-d$_6$) δ 7.82 (s, 1H), 7.77 (d, J=8.1 Hz, 1H), 7.31 (dd, J=8.2, 1.0 Hz, 1H), 7.08-7.02 (m, 2H), 6.98 (d, J=2.1 Hz, 1H), 6.91 (d, J=8.0 Hz, 1H), 6.82 (d, J=7.4 Hz, 1H), 4.92-5.05 (m, 1H), 4.87 (d, J=4.1 Hz, 1H), 4.74-4.70 (m, 2H), 4.62-4.48 (m, 3H), 3.05 (dd, J=16.2, 6.4 Hz, 1H), 2.95 (dd, J=16.0, 6.1 Hz, 1H), 2.74 (dd, J=16.0, 3.5 Hz, 1H), 2.66 (dd, J=16.0, 3.3 Hz, 1H), 2.31 (dd, J=14.1, 6.2 Hz, 1H), 1.93 (ddd, J=13.6, 10.8, 2.7 Hz, 1H); MS (ESI+) m/z 423 (M+H)$^+$, 440 (M+NH$_4$)$^+$.

Example 25

1-[(2R,4R)-7-chloro-2-(fluoromethyl)-2-methyl-3,4-dihydro-2H-chromen-4-yl]-3-(5-fluoro-2-hydroxy-2,3-dihydro-1H-inden-4-yl)urea

Example 25A 4-bromo-5-fluoro-2,3-dihydro-1H-inden-1-one

A solution of aluminum trichloride (11.10 g, 83.00 mmol) in dichloroethane (100 mL) was slowly added a solution of 5-fluoro-2,3-dihydro-1H-inden-1-one (5 g, 33.3 mmol) in dichloroethane (10 mL) at ambient temperature and stirred for 5 minutes, followed with the addition of bromine (2.57 mL, 50.0 mmol). The resulting dark red mixture was heated at 70° C. for 2 hours. The reaction mixture was cooled to ambient temperature and poured into a mixture of ice and HCl (1N, 50 mL). Diethyl ether (300 mL) was added and the mixture was partitioned. The organic portion was washed with water (75 mL) and brine (50 mL), dried (MgSO$_4$), filtered, and concentrated under reduced pressure. The resulting residue was chromatographed on silica gel (gradient elution: 0-10% EtOAc/hexanes) to provide the title compound mixed with inseparable bisbrominated side product (4,7-dibromo-5-fluoro-2,3-dihydro-1H-inden-1-one). MS (DCI) m/z 246 (M+NH$_4$)$^+$.

Example 25B 4-bromo-5-fluoro-2,3-dihydro-1H-inden-1-ol

A solution of Example 25A (9.5 g, 41.5 mmol) in MeOH (80 mL) was cooled with an ice bath and treated with NaBH$_4$ (2.04 g, 53.9 mmol). The mixture was stirred for 2 hours at ambient temperature. The reaction mixture was diluted with diethyl ether (200 mL), quenched with HCl (1N, 20 mL) and partitioned. The organic layer was washed with H$_2$O (50 mL) and brine (40 mL), dried (Na$_2$SO$_4$), filtered, and concentrated under reduced pressure. The resulting residue was chromatographed on silica gel (gradient elution: 0-15% EtOAc/hexanes) to provide the title compound. MS (DCI) m/z 248 (M+NH$_4$)$^+$

Example 25C 7-bromo-6-fluoro-1H-indene

A solution of Example 25B (923 mg, 3.99 mmol) and TsOH (45.6 mg, 0.240 mmol) in toluene (20 mL) was heated to reflux for 2 hours. The mixture was cooled to ambient temperature and was then concentrated under reduced pressure. The residue was passed through a silica gel frit to provide the title compound (670 mg, 3.14 mmol, 79%). MS (DCI) m/z 231 (M+NH$_4$)$^+$.

Example 25D 5-bromo-4-fluoro-6,6a-dihydro-1aH-1-oxa-cyclopropa[a]indene

A solution of Example 25C (500 mg, 2.347 mmol) in dichloromethane (30 mL) was cooled to 0° C. and a solution of mCPBA (631 mg, 2.82 mmol) in dichloromethane (5 mL) was added. The mixture was warmed to ambient temperature and stirred for 2 hours. The mixture was diluted with dichloromethane (50 mL), quenched with a saturated solution of Na$_2$S$_2$O$_3$ and partitioned. The organic portion was dried (MgSO$_4$), filtered, concentrated under reduced pressure. The resulting residue was purified by silica gel chromatography (elution with 10% EtOAc/hexanes) to provide the title product (316 mg, 1.38 mmol, 59%). MS (DCI) m/z 230 (M+H)$^+$.

Example 25E 4-bromo-5-fluoro-2,3-dihydro-1H-inden-2-ol

A solution of the Example 25D (1.68 g, 7.33 mmol) in diethyl ether (40 mL) was cooled to 0° C. and treated with lithium aluminum hydride (8.07 mL of a 1.0M solution in Et$_2$O, 8.07 mmol). The reaction was raised to ambient temperature and stirred for 2 hours. The mixture was diluted with ether (25 mL) and treated sequentially with H$_2$O (0.3 mL), 1N NaOH (0.3 mL), then H$_2$O (0.9 mL). The mixture was stirred for 10 minutes and filtered through a layer of Celite. The filtrate was concentrated and the residue purified by silica gel chromatorgraphy (gradient elution: 10-15% EtOAc/hexanes) to provide the title compound (1.22 g, 5.28 mmol, 72%). MS (DCI) m/z 232 (M+H)+.

Example 25F 4-amino-5-fluoro-2,3-dihydro-1H-inden-2-ol

A solution of Example 25E (950 mg, 4.11 mmol), (R)-(+)-2,2'-bis(diphenylphosphino)-1,1'-binaphthyl (154 mg, 0.247 mmol), Pd$_2$(dba)$_3$ (11 mg, 0.12 mmol), diphenylmethanimine (1.09 mL, 6.17 mmol) and Cs$_2$CO$_3$ (335 mg, 10.3 mmol) in toluene (20 mL) was heated at 85° C. for 16 hours. The mixture was cooled to ambient temperature, filtered through a layer of Celite, and washed with diethyl ether (60 mL). The filtrate was concentrated under reduced pressure and the resulting residue was purified by silica gel chromatography (gradient elution: 0-20% EtOAc/hexanes) to provide 4-(diphenylmethyleneamino)-5-fluoro-2,3-dihydro-1H-inden-2-ol (1.15 g, 3.47 mmol, 84%) which was used without further purification.

This abovementioned residue was dissolved in MeOH (10 mL) and stirred with HCl (1N, 7 mL) for 5 minutes. The mixture was diluted with diethyl ether (20 mL) and partitioned. The organic portion was washed with water (15 mL) and brine (10 mL), dried (MgSO4), and concentrated under reduced pressure. The residue was purified by silica gel chromatography (elution with 25% EtOAc/hexanes) to provide the title product. MS (DCI) m/z 168 (M+NH4)+.

Example 25G

1-[(2R,4R)-7-chloro-2-(fluoromethyl)-2-methyl-3,4-dihydro-2H-chromen-4-yl]-3-(5-fluoro-2-hydroxy-2,3-dihydro-1H-inden-4-yl)urea The title compound was prepared according to the procedure of Example 1F, substituting Example 17C for Example 1C, and substituting Example 25F for Example 1E. $^1$H NMR (300 MHz, CDCl$_3$) δ 7.22 (dd, J=8.48, 5.09 Hz, 2H), 6.94-6.81 (m, 3H), 6.08 (d, J=4.41 Hz, 1H), 5.28-5.16 (m, 1H), 4.82-4.70 (m, 2H), 4.50-4.34 (m, 1H), 4.34-4.14 (m, 1H), 3.28-2.84 (m, 4H), 2.24-2.12 (m, 1H), 1.93-1.78 (m, 1H), 1.31 (d, J=2.0 Hz, 3H); MS (DCI) m/z 440 (M+NH$_4$)$^+$.

Example 26

1-[(2R)-2-hydroxy-2,3-dihydro-1H-inden-4-yl]-3-{[6-(trifluoromethyl)-3,4-dihydro-2H-chromen-2-yl]methyl}urea

Example 26A (6-(trifluoromethyl)chroman-2-yl)methanamine

The title compound was prepared according to the procedure outlined in US 20060128689. MS (DCI) m/z 249 $(M+NH_4)^+$.

Example 26B

1-[(2R)-2-hydroxy-2,3-dihydro-1H-inden-4-yl]-3-{[6-(trifluoromethyl)-3,4-dihydro-2H-chromen-2-yl]methyl}urea The title compound was prepared according to the procedure of Example 1F, substituting Example 26A for Example 1C. $^1$H NMR (300 MHz, CDCl$_3$) δ 7.27-7.32 (m, 1H), 7.24-7.15 (m, 1H), 7.14-7.05 (m, 3H), 7.03-6.97 (m, 1H), 6.08 (s, 1H), 5.20 (s, 1H), 4.70 (s, 1H), 4.22-4.12 (m, 1H), 3.83-3.67 (m, 1H), 3.42-3.30 (m, 1H), 3.30-3.06 (m, 2H), 3.01-2.81 (m, 4H), 2.10-2.05 (m, 1H), 1.85-1.66 (m, 2H); MS (DCI) m/z 424 $(M+NH_4)^+$.

Example 27

1-[(3S)-6-chloro-3,4-dihydro-2H-chromen-3-yl]-3-[(2R)-2-hydroxy-2,3-dihydro-1H-inden-4-yl]urea

Example 27A 1-(6-chlorochroman-3-yl)-3-((R)-2-hydroxy-2,3-dihydro-1H-inden-4-yl)urea A solution of N,N-disuccinimidyl carbonate (86 mg, 0.33 mmol), acetonitrile (3 mL), pyridine (0.027 mL, 0.335 mmol), and Example 1E (50 mg, 0.33 mmol) was stirred at ambient temperature. After 30 minutes, N,N-diisopropylethylamine (0.12 mL, 0.67 mmol) and 6-chlorochroman-3-one (synthesized by the procedure described in WO 2008/079683) (62 mg, 0.335 mmol) were added. After 10 minutes, 2N HCl (20 mL) and EtOAc (100 mL) were added, the layers were separated, and the organic layer was washed with brine (20 mL). The organic layer was dried (Na$_2$SO$_4$), filtered, and concentrated. The resulting oil was triturated with methylene chloride to yield crystalline title product (70 mg, 68% yield). MS (ESI$^+$) m/z 359 $(M+H)^+$.

Example 27B

1-[(3S)-6-chloro-3,4-dihydro-2H-chromen-3-yl]-3-[(2R)-2-hydroxy-2,3-dihydro-1H-inden-4-yl]urea The product from the Example 27A was resolved via semi-preparative chiral supercritical fluid chromatography on a ChiralPak® AD-H column (Chiral technologies Inc.), 21×250 mm, 5 µm, using an outlet pressure of 100 bar, column temperature of 35° C., and mobile phase flow rate of 40 mL/min, gradient elution 10-50% MeOH:CO$_2$ over 25 min, to yield the title product. $^1$H NMR (300 MHz, DMSO-d$_6$) δ 7.79 (d, J=7.1 Hz, 1H), 7.78 (d, J=4.1 Hz, 1H), 7.21 (d, J=2.7 Hz, 1H), 7.15 (dd, J=8.6, 2.5 Hz, 1H), 7.01 (t, J=7.6 Hz, 1H), 6.85 (d, J=8.8 Hz, 1H), 6.77 (dd, J=6.9, 2.9 Hz, 2H), 4.83 (d, J=3.4 Hz, 1H), 4.48 (m, J=5.8 Hz, 1H), 4.09 (m, 3H), 3.09 (m, 1H), 3.02 (m, 1H), 2.88 (dd, J=16.1, 6.3 Hz, 1H), 2.70 (m, 2H), 2.59 (dd, J=16.3, 3.4 Hz, 1H); MS (ESI+) m/z 359 $(M+H)^+$.

Example 28

1-[(6-fluoro-3,4-dihydro-2H-chromen-3-yl)methyl]-3-[(2R)-2-hydroxy-2,3-dihydro-1H-inden-4-yl]urea

Example 28A 6-fluoro-2H-chromene-3-carbonitrile

A solution of 5-fluoro-2-hydroxybenzaldehyde (1.00 g, 8.92 mmol) and acrylonitrile (9.40 mL, 143 mmol) was refluxed overnight with DABCO (1.00 g, 8.92 mmol). The mixture was cooled and 1 M NaOH (10 mL) was added. The mixture was extracted with EtOAc (20 mL), and the organic layer was dried (MgSO$_4$), filtered, and concentrated. The resulting residue was purified by silica gel chromatography (elution with 10% EtOAc/hexanes) to provide the title compound (4.50 g) as yellow crystals. $^1$H NMR (300 MHz, CDCl$_3$) δ 7.13 (m, 1H), 6.98 (td, J=8.5, 3.0 Hz, 1H), 6.89-6.80 (m, 2H), 4.80 (d, J=1.4 Hz, 2H).

Example 28B (6-fluorochroman-3-yl)methanamine

To a solution of Example 28A (780 mg, 4.45 mmol) in 7M NH$_3$ in MeOH (5.00 mL) was added to Ra—Ni 2800 water slurry (1.56 g, 26.6 mmol) in a 50 mL pressure bottle. The reaction mixture was and stirred for 10 hours at 30 psi at ambient temperature. After 3 hours, the solution was filtered and concentrated. The resulting residue was purified by silica gel chromatography (gradient elution: 1-15% MeOH/CH$_2$Cl$_2$ with 1% NH$_4$OH) to provide the title compound. MS (DCI+) m/z 182 $(M+H)^+$.

Example 28C

1-[(6-fluoro-3,4-dihydro-2H-chromen-3-yl)methyl]-3-[(2R)-2-hydroxy-2,3-dihydro-1H-inden-4-yl]urea The title compound was prepared according to the procedure of Example 1F, substituting Example 28B for Example 1C. $^1$H NMR (300 MHz, DMSO-d$_6$) δ 7.74-7.69 (m, 2H), 7.01 (t, J=7.6 Hz, 1H), 6.94-6.91 (m, 2H), 6.79-6.71 (m, 2H), 6.66 (t, J=5.8 Hz, 1H), 4.85 (s, 1H), 4.55-4.48 (m, 1H), 4.18 (dd, J=11.4, 3.9 Hz, 1H), 3.83 (dd, J=11.0, 8.3 Hz, 1H), 3.19-3.12 (m, 2H), 3.10-3.04 (m, 1H), 3.00-2.95 (m, 2H), 2.89-2.79 (m, 1H), 2.76-2.66 (m, 2H), 2.60-2.53 (m, 1H), 2.19-2.08 (m, 1H); MS (ESI+) m/z 357 $(M+H)^+$.

Examples 29-176 were prepared using methodologies analogous to those illustrated in the general schemes and Examples 1-28:

Example 29

1-[(4R)-2,2-dimethyl-8-(trifluoromethyl)-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 1.31 (s, 3H), 1.43 (s, 3H), 1.77-1.86 (m, 1H), 2.22 (dd, J=13.3, 6.2 Hz, 1H), 2.67 (dd, J=16.1, 3.5 Hz, 1H), 2.76 (dd, J=16.0, 3.6 Hz, 1H), 2.98 (dd, J=16.1, 6.2 Hz, 1H), 3.07 (dd, J=16.1, 6.2 Hz, 1H), 4.49-4.56 (m, 1H), 5.01 (dd, J=10.8, 6.2 Hz, 1H), 6.86 (d, J=7.4 Hz, 1H), 7.07 (q, J=7.6 Hz, 2H), 7.53 (dd, J=20.8, 7.8 Hz, 2H), 7.74 (d, J=8.1 Hz, 1H). MS (ESI$^+$) m/z 421.1 (M+H).

Example 30

1-[(4R)-2,2-dimethyl-7-(trifluoromethoxy)-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 1.30 (s, 3H), 1.42 (s, 3H), 1.75 (dd, J=13.3, 10.9 Hz, 1H), 2.18 (dd, J=13.3, 6.1 Hz, 1H), 2.66 (dd, J=16.1, 3.5 Hz, 1H), 2.75 (dd, J=16.0, 3.6 Hz, 1H), 2.98 (dd, J=16.1, 6.1 Hz, 1H), 3.07 (dd, J=16.1, 6.2 Hz, 1H), 4.49-4.56 (m, 1H), 4.96 (dd, J=10.9, 6.1 Hz, 1H), 6.72 (d, J=2.3 Hz, 1H), 6.85 (d, J=7.4 Hz, 1H), 6.91 (ddd, J=8.6, 2.5, 1.3 Hz, 1H), 7.07 (t, J=7.7 Hz, 1H), 7.38 (dd, J=8.5, 1.0 Hz, 1H), 7.75 (d, J=8.1 Hz, 1H). MS (ESI$^+$) m/z 437.2 (M+H).

Example 31

1-[(4R)-2,2-bis(fluoromethyl)-7-(trifluoromethoxy)-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 1.98 (ddd, J=13.6, 10.7, 2.7 Hz, 1H), 2.33 (dd, J=13.8, 5.9 Hz, 1H), 2.66 (dd, J=16.1, 3.5 Hz, 1H), 2.75 (dd, J=16.0, 3.6 Hz, 1H), 2.98 (dd, J=16.1, 6.1 Hz, 1H), 3.07 (dd, J=16.1, 6.2 Hz, 1H), 4.49-4.74 (m, 4H), 5.01 (dd, J=10.4, 5.9 Hz, 1H), 6.86 (d, J=7.4 Hz, 1H), 6.89 (d, J=2.3 Hz, 1H), 7.00 (ddd, J=8.6, 2.5, 1.3 Hz, 1H), 7.07 (t, J=7.7 Hz, 1H), 7.41 (dd, J=8.5, 1.0 Hz, 1H), 7.73 (d, J=8.1 Hz, 1H). MS (ESI$^+$) m/z 473.1 (M+H).

Example 32

1-[(4R)-7-fluoro-2,2-dimethyl-3,4-dihydro-2H-chromen-4-yl]-3-[(2S)-2-hydroxy-2,3-dihydro-1H-inden-4-yl]urea $^1$H NMR (300 MHz, DMSO-d$_6$) δ 7.81 (d, J=8.2 Hz, 1H), 7.78 (s, 1H), 7.30 (ddd, J=8.6, 6.9, 1.0 Hz, 1H), 7.04 (t, J=7.7 Hz, 1H), 6.84 (d, J=8.6 Hz, 1H), 6.81 (d, J=7.8 Hz, 1H), 6.74 (td, J=8.6, 2.6 Hz, 1H), 6.59 (dd, J=10.6, 2.6 Hz, 1H), 5.00-4.86 (m, 1H), 4.86 (d, J=4.1 Hz, 1H), 4.57-4.45 (m, 1H), 3.05 (dd, J=16.0, 6.1 Hz, 1H), 2.94 (dd, J=16.1, 6.1 Hz, 1H), 2.74 (dd, J=16.1, 3.5 Hz, 1H), 2.65 (dd, J=16.1, 3.3 Hz, 1H), 2.16 (dd, J=13.3, 6.1 Hz, 1H), 1.70 (dd, J=13.2, 10.8 Hz, 1H), 1.40 (s, 3H), 1.29 (s, 3H). MS (DCI$^+$) m/z 388 (M+NH$_4$)$^+$.

Example 33

1-[(2R,4R)-7-chloro-2-(difluoromethyl)-2-methyl-3,4-dihydro-2H-chromen-4-yl]-3-[(2R)-2-hydroxy-2,3-dihydro-1H-inden-4-yl]urea $^1$H NMR (300 MHz, DMSO-d$_6$) δ 7.84 (s, 1H), 7.76 (d, J=8.1 Hz, 1H), 7.32 (d, J=8.3 Hz, 1H), 7.10-7.00 (m, 2H), 6.94 (dd, J=5.2, 3.0 Hz, 2H), 6.83 (d, J=7.3 Hz, 1H), 6.15 (t, J=55.2 Hz, 1H), 5.00 (dd, J=12.9 Hz, 1H), 4.86 (d, J=3.7 Hz, 1H), 4.51 (s, 1H), 3.23-2.88 (m, 2H), 2.82-2.56 (m, 2H), 2.18 (dd, J=13.0, 5.9 Hz, 1H), 1.87 (t, J=12.3 Hz, 1H), 1.37 (s, 3H); MS (DCI+) m/z 440 (M+NH$_4$)$^+$.

Example 34

1-[(4R)-2,2-dimethyl-8-(trifluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.32 (s, 3H), 1.43 (s, 3H), 1.79-1.84 (m, 2H), 2.22 (dd, J=13.3, 6.2 Hz, 1H), 2.67 (dd, J=16.1, 3.5 Hz, 1H), 2.76 (dd, J=16.1, 3.6 Hz, 1H), 3.02 (ddd, J=41.0, 16.1, 6.2 Hz, 2H), 4.48-4.57 (m, 1H), 5.01 (dd, J=10.9, 6.2 Hz, 1H), 6.86 (d, J=7.3 Hz, 1H), 6.94-7.12 (m, 2H), 7.51 (d, J=7.8 Hz, 1H), 7.56 (d, J=7.8 Hz, 1H), 7.75 (d, J=8.1 Hz, 1H). MS (ESI$^+$) m/z 421 (M+H)$^+$.

Example 35

1-[(4R)-7-chloro-8-fluoro-2,2-dimethyl-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.33 (s, 3H), 1.46 (s, 3H), 1.78 (dd, J=13.4, 11.1 Hz, 1H), 2.19 (dd, J=13.3, 6.1 Hz, 1H), 2.71 (ddd, J=36.2, 16.1, 3.6 Hz, 3H), 3.02 (ddd, J=43.2, 16.1, 6.2 Hz, 3H), 4.43-4.56 (m, 1H), 4.97 (dd, J=11.1, 6.1 Hz, 1H), 6.86 (d, J=7.4 Hz, 1H), 7.03-7.15 (m, 3H), 7.74 (d, J=8.1 Hz, 1H). MS (ESI$^+$) m/z 405 (M+H)$^+$.

Example 36

1-[(4R)-8-chloro-7-fluoro-2,2-dimethyl-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.32 (s, 3H), 1.47 (s, 3H), 1.77 (dd, J=13.3, 11.1 Hz, 1H), 2.19 (dd, J=13.3, 6.1 Hz, 1H), 2.67 (dd, J=16.0, 3.5 Hz, 1H), 2.76 (dd, J=16.1, 3.6 Hz, 1H), 2.96 (dd, J=16.1, 6.1 Hz, 1H), 3.07 (dd, J=16.1, 6.2 Hz, 1H), 3.18 (s, 1H), 4.48-4.57 (m, 1H), 4.94-5.10 (m, 1H), 6.86 (d, J=7.3 Hz, 1H), 6.96 (t, J=8.7 Hz, 1H), 7.07 (t, J=7.7 Hz, 1H), 7.28 (ddd, J=8.7, 6.4, 1.1 Hz, 1H), 7.75 (d, J=8.1 Hz, 1H). MS (ESI$^+$) m/z 405 (M+H)$^+$.

Example 37

1-[(2S)-2-hydroxy-2,3-dihydro-1H-inden-4-yl]-3-[(4R)-7-(trifluoromethoxy)-3,4-dihydro-2H-chromen-4-yl]urea $^1$H NMR (400 MHz, DMSO-d$_6$/D$_2$O) δ ppm 1.92-2.03 (m, 1H), 2.04-2.18 (m, 1H), 2.62 (dd, J=16.0, 3.4 Hz, 1H), 2.74 (dd, J=16.1, 3.7 Hz, 1H), 2.93 (dd, J=16.1, 6.2 Hz, 1H), 3.06 (dd, J=16.1, 6.2 Hz, 1H), 4.18 (ddd, J=11.4, 8.7, 2.8 Hz, 1H), 4.29-4.38 (m, 1H), 4.47-4.55 (m, 1H), 4.88 (t, J=5.4 Hz, 1H), 6.81 (d, J=2.4 Hz, 1H), 6.84 (d, J=7.4 Hz, 1H), 6.93 (ddd, J=8.5, 2.5, 1.2 Hz, 1H), 7.07 (t, J=7.7 Hz, 1H), 7.40 (d, J=8.5 Hz, 1H), 7.77 (d, J=8.1 Hz, 1H). MS (ESI$^+$) m/z 409 (M+H)$^+$.

Example 38

1-[(4R)-7,8-difluoro-2,2-dimethyl-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.33 (s, 3H), 1.46 (s, 3H), 1.72-1.86 (m, 1H), 2.19 (dd, J=13.4, 6.1 Hz, 1H), 2.71 (ddd, J=35.5, 16.1, 3.6 Hz, 2H), 2.96 (dd, J=16.1, 6.1 Hz, 1H), 3.07 (dd, J=16.1, 6.2 Hz, 1H), 4.48-4.57 (m, 1H), 4.96

(dd, J=11.0, 6.1 Hz, 1H), 6.86 (d, J=7.3 Hz, 1H), 6.89-6.99 (m, 1H), 7.03-7.14 (m, 2H), 7.75 (d, J=8.1 Hz, 1H). MS (ESI⁺) m/z 389 (M+H)⁺.

Example 39

1-[(1R)-5-chloro-2,3-dihydro-1H-inden-1-yl]-3-[(2R)-2-hydroxy-2,3-dihydro-1H-inden-4-yl]urea ¹H NMR (300 MHz, CD₃OD) δ ppm 1.79-1.94 (m, 1H), 2.52-2.66 (m, 1H), 2.78 (dd, J=16.2, 3.4 Hz, 1H), 2.83-2.92 (m, 2H), 2.99 (ddd, J=16.1, 8.6, 3.7 Hz, 1H), 3.05-3.23 (m, 2H), 4.59-4.67 (m, 1H), 5.25 (dd, J=7.6, 7.6 Hz, 1H), 6.93 (d, J=7.5 Hz, 1H), 7.11 (dd, J=7.8, 7.8 Hz, 1H), 7.17-7.22 (m, 1H), 7.23-7.26 (m, 1H), 7.30 (d, J=7.9 Hz, 1H), 7.57 (d, J=8.1 Hz, 1H). MS (ESI) m/z 343 (M+H)⁺.

Example 40

1-[(2R)-2-hydroxy-2,3-dihydro-1H-inden-4-yl]-3-[(1R)-5-(trifluoromethyl)-2,3-dihydro-1H-inden-1-yl]urea ¹H NMR (300 MHz, CD₃OD) δ ppm 1.90 (dddd, J=12.7, 8.8, 8.8, 8.8 Hz, 1H), 2.63 (dddd, J=12.6, 7.7, 7.7, 3.4 Hz, 1H), 2.80 (dd, J=16.3, 3.4 Hz, 1H), 2.84-3.00 (m, 2H), 3.01-3.23 (m, 3H), 4.60-4.67 (m, 1H), 5.35 (dd, J=7.8, 7.8 Hz, 1H), 6.94 (d, J=7.4 Hz, 1H), 7.11 (dd, J=7.7, 7.7 Hz, 1H), 7.51 (d, J=1.1 Hz, 2H), 7.54 (s, 1H), 7.55-7.59 (m, 1H). MS (ESI) m/z 377 (M+H)⁺.

Example 41

1-[(2R)-2-hydroxy-2,3-dihydro-1H-inden-4-yl]-3-[(1R)-4-(trifluoromethyl)-2,3-dihydro-1H-inden-1-yl]urea ¹H NMR (300 MHz, CD₃OD) δ ppm 1.91 (m, 1H), 2.56-2.69 (m, 1H), 2.79 (dd, J=16.3, 3.4 Hz, 1H), 2.87 (dd, J=16.2, 3.4 Hz, 1H), 2.93-3.06 (m, 1H), 3.06-3.26 (m, 3H), 4.59-4.67 (m, 1H), 5.33 (dd, J=7.7, 7.7 Hz, 1H), 6.94 (d, J=7.4 Hz, 1H), 7.11 (dd, J=7.7, 7.7 Hz, 1H), 7.39 (dd, J=7.7, 7.7 Hz, 1H), 7.53 (d, J=7.8 Hz, 1H), 7.55-7.63 (m, 2H). MS (ESI) m/z 377 (M+H)⁺.

Example 42

1-[(2R)-2-hydroxy-2,3-dihydro-1H-inden-4-yl]-3-[(4R)-7-(trifluoromethyl)-3,4-dihydrospiro[chromene-2,1'-cyclobutan]-4-yl]urea ¹H NMR (300 MHz, DMSO-d₆) δ 7.90-7.73 (m, 2H), 7.46 (d, J=8.1 Hz, 1H), 7.25 (d, J=8.1 Hz, 1H), 7.16-6.90 (m, 3H), 6.82 (d, J=7.2 Hz, 1H), 4.99 (s, 1H), 4.86 (d, J=4.1 Hz, 1H), 4.52 (dt, J=9.9, 4.8 Hz, 1H), 3.23-2.87 (m, 2H), 2.83-2.56 (m, 2H), 2.45-2.09 (m, 5H), 2.09-1.65 (m, 3H); MS (ESI⁺) m/z 433 (M+H)⁺.

Example 43

1-[(2R,4R)-2-(fluoromethyl)-2-methyl-7-(trifluoromethyl)-3,4-dihydro-2H-chromen-4-yl]-3-[(2R)-2-hydroxy-2,3-dihydro-1H-inden-4-yl]urea ¹H NMR (300 MHz, DMSO-d₆) δ 7.90-7.71 (m, 2H), 7.59-7.45 (m, 1H), 7.28 (dt, J=6.1, 3.0 Hz, 1H), 7.18-6.91 (m, 3H), 6.83 (d, J=7.4 Hz, 1H), 5.20-5.00 (m, 1H), 4.87 (d, J=4.1 Hz, 1H), 4.68-4.34 (m, 3H), 3.15-2.88 (m, 2H), 2.83-2.58 (m, 2H), 2.26-2.08 (m, 1H), 1.97-1.82 (m, 1H), 1.36-1.26 (m, 3H); MS (DCI+) m/z 456 (M+NH₄)⁺.

Example 44

1-[(2S,4R)-2-(fluoromethyl)-2-methyl-7-(trifluoromethyl)-3,4-dihydro-2H-chromen-4-yl]-3-[(2R)-2-hydroxy-2,3-dihydro-1H-inden-4-yl]urea ¹H NMR (300 MHz, DMSO-d₆) δ 7.89-7.72 (m, 2H), 7.49 (dd, J=8.8, 4.3 Hz, 1H), 7.35-7.21 (m, 1H), 7.19-6.99 (m, 2H), 6.99-6.88 (m, 1H), 6.84 (t, J=8.0 Hz, 1H), 5.12-4.93 (m, 1H), 4.86 (d, J=4.1 Hz, 1H), 4.70-4.34 (m, 3H), 3.15-2.87 (m, 2H), 2.82-2.61 (m, 2H), 2.42-2.26 (m, 1H), 1.96-1.84 (m, 1H), 1.40 (t, J=3.9 Hz, 3H); MS (DCI+) m/z 456 (M+NH₄)⁺.

Example 45

1-[(4R)-7-bromo-2,2-bis(fluoromethyl)-3,4-dihydro-2H-chromen-4-yl]-3-[(2R)-2-hydroxy-2,3-dihydro-1H-inden-4-yl]urea

Example 45A

Example 45A was prepared as described in Example 1B substituting 7-bromo-2,2-bis(fluoromethyl)chroman-4-one (WO 2010045401) for Example 1A. MS (DCI) m/z 396, 398 (M+H)⁺.

Example 45B (R)-7-bromo-2,2-bis(fluoromethyl)chroman-4-aminium chloride

The title compound was prepared as described in Example 1C substituting Example 45A for Example 1B. MS (DCI) m/z 293, 295 (M+NH₄—H₂O)⁺.

Example 45C

1-[(4R)-7-bromo-2,2-bis(fluoromethyl)-3,4-dihydro-2H-chromen-4-yl]-3-[(2R)-2-hydroxy-2,3-dihydro-1H-inden-4-yl]urea ¹H NMR (300 MHz, DMSO) δ 7.77 (d, J=8.1 Hz, 1H), 7.25 (dd, J=8.2, 0.9 Hz, 1H), 7.17 (dd, J=8.2, 1.9 Hz, 1H), 7.10 (d, J=1.9 Hz, 1H), 7.03 (d, J=7.8 Hz, 1H), 6.91 (d, J=8.0 Hz, 1H), 6.82 (d, J=7.4 Hz, 1H), 5.02-4.89 (m, 1H), 4.86 (d, J=4.1 Hz, 1H), 4.79-4.65 (m, 1H), 4.63-4.47 (m, 2H), 3.00 (ddd, J=30.7, 16.1, 6.1 Hz, 3H), 2.70 (ddd, J=25.2, 16.0, 3.5 Hz, 3H), 2.31 (dd, J=13.8, 5.9 Hz, 1H), 1.99 (s, 1H), 1.18 (t, J=7.1 Hz, 1H). MS (ESI⁺) m/z 469 (M+H)⁺.

Example 46

1-[(4R)-8-fluoro-2,2-dimethyl-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.31 (s, 3H), 1.44 (s, 3H), 2.19 (dd, J=13.3, 6.2 Hz, 1H), 2.66 (dd, J=16.1, 3.5 Hz, 1H), 2.75 (dd, J=16.0, 3.6 Hz, 1H), 2.98 (dd, J=16.1, 6.1 Hz, 1H), 3.07 (dd, J=16.1, 6.1 Hz, 1H), 4.49-4.56 (m, 1H), 4.99 (dd, J=10.9, 6.1 Hz, 1H), 6.80-6.93 (m, 2H), 7.04-7.13 (m, 3H), 7.75 (d, J=8.1 Hz, 1H). MS (ESI⁺) m/z 371 (M+H)⁺.

Example 47

1-[(4R)-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 1.96 (dtd, J=14.0, 5.8, 2.6 Hz, 1H), 2.06-2.16 (m, 1H), 2.62 (dd, J=16.0, 3.5 Hz, 1H), 2.74 (dd, J=16.0, 3.6 Hz, 1H), 2.93 (dd, J=16.1, 6.1 Hz, 1H), 3.06 (dd, J=16.1, 6.2 Hz, 1H), 4.14 (ddd, J=11.4, 9.0, 2.5 Hz, 1H), 4.24-4.31 (m, 1H), 4.47-4.55 (m, 1H), 4.85 (t, J=5.3 Hz, 1H), 6.78-6.86 (m, 2H), 6.92 (td, J=7.4, 1.2 Hz, 1H), 7.06 (t, J=7.8 Hz, 1H), 7.19 (td, J=7.7, 1.7 Hz, 1H), 7.27 (dd, J=7.7, 1.6 Hz, 1H), 7.79 (d, J=8.1 Hz, 1H). MS (ESI$^+$) m/z 325 (M+H)$^+$.

Example 48

1-[(4R)-2,2-diethyl-8-fluoro-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 0.85-0.96 (m, 6H), 1.53-1.77 (m, 5H), 2.18 (dd, J=13.5, 6.1 Hz, 1H), 2.66 (dd, J=16.1, 3.4 Hz, 1H), 2.75 (dd, J=16.0, 3.6 Hz, 1H), 2.98 (dd, J=16.1, 6.2 Hz, 1H), 3.07 (dd, J=16.1, 6.2 Hz, 1H), 4.49-4.56 (m, 1H), 4.96 (dd, J=10.9, 6.1 Hz, 1H), 6.82-6.91 (m, 2H), 7.04-7.13 (m, 3H), 7.75 (d, J=8.1 Hz, 1H). MS (ESI$^+$) m/z 399 (M+H)$^+$.

Example 49

1-[(4R)-2,2-diethyl-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 0.84-0.94 (m, 6H), 1.51-1.73 (m, 5H), 2.15 (dd, J=13.4, 6.1 Hz, 1H), 2.65 (dd, J=16.1, 3.4 Hz, 1H), 2.75 (dd, J=16.0, 3.6 Hz, 1H), 2.97 (dd, J=16.1, 6.2 Hz, 1H), 3.07 (dd, J=16.1, 6.2 Hz, 1H), 4.49-4.56 (m, 1H), 4.93 (dd, J=10.8, 6.1 Hz, 1H), 6.77 (dd, J=8.2, 1.2 Hz, 1H), 6.84 (d, J=7.3 Hz, 1H), 6.90 (td, J=7.4, 1.2 Hz, 1H), 7.07 (t, J=7.7 Hz, 1H), 7.12-7.19 (m, 1H), 7.26 (d, J=7.1 Hz, 1H), 7.77 (d, J=8.1 Hz, 1H). MS (ESI$^+$) m/z 381 (M+H)$^+$.

Example 50

1-[(1R)-5-tert-butyl-2,3-dihydro-1H-inden-1-yl]-3-[(2R)-2-hydroxy-2,3-dihydro-1H-inden-4-yl]urea $^1$H NMR (500 MHz, DMSO-d$_6$/D$_2$O) δ ppm 1.28 (s, 9H), 2.40-2.51 (m, 1H), 2.59-2.68 (m, 1H), 2.74 (dd, J=16.1, 3.6 Hz, 1H), 2.80 (dt, J=15.8, 7.9 Hz, 2H), 2.88-2.98 (m, 2H), 3.06 (dd, J=16.1, 6.2 Hz, 1H), 4.47-4.55 (m, 1H), 5.10 (t, J=7.0 Hz, 1H), 6.82 (d, J=7.2 Hz, 1H), 7.06 (t, J=7.7 Hz, 1H), 7.20-7.32 (m, 3H), 7.78 (d, J=8.1 Hz, 1H). MS (ESI$^+$) m/z 365.2 (M+H)$^+$.

Example 51

1-[(4R)-8-tert-butyl-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 1.34 (s, 9H), 1.92-2.01 (m, 1H), 2.04-2.14 (m, 1H), 2.61 (dd, J=16.1, 3.4 Hz, 2H), 2.74 (dd, J=16.1, 3.6 Hz, 1H), 2.92 (dd, J=16.1, 6.2 Hz, 1H), 3.05 (dd, J=16.1, 6.2 Hz, 1H), 4.12 (td, J=10.5, 2.6 Hz, 1H), 4.34 (dt, J=11.2, 4.3 Hz, 1H), 4.47-4.54 (m, 1H), 4.81-4.88 (m, 1H), 6.80-6.89 (m, 2H), 7.02-7.17 (m, 4H), 7.80 (d, J=8.1 Hz, 1H). MS (ESI$^+$) m/z 381.1 (M+H)$^+$.

Example 52

1-[(4R)-2,2-diethyl-7-fluoro-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 0.82-0.94 (m, 6H), 1.50-1.74 (m, 4H), 2.15 (dd, J=13.5, 6.0 Hz, 1H), 2.61-2.70 (m, 1H), 2.75 (dd, J=16.1, 3.6 Hz, 1H), 2.97 (dd, J=16.1, 6.3 Hz, 1H), 3.07 (dd, J=16.1, 6.2 Hz, 1H), 4.49-4.56 (m, 1H), 4.86-4.94 (m, 1H), 6.60 (dd, J=10.5, 2.6 Hz, 1H), 6.74 (td, J=8.5, 2.6 Hz, 1H), 6.85 (d, J=7.4 Hz, 1H), 7.07 (t, J=7.7 Hz, 1H), 7.29 (t, J=7.9 Hz, 1H), 7.76 (d, J=8.2 Hz, 1H). MS (ESI$^+$) m/z 399.2 (M+H)$^+$.

Example 53

1-[(4R)-2,2-diethyl-7-(trifluoromethyl)-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 0.85-0.96 (m, 6H), 1.54-1.78 (m, 4H), 2.18 (dd, J=13.5, 6.1 Hz, 1H), 2.66 (dd, J=16.1, 3.5 Hz, 1H), 2.76 (dd, J=16.0, 3.6 Hz, 1H), 2.98 (dd, J=16.1, 6.2 Hz, 1H), 3.07 (dd, J=16.1, 6.2 Hz, 1H), 4.49-4.57 (m, 1H), 4.95-5.03 (m, 1H), 6.86 (d, J=7.4 Hz, 1H), 7.06 (d, J=5.3 Hz, 2H), 7.05-7.11 (m, 2H), 7.24 (dd, J=8.1, 1.8 Hz, 1H), 7.49 (d, J=8.1 Hz, 1H), 7.75 (d, J=8.1 Hz, 1H). MS (ESI$^+$) m/z 449 (M+H)$^+$.

Example 54

1-[(4R)-7-chloro-2,2-diethyl-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 0.84-0.94 (m, 6H), 1.50-1.74 (m, 4H), 2.15 (dd, J=13.5, 6.1 Hz, 1H), 2.65 (dd, J=16.1, 3.4 Hz, 1H), 2.75 (dd, J=16.0, 3.6 Hz, 1H), 2.97 (dd, J=16.1, 6.1 Hz, 1H), 3.07 (dd, J=16.1, 6.2 Hz, 1H), 4.49-4.56 (m, 1H), 4.91 (dd, J=11.0, 6.1 Hz, 1H), 6.83 (d, J=2.2 Hz, 1H), 6.85 (d, J=7.2 Hz, 2H), 6.95 (dd, J=8.3, 2.2 Hz, 1H), 7.07 (t, J=7.7 Hz, 1H), 7.27 (d, J=8.3 Hz, 1H), 7.75 (d, J=8.1 Hz, 1H). MS (ESI$^+$) m/z 415 (M+H)$^+$.

Example 55

1-[(4R)-7,8-dichloro-2,2-diethyl-3,4-dihydro-2H-chromen-4-yl]-3-[(2R)-2-hydroxy-2,3-dihydro-1H-inden-4-yl]urea $^1$H NMR (500 MHz, DMSO-d$_6$/D$_2$O) δ ppm 0.85-0.98 (m, 6H), 1.49-1.62 (m, 1H), 1.60-1.78 (m, 4H), 2.19 (dd, J=13.6, 6.2 Hz, 1H), 2.66 (dd, J=16.1, 3.5 Hz, 1H), 2.75 (dd, J=16.0, 3.6 Hz, 1H), 2.98 (dd, J=16.1, 6.1 Hz, 1H), 3.07 (dd, J=16.1, 6.2 Hz, 1H), 4.49-4.56 (m, 1H), 4.96 (dd, J=11.1, 6.1 Hz, 1H), 6.86 (d, J=7.4 Hz, 1H), 7.07 (t, J=7.7 Hz, 1H), 7.16 (d, J=8.4 Hz, 1H), 7.25 (dd, J=8.4, 1.0 Hz, 1H), 7.73 (d, J=8.1 Hz, 1H). MS (ESI$^+$) m/z 449 (M+H)$^+$.

Example 56

1-[(4R)-6-fluoro-2,2-dipropyl-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 0.87 (t, J=7.2 Hz, 3H), 0.92 (t, J=7.2 Hz, 3H), 1.24-1.43 (m, 3H), 1.47-1.72 (m, 4H), 2.13 (dd, J=13.4, 6.1 Hz, 1H), 2.65 (dd, J=16.1, 3.5 Hz, 1H), 2.75 (dd, J=16.0, 3.6 Hz, 1H), 2.99 (dd, J=16.1, 6.2 Hz, 1H), 3.07 (dd, J=16.1, 6.2 Hz, 1H), 4.49-4.57 (m, 1H), 4.90 (dd, J=11.0, 6.1 Hz, 1H), 6.77 (dd, J=8.7, 4.8 Hz, 1H), 6.86 (d, J=7.4 Hz, 1H), 6.96-7.05 (m, 2H), 7.07 (t, J=7.7 Hz, 1H), 7.74 (d, J=8.1 Hz, 1H). MS (ESI⁺) m/z 427 (M+H)⁺.

Example 57

1-[(4R)-6-fluoro-2,2-bis(fluoromethyl)-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.88-1.97 (m, 1H), 2.31 (dd, J=13.7, 6.0 Hz, 1H), 2.67 (dd, J=16.1, 3.5 Hz, 1H), 2.75 (dd, J=16.1, 3.6 Hz, 1H), 3.03 (ddd, J=39.9, 16.1, 6.2 Hz, 2H), 4.49-4.63 (m, 3H), 4.62-4.73 (m, 2H), 4.98 (dd, J=10.6, 5.9 Hz, 1H), 6.86 (d, J=7.4 Hz, 1H), 6.89-6.95 (m, 1H), 7.03-7.11 (m, 3H), 7.72 (d, J=8.1 Hz, 1H). MS (ESI⁺) m/z 407 (M+H)⁺.

Example 58

1-[(4R)-2,2-diethyl-6-fluoro-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 0.83-0.94 (m, 6H), 1.50-1.72 (m, 5H), 2.14 (dd, J=13.4, 6.2 Hz, 1H), 2.66 (dd, J=16.1, 3.5 Hz, 1H), 2.75 (dd, J=16.0, 3.6 Hz, 1H), 2.99 (dd, J=16.1, 6.1 Hz, 1H), 3.07 (dd, J=16.1, 6.2 Hz, 1H), 4.49-4.57 (m, 1H), 4.91 (dd, J=11.0, 6.1 Hz, 1H), 6.79 (dd, J=8.7, 4.8 Hz, 1H), 6.86 (d, J=7.4 Hz, 1H), 6.96-7.05 (m, 2H), 7.07 (t, J=7.7 Hz, 1H), 7.75 (d, J=8.1 Hz, 1H). MS (ESI⁺) m/z 399 (M+H)⁺.

Example 59

1-[(4R)-8-fluoro-2,2-dipropyl-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 0.88 (t, J=7.2 Hz, 3H), 0.93 (t, J=7.3 Hz, 3H), 1.26-1.44 (m, 4H), 1.49-1.60 (m, 2H), 1.63-1.79 (m, 3H), 2.17 (dd, J=13.5, 6.0 Hz, 1H), 2.65 (dd, J=16.0, 3.5 Hz, 1H), 2.75 (dd, J=16.0, 3.6 Hz, 1H), 2.97 (dd, J=16.1, 6.1 Hz, 1H), 3.07 (dd, J=16.1, 6.2 Hz, 1H), 4.49-4.56 (m, 1H), 4.95 (dd, J=10.8, 6.0 Hz, 1H), 6.78-6.92 (m, 2H), 7.03-7.13 (m, 3H), 7.75 (d, J=8.1 Hz, 1H). MS (ESI⁺) m/z 427 (M+H)⁺.

Example 60

1-[(4R)-2,2-diethyl-7-(trifluoromethoxy)-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 0.85-0.95 (m, 6H), 1.51-1.75 (m, 5H), 2.16 (dd, J=13.5, 6.1 Hz, 1H), 2.65 (dd, J=16.1, 3.5 Hz, 1H), 2.75 (dd, J=16.0, 3.6 Hz, 1H), 2.97 (dd, J=16.1, 6.2 Hz, 1H), 3.07 (dd, J=16.1, 6.2 Hz, 1H), 4.49-4.56 (m, 1H), 4.93 (dd, J=10.9, 6.1 Hz, 1H), 6.74 (d, J=2.3 Hz, 1H), 6.85 (d, J=7.4 Hz, 1H), 6.87-6.93 (m, 1H), 7.07 (t, J=7.7 Hz, 1H), 7.38 (d, J=8.5, 1.0 Hz, 1H), 7.75 (d, J=8.1 Hz, 1H). MS (ESI⁺) m/z 465 (M+H)⁺.

Example 61

1-[(4R)-6-chloro-2-(difluoromethyl)-2-methyl-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.40 (d, J=21.8 Hz, 3H), 1.84-1.97 (m, 1H), 2.18 (dd, J=13.0, 5.9 Hz, 1H), 2.41 (dd, J=14.1, 6.0 Hz, 1H), 2.66 (dt, J=16.1, 4.2 Hz, 1H), 2.71-2.79 (m, 1H), 2.98 (dt, J=16.1, 6.2 Hz, 1H), 3.01-3.11 (m, 1H), 4.49-4.57 (m, 1H), 4.94-5.04 (m, 1H), 6.15 (td, J=55.0, 21.3 Hz, 1H), 6.86 (dd, J=7.3, 4.7 Hz, 1H), 6.95 (dd, J=9.0, 2.1 Hz, 1H), 7.01-7.11 (m, 2H), 7.31 (ddd, J=9.8, 8.5, 1.1 Hz, 1H), 7.73 (t, J=8.9 Hz, 1H). MS (ESI⁺) m/z 423 (M+H)⁺.

Example 62

1-[(4R)-7-fluoro-2,2,8-trimethyl-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.28 (s, 3H), 1.43 (s, 3H), 1.70 (dd, J=13.2, 10.8 Hz, 1H), 2.02 (d, J=1.8 Hz, 3H), 2.15 (dd, J=13.2, 6.2 Hz, 1H), 2.66 (dd, J=16.1, 3.5 Hz, 1H), 2.75 (dd, J=16.2, 3.7 Hz, 1H), 2.97 (dd, J=16.1, 6.1 Hz, 1H), 3.07 (dd, J=16.1, 6.1 Hz, 1H), 4.49-4.56 (m, 1H), 4.93 (dd, J=10.7, 6.2 Hz, 1H), 6.72 (t, J=8.8 Hz, 1H), 6.85 (d, J=7.4 Hz, 1H), 7.07 (t, J=7.7 Hz, 1H), 7.12 (t, J=7.6 Hz, 1H), 7.76 (d, J=8.1 Hz, 1H). MS (ESI⁺) m/z 385 (M+H)⁺.

Example 63

1-[(1R)-3,3-dimethyl-2,3-dihydro-1H-inden-1-yl]-3-[(2R)-2-hydroxy-2,3-dihydro-1H-inden-4-yl]urea ¹H NMR (500 MHz, DMSO-d₆/D₂O) δ ppm 1.20 (s, 3H), 1.36 (s, 3H), 1.67 (dd, J=12.5, 7.8 Hz, 1H), 2.36 (dd, J=12.5, 7.4 Hz, 1H), 2.64 (dd, J=16.1, 3.5 Hz, 1H), 2.75 (dd, J=16.0, 3.6 Hz, 1H), 2.95 (dd, J=16.1, 6.2 Hz, 1H), 3.07 (dd, J=16.1, 6.2 Hz, 1H), 4.48-4.56 (m, 1H), 5.21 (t, J=7.6 Hz, 1H), 6.83 (d, J=7.4 Hz, 1H), 7.07 (t, J=7.7 Hz, 1H), 7.21-7.31 (m, 4H), 7.78 (d, J=8.1 Hz, 1H). MS (ESI⁺) m/z 337 (M+H)⁺.

Example 64

1-[(4R)-6,8-difluoro-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 2.00 (dtd, J=13.9, 7.0, 3.0 Hz, 1H), 2.12-2.22 (m, 1H), 2.64 (dd, J=16.0, 3.5 Hz, 1H), 2.75 (dd, J=16.1, 3.6 Hz, 1H), 2.96 (dd, J=16.1, 6.1 Hz, 1H), 3.07 (dd, J=16.1, 6.2 Hz, 1H), 4.23 (ddd, J=11.2, 8.2, 3.0 Hz, 1H), 4.32-4.40 (m, 1H), 4.48-4.56 (m, 1H), 4.91 (t, J=5.8 Hz, 1H), 6.85 (d, J=7.4 Hz, 1H), 6.95 (dd, J=9.1, 2.8

Hz, 1H), 7.07 (t, J=7.7 Hz, 1H), 7.19 (ddd, J=11.3, 8.5, 2.9 Hz, 1H), 7.75 (d, J=8.1 Hz, 1H). MS (ESI⁺) m/z 361 (M+H)⁺.

Example 65

1-[(4R)-7-fluoro-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.92-2.01 (m, 1H), 2.05-2.15 (m, 1H), 2.62 (dd, J=16.0, 3.5 Hz, 1H), 2.74 (dd, J=16.0, 3.6 Hz, 1H), 2.93 (dd, J=16.1, 6.1 Hz, 1H), 3.06 (dd, J=16.1, 6.2 Hz, 1H), 4.16 (ddd, J=11.4, 9.0, 2.6 Hz, 1H), 4.27-4.35 (m, 1H), 4.47-4.55 (m, 1H), 4.84 (t, J=5.3 Hz, 1H), 6.67 (dd, J=10.5, 2.6 Hz, 1H), 6.73-6.81 (m, 1H), 6.83 (d, J=7.3 Hz, 1H), 6.98-7.10 (m, 1H), 7.27-7.34 (m, 1H), 7.78 (d, J=8.1 Hz, 1H). MS (ESI⁺) m/z 343 (M+H)⁺.

Example 66

1-[(2R,4R)-8-fluoro-2-(fluoromethyl)-2-methyl-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.31 (d, J=2.1 Hz, 3H), 1.90 (t, J=12.3 Hz, 1H), 2.15 (dd, J=13.2, 6.0 Hz, 1H), 2.66 (dd, J=16.1, 3.5 Hz, 1H), 2.75 (dd, J=16.0, 3.6 Hz, 1H), 2.98 (dd, J=16.1, 6.2 Hz, 1H), 3.03-3.11 (m, 1H), 4.43-4.62 (m, 3H), 5.08 (dd, J=11.4, 6.0 Hz, 1H), 6.93 (td, J=8.0, 4.9 Hz, 1H), 7.04-7.17 (m, 3H), 7.74 (d, J=8.1 Hz, 1H). MS (ESI⁺) m/z 389 (M+H)⁺.

Example 67

1-[(4R)-7-chloro-2-(fluoromethyl)-2-methyl-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.33 (dd, J=50.3, 1.9 Hz, 3H), 1.96 (m, 1H), 2.12 (dd, J=13.1, 6.1 Hz, 1H), 2.33 (dd, J=13.8, 6.2 Hz, 1H), 2.66 (dt, J=16.0, 4.2 Hz, 1H), 2.71-2.79 (m, 1H), 2.97 (dt, J=16.1, 6.0 Hz, 1H), 3.07 (dd, J=16.1, 6.1 Hz, 1H), 4.39-4.58 (m, 2H), 4.90-5.05 (m, 1H), 6.85 (dd, J=7.3, 4.0 Hz, 1H), 6.89 (dd, J=7.8, 2.2 Hz, 1H), 7.00 (dt, J=8.3, 2.0 Hz, 1H), 7.07 (td, J=7.8, 2.3 Hz, 1H), 7.26-7.33 (m, 1H), 7.74 (dd, J=8.2, 4.3 Hz, 1H). MS (ESI⁺) m/z 405 (M+H)⁺.

Example 68

1-[(4R)-6-fluoro-2,2-bis(methoxymethyl)-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.77-1.89 (m, 2H), 2.18 (dd, J=13.5, 6.0 Hz, 1H), 2.59-2.72 (m, 1H), 2.76 (dd, J=16.0, 3.6 Hz, 1H), 2.94-3.12 (m, 2H), 3.28 (s, 3H), 3.32 (s, 3H), 3.43 (dd, J=20.6, 10.1 Hz, 2H), 3.49 (s, 2H), 4.49-4.57 (m, 1H), 4.93 (dd, J=11.0, 6.0 Hz, 1H), 6.79-6.89 (m, 2H), 6.96-7.13 (m, 3H), 7.73 (d, J=8.1 Hz, 1H). MS (ESI⁺) m/z 431 (M+H)⁺.

Example 69

1-[(4R)-2,2-bis(fluoromethyl)-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 1.90-1.99 (m, 1H), 2.30 (dd, J=13.7, 5.9 Hz, 1H), 2.66 (dd, J=16.1, 3.5 Hz, 1H), 2.75 (dd, J=16.1, 3.6 Hz, 1H), 2.98 (dd, J=16.1, 6.2 Hz, 1H), 3.07 (dd, J=16.1, 6.2 Hz, 1H), 4.49-4.72 (m, 5H), 4.99 (dd, J=10.1, 5.9 Hz, 1H), 6.85 (d, J=7.3 Hz, 1H), 6.89 (dd, J=8.2, 1.0 Hz, 1H), 7.00 (td, J=7.5, 1.2 Hz, 1H), 7.07 (t, J=7.7 Hz, 1H), 7.19-7.27 (m, 1H), 7.30 (d, J=7.1 Hz, 1H), 7.75 (d, J=8.1 Hz, 1H). MS (ESI⁺) m/z 389 (M+H)⁺.

Example 70

1-[(4R)-8-fluoro-2,2-bis(fluoromethyl)-3,4-dihydro-2H-chromen-4-yl]-3-[(2R)-2-hydroxy-2,3-dihydro-1H-inden-4-yl]urea ¹H NMR (500 MHz, DMSO-d₆/D₂O) δ ppm 2.00 (ddd, J=13.6, 10.7, 2.9 Hz, 1H), 2.34 (dd, J=13.8, 5.9 Hz, 1H), 2.66 (dd, J=16.1, 3.5 Hz, 1H), 2.75 (dd, J=16.0, 3.6 Hz, 1H), 2.98 (dd, J=16.1, 6.1 Hz, 1H), 3.07 (dd, J=16.1, 6.2 Hz, 1H), 4.49-4.56 (m, 1H), 4.57-4.68 (m, 2H), 4.67-4.77 (m, 2H), 5.03 (dd, J=10.4, 5.9 Hz, 1H), 6.86 (d, J=7.4 Hz, 1H), 6.98 (td, J=8.0, 4.9 Hz, 1H), 7.07 (t, J=7.7 Hz, 1H), 7.12 (dd, J=7.9, 1.4 Hz, 1H), 7.13-7.21 (m, 1H), 7.73 (d, J=8.1 Hz, 1H). MS (ESI⁺) m/z 407 (M+H)⁺.

Example 71

1-[(4R)-8-fluoro-2,2-dimethyl-3,4-dihydro-2H-chromen-4-yl]-3-[(2S)-2-hydroxy-2,3-dihydro-1H-inden-4-yl]urea ¹H NMR (500 MHz, DMSO-d₆/D₂O) δ ppm 1.26-1.33 (m, 3H), 1.37-1.49 (m, 3H), 1.75 (dt, J=29.6, 14.8 Hz, 1H), 2.18 (dd, J=13.3, 6.2 Hz, 1H), 2.61-2.69 (m, 1H), 2.75 (dd, J=16.1, 3.5 Hz, 1H), 2.95 (dt, J=17.0, 8.6 Hz, 1H), 3.06 (dt, J=12.3, 6.1 Hz, 1H), 4.45-4.57 (m, 1H), 4.99 (dd, J=10.9, 6.2 Hz, 1H), 6.82-6.92 (m, 2H), 7.09 (ddd, J=19.6, 10.2, 5.9 Hz, 3H), 7.76 (t, J=8.5 Hz, 1H) MS (ESI⁺) m/z 371 (M+H)⁺.

Example 72

1-[(4R)-2,2-dimethyl-7-(trifluoromethoxy)-3,4-dihydro-2H-chromen-4-yl]-3-[(2S)-2-hydroxy-2,3-dihydro-1H-inden-4-yl]urea ¹H NMR (500 MHz, DMSO-d₆/D₂O) δ ppm 1.28 (d, J=22.6 Hz, 3H), 1.40 (d, J=13.2 Hz, 3H), 1.69-1.83 (m, 1H), 2.17 (dd, J=13.3, 6.2 Hz, 1H), 2.61-2.70 (m, 1H), 2.76 (dd, J=16.1, 3.5 Hz, 1H), 2.96 (dd, J=16.1, 6.1 Hz, 1H), 3.07 (dd, J=16.1, 6.1 Hz, 1H), 4.46-4.57 (m, 1H), 4.97 (dd, J=10.7, 6.2 Hz, 1H), 6.71 (t, J=9.3 Hz, 1H), 6.86 (d, J=7.3 Hz, 1H), 6.89-6.95 (m, 1H), 7.08 (dd, J=17.2, 9.6 Hz, 1H), 7.39 (dd, J=8.6, 0.8 Hz, 1H), 7.76 (d, J=8.1 Hz, 1H) MS (ESI⁺) m/z 437 (M+H)⁺.

Example 73

1-[(2S)-2-hydroxy-2,3-dihydro-1H-inden-4-yl]-3-[(4R)-8-(trifluoromethoxy)-3,4-dihydro-2H-chromen-4-yl]urea ¹H NMR (400 MHz, DMSO-d₆/D₂O) δ ppm 2.00 (dtd, J=8.8, 6.1, 2.8 Hz, 1H), 2.15 (qd, J=8.5, 3.3 Hz, 1H), 2.58-2.69 (m, 1H), 2.70-2.83 (m, 1H), 2.93 (dd, J=16.1, 6.1 Hz, 1H), 3.06 (dd, J=16.1, 6.1 Hz, 1H), 4.21 (ddd, J=11.4, 9.0, 2.7 Hz, 1H), 4.40 (ddd, J=9.7, 6.2, 3.2 Hz, 1H), 4.44-4.63 (m, 1H), 4.86-5.07 (m, 1H), 6.84 (d, J=7.3 Hz, 1H), 6.99 (dd, J=16.4, 8.5 Hz, 1H), 7.02-7.13 (m, 1H), 7.26-7.40 (m, 2H), 7.76 (t, J=10.7 Hz, 1H). MS (ESI$^+$) m/z 409 (M+H)$^+$.

Example 74

1-[(4R)-2,2-bis(fluoromethyl)-7-(trifluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.82 (s, 1H), 2.00 (ddd, J=13.6, 11.1, 2.5 Hz, 1H), 2.35 (dd, J=13.7, 6.0 Hz, 1H), 2.72 (ddd, J=31.8, 16.1, 3.5 Hz, 2H), 2.98 (dd, J=16.1, 6.1 Hz, 1H), 3.03-3.10 (m, 1H), 4.45-4.56 (m, 1H), 4.56-4.65 (m, 2H), 4.66-4.74 (m, 2H), 5.07 (dd, J=10.8, 5.9 Hz, 1H), 6.87 (d, J=7.3 Hz, 1H), 7.03-7.15 (m, 1H), 7.20 (t, J=7.2 Hz, 1H), 7.34 (dt, J=12.9, 6.4 Hz, 1H), 7.52 (d, J=8.1 Hz, 1H), 7.73 (d, J=8.1 Hz, 1H). MS (ESI$^+$ ESI$^+$) m/z 457 (M+H)$^+$.

Example 75

1-[(4R)-8-chloro-2,2-bis(fluoromethyl)-3,4-dihydro-2H-chromen-4-yl]-3-[(2S)-2-hydroxy-2,3-dihydro-1H-inden-4-yl]urea $^1$H NMR (500 MHz, DMSO-d$_6$/D$_2$O) δ ppm 1.81 (s, 1H), 1.89-2.04 (m, 1H), 2.55-2.79 (m, 2H), 2.92-3.01 (m, 2H), 3.02-3.11 (m, 1H), 3.18 (s, 1H), 4.44-4.58 (m, 1H), 4.57-4.77 (m, 3H), 4.69 (ddd, J=46.6, 10.4, 1.6 Hz, 3H), 6.79-6.93 (m, 2H), 7.01 (t, J=7.8 Hz, 1H), 7.07 (q, J=7.8 Hz, 1H), 7.24-7.41 (m, 2H), 7.75 (dd, J=24.3, 8.1 Hz, 1H). MS (ESI$^+$) m/z 423 (M+H)$^+$.

Example 76

1-[(4R)-2,2-bis(fluoromethyl)-7-(trifluoromethoxy)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.07 (t, J=7.0 Hz, 1H), 1.15-1.35 (m, 1H), 1.40 (d, J=1.9 Hz, 1H), 1.82 (s, 1H), 1.98 (ddd, J=13.4, 10.6, 2.5 Hz, 1H), 2.32 (dd, J=13.8, 5.9 Hz, 1H), 2.60-2.82 (m, 1H), 3.02 (ddd, J=41.6, 16.1, 6.1 Hz, 2H), 3.18 (s, 1H), 3.32 (d, J=20.7 Hz, 1H), 3.58-3.67 (m, 1H), 3.80-4.13 (m, 1H), 4.46-4.80 (m, 5H), 5.01 (dd, J=10.4, 5.9 Hz, 1H), 6.87 (dd, J=10.1, 4.4 Hz, 2H), 7.02 (ddt, J=14.2, 12.9, 9.8 Hz, 2H), 7.42 (dd, J=8.6, 0.8 Hz, 1H), 7.73 (d, J=7.9 Hz, 1H), 7.92 (s, 1H). MS (ESI$^+$) m/z 473 (M+H)$^+$.

Example 77

1-[(4R)-2,2-dimethyl-7-(trifluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.31 (s, 3H), 1.43 (s, 3H), 1.73-1.82 (m, 1H), 2.20 (dd, J=13.3, 6.2 Hz, 1H), 2.72 (ddd, J=34.4, 16.1, 3.6 Hz, 2H), 3.02 (ddd, J=41.5, 16.1, 6.1 Hz, 2H), 4.48-4.57 (m, 1H), 4.98-5.07 (m, 1H), 6.86 (d, J=7.4 Hz, 1H), 7.06 (d, J=2.2 Hz, 1H), 7.09 (d, J=7.7 Hz, 1H), 7.25 (dd, J=8.1, 1.8 Hz, 1H), 7.50 (d, J=8.1 Hz, 1H), 7.76 (d, J=8.1 Hz, 1H). MS (ESI$^+$) m/z 421 (M+H)$^+$.

Example 78

1-[(4R)-6-fluoro-2,2-bis(fluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.92 (ddd, J=13.6, 10.7, 2.9 Hz, 1H), 2.31 (dd, J=13.7, 6.0 Hz, 1H), 2.68 (dd, J=16.1, 3.5 Hz, 1H), 2.76 (dd, J=16.0, 3.7 Hz, 1H), 2.97 (dd, J=16.1, 6.2 Hz, 1H), 3.08 (dd, J=16.1, 6.2 Hz, 1H), 4.49-4.63 (m, 3H), 4.65-4.72 (m, 2H), 4.98 (dd, J=100.6, 5.9 Hz, 1H), 6.87 (d, J=7.3 Hz, 1H), 6.88-7.00 (m, 1H), 7.03-7.12 (m, 3H), 7.69-7.75 (m, 1H). MS (ESI$^+$) m/z 407 (M+H)$^+$.

Example 79

1-[(4R)-6,8-difluoro-2,2-bis(fluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 2.00 (ddd, J=13.7, 10.9, 2.8 Hz, 1H), 2.35 (dd, J=13.8, 5.9 Hz, 1H), 2.68 (dd, J=16.1, 3.5 Hz, 1H), 2.76 (dd, J=16.1, 3.7 Hz, 1H), 3.03 (ddd, J=39.8, 16.1, 6.2 Hz, 2H), 4.49-4.80 (m, 5H), 5.01 (dd, J=10.9, 5.9 Hz, 1H), 6.87 (d, J=7.4 Hz, 1H), 6.90-6.97 (m, 1H), 7.08 (t, J=7.7 Hz, 1H), 7.24 (ddd, J=11.2, 8.4, 2.9 Hz, 1H), 7.70 (d, J=8.1 Hz, 1H). MS (ESI$^+$) m/z 425 (M+H)$^+$.

Example 80

1-[(4R)-6-fluoro-3,4-dihydrospiro[chromene-2,1'-cyclobutan]-4-yl]-3-[(2S)-2-hydroxy-2,3-dihydro-1H-inden-4-yl]urea $^1$H NMR (400 MHz, DMSO-d$_6$/D$_2$O) δ ppm 1.67-1.90 (m, 3H), 2.04-2.34 (m, 4H), 2.34-2.44 (m, 1H), 2.67 (dd, J=16.1, 3.5 Hz, 1H), 2.76 (dd, J=16.0, 3.7 Hz, 1H), 2.97 (dd, J=16.1, 6.2 Hz, 1H), 3.07 (dd, J=16.1, 6.2 Hz, 1H), 4.48-4.57 (m, 1H), 4.94 (dd, J=10.2, 5.8 Hz, 1H), 6.79-6.89 (m, 2H), 6.96-7.12 (m, 3H), 7.75 (d, J=8.1 Hz, 1H). MS (ESI$^+$) m/z 383 (M+H)$^+$.

Example 81

1-[(4R)-7-chloro-8-fluoro-2,2-bis(fluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 2.00 (ddd, J=13.7, 10.9, 2.7 Hz, 1H), 2.35 (dd, J=13.8, 5.9 Hz, 1H), 2.67 (dd, J=16.1, 3.5 Hz, 1H), 2.76 (dd, J=16.1, 3.6 Hz, 1H), 2.97 (dd, J=16.1, 6.1 Hz, 1H), 3.07 (dd, J=16.1, 6.2 Hz, 1H), 3.18 (s, 1H), 4.48-4.57 (m, 1H), 4.58-4.70 (m, 2H), 4.70-4.89 (m, 2H), 5.03 (dd, J=10.8, 5.9 Hz, 1H), 6.87 (d, J=7.4 Hz, 1H), 7.04-7.20 (m, 3H), 7.72 (d, J=8.1 Hz, 1H). MS (ESI$^+$) m/z 441 (M+H)$^+$.

Example 82

1-[(4R)-2,2-dimethyl-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.21-1.29 (m, 3H), 1.38 (d, J=9.8 Hz, 3H), 1.60-1.77 (m, 1H), 2.15 (dd, J=13.2, 6.2 Hz, 1H), 2.59-2.79 (m, 2H), 2.91-3.04 (m, 1H), 3.07 (dd, J=16.1, 6.1 Hz, 1H), 4.46-4.59 (m, 1H), 4.90-5.15 (m, 1H), 6.67-6.80 (m, 1H), 6.81-6.99 (m, 2H), 7.07 (t, J=7.8 Hz, 1H), 7.12-7.20 (m, 1H), 7.27 (d, J=7.6 Hz, 1H), 7.77 (d, J=8.1 Hz, 1H). MS (ESI$^+$) m/z 353 (M+H)$^+$.

Example 83

1-[(4R)-6-fluoro-2,2-dimethyl-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.25 (d, J=17.4 Hz, 3H), 1.39 (s, 3H), 1.70 (dd, J=13.1, 11.2 Hz, 1H), 1.86 (s, 1H), 2.15 (dd, J=13.2, 6.3 Hz, 1H), 2.58-2.85 (m, 2H), 2.95 (dt, J=36.4, 18.2 Hz, 1H), 3.06 (dt, J=24.2, 12.1 Hz, 1H), 4.46-4.56 (m, 1H), 4.94 (dd, J=10.9, 6.2 Hz, 1H), 6.76 (ddd, J=13.7, 8.8, 4.8 Hz, 1H), 6.87 (t, J=6.7 Hz, 1H), 6.98-7.12 (m, 3H), 7.76 (t, J=9.3 Hz, 1H). MS (ESI$^+$) m/z 371 (M+H)$^+$.

Example 84

1-[(2S)-2-hydroxy-2,3-dihydro-1H-inden-4-yl]-3-[(4R)-1-methyl-7-(trifluoromethyl)-1,2,3,4-tetrahydroquinolin-4-yl]urea $^1$H NMR (400 MHz, DMSO-d$_6$/D$_2$O) δ ppm 1.88-2.05 (m, 2H), 2.62 (dd, J=16.1, 3.4 Hz, 1H), 2.72 (dd, J=12.6, 9.1 Hz, 1H), 2.88 (t, J=6.8 Hz, 1H), 2.90-2.96 (m, 4H), 3.07 (dt, J=16.1, 7.9 Hz, 1H), 3.24-3.40 (m, 2H), 4.45-4.61 (m, 1H), 4.83 (t, J=5.1 Hz, 1H), 6.77-6.86 (m, 2H), 6.86-6.94 (m, 1H), 7.07 (dd, J=15.3, 7.7 Hz, 1H), 7.31 (d, J=7.8 Hz, 1H), 7.78 (d, J=8.1 Hz, 1H). MS (ESI$^+$) m/z 406 (M+H)$^+$.

Example 85

1-[(4R)-7-chloro-2,2-dimethyl-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.29 (s, 3H), 1.41 (s, 3H), 1.84-2.02 (m, 1H), 2.55-2.71 (m, 1H), 2.75 (ddd, J=16.1, 6.3, 3.6 Hz, 1H), 2.89-3.12 (m, 4H), 3.16-3.41 (m, 1H), 4.47-4.57 (m, 1H), 4.81-4.98 (m, 1H), 6.79-7.00 (m, 3H), 7.07 (td, J=7.7, 5.8 Hz, 1H), 7.30 (t, J=8.3 Hz, 1H), 7.79 (d, J=8.7 Hz, 1H). MS (ESI$^+$) m/z 387 (M+H)$^+$.

Example 86

1-[(4R)-2,2-bis(fluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.81 (s, 1H), 1.86-1.98 (m, 1H), 2.30 (dd, J=13.8, 5.9 Hz, 1H), 2.71 (ddd, J=34.8, 16.1, 3.5 Hz, 2H), 2.96 (dd, J=16.1, 6.1 Hz, 1H), 3.07 (dd, J=16.1, 6.1 Hz, 1H), 4.48-4.60 (m, 3H), 4.57-4.74 (m, 2H), 4.93-5.01 (m, 1H), 6.79-6.91 (m, 2H), 6.93-7.01 (m, 1H), 7.07 (t, J=7.8 Hz, 1H), 7.18-7.27 (m, 1H), 7.30 (d, J=7.6 Hz, 1H), 7.75 (d, J=8.0 Hz, 1H). MS (ESI$^+$) m/z 389 (M+H)$^+$.

Example 87

1-[(4R)-8-fluoro-2,2-bis(fluoromethyl)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.81 (s, 1H), 1.99 (ddd, J=13.5, 10.6, 2.6 Hz, 1H), 2.34 (dd, J=13.8, 5.9 Hz, 1H), 2.62-2.69 (m, 1H), 2.75 (dt, J=12.4, 6.2 Hz, 1H), 2.97 (dd, J=16.1, 6.1 Hz, 1H), 3.07 (dd, J=16.1, 6.1 Hz, 1H), 4.51 (dd, J=6.2, 3.6 Hz, 1H), 4.56-4.66 (m, 2H), 4.69-4.79 (m, 2H), 5.03 (dd, J=10.4, 5.9 Hz, 1H), 6.86 (d, J=7.3 Hz, 1H), 6.98 (td, J=8.0, 5.0 Hz, 1H), 7.03-7.21 (m, 3H), 7.73 (d, J=7.9 Hz, 1H). MS (ESI$^+$) m/z 407 (M+H)$^+$.

Example 88

1-[(4R)-2,2-dimethyl-8-(trifluoromethoxy)-3,4-dihydro-2H-chromen-4-yl]-3-[(2S)-2-hydroxy-2,3-dihydro-1H-inden-4-yl]urea $^1$H NMR (400 MHz, DMSO-d$_6$/D$_2$O) δ ppm 1.30 (s, 3H), 1.43 (s, 3H), 1.78 (dd, J=13.4, 10.8 Hz, 1H), 2.20 (dd, J=13.3, 6.2 Hz, 1H), 2.71 (ddd, J=36.6, 16.1, 3.6 Hz, 2H), 2.96 (dd, J=16.1, 6.1 Hz, 1H), 3.07 (dd, J=16.1, 6.2 Hz, 1H), 4.48-4.57 (m, 1H), 5.01 (dd, J=10.8, 6.2 Hz, 1H), 6.86 (d, J=7.3 Hz, 1H), 6.98 (t, J=7.9 Hz, 1H), 7.08 (t, J=7.7 Hz, 1H), 7.21-7.27 (m, 1H), 7.31 (dt, J=7.8, 1.2 Hz, 1H), 7.75 (d, J=8.1 Hz, 1H). MS (ESI$^+$) m/z 437 (M+H)$^+$.

Example 89

1-[(3R)-6-chloro-3,4-dihydro-2H-chromen-3-yl]-3-[(2R)-2-hydroxy-2,3-dihydro-1H-inden-4-yl]urea $^1$H NMR (300 MHz, DMSO-d$_6$) δ 7.85-7.70 (m, 2H), 7.22 (d, J=2.6 Hz, 1H), 7.15 (dd, J=8.7, 2.7 Hz, 1H), 7.01 (t, J=7.8 Hz, 1H), 6.85 (d, J=8.6 Hz, 1H), 6.81-6.71 (m, 2H), 4.82 (d, J=4.1 Hz, 1H), 4.48 (d, J=3.7 Hz, 1H), 4.11 (dd, J=20.6, 11.0 Hz, 3H), 3.06 (ddd, J=22.0, 16.4, 5.4 Hz, 2H), 2.89 (dd, J=16.1, 6.1 Hz, 1H), 2.70 (dd, J=16.2, 2.8 Hz, 2H), 2.61-2.55 (m, 1H); MS (LCMS) m/z 359 (M+H)$^+$.

Example 90

1-[(2S,4R)-7-chloro-8-fluoro-2-(fluoromethyl)-2-methyl-3,4-dihydro-2H-chromen-4-yl]-3-[(2R)-2-hydroxy-2,3-dihydro-1H-inden-4-yl]urea $^1$H NMR (300 MHz, DMSO-d$_6$) δ 7.83 (s, 1H), 7.77 (d, J=8.1 Hz, 1H), 7.17-7.07 (m, 2H), 7.04 (t, J=7.5 Hz, 1H), 6.90 (d, J=8.2 Hz, 1H), 6.82 (d, J=7.4 Hz, 1H), 5.04-4.92 (m, 1H), 4.85 (d, J=4.0 Hz, 1H), 4.70-4.38 (m, 3H), 3.05 (dd, J=16.1, 5.9 Hz, 1H), 2.96 (dd, J=16.0, 6.0 Hz, 1H), 2.73 (dd, J=16.2, 3.6 Hz, 1H), 2.64 (dd, J=16.1, 3.2 Hz, 1H), 2.37 (dd, J=13.8, 5.9 Hz, 1H), 1.92 (ddd, J=13.7, 10.1, 2.4 Hz, 1H), 1.43 (d, J=2.0 Hz, 3H). MS (ESI$^+$) m/z 388 (M+H)$^+$.

Example 91

1-(6-fluoro-2,2-dimethyl-3,4-dihydro-2H-chromen-3-yl)-3-[(2R)-2-hydroxy-2,3-dihydro-1H-inden-4-yl]urea $^1$H NMR (300 MHz, DMSO-d$_6$) δ 7.86-7.75 (m, 2H), 7.04-6.90 (m, 3H), 6.85-6.73 (m, 2H), 6.68-6.59 (m, 1H), 4.84-4.77 (m, 1H), 4.53-4.42 (m, 1H), 3.99-3.91 (m, 1H), 3.13-2.98 (m, 2H), 2.95-2.83 (m, 1H), 2.76-2.56 (m, 3H), 1.30 (s, 3H), 1.25 (s, 3H); MS (ESI$^+$) m/z 371 (M+H)$^+$.

Example 92

1-[(1R)-5-fluoro-2,3-dihydro-1H-inden-1-yl]-3-[(2R)-2-hydroxy-2,3-dihydro-1H-inden-4-yl]urea $^1$H NMR (300 MHz, CD$_3$OD) δ ppm 1.81-1.95 (m, 1H), 2.53-2.66 (m, 1H), 2.78 (dd, J=16.2, 3.5 Hz, 1H), 2.83-3.10 (m, 3H), 3.10-3.23 (m, 2H), 4.58-4.67 (m, 1H), 5.24 (dd, J=7.2, 7.2 Hz, 1H), 6.88-7.00 (m, 3H), 7.11 (dd, J=7.8, 7.8 Hz, 1H), 7.28-7.35 (m, 1H), 7.57 (d, J=8.2 Hz, 1H). MS (ESI$^+$) m/z 327 (M+H)$^+$.

Example 93

1-[(2R)-2-hydroxy-2,3-dihydro-1H-inden-4-yl]-3-[(4S)-7-(trifluoromethoxy)-3,4-dihydro-2H-chromen-4-yl]urea $^1$H NMR (300 MHz, CD$_3$OD) δ ppm 2.01-2.12 (m, 1H), 2.15-2.27 (m, 1H), 2.77 (dd, J=16.3, 3.4 Hz, 1H), 2.87 (dd, J=16.3, 3.4 Hz, 1H), 3.08 (dd, J=16.3, 6.1 Hz, 1H), 3.18 (dd, J=16.3, 6.1 Hz, 1H), 4.19-4.28 (m, 1H), 4.28-4.37 (m, 1H), 4.58-4.66 (m, 1H), 4.99 (dd, J=5.4, 5.4 Hz, 1H), 6.68-6.71 (m, 1H), 6.81 (ddq, J=8.6, 2.3, 1.1 Hz, 1H), 6.93 (d, J=7.4 Hz, 1H), 7.11 (dd, J=7.8, 7.8 Hz, 1H), 7.38 (dd, J=8.5, 0.5 Hz, 1H), 7.57 (d, J=8.1 Hz, 1H). MS (ESI$^+$) m/z 409 (M+H)$^+$.

Example 94

1-[(2S)-2-hydroxy-2,3-dihydro-1H-inden-4-yl]-3-[(4S)-7-(trifluoromethoxy)-3,4-dihydro-2H-chromen-4-yl]urea $^1$H NMR (300 MHz, CD$_3$OD) δ ppm 2.01-2.12 (m, 1H), 2.15-2.27 (m, 1H), 2.77 (dd, J=16.3, 3.4 Hz, 1H), 2.87 (dd, J=16.3, 3.4 Hz, 1H), 3.09 (dd, J=16.3, 6.1 Hz, 1H), 3.18 (dd, J=16.3, 6.1 Hz, 1H), 4.19-4.28 (m, 1H), 4.28-4.37 (m, 1H), 4.59-4.67 (m, 1H), 4.99 (dd, J=5.5, 5.5 Hz, 1H), 6.67-6.71 (m, 1H), 6.81 (ddq, J=8.6, 2.3, 1.1 Hz, 1H), 6.93 (d, J=7.3 Hz, 1H), 7.11 (dd, J=7.8, 7.8 Hz, 1H), 7.38 (dd, J=8.5, 0.5 Hz, 1H), 7.57 (d, J=8.1 Hz, 1H). MS (ESI$^+$) m/z 409 (M+H)$^+$.

Example 95

1-[(4R)-2,2-bis(fluoromethyl)-7-(trifluoromethyl)-3,4-dihydro-2H-chromen-4-yl]-3-[(2S)-5-fluoro-2-hydroxy-2,3-dihydro-1H-inden-4-yl]urea

Example 95A (S)-4-amino-5-fluoro-2,3-dihydro-1H-inden-2-ol

Example 25F was separated on a Chiralpak AD-H column (Chiral technologies Inc., eluting with 40-55% IPA/hexanes, 25 mL/min, 5 mL/injection) to provide Example 95A as the second eluting enantiomer. MS (DCI) m/z 185 (M+NH$_4$)$^+$.

Example 95B

1-[(4R)-2,2-bis(fluoromethyl)-7-(trifluoromethyl)-3,4-dihydro-2H-chromen-4-yl]-3-[(2S)-5-fluoro-2-hydroxy-2,3-dihydro-1H-inden-4-yl]urea The title compound was prepared as described in Example 1F substituting Example 95A for Example 1E, and Example 7A for Example 1C. $^1$H NMR (300 MHz, CDCl$_3$) δ 7.44 (d, J=8.1 Hz, 1H), 7.24-7.12 (m, 3H), 6.90 (t, J=8.4 Hz, 1H), 6.18 (s, 1H), 5.39-5.16 (m, 1H), 4.91-4.75 (m, 2H), 4.64-4.54 (m, 2H), 4.51-4.40 (m, 2H), 3.32-2.88 (m, 4H), 2.54-2.35 (m, 1H), 2.01-1.85 (m, 1H). MS (DCI/NH$_3$) m/z 492 (M+NH$_4$)$^+$.

Example 96

1-[(4R)-2,2-bis(fluoromethyl)-7-(trifluoromethyl)-3,4-dihydro-2H-chromen-4-yl]-3-[(2R)-5-fluoro-2-hydroxy-2,3-dihydro-1H-inden-4-yl]urea

Example 96A (R)-4-amino-5-fluoro-2,3-dihydro-1H-inden-2-ol

Example 25F was separated on a Chiralpak AD-H column (Chiral technologies Inc., eluting with 40-55% IPA/hexanes, 25 mL/min, 5 mL/injection) to provide Example 96A as the first eluting enantiomer. MS (DCI) m/z 185 (M+NH$_4$)$^+$.

Example 96B

1-[(4R)-2,2-bis(fluoromethyl)-7-(trifluoromethyl)-3,4-dihydro-2H-chromen-4-yl]-3-[(2R)-5-fluoro-2-hydroxy-2,3-dihydro-1H-inden-4-yl]urea The title compound was prepared as described in Example 1F substituting Example 96A for Example 1E, and Example 7A for Example 1C. $^1$H NMR (300 MHz, CDCl$_3$) δ 7.52 (d, J=8.1 Hz, 1H), 7.22-7.11 (m, 3H), 6.93 (t, J=8.4 Hz, 1H), 5.96 (s, 1H), 5.35-5.22 (m, 1H), 4.84-4.69 (m, 1H), 4.65-4.54 (m, 2H), 4.48-4.40 (m, 2H), 4.08-3.99 (m, 1H), 3.32-3.14 (m, 2H), 3.12-2.83 (m, 2H), 2.49-2.36 (m, 1H), 1.99-1.87 (m, 1H). MS (DCI/NH$_3$) m/z 492 (M+NH$_4$)$^+$.

Example 97

1-[(4S)-7-chloro-2,2-bis(fluoromethyl)-3,4-dihydro-2H-chromen-4-yl]-3-[(2R)-2-hydroxy-2,3-dihydro-1H-inden-4-yl]urea $^1$H NMR (300 MHz, DMSO-d$_6$) δ 7.86-7.70 (m, 2H), 7.31 (dd, J=8.3, 0.8 Hz, 1H), 7.12-6.76 (m, 5H), 4.86 (d, J=4.1 Hz, 1H), 4.79-4.65 (m, 1H), 4.64-4.44 (m, 1H), 4.12-3.94 (m, 1H), 3.14-2.86 (m, 1H), 2.83-2.56 (m, 2H), 2.31 (dt, J=9.1, 4.7 Hz, 1H), 2.04-1.96 (m, 2H), 1.96-1.87 (m, 2H), 1.25-1.10 (m, 1H). MS (ESI$^+$) m/z 423 (M+H)$^+$.

Example 98

1-[(4S)-7-chloro-2,2-bis(fluoromethyl)-3,4-dihydro-2H-chromen-4-yl]-3-[(2S)-2-hydroxy-2,3-dihydro-1H-inden-4-yl]urea $^1$H NMR (300 MHz, DMSO-d$_6$) δ 7.77 (d, J=8.1 Hz, 2H), 7.31 (dd, J=8.3, 1.0 Hz, 1H), 7.09-7.00 (m, 3H), 6.98 (d, J=2.2 Hz, 1H), 6.91 (d, J=8.0 Hz, 1H), 6.82 (d, J=7.3 Hz, 1H), 5.03-4.91 (m, 4H), 4.86 (d, J=4.1 Hz, 1H), 3.01 (ddd, J=27.7, 16.0, 6.1 Hz, 1H), 2.69 (ddd, J=27.0, 16.0, 3.5 Hz, 3H), 2.37-2.26 (m, 1H), 1.99 (s, 1H), 1.17 (t, J=7.1 Hz, 1H). MS (ESI$^+$) m/z 423 (M+H)$^+$.

Example 99

1-(7-chloro-3,4-dihydro-2H-chromen-3-yl)-3-[(2R)-2-hydroxy-2,3-dihydro-1H-inden-4-yl]urea $^1$H NMR (300 MHz, DMSO-d$_6$) δ 7.85-7.71 (m, 2H), 7.15 (d, J=7.9 Hz, 1H), 7.07-6.87 (m, 3H), 6.76 (t, J=7.1 Hz, 2H), 4.83 (s, 1H), 4.48 (s, 1H), 4.10 (dt, J=10.9, 6.3 Hz, 3H), 3.14-2.81 (m, 3H), 2.75-2.56 (m, 3H); MS (ESI+) m/z 359 (M+H)$^+$.

Example 100

1-[(2R,4R)-7-chloro-2-(fluoromethyl)-2-methyl-3,4-dihydro-2H-chromen-4-yl]-3-[(2S)-5-fluoro-2-hydroxy-2,3-dihydro-1H-inden-4-yl]urea $^1$H NMR (300 MHz, CDCl$_3$) δ 7.24-7.17 (m, 2H), 6.89 (td, J=8.5, 4.4 Hz, 2H), 6.83 (d, J=2.1 Hz, 1H), 5.97 (s, 1H), 5.25 (s, 1H), 4.79 (s, 1H), 4.35 (ddd, J=40.1, 30.9, 9.7 Hz, 1H), 4.09-4.01 (m, 1H), 3.30-3.09 (m, 1H), 2.96 (dd, J=24.7, 17.5 Hz, 1H), 2.19 (s, 1H), 1.92-1.76 (m, 1H), 1.33 (s, 3H). MS (DCI/NH$_3$) m/z 440 (M+NH$_4$)$^+$.

Example 101

1-[(4S)-6-fluoro-3,4-dihydrospiro[chromene-2,1'-cyclobutan]-4-yl]-3-[(2R)-2-hydroxy-2,3-dihydro-1H-inden-4-yl]urea $^1$H NMR (300 MHz, DMSO-$d_6$) δ 7.84-7.76 (m, 2H), 7.10-6.95 (m, 3H), 6.92 (d, J=8.2 Hz, 1H), 6.86-6.77 (m, 2H), 5.00-4.87 (m, 1H), 4.86 (d, J=4.1 Hz, 1H), 4.57-4.46 (m, 1H), 3.06 (dd, J=16.0, 6.2 Hz, 1H), 2.95 (dd, J=16.0, 6.1 Hz, 1H), 2.79-2.61 (m, 2H), 2.43-2.03 (m, 5H), 1.89-1.66 (m, 3H). MS (ESI$^+$) m/z 383 (M+H)$^+$.

Example 102

1-[(4S)-6-fluoro-3,4-dihydrospiro[chromene-2,1'-cyclobutan]-4-yl]-3-[(2S)-2-hydroxy-2,3-dihydro-1H-inden-4-yl]urea $^1$H NMR (300 MHz, DMSO-$d_6$) δ 7.83-7.76 (m, 2H), 7.10-6.95 (m, 3H), 6.92 (d, J=8.2 Hz, 1H), 6.84 (d, J=1.3 Hz, 1H), 6.82 (d, J=4.1 Hz, 2H), 4.99-4.87 (m, 1H), 4.85 (d, J=4.0 Hz, 1H), 4.58-4.46 (m, 1H), 3.12-2.92 (m, 1H), 2.79-2.69 (m, 1H), 2.64 (dd, J=16.0, 3.4 Hz, 1H), 2.38 (dd, J=13.3, 5.8 Hz, 1H), 2.32-2.07 (m, 4H), 1.90-1.63 (m, 3H). MS (ESI$^+$) m/z 383 (M+H)$^+$.

Example 103

1-[(4S)-6-fluoro-2,2-dimethyl-3,4-dihydro-2H-chromen-4-yl]-3-[(2S)-2-hydroxy-2,3-dihydro-1H-inden-4-yl]urea $^1$H NMR (300 MHz, DMSO-$d_6$) δ 7.82-7.75 (m, 2H), 7.09-6.93 (m, 3H), 6.88 (d, J=8.2 Hz, 1H), 6.82 (d, J=7.3 Hz, 1H), 6.81-6.72 (m, 1H), 4.99-4.87 (m, 1H), 4.86 (d, J=4.1 Hz, 1H), 4.56-4.45 (m, 1H), 3.05 (dd, J=16.0, 6.2 Hz, 1H), 2.95 (dd, J=16.0, 6.1 Hz, 1H), 2.70 (ddd, J=21.9, 16.1, 3.6 Hz, 2H), 2.16 (dd, J=13.2, 6.2 Hz, 1H), 1.69 (dd, J=13.2, 10.9 Hz, 1H), 1.39 (s, 3H), 1.27 (s, 3H). MS (ESI$^+$) m/z 371 (M+H)$^+$.

Example 104

1-[(4S)-6-fluoro-2,2-dimethyl-3,4-dihydro-2H-chromen-4-yl]-3-[(2R)-2-hydroxy-2,3-dihydro-1H-inden-4-yl]urea $^1$H NMR (300 MHz, DMSO-$d_6$) δ 7.82-7.75 (m, 2H), 7.09-6.94 (m, 3H), 6.88 (d, J=8.3 Hz, 1H), 6.82 (d, J=7.3 Hz, 1H), 6.77 (dd, J=8.8, 4.9 Hz, 1H), 5.00-4.87 (m, 1H), 4.86 (d, J=4.0 Hz, 1H), 4.58-4.46 (m, 1H), 3.02 (ddd, J=24.5, 16.1, 6.1 Hz, 2H), 2.69 (ddd, J=27.5, 16.0, 3.5 Hz, 2H), 2.16 (dd, J=13.2, 6.2 Hz, 1H), 1.69 (dd, J=13.2, 10.9 Hz, 1H), 1.39 (s, 3H), 1.27 (s, 3H). MS (ESI$^+$) m/z 371 (M+H)$^+$.

Example 105

1-[(4R)-2,2-dimethyl-7-(trifluoromethyl)-3,4-dihydro-2H-pyrano[2,3-b]pyridin-4-yl]-3-[(2R)-2-hydroxy-2,3-dihydro-1H-inden-4-yl]urea

Example 105A sodium 3-acetyl-6-(trifluoromethyl)pyridin-2-olate

A solution of 4-ethoxy-1,1,1-trifluoro-3-buten-2-one (4.21 g, 22.5 mmol), EtOH (42 mL), acetoacetamide (2.28 g, 22.5 mmol), and sodium ethoxide (21 weight % in EtOH, 8.41 mL, 22.5 mmol) was heated to 75° C. After 12 hours, the mixture was cooled to room temperature over 30 minutes, stirred for 4 hours, then cooled to <5° C. After 10 minutes, the white slurry was filtered, washing with cold EtOH (5 mL). The white solid was dried in a vacuum oven at 60° C. to provide the title compound (4.39 g, 19.3 mmol, 86% yield).

Example 105B 2,2-dimethyl-7-(trifluoromethyl)-2H-pyrano[2,3-b]pyridin-4(3H)-one A mixture of Example 105A (2.62 g, 12.8 mmol), acetone (26 mL), 3 Å molecular sieves (1.55 g), and pyrrolidine (0.211 ml, 2.55 mmol) was stirred at ambient temperature for four days. The volatiles were removed in vacuo and the mixture was purified by flash column chromatography (SiO$_2$, 0-50% EtOAc/hexanes gradient) provided the title compound (1.52 g, 6.20 mmol, 49% yield). MS (DCI$^+$) m/z 246 (M+H)$^+$.

Example 105C

A solution of Example 105B (1.52 g, 6.20 mmol), (R)-2-methylpropane-2-sulfinamide (1.13 g, 9.30 mmol), 2-methyltetrahydrofuran (20 mL), and tetraethoxytitanium (5.20 mL, 24.8 mmol) was heated to 70° C. After 3 hours the mixture was cooled to −10° C. and sodium borohydride (0.469 g, 12.40 mmol) was added. The mixture was warmed to room temperature, stirred for 2.0 hours then cooled to <5° C. A solution of 10% aqueous citric acid (50 mL) was added dropwise followed by 2-methyltetrahydrofuran (300 mL). The mixture was stirred vigorously overnight then diluted with MTBE (500 mL). The layers were separated and the organic extract was washed with water and brine, dried (Na$_2$SO$_4$), and concentrated. Purification by flash column chromatography (SiO$_2$, 20-100% hexanes/ethyl acetate gradient) afforded the title compound (2.14 g, 6.11 mmol, 99% yield). MS (DCI$^+$) m/z 349 (M+H)$^+$.

Example 105D (R)-2,2-dimethyl-7-(trifluoromethyl)-3,4-dihydro-2H-pyrano[2,3-b]pyridin-4-aminium chloride A solution of methanolic HCl was formed by adding acetyl chloride (0.868 mL, 12.2 mmol) dropwise to methanol (2.22 mL, 55.0 mmol) at <5° C. This was added to a solution of Example 105C in MTBE (20 mL) at room temperature. After 2 hours the solid was collected by filtration (200 mL MTBE wash) and dried in a vacuum oven at 60° C. to afford the title compound (2.14 g, 6.11 mmol). $^1$H NMR (300 MHz, DMSO) δ 8.97 (bs, 2H), 8.43 (d, J=7.8 Hz, 1H), 7.62 (d, J=7.7 Hz, 1H), 4.75-4.66 (m, 1H), 2.51-2.36 (m, 2H), 1.50 (s, 3H), 1.30 (s, 3H). MS (ESI$^+$) m/z 247 (M+NH$_4$—H$_2$O)$^+$.

Example 105E

1-[(4R)-2,2-dimethyl-7-(trifluoromethyl)-3,4-dihydro-2H-pyrano[2,3-b]pyridin-4-yl]-3-[(2R)-2-hydroxy-2,3-dihydro-1H-inden-4-yl]urea $^1$H NMR (300 MHz, DMSO-$d_6$) δ 7.93 (d, J=7.7 Hz, 2H), 7.76 (d, J=8.1 Hz, 1H), 7.47 (d, J=7.7 Hz, 1H), 7.05 (t, J=7.7 Hz, 1H), 6.95 (d, J=8.3 Hz, 1H), 6.83 (d, J=7.4 Hz, 1H), 5.14-5.00 (m, 1H), 4.86 (d, J=4.0 Hz, 1H), 4.52 (td, J=6.3, 3.3 Hz, 1H), 3.12-2.92 (m, 1H), 2.79-2.61 (m, 1H), 2.23 (dd, J=13.3, 6.0 Hz, 1H), 2.02-1.96 (m, 1H), 1.85 (t, J=12.5 Hz, 1H), 1.48 (s, 3H), 1.36 (s, 3H), 1.18 (t, J=7.1 Hz, 1H). MS (ESI$^+$) m/z 422 (M+H)$^+$.

Example 106

1-[(2R)-2-hydroxy-2,3-dihydro-1H-inden-4-yl]-3-[(1R)-5-(trifluoromethoxy)-2,3-dihydro-1H-inden-1-yl]urea $^1$H NMR (300 MHz, CD$_3$OD) δ ppm 1.83-1.97 (m, 1H), 2.55-2.67 (m, 1H), 2.79 (dd, J=16.2, 3.4 Hz, 1H), 2.83-2.96 (m, 2H), 2.97-3.23 (m, 3H), 4.59-4.67 (m, 1H), 5.29 (dd, J=7.6, 7.6 Hz, 1H), 6.93 (d, J=7.4 Hz, 1H), 7.07-7.14 (m, 2H), 7.15 (s, 1H), 7.40 (d, J=8.2 Hz, 1H), 7.57 (d, J=8.1 Hz, 1H). MS (ESI$^+$) m/z 393 (M+H)$^+$.

Example 107

1-(2-hydroxy-2,3-dihydro-1H-inden-4-yl)-3-(7-methoxy-3,4-dihydro-2H-chromen-4-yl)urea $^1$H NMR (500 MHz, DMSO-d$_6$/D$_2$O) δ ppm 1.88-1.97 (m, 1H), 2.02-2.12 (m, 1H), 2.58-2.69 (m, 1H), 2.74 (dd, J=16.1, 3.6 Hz, 1H), 2.88-3.00 (m, 1H), 3.01-3.13 (m, 1H), 3.7 (s, 3H), 4.07-4.15 (m, 1H), 4.22-4.29 (m, 1H), 4.46-4.55 (m, 1H), 4.74-4.81 (m, 1H), 6.36 (d, J=2.5 Hz, 1H), 6.53 (ddd, J=8.5, 2.6, 1.3 Hz, 1H), 6.83 (d, J=7.4 Hz, 1H), 7.06 (t, J=7.7 Hz, 1H), 7.17 (dd, J=8.5, 2.2 Hz, 1H), 7.78 (d, J=8.1 Hz, 1H). MS (ESI$^+$) m/z 355 (M+H)$^+$.

Example 108

1-(2-hydroxy-2,3-dihydro-1H-inden-4-yl)-3-(3-phenyl-3,4-dihydro-2H-chromen-4-yl)urea $^1$H NMR (500 MHz, DMSO-d$_6$/D$_2$O) δ ppm 2.56-2.63 (m, 1H), 2.68-2.75 (m, 1H), 2.79-2.94 (m, 1H), 3.03 (dt, J=16.0, 6.5 Hz, 1H), 3.26 (ddd, J=11.3, 8.1, 3.0 Hz, 1H), 3.46-3.52 (m, 1H), 4.25-4.41 (m, 2H), 4.44-4.57 (m, 1H), 5.18 (dd, J=8.1, 4.9 Hz, 1H), 5.28 (d, J=4.7 Hz, 1H), 6.74-6.90 (m, 2H), 6.99 (ddd, J=21.3, 15.3, 7.6 Hz, 2H), 7.17-7.39 (m, 7H), 7.58 (dd, J=8.1, 4.3 Hz, 1H), 7.69 (d, J=8.1 Hz, 1H). MS (ESI$^+$) m/z 401 (M+H)$^+$.

Example 109

1-[3-(3,4-dimethoxybenzyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.23 (d, J=3.1 Hz, 2H), 2.61-2.77 (m, 4H), 2.85-3.00 (m, 2H), 3.06 (dd, J=15.9, 6.0 Hz, 1H), 3.71 (s, 3H), 3.75 (s, 3H), 3.95 (dd, J=11.3, 5.8 Hz, 1H), 3.71 (bs, 3H), 3.75 (bs, 3H), 4.10 (t, J=10.5 Hz, 1H), 4.45-4.58 (m, 1H), 4.65 (t, J=5.4 Hz, 1H), 6.72 (dd, J=8.1, 1.7 Hz, 1H), 6.81-6.91 (m, 6H), 6.94 (dd, J=16.1, 8.7 Hz, 1H), 7.02-7.15 (m, 2H), 7.20 (dd, J=17.0, 8.3 Hz, 1H), 7.60-7.78 (m, 1H). MS (ESI$^+$) m/z 475 (M+H)$^+$.

Example 110

1-[2-(3-chlorophenyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.24 (dd, J=6.9, 4.0 Hz, 1H), 2.56-2.71 (m, 2H), 2.71-2.79 (m, 1H), 2.90-3.03 (m, 1H), 3.02-3.11 (m, 1H), 4.48-4.56 (m, 1H), 5.15-5.29 (m, 1H), 6.81-6.92 (m, 2H), 6.94-7.04 (m, 2H), 7.07 (td, J=7.7, 5.0 Hz, 1H), 7.17-7.25 (m, 1H), 7.24-7.38 (m, 2H), 7.40-7.58 (m, 5H), 7.69-7.81 (m, 1H). MS (ESI$^+$) m/z 434 (M+H)$^+$.

Example 111

1-(3-benzyl-3,4-dihydro-2H-chromen-4-yl)-3-(2-hydroxy-2,3-dihydro-1H-inden-4-yl)urea $^1$H NMR (500 MHz, DMSO-d$_6$/D$_2$O) δ ppm 2.26-2.33 (m, 1H), 2.58-2.69 (m, 1H), 2.69-2.78 (m, 3H), 2.88-2.97 (m, 2H), 3.06 (dd, J=16.1, 6.2 Hz, 1H), 3.97 (dd, J=11.4, 5.7 Hz, 1H), 4.08 (dd, J=11.4, 2.6 Hz, 1H), 4.47-4.55 (m, 1H), 4.58-4.67 (m, 1H), 6.81-6.88 (m, 3H), 6.93-7.10 (m, 2H), 7.49-7.59 (m, 7H), 7.67-7.79 (m, 1H). MS (ESI$^+$) m/z 415 (M+H)$^+$.

Example 112

1-[3-(3,4-dichlorobenzyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.26-2.33 (m, 1H), 2.58-2.69 (m, 1H), 2.69-2.78 (m, 2H), 2.88-2.97 (m, 1H), 3.06 (dd, J=16.1, 6.2 Hz, 1H), 3.97 (dd, J=11.4, 5.7 Hz, 1H), 4.08 (dd, J=11.4, 2.6 Hz, 1H), 4.47-4.55 (m, 1H), 4.58-4.67 (m, 1H), 6.81-6.88 (m, 2H), 6.93-7.10 (m, 3H), 7.19-7.28 (m, 3H), 7.49-7.59 (m, 2H), 7.67-7.79 (m, 1H). MS (ESI$^+$) m/z 482 (M+H)$^+$.

Example 113

1-[2-(3,4-dimethoxyphenyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.14-2.42 (m, 1H), 2.59-2.71 (m, 1H), 2.70-2.79 (m, 1H), 2.89-3.02 (m, 1H), 3.02-3.11 (m, 1H), 3.75-3.80 (m, 6H), 4.48-4.55 (m, 1H), 5.19-5.28 (m, 1H), 6.81-7.11 (m, 6H), 7.16-7.29 (m, 1H), 7.28-7.38 (m, 1H), 7.68-7.82 (m, 1H). MS (ESI$^+$) m/z 461 (M+H)$^+$.

Example 114

1-[3-(3,4-dichlorobenzyl)-7-methoxy-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.22-2.31 (m, 1H), 2.64-2.78 (m, 2H), 2.92 (dt, J=16.0, 5.6 Hz, 1H), 3.05 (dd, J=16.1, 6.2 Hz, 1H), 3.91-3.99 (m, 1H), 4.06 (dd, J=11.4, 2.6 Hz, 1H), 4.47-4.56 (m, 2H), 6.39-6.43 (m, 1H), 6.57 (dd, J=8.5, 2.6 Hz, 1H), 6.83 (d, J=7.4 Hz, 1H), 7.06 (t, J=7.8 Hz, 1H), 7.15 (d, J=8.5 Hz, 1H), 7.23 (dd, J=8.2, 2.0 Hz, 1H), 7.55 (dd, J=8.2, 5.8 Hz, 1H), 7.76 (d, J=8.2 Hz, 1H). MS (ESI$^+$) m/z 513 (M+H)$^+$.

Example 115

1-[3-(4-chlorophenyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.68-2.76 (m, 1H), 2.78-2.95 (m, 1H), 3.03 (dd, J=16.1, 6.2 Hz, 1H), 3.49-3.56 (m, 1H), 4.25-4.41 (m, 1H), 4.45-4.53 (m, 2H), 5.25 (d, J=5.0 Hz, 1H), 6.81 (d, J=7.4 Hz, 1H), 6.84-6.93 (m, 1H), 6.93-7.14 (m, 2H), 7.19-7.30 (m, 4H), 7.31-7.41 (m, 2H), 7.55 (dd, J=8.2, 4.1 Hz, 1H). MS (ESI$^+$) m/z 435 (M+H)$^+$.

Example 116

1-(2-hydroxy-2,3-dihydro-1H-inden-4-yl)-3-[3-(4-methoxyphenyl)-3,4-dihydro-2H-chromen-4-yl]urea $^1$H NMR (500 MHz, DMSO-d$_6$/D$_2$O) δ ppm 2.68-2.76 (m, 1H), 2.78-2.95 (m, 1H), 3.03 (dd, J=16.1, 6.2 Hz, 1H), 3.49-3.56 (m, 1H), 3.72 (s, 3H), 4.25-4.41 (m, 1H), 4.45-4.53 (m, 2H), 5.25 (d, J=5.0 Hz, 1H), 6.81 (d, J=7.4 Hz, 1H), 6.84-6.93 (m, 1H), 6.93-7.14 (m, 2H), 7.19-7.30 (m, 4H), 7.31-7.41 (m, 2H), 7.55 (dd, J=8.2, 4.1 Hz, 1H). MS (ESI$^+$) m/z 431 (M+H)$^+$.

Example 117

1-[2-(4-chlorophenyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 1.88-1.99 (m, 1H), 2.41 (ddd, J=13.0, 6.0, 1.9 Hz, 1H), 2.65 (dd, J=16.1, 3.5 Hz, 1H), 2.75 (dd, J=16.0, 3.6 Hz, 1H), 2.98 (dd, J=16.1, 6.2 Hz, 1H), 3.07 (dd, J=16.1, 6.2 Hz, 1H), 4.48-4.56 (m, 1H), 5.24 (dd, J=11.4, 5.9 Hz, 1H), 5.32-5.39 (m, 1H), 6.82-6.92 (m, 2H), 6.98 (td, J=7.4, 1.2 Hz, 1H), 7.07 (t, J=7.7 Hz, 1H), 7.21 (td, J=7.7, 1.6 Hz, 1H), 7.31 (d, J=7.7 Hz, 1H), 7.46-7.57 (m, 4H), 7.74 (d, J=8.1 Hz, 1H). MS (ESI$^+$) m/z 435 (M+H)$^+$.

Example 118

1-(2-hydroxy-2,3-dihydro-1H-inden-4-yl)-3-(2-phenyl-3,4-dihydro-2H-chromen-4-yl)urea $^1$H NMR (500 MHz, DMSO-d$_6$/D$_2$O) δ ppm 2.57-2.71 (m, 1H), 2.71-2.79 (m, 1H), 2.90-3.02 (m, 1H), 3.02-3.11 (m, 1H), 4.48-4.56 (m, 1H), 5.12-5.30 (m, 1H), 6.81-7.02 (m, 3H), 7.03-7.11 (m, 1H), 7.17-7.31 (m, 1H), 7.29-7.41 (m, 2H), 7.41-7.56 (m, 3H), 7.69-7.82 (m, 1H). MS (ESI$^+$) m/z 401 (M+H)$^+$.

Example 119

1-[2-(4-fluorophenyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.18-2.27 (m, 1H), 2.58-2.70 (m, 1H), 2.70-2.78 (m, 1H), 2.90-3.02 (m, 1H), 3.02-3.11 (m, 1H), 4.48-4.54 (m, 1H), 5.12-5.28 (m, 1H), 6.81-6.88 (m, 2H), 6.90-7.03 (m, 2H), 7.03-7.11 (m, 1H), 7.17-7.38 (m, 5H), 7.54 (dd, J=23.8, 5.5 Hz, 2H), 7.54 (t, J=6.2 Hz, 2H), 7.71-7.82 (m, 1H). MS (ESI$^+$) m/z 419 (M+H)$^+$.

Example 120

1-[2-(2-chlorophenyl)-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 2.00-2.09 (m, 1H), 2.34-2.42 (m, 1H), 2.61-2.66 (m, 1H), 2.74 (dd, J=16.1, 3.6 Hz, 1H), 2.93 (dt, J=16.1, 6.0 Hz, 1H), 3.06 (dd, J=16.1, 6.2 Hz, 1H), 4.47-4.55 (m, 1H), 4.87 (t, J=2.9 Hz, 1H), 5.48 (dd, J=11.3, 2.1 Hz, 1H), 6.84 (d, J=7.4 Hz, 1H), 6.98 (dd, J=8.2, 1.1 Hz, 1H), 6.99-7.10 (m, 2H), 7.26-7.33 (m, 1H), 7.34-7.45 (m, 2H), 7.43-7.54 (m, 2H), 7.66 (dd, J=7.7, 1.7 Hz, 1H), 7.71-7.77 (m, 1H). MS (ESI$^+$) m/z 435 (M+H)$^+$.

Example 121

1-(2-hydroxy-2,3-dihydro-1H-inden-4-yl)-3-{2-[4-(trifluoromethyl)phenyl]-3,4-dihydro-2H-chromen-4-yl}urea $^1$H NMR (500 MHz, DMSO-d$_6$/D$_2$O) δ ppm 1.89-2.00 (m, 1H), 2.66 (ddd, J=16.1, 7.1, 3.6 Hz, 1H), 2.71-2.79 (m, 1H), 2.91-3.02 (m, 1H), 3.07 (ddd, J=16.1, 6.1, 3.1 Hz, 1H), 4.48-4.56 (m, 1H), 5.28 (dd, J=11.3, 5.9 Hz, 1H), 5.44-5.50 (m, 1H), 6.83-6.93 (m, 2H), 6.97-7.04 (m, 1H), 7.07 (t, J=7.7 Hz, 1H), 7.23 (t, J=7.7 Hz, 1H), 7.33 (dd, J=7.7, 1.7 Hz, 1H), 7.72-7.78 (m, 3H), 7.78-7.83 (m, 2H). MS (ESI$^+$) m/z 469 (M+H)$^+$.

Example 122

1-[2-(4-chlorophenyl)-7-methoxy-3,4-dihydro-2H-chromen-4-yl]-3-(2-hydroxy-2,3-dihydro-1H-inden-4-yl)urea $^1$H NMR (500 MHz, DMSO-d$_6$/D$_2$O) δ ppm 1.83-1.94 (m, 1H), 2.36-2.44 (m, 1H), 2.65 (ddd, J=16.1, 6.6, 3.4 Hz, 1H), 2.71-2.79 (m, 1H), 2.91-3.01 (m, 1H), 3.07 (ddd, J=16.1, 6.1, 2.6 Hz, 1H), 3.72 (s, 3H), 4.48-4.56 (m, 1H), 5.16 (dd, J=11.2, 5.9 Hz, 1H), 5.29-5.36 (m, 1H), 6.43 (d, J=2.5 Hz, 1H), 6.59 (dt, J=8.6, 2.2 Hz, 1H), 6.85 (d, J=7.4 Hz, 1H), 7.07 (t, J=7.7 Hz, 1H), 7.20 (d, J=8.6 Hz, 1H), 7.46-7.52 (m, 2H), 7.50-7.56 (m, 2H), 7.74 (dd, J=8.1, 3.2 Hz, 1H). MS (ESI$^+$) m/z 465 (M+H)$^+$.

Example 123

1-(3,4-dihydrospiro[chromene-2,1'-cyclohexan]-4-yl)-3-(2-hydroxy-2,3-dihydro-1H-inden-4-yl)urea $^1$H NMR (500 MHz, DMSO-d$_6$/D$_2$O) δ ppm 1.32-1.77 (m, 12H), 2.20 (ddd, J=13.4, 6.3, 2.1 Hz, 1H), 2.65 (ddd, J=16.1, 6.2, 3.5 Hz, 1H), 2.71-2.79 (m, 1H), 2.91-3.01 (m, 1H), 3.07 (dd, J=16.1, 6.2 Hz, 1H), 4.52 (dh, J=6.2, 3.1 Hz, 1H), 4.91-4.99 (m, 1H), 6.76-6.94 (m, 3H), 7.07 (t, J=7.8 Hz, 1H), 7.17 (td, J=7.7, 1.6 Hz, 1H), 7.23-7.29 (m, 1H), 7.77 (dd, J=8.1, 3.5 Hz, 1H). MS (ESI$^+$) m/z 393 (M+H)$^+$.

Example 124

1-[2-(3,4-dichlorobenzyl)-2,3-dihydro-1H-inden-1-yl]-3-(2-hydroxy-2,3-dihydro-1H-inden-4-yl)urea $^1$H NMR (500 MHz, DMSO-d$_6$/D$_2$O) δ ppm 2.59-2.68 (m, 2H), 2.70-2.99 (m, 4H), 2.98-3.12 (m, 1H), 4.48-4.55 (m, 1H), 5.19-5.24 (m, 1H), 6.83 (d, J=7.4 Hz, 1H), 7.06 (t, J=7.8 Hz, 1H), 7.19-7.35 (m, 5H), 7.48-7.59 (m, 2H), 7.70-7.80 (m, 1H). MS (ESI$^+$) m/z 467 (M+H)$^+$.

Example 125

1-(2-benzyl-2,3-dihydro-1H-inden-1-yl)-3-(2-hydroxy-2,3-dihydro-1H-inden-4-yl)urea $^1$H NMR (500 MHz, DMSO-d$_6$/D$_2$O) δ ppm 2.27-2.44 (m, 1H), 2.58-2.69 (m, 2H), 2.71-2.87 (m, 3H), 2.88-3.01 (m, 2H), 3.03-3.13 (m, 1H), 4.52 (ddd, J=9.7, 6.4, 3.6 Hz, 1H),

Example 126

1-[(2S,4R)-2-(difluoromethyl)-2-methyl-3,4-dihydro-2H-chromen-4-yl]-3-[(2R)-2-hydroxy-2,3-dihydro-1H-inden-4-yl]urea $^1$H NMR (300 MHz, DMSO-$d_6$) δ 7.84-7.77 (m, 2H), 7.30 (d, J=7.7 Hz, 1H), 7.21 (td, J=7.7, 1.7 Hz, 1H), 7.09-6.78 (m, 5H), 5.06-4.93 (m, 1H), 4.85 (d, J=4.0 Hz, 1H), 4.57-4.46 (m, 1H), 3.00 (ddd, J=29.6, 16.1, 6.1 Hz, 2H), 2.73 (dd, J=16.0, 3.5 Hz, 1H), 2.64 (dd, J=16.0, 3.4 Hz, 1H), 2.43-2.33 (m, 3H), 1.41 (s, 3H). MS (ESI$^+$) m/z 389 (M+H)$^+$.

Example 127

1-[(2R,4R)-2-(difluoromethyl)-2-methyl-3,4-dihydro-2H-chromen-4-yl]-3-[(2R)-2-hydroxy-2,3-dihydro-1H-inden-4-yl]urea $^1$H NMR (300 MHz, DMSO-$d_6$) δ 7.83-7.79 (m, 2H), 7.78 (d, J=8.2 Hz, 1H), 7.32 (dt, J=7.6, 1.3 Hz, 1H), 7.26-7.16 (m, 1H), 7.09-6.89 (m, 2H), 6.88-6.79 (m, 2H), 5.09-4.96 (m, 1H), 4.85 (d, J=4.1 Hz, 1H), 4.58-4.46 (m, 1H), 2.69 (ddd, J=26.5, 16.1, 3.4 Hz, 2H), 2.19 (dd, J=12.9, 5.8 Hz, 2H), 1.86 (t, J=12.1 Hz, 1H), 1.36 (s, 3H), 1.34-0.99 (m, 2H). MS (ESI$^+$) m/z 389 (M+H)$^+$.

Example 128

1-[(4R)-3,4-dihydrospiro[chromene-2,1'-cyclopentan]-4-yl]-3-[(2R)-2-hydroxy-2,3-dihydro-1H-inden-4-yl]urea $^1$H NMR (300 MHz, DMSO-$d_6$) δ 7.88-7.70 (m, 2H), 7.27 (d, J=7.5 Hz, 1H), 7.19-6.97 (m, 2H), 6.96-6.66 (m, 4H), 4.95 (dd, J=14.8, 8.9 Hz, 1H), 4.84 (d, J=4.1 Hz, 1H), 4.52 (dt, J=9.8, 4.8 Hz, 1H), 3.00 (ddd, J=29.9, 16.0, 6.1 Hz, 2H), 2.82-2.60 (m, 2H), 2.17 (dd, J=13.2, 6.0 Hz, 1H), 2.02-1.54 (m, 9H); MS (DCI+) m/z 396 (m+NH$_4$)$^+$.

Example 129

1-[(4R)-7-fluoro-2,2-bis(fluoromethyl)-3,4-dihydro-2H-chromen-4-yl]-3-[(2R)-2-hydroxy-2,3-dihydro-1H-inden-4-yl]urea $^1$H NMR (300 MHz, DMSO-$d_6$) δ 7.80-7.76 (m, 1H), 7.78 (d, J=8.0 Hz, 2H), 7.37-7.28 (m, 1H), 7.05 (t, J=7.8 Hz, 1H), 6.93-6.72 (m, 3H), 5.02-4.90 (m, 1H), 4.85 (d, J=4.0 Hz, 1H), 4.80-4.65 (m, 2H), 4.63-4.47 (m, 2H), 3.21-2.91 (m, 2H), 2.69 (ddd, J=27.9, 16.0, 3.5 Hz, 2H), 2.31 (dd, J=13.8, 5.9 Hz, 1H), 2.01-1.92 (m, 1H); MS (DCI+) m/z 424 (M+NH$_4$)$^+$.

Example 130

1-[(4R)-7-(difluoromethyl)-2,2-bis(fluoromethyl)-3,4-dihydro-2H-chromen-4-yl]-3-[(2R)-2-hydroxy-2,3-dihydro-1H-inden-4-yl]urea

Example 130A

To a solution of Example 45A (212 mg, 0.535 mmol) in THF (4 mL) at <−70° C. was added methyllithium (0.669 mL of a 1.6 M solution in diethyl ether, 1.07 mmol). After 5 minutes n-BuLi (0.257 mL of a 1.6 M solution in hexanes, 0.642 mmol) was added, followed by DMF (0.166 mL, 2.14 mmol). The mixture was diluted with saturated aqueous NH$_4$Cl, extracted with MTBE, and the layers separated. The organic extract was dried (Na$_2$SO$_4$), concentrated, and then purified by flash column chromatography (50-100% EtOAc/hexanes) to give the title compound (147 mg, 0.426 mmol, 80% yield).

Example 130B

To a solution of Example 130A (146 mg, 0.423 mmol) in dichloromethane (3 mL) at <5° C. was added diethylaminosulfur trifluoride (0.279 mL, 2.11 mmol) and the mixture was stirred for 50 minutes at <5° C. The mixture was warmed to room temperature and stirred for 2 hours, then cooled to <5° C. and quenched with EtOH (5 mL). The mixture dichloromethane diluted with MTBE, washed with saturated aqueous NaHCO$_3$ and brine, dried (Na$_2$SO$_4$), and concentrated. Purification of the residue by flash column chromatography (25-75% EtOAc/hexanes) gave the title compound (70 mg, 0.191 mmol, 45.1% yield).

Example 130C (R)-7-(difluoromethyl)-2,2-bis(fluoromethyl)chroman-4-aminium chloride Methanol (0.070 mL, 1.739 mmol) was cooled to <0° C. and acetyl chloride (0.027 mL, 0.386 mmol) added dropwise. In a separate flask, Example 130B (71 mg, 0.193 mmol) in MTBE (2 mL) was stirred at room temperature and the methanolic solution of HCl was added. The solid was collected by filtration (MTBE wash) then diluted with MeOH and concentrated to provide the title compound (47 mg, 0.157 mmol, 81% yield).

Example 130D

1-[(4R)-7-(difluoromethyl)-2,2-bis(fluoromethyl)-3,4-dihydro-2H-chromen-4-yl]-3-[(2R)-2-hydroxy-2,3-dihydro-1H-inden-4-yl]urea The title compound was prepared as described in Example 1F substituting Example 130C for Example 1C. $^1$H NMR (300 MHz, DMSO) δ 7.83 (s, 1H), 7.78 (d, J=8.1 Hz, 1H), 7.44 (d, J=8.0 Hz, 1H), 7.22-7.13 (m, 1H), 7.07 (d, J=4.8 Hz, 2H), 7.04 (d, J=8.2 Hz, 2H), 6.95 (d, J=8.2 Hz, 1H), 6.83 (d, J=7.4 Hz, 1H), 5.10-4.97 (m, 1H), 4.87 (d, J=3.9 Hz, 1H), 4.80-4.70 (m, 2H), 4.64-4.47 (m, 3H), 3.01 (ddd, J=30.1, 16.0, 6.1 Hz, 2H), 2.79-2.61 (m, 2H), 2.34 (dd, J=13.8, 5.9 Hz, 1H), 1.95 (ddd, J=13.6, 10.7, 2.8 Hz, 1H); MS (DCI+) m/z 456 (M+NH$_4$)$^+$.

Example 131

1-[(2R,4R)-7-chloro-2-(fluoromethyl)-2-methyl-3,4-dihydro-2H-chromen-4-yl]-3-(8-hydroxybicyclo[4.2.0]octa-1,3,5-trien-3-yl)urea

Example 131A 5-aminocyclobutabenzen-1(2H)-one

To a solution of 5-nitrocyclobutabenzen-1(2H)-one (900 mg, 5.52 mmol) in ethanol (25 mL) under a stream of nitrogen was added palladium on carbon (587 mg, 10%, 0.55 mmol). The mixture was placed under a hydrogen atmosphere (balloon) and stirred at ambient temperature for 16 hours. The reaction vessel was charged with nitrogen and the mixture filtered (ethanol wash). The filtrate was concentrated and purified by chromatography (silica gel, 20% EtOAc/hexanes) to provide the title compound. MS (DCI/NH$_3$) m/z 151 (M+NH$_4$)$^+$.

Example 131B tert-butyl 2-oxo-1,2-dihydrocyclobutabenzen-4-ylcarbamate

To a 0° C. solution of Example 131A (340 mg, 2.55 mmol) in anhydrous THF (20 mL) was added diethylisopropylamine (1.34 ml, 7.66 mmol) and di-tert-butyl dicarbonate (1.1 g 5.11 mmol). The reaction mixture was stirred at ambient temperature for 16 hours then diluted with ether and washed with water and brine. The organic extract was dried (MgSO$_4$), filtered and concentrated under reduced pressure. The residue was purified by chromatographgy (silica gel, 30% EtOAc/hexanes) to provide the title compound. MS (DCI/NH$_3$) m/z 268 (M+2NH$_4$)$^+$.

Example 131C 5-amino-1,2-dihydrocyclobutabenzen-1-ol

To a solution of Example 131B (190 mg, 0.815 mmol) in MeOH (15 mL) at 0° C. was added sodium borohydride (41 mg, 1.06 mmol) and the mixture was stirred at room temperature for 2 hours. The mixture was diluted with ethyl acetate (30 mL) and washed with a saturated aqueous NaHCO$_3$ and brine, dried (MgSO$_4$), filtered and concentrated. The residue was treated with trifluoroacetic acid (2 mL) and stirred for several minutes. The solution was concentrated under reduced pressure and the residue was purified by chromatography (silica gel, 20-40% EtOAc/hexanes gradient) to provide the title compound. MS (DCI/NH$_3$) m/z 153 (M+NH$_4$)$^+$.

Example 131D

1-[(2R,4R)-7-chloro-2-(fluoromethyl)-2-methyl-3,4-dihydro-2H-chromen-4-yl]-3-(8-hydroxybicyclo [4.2.0]octa-1,3,5-trien-3-yl)urea $^1$H NMR (300 MHz, CDCl$_3$) δ 7.25-7.12 (m, 3H), 7.08 (d, J=7.7 Hz, 1H), 6.89-6.82 (m, 2H), 6.54 (s, 1H), 5.24 (dd, J=4.5, 1.8 Hz, 1H), 5.00-4.88 (m, 1H), 4.52-4.18 (m, 2H), 3.60-3.51 (m, 1H), 3.05-2.93 (m, 1H), 2.22-2.11 (m, 1H), 1.84 (tt, J=5.7, 3.3 Hz, 2H), 1.31 (d, J=2.1 Hz, 3H). MS (DCI/NH$_3$) m/z 408 (M+NH$_4$)$^+$.

Example 132

1-[(2R,4R)-2-(fluoromethyl)-2-methyl-3,4-dihydro-2H-chromen-4-yl]-3-(8-hydroxybicyclo[4.2.0]octa-1,3,5-trien-3-yl)urea $^1$H NMR (300 MHz, CDCl$_3$) δ 7.31 (dd, J=8.0, 4.3 Hz, 1H), 7.23-7.12 (m, 3H), 7.09 (dd, J=9.1, 5.1 Hz, 1H), 6.94-6.86 (m, 1H), 6.83 (dd, J=6.1, 2.3 Hz, 1H), 6.42 (s, 1H), 5.32-5.20 (m, 1H), 4.91-4.77 (m, 1H), 4.53-4.20 (m, 2H), 3.55 (dd, J=7.2, 2.1 Hz, 1H), 3.05-2.95 (d, J=2.8 Hz, 1H), 2.29-2.16 (m, 1H), 1.94-1.82 (m, 1H), 1.34 (d, J=2.4 Hz, 3H). MS (DCI/NH$_3$) m/z 374 (M+NH$_4$)$^+$.

Example 133

1-[(4R)-7-chloro-2,2-bis(fluoromethyl)-3,4-dihydro-2H-chromen-4-yl]-3-[(2R)-7-fluoro-2-hydroxy-2,3-dihydro-1H-inden-4-yl]urea Example 133A 4-bromo-7-fluoro-2,3-dihydro-1H-inden-1-one To a room temperature solution of aluminum chloride (11.77 g, 88 mmol) in dichloroethane (100 mL) was added 7-fluoro-2,3-dihydro-1H-inden-1-one (5.3 g, 35.3 mmol) followed with bromine (1.91 mL, 37.1 mmol). The mixture was heated at 65° C. for 16 hours, then cooled to ambient temperature and poured into a mixture of ice and HCl (1N aqueous). The mixture was extracted twice with ether (200 mL). The combined organic extracts were dried (MgSO$_4$), filtered, and concentrated under reduced pressure. The residue was purified by chromatography (silica gel column eluting with 0-10% EtOAc/hexanes) to provide the title compound (5.2 g, 64%). MS (DCI/NH$_3$) m/z 246 (M+NH$_4$)$^+$.

Example 133B 4-bromo-7-fluoro-2,3-dihydro-1H-inden-1-ol

To a 0° C. solution of Example 133A (5.0 g, 21.8 mmol) in MeOH (80 mL) was slowly added sodium borohydride (1.16 g, 31.0 mmol). The mixture was stirred at ambient temperature for 2 hours, concentrated under reduced pressure and then diluted with EtOAc (150 mL) and saturated aqueous NaHCO$_3$ (50 mL). The organic layer was separated, washed with brine, dried (MgSO$_4$), filtered, and concentrated under reduced pressure. The residue was purified by chromatography (silica gel column eluting with 0-20% EtOAc/hexanes) to provide the title compound (5 g, 99%). MS (DCI/NH$_3$) m/z 248 (m+NH$_4$)$^+$.

Example 133C 7-bromo-4-fluoro-1H-indene

A mixture of Example 133B (5.3 g, 22.94 mmol) and p-toluenesulfonic acid monohydrate (0.262 g, 1.38 mmol) in toluene (60 mL) was refluxed for 2 hours. The mixture was cooled to ambient temperature, diluted with ether (100 mL) and washed with saturated aqueous K$_2$CO$_3$. The organic extract was dried (MgSO$_4$), filtered, and concentrated under reduced pressure to provide the title compound. (DCI/NH$_3$) m/z 230 (M+NH$_4$)$^+$.

Example 133D 5-bromo-2-fluoro-6,6a-dihydro-1aH-indeno[1,2-b] oxirene

To a 0° C. solution of Example 133C (4.4 g, 20.65 mmol) in anhydrous dichloromethane (40 mL) was added 3-chloroperbenzoic acid (6.02 g, 26.8 mmol). The ice bath was removed and the mixture stirred for 16 hours. The mixture was diluted with dichloromethane (100 mL) and treated with a saturated aqueous Na$_2$S$_2$O$_3$. The organic extract was dried (MgSO$_4$), filtered, and concentrated under reduced pressure. The residue was purified by chromatography (silica gel column eluting with 0-10% EtOAc/hexanes) to provide the title compound (4.55 g, 96%). (DCI/NH$_3$) m/z 246 (M+NH$_4$)$^+$.

Example 133E 4-bromo-7-fluoro-2,3-dihydro-1H-inden-2-ol

To a 0° C. solution of Example 133D (4.55 g, 19.87 mmol) in anhydrous diethyl ether (40 mL) was added lithium aluminum hydride (21.9 mL, 1M in THF). After stirring at ambient temperature for 2 hours the mixture was diluted with ether (50 mL) and H$_2$O (0.3 mL), 1N aqueous NaOH (0.3 mL) and H$_2$O (0.9 mL) were added sequentially. The mixture was stirred for 10 minutes then filtered (Et$_2$O wash). The filtrate was concentrated under reduced pressure and purified by chromatography (silica gel column eluting with 10-15% EtOAc/hexanes) to provide the title compound. (DCI/NH$_3$) m/z 248 (M+NH$_4$)$^+$.

Example 133F 4-(diphenylmethyleneamino)-7-fluoro-2,3-dihydro-1H-inden-2-ol

A mixture of Example 133E (4.08 g, 17.66 mmol), diphenylmethanimine (4.68 mL, 26.5 mmol), Cs$_2$CO$_3$ (14.38 g, 44.1 mmol), (R)-(+)-2,2'-bis(diphenylphosphino)-1,1'-binaphthyl (0.66 g, 1.096 mmol), and Pd$_2$(dba)$_3$ in toluene (20 mL) was heated at 85° C. for 16 hours. The mixture was cooled to room temperature and filtered (ether wash). The filtrate was concentrated under reduced pressure and the residue purified by chromatography (silica gel column eluting with 0-20% EtOAc/hexanes) to provide the title compound. (DCI/NH$_3$) m/z 349 (M+NH$_4$)$^+$.

Example 133G (R)-4-amino-7-fluoro-2,3-dihydro-1H-inden-2-ol

A solution of Example 133F (1.15 g, 3.47 mmol) in MeOH (10 mL) was treated with 1N aqueous hydrochloric acid (10 mL) and stirred for 30 minutes. The mixture was diluted with ether (100 mL), washed with H$_2$O and brine, dried (MgSO$_4$), filtered, and concentrated under reduced pressure. The residue was purified by chromatography (silica gel column eluting with 0-30% EtOAc/hexanes) to provide a racemic mixture of the title compounds. This racemate was separated on a Chiralpak AD-H prep column (Chiral technologies Inc., eluting with 40-55% IPA/hexanes mobile phase, 25 mL/min, 5 mL/injection) to provide Example 133G as the second eluting enantiomer. MS (DCI) m/z 185 (M+NH$_4$)$^+$.

Example 133H

1-[(4R)-7-chloro-2,2-bis(fluoromethyl)-3,4-dihydro-2H-chromen-4-yl]-3-[(2R)-7-fluoro-2-hydroxy-2,3-dihydro-1H-inden-4-yl]urea The title compound was prepared using the procedure described in Example 1F substituting Example 133G for Example 1E, and substituting Example 4B for Example 1C. $^1$H NMR (300 MHz, CDCL$_3$) δ 7.21 (d, J=8.0 Hz, 2H), 6.90 (t, J=8.3 Hz, 3H), 6.03 (s, 1H), 5.19 (s, 1H), 4.78 (s, 2H), 4.58 (dd, J=14.7, 8.5 Hz, 2H), 4.48-4.34 (m, 2H), 3.34-2.83 (m, 4H), 2.38 (s, 1H), 1.90 (s, 1H). MS (DCI/NH$_3$) m/z 458 (M+NH$_4$)$^+$.

Example 134

1-[(4R)-7-chloro-2,2-bis(fluoromethyl)-3,4-dihydro-2H-chromen-4-yl]-3-[(2S)-7-fluoro-2-hydroxy-2,3-dihydro-1H-inden-4-yl]urea

Example 134A (S)-4-amino-7-fluoro-2,3-dihydro-1H-inden-2-ol

The title compound was isolated as the first eluting enantiomer from the chiral separation of the racemate as described in Example 133G.

Example 134B

1-[(4R)-7-chloro-2,2-bis(fluoromethyl)-3,4-dihydro-2H-chromen-4-yl]-3-[(2S)-7-fluoro-2-hydroxy-2,3-dihydro-1H-inden-4-yl]urea The title compound was prepared using the procedure described in Example 1F substituting Example 134A for Example 1E, and substituting Example 4B for Example 1C. $^1$H NMR (300 MHz, CDCl$_3$) δ 7.24-7.16 (m, 2H), 6.98-6.83 (m, 3H), 6.09-5.89 (m, 1H), 5.26-5.10 (m, 1H), 4.84-4.66 (m, 2H), 4.62-4.49 (m, 2H), 4.45-4.32 (m, 2H), 3.29-2.84 (m, 4H), 2.47-2.33 (m, 1H). MS (DCI/NH$_3$) m/z 458 (M+NH$_4$)$^+$.

Example 135

1-[(4R)-2,2-dimethyl-8-(trifluoromethyl)-3,4-dihydro-2H-chromen-4-yl]-3-[(2S)-7-fluoro-2-hydroxy-2,3-dihydro-1H-inden-4-yl]urea $^1$H NMR (500 MHz, DMSO-d$_6$/D$_2$O) δ ppm 1.31 (s, 3H), 1.43 (s, 3H), 1.81 (dd, J=13.27, 11.14 Hz, 1H), 2.21 (dd, J=13.27, 6.26 Hz, 1H), 2.69-2.81 (m, 2H), 3.01 (dd, J=16.48, 6.10 Hz, 1H), 3.09 (dd, J=16.32, 5.95 Hz, 1H), 4.55-4.60 (m, 1H), 5.00 (dd, J=10.98, 6.41 Hz, 1H), 6.92 (t, J=8.70 Hz, 1H), 7.06 (t, J=7.78 Hz, 1H), 7.53 (dd, J=17.85, 7.48 Hz, 2H), 7.69 (dd, J=8.85, 4.58 Hz, 1H). ESI$^+$ m/z 439 (M+H)$^+$.

Example 136

1-[(4R)-8-fluoro-2,2-dimethyl-3,4-dihydro-2H-chromen-4-yl]-3-[(2S)-7-fluoro-2-hydroxy-2,3-dihydro-1H-inden-4-yl]urea $^1$H NMR (500 MHz, DMSO-d$_6$/D$_2$O) δ ppm 1.31 (s, 3H), 1.44 (s, 3H), 1.77 (dd, J=13.27, 11.14 Hz, 1H), 2.17 (dd, J=13.43, 6.10 Hz, 1H), 2.69-2.81 (m, 2H), 3.00 (dd, J=16.32, 5.95 Hz, 1H), 3.06-3.12 (m, 1H), 4.56-4.59 (m, 1H), 4.98 (dd, J=10.98, 6.10 Hz, 1H), 6.86-6.93 (m, 2H), 7.07-7.12 (m, 2H), 7.70 (dd, J=8.85, 4.58 Hz, 1H). ESI$^+$ m/z 389 (M+H)$^+$.

Example 137

1-[(2S)-7-fluoro-2-hydroxy-2,3-dihydro-1H-inden-4-yl]-3-[(4R)-8-(trifluoromethoxy)-3,4-dihydro-2H-chromen-4-yl]urea $^1$H NMR (500 MHz, DMSO-d$_6$/D$_2$O) δ ppm 1.96-2.04 (m, 1H), 2.11-2.18 (m, 1H), 2.67 (dd, J=16.48, 3.05 Hz, 1H), 2.77 (dd, J=16.32, 2.90 Hz, 1H), 2.97 (dd, J=16.32, 5.95 Hz, 1H), 3.08 (dd, J=16.32, 5.95 Hz, 1H), 4.19-4.25 (m, 1H), 4.37-4.42 (m, 1H), 4.55-4.58 (m, 1H), 4.93 (q, J=5.49 Hz, 1H), 6.91 (t, J=8.70 Hz, 1H), 6.98-7.02 (m, 2H), 7.29 (dd, J=19.99, 7.78 Hz, 2H), 7.72 (dd, J=8.85, 4.58 Hz, 1H). ESI+ m/z 427 (M+H)+.

Example 138

1-[(4R)-7-fluoro-2,2-dimethyl-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.29 (s, 3H), 1.40 (s, 3H), 1.71 (dd, J=13.27, 11.14 Hz, 1H), 2.15 (dd, J=13.12, 6.10 Hz, 1H), 2.68-2.81 (m, 2H), 2.97-3.12 (m, 2H), 4.55-4.61 (m, 1H), 4.87-4.99 (m, 1H), 6.58 (dd, J=10.53, 2.59 Hz, 1H), 6.71-6.81 (m, 2H), 6.91 (t, J=8.70 Hz, 1H), 7.27-7.31 (m, 1H), 7.71 (dd, J=8.85, 4.58 Hz, 1H). ESI+ m/z 389 (M+H)+.

Example 139

1-[(4R)-2,2-bis(fluoromethyl)-7-(trifluoromethoxy)-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.95-2.02 (m, 1H), 2.31 (dd, J=13.73, 5.80 Hz, 1H), 2.71 (dd, J=16.32, 2.90 Hz, 1H), 2.78 (dd, J=16.17, 2.75 Hz, 1H), 3.01 (dd, J=16.32, 5.95 Hz, 1H), 3.09 (dd, J=16.48, 6.10 Hz, 1H), 4.56-4.75 (m, 5H), 5.00 (dd, J=10.37, 5.80 Hz, 1H), 6.89 (d, J=1.53 Hz, 1H), 6.91 (t, J=8.70 Hz, 1H), 6.99-7.02 (m, 1H), 7.41 (d, J=8.54 Hz, 1H), 7.68 (dd, J=8.85, 4.58 Hz, 1H). ESI+ m/z 491 (M+H)+.

Example 140

1-[(4R)-2,2-dimethyl-7-(trifluoromethyl)-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.31 (s, 3H), 1.43 (s, 3H), 1.78 (dd, J=13.12, 11.60 Hz, 1H), 2.18 (dd, J=13.27, 6.26 Hz, 1H), 2.69-2.81 (m, 2H), 3.01 (dd, J=16.48, 6.10 Hz, 1H), 3.09 (dd, J=16.32, 5.95 Hz, 2H), 4.56-4.60 (m, 1H) 5.02 (dd, J=11.14, 6.26 Hz, 1H), 6.92 (t, J=8.85 Hz, 1H), 7.05 (d, J=1.53 Hz, 1H), 7.25 (d, J=8.24 Hz, 1H), 7.49 (d, J=8.24 Hz, 1H), 7.70 (dd, J=8.85, 4.58 Hz, 1H). ESI+ m/z 439 (M+H)+.

Example 141

1-[(4R)-6-fluoro-2,2-bis(fluoromethyl)-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.89-1.96 (m, 1H), 2.29 (dd, J=13.73, 5.80 Hz, 1H), 2.70-2.81 (m, 2H), 3.01 (dd, J=16.32, 5.95 Hz, 1H), 3.09 (dd, J=16.17, 6.10 Hz, 1H), 4.54-4.61 (m, 3H), 4.63-4.71 (m, 2H), 4.97 (dd, J=10.53, 5.95 Hz, 1H), 6.90-6.94 (m, 2H), 7.04-7.10 (m, 2H), 7.67 (dd, J=8.85, 4.58 Hz, 1H). ESI+ m/z 425 (M+H)+.

Example 142

1-[(4R)-6,8-difluoro-2,2-bis(fluoromethyl)-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.97-2.04 (m, 1H), 2.34 (dd, J=13.73, 6.10 Hz, 1H), 2.70-2.81 (m, 2H), 3.01 (dd, J=16.32, 5.95 Hz, 1H), 3.09 (dd, J=16.32, 5.95 Hz, 1H), 4.56-4.76 (m, 5H), 5.00 (dd, J=10.83, 5.95 Hz, 1H), 6.92 (t, J=8.70 Hz, 2H), 7.21-7.26 (m, 1H), 7.65 (dd, J=8.85, 4.58 Hz, 1H). ESI+ m/z 442 (M+H)+.

Example 143

1-[(4R)-6-fluoro-3,4-dihydrospiro[chromene-2,1'-cyclobutan]-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.69-1.78 (m, 1H), 1.81-1.87 (m, 2H), 2.06-2.21 (m, 3H), 2.28 (q, J=9.97 Hz, 1H), 2.37 (dd, J=13.12, 5.80 Hz, 1H), 2.70-2.81 (m, 2H), 3.01 (dd, J=16.48, 6.10 Hz, 1H), 3.10 (dd, J=16.48, 6.10 Hz, 1H), 4.56-4.61 (m, 1H), 4.93 (dd, J=10.07, 5.80 Hz, 1H), 6.82 (dd, J=8.85, 4.88 Hz, 1H), 6.92 (t, J=8.85 Hz, 1H), 6.98-7.04 (m, 2H), 7.70 (dd, J=8.85, 4.58 Hz, 1H). ESI+ m/z 401 (M+H)+.

Example 144

1-[(4R)-7-chloro-8-fluoro-2,2-bis(fluoromethyl)-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.97-2.04 (m, 1H), 2.34 (dd, J=13.73, 5.80 Hz, 1H), 2.69-2.81 (m, 2H), 2.99-3.03 (m, 1H), 3.09 (dd, J=16.48, 6.10 Hz, 1H), 4.56-4.78 (m, 5H), 5.02 (dd, J=10.83, 5.95 Hz, 1H), 6.91 (t, J=8.70 Hz, 1H), 7.12-7.18 (m, 2H), 7.66 (dd, J=8.85, 4.58 Hz, 1H). ESI+ m/z 458 (M+H)+.

Example 145

1-[(4R)-2,2-dimethyl-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.28 (s, 3H), 1.39 (s, 3H), 1.67-1.73 (m, 1H), 2.14 (dd, J=13.12, 6.10 Hz, 1H), 2.69-2.80 (m, 2H), 3.00 (dd, J=16.48, 6.10 Hz, 1H), 3.05-3.11 (m, 1H), 4.55-4.60 (m, 1H), 4.95 (dd, J=10.83, 6.26 Hz, 1H), 6.74 (d, J=7.93 Hz, 1H), 6.89-6.93 (m, 2H), 7.14-7.18 (m, 1H), 7.26 (d, J=7.63 Hz, 1H), 7.72 (dd, J=8.85, 4.58 Hz, 1H). ESI+ m/z 371 (M+H)+.

Example 146

1-[(4R)-6-fluoro-2,2-dimethyl-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.27 (s, 3H), 1.39 (s, 3H), 1.70 (dd, J=13.12, 11.29 Hz, 1H), 2.14 (dd, J=13.27, 6.26 Hz, 1H), 2.70-2.81 (m, 2H), 3.01 (dd, J=16.48, 5.80 Hz, 1H), 3.09 (dd, J=16.48, 6.10 Hz, 1H), 4.56-4.60 (m, 1H), 4.93 (dd, J=10.98, 6.10 Hz, 1H), 6.77 (dd, J=8.70, 4.73 Hz, 1H), 6.92 (t, J=8.70 Hz, 1H), 6.98-7.04 (m, 2H), 7.69 (dd, J=8.85, 4.58 Hz, 1H). ESI+ m/z 389 (M+H)+.

Example 147

1-[(4R)-8-chloro-7-fluoro-2,2-dimethyl-3,4-dihydro-2H-chromen-4-yl]-3-[(2S)-7-fluoro-2-hydroxy-2,3-dihydro-1H-inden-4-yl]urea $^1$H NMR (500 MHz, DMSO-$d_6$/D$_2$O) δ ppm 1.32 (s, 3H), 1.47 (s, 3H), 1.78 (dd, J=13.43, 11.29 Hz, 1H), 2.18 (dd, J=13.27, 6.26 Hz, 1H), 2.69-2.81 (m, 2H), 3.00 (dd, J=16.48, 6.10 Hz, 1H), 3.09 (dd, J=16.17, 6.10 Hz, 1H), 4.56-4.60 (m, 1H), 4.97 (dd, J=10.98, 6.10 Hz, 1H), 6.89-6.98 (m, 2H), 7.27 (dd, J=7.78, 6.56 Hz, 1H), 7.69 (dd, J=8.85, 4.58 Hz, 1H). ESI$^+$ m/z 423 (M+H)$^+$.

Example 148

1-[(2S)-7-fluoro-2-hydroxy-2,3-dihydro-1H-inden-4-yl]-3-[(4R)-1-methyl-7-(trifluoromethyl)-1,2,3,4-tetrahydroquinolin-4-yl]urea $^1$H NMR (500 MHz, DMSO-d$_6$/D$_2$O) δ ppm 1.90-2.03 (m, 2H), 2.66 (dd, J=16.32, 2.90 Hz, 1H), 2.77 (dd, J=16.32, 2.90 Hz, 1H), 2.94 (s, 3H), 2.94-2.99 (m, 1H), 3.08 (dd, J=16.32, 5.95 Hz, 1H), 3.23-3.29 (m, 1H), 3.33-3.38 (m, 1H), 4.54-4.59 (m, 1H), 4.83 (t, J=5.03 Hz, 1H), 6.81 (s, 1H), 6.88-6.92 (m, 2H), 7.30 (d, J=7.93 Hz, 1H), 7.73 (dd, J=9.00, 4.42 Hz, 1H). ESI$^+$ m/z 424 (M+H)$^+$.

Example 149

1-[(4R)-7-chloro-2,2-dimethyl-3,4-dihydro-2H-chromen-4-yl]-3-[(2S)-7-fluoro-2-hydroxy-2,3-dihydro-1H-inden-4-yl]urea $^1$H NMR (500 MHz, DMSO-d$_6$/D$_2$O) δ ppm 1.28 (s, 3H), 1.40 (s, 3H), 1.72 (dd, J=13.12, 11.29 Hz, 1H), 2.15 (dd, J=13.27, 6.26 Hz, 1H), 2.71 (dd, J=16.48, 2.75 Hz, 1H), 2.78 (dd, J=16.32, 2.90 Hz, 1H), 3.00 (dd, J=16.48, 6.10 Hz, 1H), 3.09 (dd, J=16.32, 5.95 Hz, 1H), 4.55-4.61 (m, 1H), 4.93 (dd, J=10.98, 6.10 Hz, 1H), 6.81 (d, J=2.14 Hz, 1H), 6.91 (t, J=8.85 Hz, 1H), 6.96 (dd, J=8.54, 2.14 Hz, 1H), 7.28 (d, J=9.15 Hz, 1H), 7.70 (dd, J=8.85, 4.58 Hz, 1H). ESI$^+$ m/z 405 (M+H)$^+$.

Example 150

1-[(2S)-7-fluoro-2-hydroxy-2,3-dihydro-1H-inden-4-yl]-3-[(4R)-7-(trifluoromethoxy)-3,4-dihydro-2H-chromen-4-yl]urea $^1$H NMR (500 MHz, DMSO-d$_6$/D$_2$O) δ ppm 1.94-2.01 (m, 1H), 2.08-2.16 (m, 1H), 2.67 (dd, J=16.48, 3.05 Hz, 1H), 2.77 (dd, J=16.17, 2.75 Hz, 1H), 2.97 (dd, J=16.32, 5.95 Hz, 1H), 3.08 (dd, J=16.48, 6.10 Hz, 1H), 4.15-4.21 (m, 1H), 4.30-4.36 (m, 1H), 4.54-4.59 (m, 1H), 4.88 (q, J=5.59 Hz, 1H), 6.80 (d, J=1.53 Hz, 1H), 6.88-6.99 (m, 2H), 7.40 (d, J=8.54 Hz, 1H), 7.72 (dd, J=9.00, 4.42 Hz, 1H). ESI$^+$ m/z 427 (M+H)$^+$.

Example 151

1-[(4R)-2,2-bis(fluoromethyl)-3,4-dihydro-2H-chromen-4-yl]-3-[(2S)-7-fluoro-2-hydroxy-2,3-dihydro-1H-inden-4-yl]urea $^1$H NMR (500 MHz, DMSO-d$_6$/D$_2$O) δ ppm 1.91-1.98 (m, 1H), 2.29 (dd, J=13.88, 5.95 Hz, 1H), 2.69-2.81 (m, 2H), 3.00 (dd, J=16.48, 6.10 Hz, 1H), 3.09 (dd, J=16.32, 5.95 Hz, 1H), 4.54-4.61 (m, 1H), 4.62-4.71 (m, 2H), 4.98 (dd, J=10.22, 5.95 Hz, 1H), 6.87-6.93 (m, 2H), 7.00 (t, J=7.32 Hz, 1H), 7.23 (t, J=6.87 Hz, 1H), 7.29 (d, J=7.63 Hz, 1H), 7.70 (dd, J=8.85, 4.58 Hz, 1H). ESI$^+$ m/z 407 (M+H)$^+$.

Example 152

1-[(4R)-8-fluoro-2,2-bis(fluoromethyl)-3,4-dihydro-2H-chromen-4-yl]-3-[(2S)-7-fluoro-2-hydroxy-2,3-dihydro-1H-inden-4-yl]urea $^1$H NMR (500 MHz, DMSO-d$_6$/D$_2$O) δ ppm 1.97-2.03 (m, 1H), 2.33 (dd, J=13.88, 5.95 Hz, 1H), 2.69-2.81 (m, 2H), 3.01 (dd, J=16.48, 6.10 Hz, 1H), 3.09 (dd, J=16.32, 5.95 Hz, 1H), 4.56-4.76 (m, 5H), 5.03 (dd, J=10.53, 5.95 Hz, 1H), 6.91 (t, J=8.70 Hz, 1H), 6.95-7.00 (m, 1H), 7.11 (d, J=7.32 Hz, 1H) 7.15-7.19 (m, 1H), 7.68 (dd, J=8.85, 4.58 Hz, 1H). ESI$^+$ m/z 425 (M+H)$^+$.

Example 153

1-[(4R)-7,8-difluoro-2,2-dimethyl-3,4-dihydro-2H-chromen-4-yl]-3-[(2S)-7-fluoro-2-hydroxy-2,3-dihydro-1H-inden-4-yl]urea $^1$H NMR (500 MHz, DMSO-d$_6$/D$_2$O) δ ppm 1.33 (s, 3H), 1.46 (s, 3H), 1.78 (dd, J=13.27, 11.44 Hz, 1H), 2.18 (dd, J=13.43, 6.10 Hz, 1H), 2.69-2.80 (m, 2H), 3.00 (dd, J=16.32, 5.95 Hz, 1H), 3.09 (dd, J=16.32, 5.95 Hz, 1H), 4.55-4.61 (m, 1H), 4.91-5.02 (m, 1H), 6.80-6.83 (m, 1H), 6.89-6.97 (m, 2H), 7.06-7.14 (m, 1H), 7.66-7.72 (m, 1H). ESI$^+$ m/z 407 (M+H)$^+$.

Example 154

1-[(4R)-2,2-dimethyl-8-(trifluoromethoxy)-3,4-dihydro-2H-chromen-4-yl]-3-[(2S)-7-fluoro-2-hydroxy-2,3-dihydro-1H-inden-4-yl]urea $^1$H NMR (500 MHz, DMSO-d$_6$/D$_2$O) δ ppm 1.29 (s, 3H), 1.43 (s, 3H), 1.78 (dd, J=13.43, 10.98 Hz, 1H), 2.19 (dd, J=13.43, 6.41 Hz, 1H), 2.68-2.81 (m, 2H), 3.00 (dd, J=16.32, 5.95 Hz, 1H), 3.09 (dd, J=16.32, 5.95 Hz, 1H), 4.55-4.60 (m, 1H), 5.00 (dd, J=10.83, 6.26 Hz, 1H), 6.91 (t, J=8.70 Hz, 1H), 6.96-7.00 (m, 1H), 7.24 (d, J=7.93 Hz, 1H), 7.30 (d, J=7.63 Hz, 1H), 7.70 (dd, J=8.85, 4.58 Hz, 1H). ESI$^+$ m/z 454 (M+H)$^+$.

Example 155

1-(7-fluoro-2-hydroxy-2,3-dihydro-1H-inden-4-yl)-3-[5-(trifluoromethyl)-2,3-dihydro-1H-inden-1-yl]urea $^1$H NMR (500 MHz, DMSO-d$_6$/D$_2$O) δ ppm 1.78-1.88 (m, 1H), 2.48-2.52 (m, 1H), 2.69 (dd, J=16.32, 2.90 Hz, 1H), 2.78 (dd, J=16.32, 2.90 Hz, 1H), 2.86-2.93 (m, 1H), 2.96-3.05 (m, 2H), 3.09 (dd, J=16.32, 5.95 Hz, 1H), 4.55-4.61 (m, 1H), 5.22 (t, J=7.78 Hz, 1H), 6.91 (t, J=8.85 Hz, 1H), 7.49 (d, J=7.93 Hz, 1H), 7.58 (d, J=7.93 Hz, 1H), 7.63 (s, 1H), 7.71 (dd, J=8.85, 4.58 Hz, 1H). ESI$^+$ m/z 395 (M+H)$^+$.

Example 156

1-[(4R)-2,2-dimethyl-8-(trifluoromethyl)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.31 (s, 3H), 1.43 (s, 3H), 1.82 (dd, J=13.27, 11.14 Hz, 1H), 2.21 (dd, J=13.27, 6.26 Hz, 1H), 2.71 (dd, J=16.48, 2.75 Hz, 1H), 2.78 (dd, J=16.32, 2.90 Hz, 1H), 3.02 (dd, J=16.63, 5.95 Hz, 1H), 3.09 (dd, J=16.48, 6.10 Hz, 1H), 4.56-4.61 (m, 1H), 5.00 (dd, J=10.98, 6.41 Hz, 1H), 6.92 (t, J=8.70 Hz, 1H), 7.06 (t, J=7.78 Hz, 1H), 7.53 (dd, J=16.94, 7.48 Hz, 2H), 7.68 (dd, J=8.85, 4.58 Hz, 1H). ESI+ m/z 439 (M+H)+.

Example 157

1-[(4R)-8-fluoro-2,2-dimethyl-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.31 (s, 3H), 1.44 (s, 3H), 1.77 (dd, J=13.27, 11.14 Hz, 1H), 2.15-2.21 (m, 1H), 2.70 (dd, J=16.48, 2.75 Hz, 1H), 2.78 (dd, J=16.48, 2.75 Hz, 1H), 3.02 (dd, J=16.63, 5.95 Hz, 1H), 3.09 (dd, J=16.32, 5.95 Hz, 1H), 4.56-4.60 (m, 1H), 4.98 (dd, J=10.98, 6.10 Hz, 1H), 6.86-6.93 (m, 2H), 7.08-7.12 (m, 2H), 7.69 (dd, J=8.85, 4.58 Hz, 1H). ESI+ m/z 389 (M+H)+.

Example 158

1-[(4R)-7-fluoro-2,2-dimethyl-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.28 (s, 3H), 1.40 (s, 3H), 1.71 (dd, J=13.12, 10.98 Hz, 1H), 2.15 (dd, J=13.43, 6.10 Hz, 1H), 2.70 (dd, J=16.32, 2.90 Hz, 1H), 2.78 (dd, J=16.48, 2.75 Hz, 1H), 3.01 (dd, J=16.63, 5.95 Hz, 1H), 3.09 (dd, J=16.48, 6.10 Hz, 1H), 4.56-4.60 (m, 1H), 4.92 (dd, J=10.68, 6.10 Hz, 1H), 6.59 (dd, J=10.53, 2.59 Hz, 1H), 6.73-6.77 (m, 1H), 6.91 (t, J=8.70 Hz, 1H), 7.26-7.30 (m, 1H), 7.70 (dd, J=8.85, 4.58 Hz, 1H). ESI+ m/z 427 (M+H)+.

Example 159

1-[(4R)-2,2-bis(fluoromethyl)-7-(trifluoromethoxy)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.95-2.02 (m, 1H), 2.31 (dd, J=13.73, 5.80 Hz, 1H), 2.70 (dd, J=16.32, 2.90 Hz, 1H), 2.78 (dd, J=16.48, 2.75 Hz, 1H), 2.99-3.05 (m, 1H), 3.09 (dd, J=16.17, 6.10 Hz, 1H), 4.56-4.74 (m, 5H), 5.00 (dd, J=10.53, 5.95 Hz, 1H), 6.89 (d, J=1.53 Hz, 1H), 6.91 (t, J=8.85 Hz, 1H), 7.00 (dd, J=8.54, 1.53 Hz, 1H), 7.40 (d, J=8.54 Hz, 1H), 7.67 (dd, J=8.85, 4.58 Hz, 1H). ESI+ m/z 490 (M+H)+.

Example 160

1-[(4R)-2,2-dimethyl-7-(trifluoromethyl)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.31 (s, 3H), 1.43 (s, 3H), 1.78 (dd, J=13.12, 11.60 Hz, 1H), 2.19 (dd, J=13.27, 6.26 Hz, 1H), 2.71 (dd, J=16.48, 2.75 Hz, 1H), 2.79 (dd, J=16.17, 2.75 Hz, 1H), 3.02 (dd, J=16.63, 5.95 Hz, 1H), 3.10 (dd, J=16.32, 5.95 Hz, 1H), 4.56-4.61 (m, 1H), 5.01 (dd, J=11.14, 6.26 Hz, 1H), 6.92 (t, J=8.70 Hz, 1H), 7.05 (d, J=1.53 Hz, 1H), 7.23-7.26 (m, 1H), 7.49 (d, J=7.93 Hz, 1H), 7.69 (dd, J=8.85, 4.58 Hz, 1H). ESI+ m/z 439 (M+H)+.

Example 161

1-[(4R)-6-fluoro-2,2-bis(fluoromethyl)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.89-1.96 (m, 1H), 2.30 (dd, J=13.73, 5.80 Hz, 1H), 2.71 (dd, J=16.32, 2.90 Hz, 1H), 2.78 (dd, J=16.32, 2.90 Hz, 1H), 3.03 (dd, J=16.48, 6.10 Hz, 1H), 3.10 (dd, J=16.32, 5.95 Hz, 1H), 4.54-4.61 (m, 3H), 4.63-4.71 (m, 2H), 4.97 (dd, J=10.68, 6.10 Hz, 1H), 6.89-6.94 (m, 2H), 7.03-7.09 (m, 2H), 7.66 (dd, J=8.85, 4.58 Hz, 1H). ESI+ m/z 424 (M+H)+.

Example 162

1-[(4R)-6,8-difluoro-2,2-bis(fluoromethyl)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.97-2.04 (m, 1H), 2.34 (dd, J=13.73, 5.80 Hz, 1H), 2.71 (dd, J=16.32, 2.90 Hz, 1H), 2.78 (dd, J=16.17, 2.75 Hz, 1H), 3.03 (dd, J=16.48, 6.10 Hz, 1H), 3.09 (dd, J=16.32, 5.95 Hz, 1H), 4.56-4.61 (m, 2H), 4.63-4.77 (m, 3H), 5.00 (dd, J=10.98, 6.10 Hz, 1H), 6.89-6.94 (m, 2H), 7.20-7.27 (m, 1H), 7.64 (dd, J=9.00, 4.73 Hz, 1H). ESI+ m/z 442 (M+H)+.

Example 163

1-[(4R)-6-fluoro-3,4-dihydrospiro[chromene-2,1'-cyclobutan]-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.67-1.78 (m, 1H), 1.80-1.86 (m, 2H), 2.06-2.21 (m, 3H), 2.25-2.32 (m, 1H), 2.37 (dd, J=13.27, 5.95 Hz, 1H), 2.70 (dd, J=16.48, 2.75 Hz, 1H), 2.79 (dd, J=16.17, 2.75 Hz, 1H), 3.03 (dd, J=16.48, 6.10 Hz, 1H), 3.10 (dd, J=16.32, 5.95 Hz, 1H), 4.57-4.61 (m, 1H), 4.93 (dd, J=10.22, 5.95 Hz, 1H), 6.82 (dd, J=8.85, 4.88 Hz, 1H), 6.92 (t, J=8.70 Hz, 1H), 6.97-7.03 (m, 2H), 7.70 (dd, J=8.85, 4.58 Hz, 1H). ESI+ m/z 401 (M+H)+.

Example 164

1-[(4R)-2,2-dimethyl-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.28 (s, 3H), 1.39 (s, 3H), 1.71 (dd, J=13.12, 10.98 Hz, 1H), 2.14 (dd, J=13.12, 6.10 Hz, 1H), 2.70 (dd, J=16.32, 2.90 Hz, 1H), 2.78 (dd, J=16.17, 2.75 Hz, 1H), 3.01 (dd, J=16.48, 6.10 Hz, 1H), 3.09 (dd, J=16.32, 5.95 Hz, 1H), 4.55-4.61 (m, 1H), 4.95 (dd, J=10.68, 6.10 Hz, 1H), 6.74 (d, J=8.24 Hz, 1H), 6.88-6.93 (m, 2H), 7.13-7.18 (m, 1H), 7.26 (d, J=7.63 Hz, 1H), 7.71 (dd, J=8.85, 4.58 Hz, 1H). ESI+ m/z 371 (M+H)+.

Example 165

1-[(4R)-6-fluoro-2,2-dimethyl-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.27 (s, 3H), 1.39 (s, 3H), 1.70 (dd, J=13.12, 11.29 Hz, 1H), 2.14 (dd, J=13.12, 6.10 Hz, 1H), 2.70 (dd, J=16.48, 2.75 Hz, 1H), 2.78

(dd, J=16.32, 2.90 Hz, 1H), 3.03 (dd, J=16.63, 5.95 Hz, 1H), 3.10 (dd, J=16.32, 5.95 Hz, 1H), 4.56-4.61 (m, 1H), 4.93 (dd, J=10.98, 6.41 Hz, 1H), 6.77 (dd, J=9.00, 5.03 Hz, 1H), 6.92 (t, J=8.70 Hz, 1H), 6.98-7.03 (m, 2H), 7.68 (dd, J=8.85, 4.58 Hz, 1H). ESI$^+$ m/z 389 (M+H)$^+$.

Example 166

1-[(4R)-8-chloro-7-fluoro-2,2-dimethyl-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.31 (s, 3H), 1.47 (s, 3H), 1.78 (dd, J=13.12, 11.29 Hz, 1H), 2.19 (dd, J=13.43, 6.10 Hz, 1H), 2.70 (dd, J=16.32, 2.90 Hz, 1H), 2.78 (dd, J=16.17, 2.75 Hz, 1H), 3.02 (dd, J=16.48, 5.80 Hz, 1H), 3.09 (dd, J=16.32, 5.95 Hz, 1H), 4.56-4.60 (m, 1H), 4.94-5.00 (m, 1H), 6.82 (dd, J=8.54, 4.27 Hz, 1H), 6.89-6.97 (m, 2H), 7.26 (dd, J=8.39, 6.87 Hz, 1H), 7.65-7.71 (m, 1H). ESI$^+$ m/z 423 (M+H)$^+$.

Example 167

1-[(4R)-7-chloro-2,2-dimethyl-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.28 (s, 3H), 1.40 (s, 3H), 1.72 (dd, J=13.27, 11.14 Hz, 1H), 2.15 (dd, J=13.12, 6.10 Hz, 1H), 2.70 (dd, J=16.48, 3.05 Hz, 1H), 2.78 (dd, J=16.32, 2.90 Hz, 1H), 3.01 (dd, J=16.48, 6.10 Hz, 1H), 3.09 (dd, J=16.32, 5.95 Hz, 1H), 4.55-4.59 (m, 1H), 4.93 (dd, J=10.68, 6.41 Hz, 1H), 6.81 (d, J=2.14 Hz, 1H), 6.91 (t, J=8.70 Hz, 1H), 6.94-6.98 (m, 1H) 7.27 (d, J=8.24 Hz, 1H), 7.69 (dd, J=8.85, 4.58 Hz, 1H). ESI$^+$ m/z 405 (M+H)$^+$.

Example 168

1-[(2R)-7-fluoro-2-hydroxy-2,3-dihydro-1H-inden-4-yl]-3-[(4R)-7-(trifluoromethoxy)-3,4-dihydro-2H-chromen-4-yl]urea $^1$H NMR (500 MHz, DMSO-d$_6$/D$_2$O) δ ppm 1.95-2.01 (m, 1H), 2.08-2.16 (m, 1H), 2.67 (dd, J=16.32, 2.90 Hz, 1H), 2.77 (dd, J=16.32, 2.90 Hz, 1H), 2.98 (dd, J=16.48, 6.10 Hz, 1H), 3.08 (dd, J=16.32, 5.95 Hz, 1H), 4.16-4.21 (m, 1H), 4.30-4.36 (m, 1H), 4.54-4.59 (m, 1H), 4.88 (t, J=5.49 Hz, 1H), 6.80 (d, J=1.22 Hz, 1H), 6.88-6.94 (m, 2H), 7.39 (d, J=9.15 Hz, 1H), 7.72 (dd, J=9.00, 4.73 Hz, 1H). ESI$^+$ m/z 427 (M+H)$^+$.

Example 169

1-[(4R)-2,2-bis(fluoromethyl)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.90-1.98 (m, 1H), 2.27-2.32 (m, 1H), 2.70 (dd, J=16.02, 2.90 Hz, 1H), 2.78 (dd, J=16.02, 2.90 Hz, 1H), 3.02 (dd, J=16.32, 6.26 Hz, 1H), 3.09 (dd, J=16.17, 5.80 Hz, 1H), 4.63-4.61 (m, 3H), 4.53-4.61 (m, 2H), 4.95-5.00 (m, 1H), 6.87-6.93 (m, 2H), 6.98-7.01 (m, 1H), 7.23 (t, J=7.48 Hz, 1H), 7.29 (d, J=7.63 Hz, 1H), 7.69 (dd, J=8.54, 4.58 Hz, 1H). ESI$^+$ m/z 407 (M+H)$^+$.

Example 170

1-[(4R)-8-fluoro-2,2-bis(fluoromethyl)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.97-2.03 (m, 1H), 2.33 (dd, J=13.88, 5.95 Hz, 1H), 2.70 (dd, J=16.32, 2.90 Hz, 1H), 2.78 (dd, J=16.32, 2.90 Hz, 1H), 3.02 (dd, J=16.63, 5.95 Hz, 1H), 3.09 (dd, J=16.32, 5.95 Hz, 1H), 4.56-4.60 (m, 1H), 4.60-4.76 (m, 4H), 5.02 (dd, J=10.53, 5.95 Hz, 1H), 6.91 (t, J=8.70 Hz, 1H), 6.95-6.99 (m, 1H), 7.11 (d, J=7.93 Hz, 1H), 7.17 (dd, J=10.83, 8.39 Hz, 1H), 7.67 (dd, J=8.85, 4.58 Hz, 1H). ESI$^+$ m/z 425 (M+H)$^+$.

Example 171

1-[(4R)-7,8-difluoro-2,2-dimethyl-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.32 (s, 3H), 1.46 (s, 3H), 1.78 (dd, J=13.43, 11.29 Hz, 1H), 2.18 (dd, J=13.43, 6.10 Hz, 1H), 2.70 (dd, J=16.32, 2.90 Hz, 1H), 2.78 (dd, J=16.17, 2.75 Hz, 1H), 3.01 (dd, J=16.48, 6.10 Hz, 1H), 3.09 (dd, J=16.17, 6.10 Hz, 1H), 4.55-4.61 (m, 1H), 4.95 (dd, J=10.98, 6.10 Hz, 1H), 6.88-6.98 (m, 2H), 7.09 (t, J=7.48 Hz, 1H), 7.68 (dd, J=8.85, 4.58 Hz, 1H). ESI$^+$ m/z 407 (M+H)$^+$.

Example 172

1-[(4R)-2,2-dimethyl-8-(trifluoromethoxy)-3,4-dihydro-2H-chromen-4-yl]-3-[(2R)-7-fluoro-2-hydroxy-2,3-dihydro-1H-inden-4-yl]urea $^1$H NMR (500 MHz, DMSO-d$_6$/D$_2$O) δ ppm 1.90-1.98 (m, 1H), 2.30 (dd, J=13.73, 5.80 Hz, 1H), 2.70 (dd, J=16.32, 2.90 Hz, 1H), 2.78 (dd, J=16.17, 2.75 Hz, 1H), 3.02 (dd, J=16.32, 5.95 Hz, 1H), 3.09 (dd, J=16.17, 6.10 Hz, 1H), 4.54-4.61 (m, 3H), 4.62-4.73 (m, 2H), 4.97 (dd, J=10.68, 5.80 Hz, 1H), 6.91 (t, J=8.85 Hz, 1H), 6.97 (d, J=2.14 Hz, 1H) 7.04-7.06 (m, 1H), 7.30 (d, J=8.54 Hz, 1H), 7.67 (dd, J=8.85, 4.58 Hz, 1H). ESI$^+$ m/z 440 (M+H)$^+$.

Example 173

1-[(2R)-7-fluoro-2-hydroxy-2,3-dihydro-1H-inden-4-yl]-3-[(4R)-8-(trifluoromethyl)-3,4-dihydro-2H-chromen-4-yl]urea $^1$H NMR (500 MHz, DMSO-d$_6$/D$_2$O) δ ppm 1.29 (s, 3H), 1.43 (s, 3H), 1.78 (dd, J=13.12, 10.98 Hz, 1H), 2.19 (dd, J=13.43, 6.10 Hz, 1H), 2.70 (dd, J=16.48, 2.75 Hz, 1H), 2.78 (dd, J=16.48, 2.75 Hz, 1H), 3.02 (dd, J=16.48, 5.80 Hz, 1H), 3.09 (dd, J=16.32, 5.95 Hz, 1H), 4.55-4.61 (m, 1H), 4.99 (dd, J=10.83, 6.26 Hz, 1H), 6.84-6.87 (m, 1H), 6.91 (t, J=8.70 Hz, 1H), 6.98 (t, J=7.93 Hz, 1H), 7.24 (d, J=7.93 Hz, 1H), 7.30 (d, J=7.93 Hz, 1H), 7.68 (dd, J=9.00, 4.73 Hz, 1H). ESI$^+$ m/z 454 (M+H)$^+$.

Example 174

1-(5-chloro-2,3-dihydro-1H-inden-1-yl)-3-(7-fluoro-2-hydroxy-2,3-dihydro-1H-inden-4-yl)urea $^1$H NMR (500 MHz, DMSO-d$_6$/D$_2$O) δ ppm 1.99-2.06 (m, 1H), 2.12-2.20 (m, 1H), 2.67 (dd, J=16.32, 2.90 Hz, 1H), 2.77

(dd, J=16.48, 2.75 Hz, 1H), 2.98 (dd, J=16.48, 6.10 Hz, 1H), 3.08 (dd, J=16.32, 5.95 Hz, 1H), 4.24-4.29 (m, 1H), 4.40-4.45 (m, 1H), 4.54-4.60 (m, 1H), 4.94 (t, J=5.49 Hz, 1H), 6.91 (t, J=8.70 Hz, 1H), 7.08 (t, J=7.63 Hz, 1H), 7.55 (t, J=7.63 Hz, 2H), 7.72 (dd, J=8.85, 4.58 Hz, 1H). ESI+ m/z 410 (M+H)$^+$.

Example 175

1-[(4R)-7-chloro-2,2-bis(fluoromethyl)-3,4-dihydro-2H-chromen-4-yl]-3-[(2R)-5-fluoro-2-hydroxy-2,3-dihydro-1H-inden-4-yl]urea $^1$H NMR (300 MHz, DMSO-d$_6$) δ 7.98 (s, 1H), 7.29 (d, J=8.3 Hz, 1H), 7.09-6.91 (m, 4H), 6.68 (d, J=8.4 Hz, 1H), 5.03-4.90 (m, 1H), 4.85 (d, J=3.9 Hz, 1H), 4.74-4.67 (m, 2H), 4.54 (bs, 2H), 3.11-2.98 (m, 2H), 2.77-2.65 (m, 2H), 2.26 (dd, J=13.6, 6.1 Hz, 1H), 1.22 (d, J=11.0 Hz, 1H), 1.16 (d, J=7.1 Hz, 1H). MS (ESI$^+$) m/z 441 (M+H)$^+$.

Example 176

1-[(4R)-7-chloro-2,2-bis(fluoromethyl)-3,4-dihydro-2H-chromen-4-yl]-3-[(2S)-5-fluoro-2-hydroxy-2,3-dihydro-1H-inden-4-yl]urea $^1$H NMR (400 MHz, DMSO-d$_6$) δ 7.98 (s, 1H), 7.29 (dd, J=8.3, 1.0 Hz, 1H), 7.08-6.93 (m, 4H), 6.68 (d, J=8.4 Hz, 1H), 5.01-4.91 (m, 1H), 4.86 (d, J=4.0 Hz, 1H), 4.73-4.66 (m, 2H), 4.61-4.45 (m, 2H), 3.09-2.99 (m, 2H), 2.76-2.65 (m, 2H), 2.26 (dd, J=13.7, 6.0 Hz, 1H), 2.05-1.94 (m, 1H), 1.17 (t, J=7.1 Hz, 1H). MS (DCI$^+$) m/z 458 (M+NH$_4$)$^+$.

E. BIOLOGICAL DATA (i) Capsaicin Activation Assay

Dulbecco's modified Eagle medium (DMEM) (with 4.5 mg/mL glucose) and fetal bovine serum were obtained from Hyclone Laboratories, Inc. (Logan, Utah). Dulbecco's phosphate-buffered saline (DPBS) (with 1 mg/mL glucose and 3.6 mg/l Na pyruvate, without phenol red), L-glutamine, hygromycin B, and Lipofectamine® were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)-methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNA for human TRPV1 (hTRPV1) was isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pCIneo mammalian expression vector (Promega) and fully sequenced using fluorescent dye-terminator reagents (Prism, PerkinElmer Applied Biosystems Division) and a PerkinElmer Applied Biosystems Model 373 DNA sequencer or Model 310 genetic analyzer. Expression plasmids encoding the hTRPV1 cDNA were transfected into HEK293 cells using Lipofectamine®. Forty-eight hours after transfection, the neomycin-resistant cells were selected with growth medium containing 800 µg/mL Geneticin (Life Technologies, formerly Gibco BRL). Surviving individual colonies were isolated and screened for TRPV1 activity. Cells expressing recombinant TRPV1 were maintained at 37° C. in DMEM containing 4 mM L-glutamine, 300 µg/mL G418 (Calbiochem) and 10% fetal bovine serum under a humidified 5% CO$_2$ atmosphere.

The functional activity of compounds at the TRPV1 receptor was determined by measurement of intracellular Ca$^{2+}$ levels ([Ca$^{2+}$]$_i$) using the Fluorescence Imaging Plate Reader (FLIPR)TETRA®. All compounds were tested over a 12-point one-third-log concentration range. Compound stocks, 10 mM, were prepared in DMSO, and diluted serially across a 384-well plate using a Bravo BenchCel workstation (Agilent Technologies, Santa Clara, Calif.). A stock concentration of capsaicin (10 mM) was made in DMSO, and diluted in DPBS to a final concentration of 200 nM (4×). On the day prior to the experiment, the recombinant HEK293 cells expressing human TRPV1 (hTRPV1) were removed from tissue culture flasks and plated in growth medium into black-walled clear-bottom 384-well Biocoat™ poly-D-lysine assay plates (BD Biosciences, Bedford, Mass.) using a Multidrop® dispenser (ThermoScientific, Waltham, Mass.). On the day of the experiment, growth medium was removed, and the no-wash FLIPR® Calcium-4 dye ($\lambda_{EX}$=470-495 nm, $\lambda_{EM}$=515-575 nm; Molecular Devices, Sunnyvale, Calif.) was added to each well using the Multidrop® dispenser. The plated cells were incubated for 90-120 minutes in the dark at room temperature and then test compound was added to each well. Three minutes later, 200 nM capsaicin (4×) solution was added to each well in an amount sufficient to provide a final assay volume of 80 µL and capsaicin concentration of 50 nM. Fluorescence readings were made at 1 to 5 second intervals over the course of the experimental run. The peak increase in relative fluorescence units (minus baseline) was calculated, and expressed as a percentage of the 50 nM capsaicin (control) response. Curve-fits of the data were solved using a four-parameter logistic Hill equation in GraphPad Prism® (GraphPad Software, Inc., San Diego, Calif.), and IC$_{50}$ values (concentration of the test compounds that inhibits 50% of the intracellular Ca$^{2+}$ concentration increase induced by capsaicin) were calculated.

Selected compounds also were tested in 1321N1 cells expressing recombinant human TRPV1 as a confirmation of potency in a cell line of neuronal lineage. The cDNA for human TRPV1 (hTRPV1) was isolated and the resulting cDNA PCR products were subcloned into pCIneo mammalian expression vector (Promega) as discussed above. Expression plasmids encoding the hTRPV1 cDNA were transfected into 1321N1 human astrocytoma cells using Lipofectamine®. Forty-eight hours after transfection, the neomycin-resistant cells were selected with growth medium containing 800 µg/mL Geneticin (Life Technologies, formerly Gibco BRL). Surviving individual colonies were isolated and screened for TRPV1 activity. Cells expressing recombinant TRPV1 were maintained at 37° C. in DMEM containing 4 mM L-glutamine, 300 µg/mL G418 (Calbiochem) and 10% fetal bovine serum under a humidified 5% CO$_2$ atmosphere.

Table 1 reports the IC$_{50}$ values calculated for the compounds tested in the recombinant HEK293 cell assay. Many of the compounds exhibited an IC$_{50}$ (cap) value less than about 1000 nM, for example, in the range of about 500 nM to about 1000 nM, or in the range of about 100 to about 500 nM, or in the range of about less than 100 nM. As illustrated by the data in Table 1, the claimed compounds are TRPV1 antagonists that inhibit an increase in cellular calcium in response to capsaicin (50 nM) addition.

(ii) Acid Activation Assay

Dulbecco's modified Eagle's medium (DMEM) with 4.5 mg/mL D-glucose, fetal bovine serum, L-glutamine, and 2-morpholinoethanesulfonic acid (MES) were purchased from Sigma-Aldrich Co. (St. Louis, Mo.). Dulbecco's phosphate-buffered saline (DPBS) with $Ca^{2+}$, $Mg^{2+}$, and 1 mg/mL D-glucose (pH 7.4), Geneticin®, 0.25% trypsin-1 mM EDTA, and penicillin-streptomycin were purchased from Invitrogen Corp. (Carlsbad, Calif.). The FLIPR® Calcium 4 assay kit was purchased from Molecular Devices (Sunnyvale, Calif.).

The cDNA for human TRPV1 (hTRPV1) was isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pCIneo mammalian expression vector (Promega) and fully sequenced using fluorescent dye-terminator reagents (Prism, PerkinElmer Applied Biosystems Division) and a PerkinElmer Applied Biosystems Model 373 DNA sequencer or Model 310 genetic analyzer. Expression plasmids encoding the hTRPV1 cDNA were transfected into HEK293 cells using Lipofectamine®. Forty-eight hours after transfection, the neomycin-resistant cells were selected with growth medium containing 800 μg/mL Geneticin (Life Technologies, formerly Gibco BRL). Surviving individual colonies were isolated and screened for TRPV1 activity. Cells expressing recombinant TRPV1 were maintained at 37° C. in DMEM containing 4 mM L-glutamine, 300 μg/mL G418 (Calbiochem) and 10% fetal bovine serum under a humidified 5% $CO_2$ atmosphere.

The functional activity of compounds at the TRPV1 receptor was determined by measurement of intracellular $Ca^{2+}$ levels ($[Ca^{2+}]_i$) using the Fluorescence Imaging Plate Reader (FLIPR)TETRA®. All compounds were tested over a 12-point one-half-log concentration range with 37.5 μM being the maximum concentration tested. Compound stocks, 10 mM, were prepared in DMSO, and diluted serially across a 384-well plate using a Bravo BenchCel workstation (Agilent Technologies, Santa Clara, Calif.). On the day prior to the experiment, the recombinant HEK293 cells expressing human TRPV1 (hTRPV1) were removed from tissue culture flasks and plated in growth medium into black-walled clear-bottom 384-well Biocoat™ poly-D-lysine assay plates (BD Biosciences, Bedford, Mass.) using a Multidrop® dispenser (ThermoScientific, Waltham, Mass.). On the day of the experiment growth medium was removed, and the no-wash FLIPR® Calcium-4 dye ($\lambda_{Ex}$=470-495 nm, $\lambda_{EM}$=515-575 nm) was added to each well using the Multidrop® dispenser. The plated cells were incubated for 90-120 min in the dark at 25° C. The test compounds dissolved in DMSO were then added to the plates using an Agilent Bravo workstation (Agilent Technologies Inc., Santa Clara, Calif.). Three minutes later, a pH 5.0 solution was added to each well. Reagents were delivered at a rate of 40 μL/sec, and the final assay volume was 80 μL. Acidic pH solutions were prepared by titration of DPBS/MES with 1 N HCl. The intensity of the fluorescence was captured and digitally transferred to an interfaced PC. The maximum peak measured for the concentration range tested was used to calculate the corresponding peak increase in fluorescence over baseline (relative fluorescence units) which was expressed as the percentage (max % remain) of the maximal pH 5.0-induced response.

Table 1 reports the percentage (max % remain) of the maximal pH 5.0-induced response measured for the compounds tested in the recombinant HEK293 cell assay. Most of the compounds tested inhibited calcium flux only partially following TRPV1 activation by the pH 5.0 solution. For example, the maximum % remaining for many of the compounds tested was at least 25% (i.e., the compounds blocked the pH 5.0 induced activation of TRPV1 by no more than 75%).

(iii) Rat Tail Immersion Protocol:

Compounds were tested for their effects on noxious thermosensation using the tail immersion assay. Testing was performed one hour following oral administration of 100 μmol/kg of the compound in 10% ethanol/20% Tween-80/70% PEG-400 (2 mL/kg). Mophine (6 mg/kg) was administered interperitoneally (i.p.) using saline (2 mL/kg) as the vehicle. For testing, a circulating water bath was heated to 55° C. Thirty to sixty minutes post dosing, the rats were handled for a few seconds to calm them down and then cupped with their back against the testers hand at a slight angle with head facing away from tester. With rat in one hand and a 0.01 second stopwatch in the other hand, the tail was quickly immersed 6-8 cm in water bath or to a distance leaving 2-3 cm of tail out of water. The timer was started simultaneously. When the rat flinched or attempted withdrawal, timer was immediately stopped and the rat's tail was quickly removed from water bath. This response latency (in seconds) was recorded. Process was repeated 3 times with 3-4 minutes between readings for a final average.

For a given compound, a percent increase in the average response latency (in seconds) for tail withdrawal relative to a vehicle control was determined % increase=$[(t_c-t_v)/t_v]\times 100\%$ $t_c$=response time (in seconds) with oral dosing of compounds $t_v$=response time (in seconds) with oral dosing of vehicle The % increases in tail withdrawal latency relative to vehicle control were divided into the following categories:

+++=greater than or equal to 25% increase

++=greater than or equal to 10% but <25% increase

+=<10% increase

−=no statistically significant increase relative to vehicle control

Table 1 reports the % increase in tail withdrawal latency measured for the compounds tested. Specifically, Examples 1-24 and 29-45, Examples A-E (shown below), and morphine were tested in the rat tail immersion assay at one hour post dosing (100 μmol/kg). Many of the compounds tested imparted little or no impairment of the subject's ability to sense noxious temperature. For example, many of the compounds tested showed less than a 10% increase in tail withdrawal latency in rats when administered orally, relative to those that were dosed with vehicle.

TABLE 1

| Example | human TRPV1 capsaicin $IC_{50}$ (nM) | human TRPV1 $H^+$ (max % remain) | % Increase in Tail Withdrawal Latency |
|---|---|---|---|
| A | 20 | 10 | +++ |
| B | 55 | 1 | +++ |
| C | 35 | 1 | +++ |
| D | 180 | 3 | +++ |
| E | 100 | 2 | +++ |
| Morphine |  |  | +++ |
| 1 | 300 | 61 | − |
| 2 | 160 | 80 | − |
| 3 | 27 | 55 | − |
| 4 | 40 | 57 | − |

TABLE 1-continued

| Example | human TRPV1 capsaicin IC$_{50}$ (nM) | human TRPV1 H$^+$ (max % remain) | % Increase in Tail Withdrawal Latency |
|---|---|---|---|
| 5 | 32 | 76 | − |
| 6 | 16 | 67 | − |
| 7 | 47 | 48 | − |
| 8 | 35 | 50 | − |
| 9 | 60 | 82 | − |
| 10 | 27 | 74 | − |
| 11 | 56 | 64 | − |
| 12 | 36 | 77 | − |
| 13 | 28 | 62 | − |
| 14 | 44 | 48 | − |
| 15 | 60 | 63 | − |
| 16 | 37 | 57 | − |
| 17 | 240 | 82 | − |
| 18 | 26 | 58 | − |
| 19 | 14 | 71 | − |
| 20 | 36 | 64 | − |
| 21 | 89 | 74 | − |
| 22 | 78 | 73 | − |
| 23 | 51 | 74 | − |
| 24 | 27 | 6 | +++ |
| 25 | 41 | 30 | |
| 26 | 770 | 66 | |
| 27 | 97 | 11 | |
| 28 | 290 | 58 | |
| 29 | 15 | 72 | − |
| 30 | 42 | 39 | ++ |
| 31 | 41 | 30 | ++ |
| 32 | 74 | 33 | − |
| 33 | 27 | 51 | +++ |
| 34 | 12 | 18 | − |
| 35 | 11 | 14 | ++ |
| 36 | 26 | 32 | − |
| 37 | 17 | 4 | − |
| 38 | 37 | 43 | − |
| 39 | 25 | 46 | − |
| 40 | 7 | 30 | − |
| 41 | 13 | 56 | − |
| 42 | 54 | 20 | − |
| 43 | 18 | 48 | +++ |
| 44 | 42 | 52 | +++ |
| 45 | 43 | 58 | − |
| 46 | 430 | 87 | |
| 47 | 4100 | 81 | |
| 48 | 24 | 89 | |
| 49 | 22 | 75 | |
| 50 | 32 | 69 | |
| 51 | 18 | 70 | |
| 52 | 13 | 73 | |
| 53 | 51 | 37 | |
| 54 | 76 | 59 | |
| 55 | 240 | 72 | |
| 56 | 46 | 96 | |
| 57 | 570 | 63 | |
| 58 | 24 | 67 | |
| 59 | 23 | 99 | |
| 60 | 52 | 23 | |
| 61 | 20 | 69 | |
| 62 | 20 | 86 | |
| 63 | 140 | 86 | |
| 64 | 4800 | 90 | |
| 65 | 270 | 73 | |
| 66 | 280 | 86 | |
| 67 | 17 | 72 | |
| 68 | 970 | 79 | |
| 69 | 400 | 91 | |
| 70 | 220 | 99 | |
| 71 | 520 | 52 | |
| 72 | 27 | 0 | |
| 73 | 25 | 18 | |
| 74 | 14 | 2 | |
| 75 | 120 | 40 | |
| 76 | 32 | 1 | |
| 77 | 12 | 1 | |
| 78 | 1400 | 12 | |
| 79 | 710 | 15 | |
| 80 | 110 | 4 | |
| 81 | 59 | 11 | |
| 82 | 510 | 56 | |
| 83 | 790 | 27 | |
| 84 | 80 | 13 | |
| 85 | 24 | 12 | |
| 86 | 1600 | 46 | |
| 87 | 1200 | 50 | |
| 88 | 16 | 23 | |
| 89 | 560 | 91 | |
| 91 | 82 | 78 | |
| 92 | 270 | 60 | |
| 93 | 41009 | 57 | |
| 94 | 5900 | 47 | |
| 95 | 170 | 46 | |
| 96 | 62 | 2 | |
| 97 | 1100 | 58 | |
| 98 | 500 | 13 | |
| 99 | 570 | 75 | |
| 100 | 33 | 30 | |
| 101 | 1200 | 90 | |
| 102 | 2800 | 63 | |
| 103 | 28000 | 99 | |
| 104 | >38000 | 100 | |
| 105 | 150 | 39 | |
| 106 | 56 | 26 | |
| 107 | 2200 | 55 | |
| 108 | 8000 | 97 | |
| 109 | 3100 | 89 | |
| 110 | 240 | 59 | |
| 111 | 2200 | 94 | |
| 112 | 980 | 77 | |
| 113 | >38000 | 74 | |
| 114 | 720 | 43 | |
| 115 | 1100 | 94 | |
| 116 | 4100 | 94 | |
| 117 | 130 | 45 | |
| 118 | 61 | 67 | |
| 119 | 430 | 72 | |
| 120 | 1600 | 51 | |
| 121 | 680 | 57 | |
| 122 | 710 | 14 | |
| 123 | 140 | 61 | |
| 124 | >38000 | 63 | |
| 125 | 3500 | 83 | |
| 126 | 1400 | 88 | |
| 127 | 260 | 62 | |
| 128 | 410 | 75 | |
| 129 | 360 | 53 | |
| 130 | 34000 | 85 | |
| 131 | 1000 | 92 | |
| 132 | 31000 | 95 | |
| 133 | 220 | 36 | |
| 134 | 349 | 3 | |
| 135 | 42 | 3 | |
| 136 | 2800 | 5 | |
| 137 | 350 | 4 | |
| 138 | 820 | 4 | |
| 139 | 370 | 2 | |
| 140 | 58 | 2 | |
| 141 | 3900 | 5 | |
| 142 | 4000 | 4 | |
| 143 | 1100 | 3 | |
| 144 | 400 | 2 | |
| 145 | 3200 | 7 | |
| 146 | 2800 | 7 | |
| 147 | 440 | 2 | |
| 148 | 3100 | 21 | |
| 149 | 540 | 2 | |
| 150 | 1600 | 3 | |
| 151 | 6600 | 6 | |
| 152 | 5500 | 3 | |
| 153 | 760 | 2 | |
| 154 | 82 | 3 | |
| 155 | 42 | 19 | |
| 156 | 61 | 40 | |
| 157 | 1800 | 59 | |

TABLE 1-continued

| Example | human TRPV1 capsaicin IC$_{50}$ (nM) | human TRPV1 H$^+$ (max % remain) | % Increase in Tail Withdrawal Latency |
|---|---|---|---|
| 158 | 600 | 48 | |
| 159 | 420 | 36 | |
| 160 | 130 | 61 | |
| 161 | 3900 | 47 | |
| 162 | 3400 | 50 | |
| 163 | 690 | 38 | |
| 164 | 1500 | 61 | |
| 165 | 2600 | 49 | |
| 166 | 65 | 43 | |
| 167 | 200 | 51 | |
| 168 | 850 | 70 | |
| 169 | 3400 | 57 | |
| 170 | 3500 | 58 | |
| 171 | 400 | 47 | |
| 172 | 32 | 47 | |
| 173 | 210 | 39 | |
| 174 | 420 | 29 | |
| 175 | 470 | 37 | |
| 176 | 210 | 4 | |

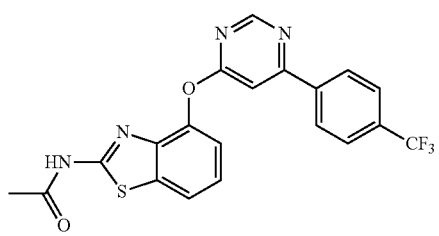

Example A

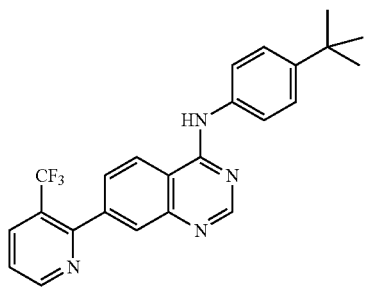

Example B

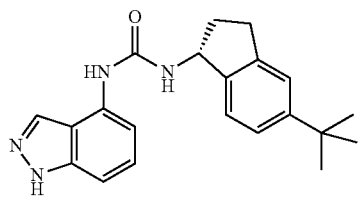

Example C

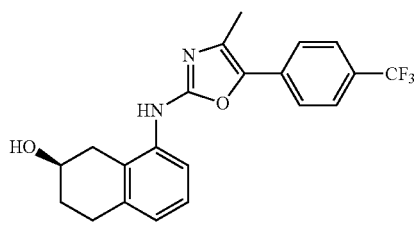

Example D

TABLE 1-continued

| Example | human TRPV1 capsaicin IC$_{50}$ (nM) | human TRPV1 H$^+$ (max % remain) | % Increase in Tail Withdrawal Latency |
|---|---|---|---|

Example E

There are numerous recognized animal models for studying pain. Generally, these pain models mimic one of the mechanisms of pain (e.g. nociceptive, inflammatory, or neuropathic), rather than the pain associated with any one disease or injury. Such models provide evidence of whether a drug or therapy would be effective in treating any of a number of injuries, diseases, or conditions that generate pain via a particular mechanism. Exemplary animal models of pain include, but are not limited to, the rat acute capsaicin-induced flinching behavior and sodium iodoacetate-induced knee joint osteoarthritic pain model discussed below.

(iv) Rat Acute Capsaicin-Induced Flinching Behavior

Rats were placed in individual observation cages. Following an acclimation period of 30 minutes, selected compounds were administered orally at a dose of 100 μmol/kg orally in a vehicle (10% ethanol/20% Tween 80/70% polyethylene glycol-400) at a volume of 2 mL/kg. One hour after administration of the compound, 2.5 μg of capsaicin in a 10 μL solution of 10% ethanol/90% hydroxypropyl-β-cyclodextrin was injected subcutaneously into the dorsal aspect of the right hind paw. The observation cage was then suspended above mirrors in order to facilitate observation. Rats were observed for a continuous period of five minutes. The number of flinching behaviors of the injured paw was recorded during the five minute observation period (Gilchrist, H. D.; Allard, B. L.; Simone, D. A.; Enhanced withdrawal responses to heat and mechanical stimuli following intraplantar injection of capsaicin in rats. *Pain*, 1996, 67, 179-188). The percent reduction in the number of flinching behaviors produced from oral administration of the test compounds relative to control-treated animals (% effect) is reported in Table 2.

TABLE 2

| Example | % effect |
|---|---|
| 4 | 54 |
| 7 | 94 |
| 9 | 76 |
| 12 | 53 |
| 36 | 71 |
| 88 | 69 |

(v) Sodium Iodoacetate-Induced Knee Joint Osteoarthritic Pain Model

Unilateral knee joint osteoarthritis was induced in the rats by a single intra-articular (i.a.) injection of sodium iodoacetate (3 mg in 0.05 mL sterile isotonic saline) into the right knee joint cavity under light isoflurane anesthesia using a 26G needle. The dose of the sodium iodoacetate (3 mg/i.a.injection) was selected based on results obtained from preliminary studies wherein an optimal pain behavior was observed at this dose. Pain behavioral assessment of hind limb grip force was conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CF-max) (gram force)/kg body weight for each animal. The analgesic effects of test compounds were determined 20 days following the i.a. injection of sodium iodoacetate. The vehicle control group for each compound being tested was assigned 0% whereas the age matched naïve group was assigned as being 100% (normal). The % effect for each dose group was then expressed as % return to normalcy compared to the naïve group. Test compounds were administered orally in 10% ethanol/20% Tween 80/70% polyethylene glycol-400 vehicle at a volume of 2 mL/kg. The assessment of the analgesic effects of test compounds was made 1 hour following oral administration. The assessment of the analgesic effects of test compounds can be made following a single dose or following repeated administration wherein the frequency of dosing is 1 to 2 times daily. The duration of such repeated daily dosing may last for any time greater than one day. A typical duration of repeated daily dosing is about 5 days to about 12 days. Table 3 illustrates that representative compounds tested showed a statistically significant change in hind limb grip force strength versus a vehicle-dosed control after administration of a single acute oral dose.

TABLE 3

| Example | Dose (µmol/kg, po) | % effect |
|---------|--------------------|---------| 
| 4 | 100 | 67 |
| 5 | 100 | 57 |
| 7 | 100 | 68 |
| 9 | 100 | 67 |
| 10 | 17 | 49 |
| 13 | 30 | 52 |
| 14 | 30 | 54 |
| 36 | 100 | 46 |
| 40 | 30 | 57 |
| 43 | 30 | 38 |

(vi) Drug-Induced Thermosensory Impairment in Human Subjects (Water Bath Test)

Compounds can be tested for drug-induced thermosensory impairment in human subjects using a temperature-controlled water bath. Specifically, a temperature-controlled water bath is maintained at a constant temperature of 49° C. The subject immerses his or her hand (dominant hand preferred) in the water bath up to the distal wrist crease with the palm side down and withdraws the hand from the water upon first experiencing discomfort. The time taken by the subject to withdraw his or her hand from the water bath is recorded. The water bath test is performed once on the day prior to initial dosing of test compound and again on the morning of initial dosing but prior to administration of the test compound. Test compound is administered daily and the water bath test is performed at a time that corresponds to maximal exposure of the test compound.

The data in Tables 1, 2, and 3 demonstrate that the present compounds are TRPV1 antagonists and are expected to have promising effect of treating or preventing the various diseases and conditions described herein.

One embodiment provides a method for treating a disorder that can be ameliorated by suppressing activation of the vanilloid receptor subtype 1 (TRPV1) receptor in a host mammal in need of such treatment. The method comprises administering therapeutically effective amounts of a compound described herein or a pharmaceutically acceptable salt, prodrug, solvate, salt of a solvate, or solvate of a salt thereof, with or without a pharmaceutically acceptable carrier, and alone, or in combination with an analgesic (e.g. acetaminophen, opioids such as morphine), or an NSAIDs, or combinations thereof.

Another embodiment provides a method for treating pain in a mammal in need of such treatment. The method comprises administering therapeutically effective amount of a compound described herein or a pharmaceutically acceptable salt, prodrug, or solvate thereof, with or without a pharmaceutically acceptable carrier, and alone, or in combination with an analgesic (e.g. acetaminophen, opioids), or with an NSAID, or a combination thereof.

Yet another embodiment provides a method for treating pain including, but not limited to, chronic pain, neuropathic pain, nociceptive pain, allodynia, inflammatory pain, inflammatory hyperalgesia, post herpetic neuralgia, post operative pain, post stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain (e.g. bone cancer pain), dental pain, headache, migraine, carpal tunnel syndrome, fibromyalgia, neuritis, sciatica, pelvic hypersensitivity, pelvic pain, menstrual pain, bladder disease, such as incontinence and bladder overactivity, micturition disorder, renal colic; and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and bronchoconstriction; gastrointestinal disease such as gastro esophageal reflux disease (GERD), dysphagia, ulcer, irritable bowel syndrome (IBS), inflammatory bowel disease (IBD), colitis and Crohn's disease; ischemia such as cerebrovascular ischemia, acute cerebral ischemia; emesis such as cancer chemotherapy-induced emesis, and obesity, in mammals, especially humans. For example, the present compounds are useful for the treatment of pain, particularly inflammatory pain (e.g. osteoarthritic pain). The method comprises administering therapeutically effective amount of a compound described herein or a pharmaceutically acceptable salt, prodrug, or solvates thereof, with or without a pharmaceutically acceptable carrier, and alone, or in combination with an analgesic (e.g. acetaminophen, opioid), or with an NSAID, or a combination thereof.

The present compounds can be used to treat pain as demonstrated by Nolano, M. et al., Pain, 1999, 81, 135-145; Caterina, M. J. and Julius, D., Annu. Rev. Neurosci., 2001, 24, 487-517; Caterina, M. J. et al., Science, 2000, 288, 306-313; Caterina, M. J. et al., Nature, 1997, 389, 816-824.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan in Prog. Neurobiol., 1999, 57, 1-164 for a review). These sensory fibers are known as nociceptors and are characteristically small-diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain can generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain, these mechanisms can be useful in promoting protective behaviors that can better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, *Science,* 2000, 288, 1765-1768).

Clinical pain is present when discomfort and abnormal sensitivity feature among the patient's symptoms. Patients tend to be quite heterogeneous and can present with various pain symptoms. Such symptoms include: 1) spontaneous pain which can be dull, burning, or stabbing; 2) exaggerated pain responses to noxious stimuli (hyperalgesia); and 3) pain produced by normally innocuous stimuli (allodynia: Meyer et al. Textbook of Pain, 13-44 (1994)). Although patients suffering from various forms of acute and chronic pain can have similar symptoms, the underlying mechanisms can be different and can, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury.

Pain afferents are activated by transduction of stimuli by nociceptors at the site of injury and activate neurons in the spinal cord at the level of their termination. This is then relayed up the spinal tracts to the brain where pain is perceived (Meyer et al., Textbook of Pain, 13-44 (1994). The activation of nociceptors activates two types of afferent nerve fibers. Myelinated A-delta fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e.g. bone pain, headache, facial pain or visceral pain) or pain associated with cancer therapy (e.g. post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament. Back pain can resolve naturally but in some patients, where it lasts over 12 weeks, it becomes a chronic condition, which can be particularly debilitating.

Neuropathic pain is currently defined as pain initiated or caused by a primary lesion or dysfunction in the nervous system. Nerve damage can be caused by trauma and disease and thus the term neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological, as it has no protective role. It is often present well after the original cause has dissipated, commonly lasting for years, significantly decreasing a patient's quality of life (Woolf and Mannion *Lancet* 1999, 353, 1959-1964). The symptoms of neuropathic pain are difficult to treat, as they are often heterogeneous even between patients with the same disease (Woolf and Decosterd *Pain Supp.* 1999, 6, S141-S147; Woolf and Mannion *Lancet* 1999, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, Textbook of Pain, 45-56 (1994)). Arthritic pain is the most common inflammatory pain.

Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors can be important (Grennan & Jayson, Textbook of Pain, 397-407 (1994)). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder *Ann. Pharmacother.* 2002, 36, 679-686; McCarthy et al., Textbook of Pain, 387-395 (1994)). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs. Fernihough, J. et al. describe in *Neurosci. Lett.* 2005, 75-80a potential role for TRPV1 in the manifestation of pain behavior accompanied by osteoarthritis changes in the knee.

Compounds described herein are TRPV1 antagonists and thus are useful in ameliorating acute and chronic inflammatory pain and postoperative pain as demonstrated in Honore, P. et al., *J. Pharmacol. Exp. Ther.* 2005, 410-421.

Another type of inflammatory pain is visceral pain, which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain.

Commonly encountered gastrointestinal (GI) disorders that cause pain include functional bowel disorder (FBD) and inflammatory bowel disease (IBD). These GI disorders include a wide range of disease states that are currently only moderately controlled, including, with respect to FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Elevated TRPV1 immunoreactivity has been observed in colonic sensory nerve fibers in patients with IBD (Szallasi, A. et al., *Nature Rev.*, 2007, 6, 357-373).

Other types of visceral pain include the pain associated with dysmenorrheal, cystitis and pancreatitis and pelvic pain.

It should be noted that some types of pain have multiple etiologies and thus can be classified in more than one area, e.g. back pain and cancer pain have both nociceptive and neuropathic components.

Other types of pain include: pain resulting from muscular-skeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardial infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, optic pain, burning mouth syndrome and temporomandibular myofascial pain. It has been shown that CGRP-receptor antagonists block the vasodilatation effects of CGRP and exhibits efficacy in patients with migraine and cluster headaches. CGRP is strongly co-expressed in many TRPV1 expressing nerve fibers, it is plausible that activation of TRPV1 could partially underlie a neurogenic-mediated component of headache.

Another type of pain is ocular pain (eye pain), which includes pain associated with dry eye syndrome, increased intraocular pressure, glaucoma, accidental trauma, and surgical procedures. intraocular pressure. Activation of TRPV1 induces inflammatory cytokine release in corneal epithelium in the eye (Zhang, F. et al., *J. Cell. Physiol.*, 2007, 213, 730; Murata, Y. et al., *Brain Res.*, 2006, 1085, 87). Retinal ganglion cell apoptosis induced by elevated hydrostatic pressure arises substantially through TRPV1, likely through the influx of extracellular $Ca^{2+}$ (Sappington, R. M. et al., Invest. Ophth. Vis. Sci., 2009, 50, 717). TRPV1 antagonists can effectively reduce symptoms of dry eye without causing anesthesia effects on the ocular surface (US2009/0131449). Silencing of TRPV1 by administration of siRNA can be a useful therapy in the treatment of ocular pain associated with dry eye syndrome and could reduce side effects associated with medications currently used to treat patients suffering from this pathology. Investigators at Sylentis have reported data indicating that an siRNA targeting TRPV1 could be used to decrease the behavioral response of guinea pigs to ocular surface irritation (Association for Research in Vision and Ophthalmology Meeting, 2008). Administration of the TRPV1 agonist capsaicin resulted in a significant increase in irritation parameters compared with saline and that topical administration of TRPV1 siRNA twice a day for three days resulted in reduced scratching and wiping movements for up to nine days in the treated eyes. The reported analgesic effect was greater than that observed using the reference standard capsazepine.

It is known that capsaicin, a TRPV1 agonist, induces cough and reduced airway conductance in human clinical trials. TRPV1 antagonists such as capsazepine have been shown to block capsaicin and citric acid-induced cough responses in guinea pigs as demonstrated by Geppetti P. et al., *Eur. J. Pharmacol.*, 2006, 533, 207-214. Thus, TRPV1 antagonists demonstrate potential in the treatment of asthma, cough, chronic obstructive pulmonary disease (COPD) and bronchoconstriction as demonstrated by Watanabe N. et al., *Pulmonary Pharmacol. Ther.*, 2005, 18, 187-197; and Jia Y. et al., *Br. J. Pharmacol.*, 2002, 137, 831-836.

Present compounds can be used to treat bladder overactivity and/or urinary incontinence as demonstrated by Fowler, C., *Urology*, 2005, 65, 400-405.

Present compounds can be used to treat inflammatory thermal hyperalgesia as demonstrated by Davis, J. et al., *Nature*, 2000, 405, 183-187.

Present compounds can be used for the treatment of anxiety-related disorders as demonstrated by Marsch, R. et al., *J. Neurosci.*, 2007, 27, 832-839.

Present compounds can be used for the treatment of disorders associated with hyperdopaminergia such as psychosis, attention deficit hyperactivity disorder and schizophrenia as demonstrated by Tzvara, E. et al., *Biol. Psych.*, 2006, 59, 508-515.

Present compounds can be used for the treatment of diabetes and obesity as demonstrated by Suni, A. and Sallazi, A., *Trends Pharmacol. Sci.*, 2008, 29, 29-36.

Ischemia (e.g. cerebral ischemia) is the shortage or inadequate of oxygenated blood flow to body parts and organs, and often results in dysfunction or damage of tissue. The neuroprotective efficacy of induced hypothermia following or during cerebral ischemia is evident in experimental anima models of stroke (Barone, F. C. et al., *Neurosci. Biobehav. Rev.*, 1997; 2(1), 31-44; Onesti, S. T. et al., *Neurosurgery*, 1991, 29, 369; Coimbra, C. et al., *Acta Neuropathol.* (*Berl*), 1994; 87, 325; Zhang, Y. et al., *Acta Anaesthesiol. Sin.*, 2001, 39, 65; Yamashita, K. et al., Stroke, 1991, 22, 1574; Ooboshi, H. et al., *Brain Res.*, 2000, 884, 23; Colbourne, F. et al., *J. Cereb. Blood Flow Metab.*, 2000, 20(1-2), 1702; Kawai, N. et al., *Stroke*, 2000, 3, 1982; Maier, C. M. et al., *J. Neurosurg.*, 2001, 94, 90; Maier, C. M. et al., *Stroke*, 1998, 29, 2171). Two trials conducted in cardiac arrest patients have demonstrated improved neurological outcome of inducing hypothermia (Mild therapeutic hypothermia to improve the neurologic outcome after cardiac arrest: Bernard, S. A. et al., *N. Engl. J. Med.*, 2002, 346, 549; and *N Engl. J. Med.*, 2002, 346, 557). Induction of hypothermia by lowering of the core temperature has been attempted by mechanical devices such as surface cooling using catheters placed in a large vessel. However, such mechanical devices have been shown to have considerable side effects, including shivering, serious infections, and lung puncture. Regulation of the core body temperature by pharmaceutical compositions comprising TRPV1 agonists as a safer and less expensive alternative to the mechanical method was discussed in WO2008/040360 and WO2008/040361. Such treatments can have unintended side effects such as the sensation of burning pain, known to be elicited by TRPV1 agonists. TRPV1 antagonists that are capable of inducing hypothermia can be used for the treatment of ischemia without the pungent effects.

Present compounds can be administered alone, or in combination with one or more other compounds described herein, or in combination (i.e. co-administered) with one or more additional pharmaceutical agents. For example, a compound of the present invention, or a pharmaceutically acceptable salt, prodrug, or solvate thereof, can be administered in combination with an analgesic (e.g. acetaminophen, or an opioid such as morphine), or with a nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac; or administered with a combination of an analgesic (e.g. acetaminophen, opioids) and an NSAID. In certain embodiments, the nonsteroidal anti-inflammatory drug (NSAID) is ibuprofen. In certain embodiments, the analgesic is acetaminophen. Combination therapy includes administration of a single pharmaceutical dosage formulation containing one or more of the compounds described herein and one or more additional pharmaceutical agents, as well as administration of the compounds of the invention and each additional pharmaceutical agent, in its own separate pharmaceutical dosage formulation. For example, a compound of formula (I) and one or more additional pharmaceutical agent(s) can be administered to the patient together, in a single oral dosage composition having a fixed ratio of each active ingredient, such as a tablet or capsule; or each agent can be administered in separate oral dosage formulations.

Where separate dosage formulations are used, the present compounds and one or more additional pharmaceutical agents can be administered at essentially the same time (e.g., concurrently) or at separately staggered times (e.g., sequentially).

Actual dosage levels of active ingredients in the pharmaceutical compositions can be varied so as to obtain an amount of the active compound that is effective to achieve the desired therapeutic response for a particular patient, compositions and mode of administration. The selected dosage level can depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds can be employed in pure form or, where such forms exist, in pharmaceutically acceptable salts thereof. The present compounds can also be administered as a pharmaceutical composition comprising the compound of interest in combination with a pharmaceutically acceptable carrier. The phrase "therapeutically effective amount" of the compound of the invention means a sufficient amount of the compound to treat disorders, at a reasonable benefit/risk ratio applicable to any medical treatment. It can be understood, however, that the total daily usage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds administered to a human or lower animal range from about 0.10 µg/kg body weight to about 25 mg/kg body weight. More preferable doses can be in the range of from about 0.10 µg/kg body weight to about 1 mg/kg body weight. If desired, the effective daily dose can be divided into multiple doses for purposes of administration. Consequently, single dose compositions can contain such amounts or submultiples thereof to make up the daily dose.

F. PHARMACEUTICAL COMPOSITIONS

Described herein are also pharmaceutical compositions comprising of a compound described herein, or a pharmaceutically acceptable salt, prodrug, or solvate thereof, formulated together with a pharmaceutically acceptable carrier. The pharmaceutical compositions can be formulated for oral administration in solid or liquid form, for parenteral injection or for rectal administration.

The compounds identified by the methods described herein can be administered as the sole pharmaceutical agent or in combination with one or more other pharmaceutical agents. For example, the compounds or salts or solvate thereof can be combined with an analgesic, or with a nonsteroidal anti-inflammatory drug (NSAID, or with a combination of an analgesic and an NSAID. Thus, the present invention also includes pharmaceutical compositions which are comprised of therapeutically effective amount of a compound identified by the methods described herein, or pharmaceutically acceptable salt, prodrug, or solvate thereof, a pharmaceutical agent as disclosed hereinabove, and a pharmaceutically acceptable carrier.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition can be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, can depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They can be sterilized, for example, by filtration through a bacteria-retaining filter or by incorporation of sterilizing agents in the form of sterile solid compositions, which can be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration include ointments, pastes, creams, lotions, gels, powders, solutions, sprays, inhalants or patches. A desired compound of the invention is admixed under sterile conditions with a pharmaceutically acceptable carrier and any needed preservatives or buffers as can be required. Ophthalmic formulation, eardrops, eye ointments, powders and solutions are also contemplated as being within the scope of this invention.

The ointments, pastes, creams and gels can contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of interest, lactose, talc, silicic acid, aluminum hydroxide, calcium silicates and polyamide powder, or mixtures of these substances. Sprays can additionally contain customary propellants such as chlorofluorohydrocarbons.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of interest, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., p 33 et seq (1976).

Dosage forms for topical administration include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds can be used in the form of pharmaceutically acceptable salts derived from inorganic or organic acids. The term "pharmaceutically acceptable salts" as used herein, include salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by mixing together solutions of the compounds of invention and a suitable acid or base. The salt can precipitate from the solution and be collected by filtration or can be recovered by evaporation of the solvent. The degree of ionization in the salt can vary from completely ionized to almost non-ionized.

Suitable acid addition salts are formed from acids which form non-toxic salts. Representative acid addition salts include, but are not limited to acetate, adipate, alginate, citrate, aspartate, benzoate, benzenesulfonate, bisulfate, bicarbonate, butyrate, camphorate, camphorsulfonate, carbonate, citrate, digluconate, glycerophosphate, hemisulfate, heptanoate, hexanoate, formate, fumarate, gluconate, glucuronate, glutamate, hydrochloride, hydrobromide, hydroiodide, 2-hydroxyethansulfonate (isethionate), lactate, maleate, malate, malonate, methanesulfonate, nicotinate, 2-naphthalenesulfonate, nicotinate-nitrate, orotate, oxalate, palmitate, pamoate, pectinate, persulfate, 3-phenylpropionate, picrate, pivalate, propionate, saccharate, stearate, succinate, sulfate, tartrate, thiocyanate, phosphate, hydrogenphosphate, dihydrogen phosphate, p-toluenesulfonate, trifluoroacetate, and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium, zinc, and aluminum salts, and the like, and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrug" or "prodrug" as used herein, represents those prodrugs of the compounds of the invention which are, within the scope of sound medical judgment, suitable for use in contact with the tissues of humans and animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof can be converted through in vivo biotransformation into compounds of the invention.

The compounds of the invention can exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:
1. A compound of formula (I):

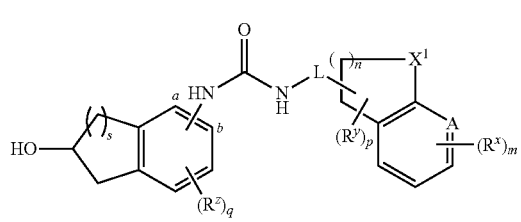

or a salt thereof, wherein:
L is a bond or $CH_2$, and is bound to any one of the carbon atom of the monocyclic ring containing $X^1$;
$X^1$ is O;
n is 1 or 2;
A is CH;
m is 0, 1, or 2;
$R^x$, at each occurrence, represents an optional substituent on any substitutable carbon atom of the ring containing A and each $R^x$ is independently alkyl, halogen, haloalkyl, OH, O(alkyl), O(haloalkyl), $NH_2$, N(H)(alkyl), or $N(alkyl)_2$;
p is 0, 1, or 2;
$R^y$, at each occurrence, represents an optional substituent on any substitutable carbon atom of the ring containing $X^1$ and each $R^y$ is independently alkyl, haloalkyl, —($C_1$-$C_6$ alkylenyl)-O(alkyl), $G^1$, and —($C_1$-$C_6$ alkylenyl)-$G^1$; wherein $G^1$, at each occurrence, is independently an aryl, optionally substituted with 1, 2, 3, or 4 substituents independently selected from the group consisting of alkyl, halogen, haloalkyl, O(alkyl), and O(haloalkyl);
two $R^y$ groups that are attached to the same carbon atom, together with said carbon atom to which they are attached, optionally form a $C_3$-$C_6$ monocyclic cycloalkyl ring, wherein the monocyclic cyclcoalkyl ring is optionally substituted with 1, 2, or 3 substituents independently selected from the group consisting of alkyl, oxo, halogen, and haloalkyl;
s is 0 or 1;
The alphabets a and b on the bicyclic ring independently represent the positions at which the —NH— of the urea moiety and a carbon atom of the ring are bound to each other, provided that when s is 1, the binding position for —NH— is at position a; and when s is 0, the binding position for —NH— is at position b;
$R^z$, at each occurrence, represents an optional substituent on any substitutable position of the bicyclic ring and is independently halogen, haloalkyl, or alkyl; and
q is 0 or 1.
2. The compound or salt according to claim 1, wherein n is 2.
3. The compound or salt according to claim 1, wherein n is 1.
4. The compound or salt according to claim 1, wherein L is $CH_2$.
5. The compound or salt according to claim 1, wherein L is a bond.
6. The compound or salt according to claim 2, wherein L is a bond.
7. The compound or salt according to claim 2, wherein L is $CH_2$.

8. The compound or salt according to claim 1 having formula (I-a):

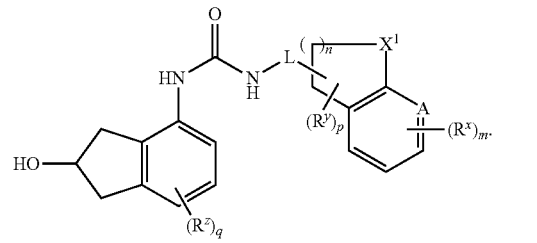

9. The compound or salt according to claim 8, wherein:
n is 2; and
L is a bond.
10. The compound or salt according to claim 8, wherein:
n is 2; and
L is $CH_2$.
11. The compound or salt according to claim 8, wherein:
n is 1; and
L is a bond.
12. The compound or salt according to claim 1 having formula (I-b):

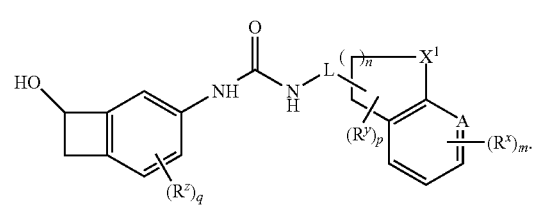

13. The compound or salt according to claim 12, wherein:
n is 2; and
L is a bond.
14. The compound or salt according to claim 1, wherein the compound is selected from the group consisting of:
1-[(4R)-6,8-difluoro-2,2-bis(fluoromethyl)-3,4-dihydro-2H-chromen-4-yl]-3-[(2R)-2-hydroxy-2,3-dihydro-1H-inden-4-yl]urea;
1-[(4R)-8-chloro-2,2-bis(fluoromethyl)-3,4-dihydro-2H-chromen-4-yl]-3-[(2R)-2-hydroxy-2,3-dihydro-1H-inden-4-yl]urea;
1-[(4R)-2,2-dimethyl-7-(trifluoromethyl)-3,4-dihydro-2H-chromen-4-yl]-3-[(2R)-2-hydroxy-2,3-dihydro-1H-inden-4-yl]urea;
1-[(4R)-7-chloro-2,2-bis(fluoromethyl)-3,4-dihydro-2H-chromen-4-yl]-3-[(2R)-2-hydroxy-2,3-dihydro-1H-inden-4-yl]urea;
1-[(4R)-7-fluoro-2,2-dimethyl-3,4-dihydro-2H-chromen-4-yl]-3-[(2R)-2-hydroxy-2,3-dihydro-1H-inden-4-yl]urea;
1-[(2R)-2-hydroxy-2,3-dihydro-1H-inden-4-yl]-3-[(4R)-8-(trifluoromethoxy)-3,4-dihydro-2H-chromen-4-yl]urea;
1-[(4R)-2,2-bis(fluoromethyl)-7-(trifluoromethyl)-3,4-dihydro-2H-chromen-4-yl]-3-[(2R)-2-hydroxy-2,3-dihydro-1H-inden-4-yl]urea;

1-[(4R)-6-fluoro-3,4-dihydrospiro[chromene-2,1'-cyclobutan]-4-yl]-3-[(2R)-2-hydroxy-2,3-dihydro-1H-inden-4-yl]urea;

1-[(4R)-7,8-difluoro-2,2-dimethyl-3,4-dihydro-2H-chromen-4-yl]-3-[(2R)-2-hydroxy-2,3-dihydro-1H-inden-4-yl]urea;

1-[(4R)-7-chloro-8-fluoro-2,2-dimethyl-3,4-dihydro-2H-chromen-4-yl]-3-[(2R)-2-hydroxy-2,3-dihydro-1H-inden-4-yl]urea;

1-[(4R)-7-chloro-8-fluoro-2,2-bis(fluoromethyl)-3,4-dihydro-2H-chromen-4-yl]-3-[(2R)-2-hydroxy-2,3-dihydro-1H-inden-4-yl]urea;

1-[(4R)-8-chloro-7-fluoro-2,2-dimethyl-3,4-dihydro-2H-chromen-4-yl]-3-[(2R)-2-hydroxy-2,3-dihydro-1H-inden-4-yl]urea;

1-[(4R)-7-chloro-2,2-dimethyl-3,4-dihydro-2H-chromen-4-yl]-3-[(2R)-2-hydroxy-2,3-dihydro-1H-inden-4-yl]urea;

1-[(2R)-2-hydroxy-2,3-dihydro-1H-inden-4-yl]-3-[(4R)-7-(trifluoromethoxy)-3,4-dihydro-2H-chromen-4-yl]urea;

1-[(2R,4R)-7-chloro-2-(fluoromethyl)-2-methyl-3,4-dihydro-2H-chromen-4-yl]-3-[(2R)-2-hydroxy-2,3-dihydro-1H-inden-4-yl]urea;

1-[(2S,4R)-7-chloro-2-(fluoromethyl)-2-methyl-3,4-dihydro-2H-chromen-4-yl]-3-[(2R)-2-hydroxy-2,3-dihydro-1H-inden-4-yl]urea;

1-[(4R)-2,2-dimethyl-3,4-dihydro-2H-chromen-4-yl]-3-[(2R)-2-hydroxy-2,3-dihydro-1H-inden-4-yl]urea;

1-[(2R)-2-hydroxy-2,3-dihydro-1H-inden-4-yl]-3-[(4R)-8-(trifluoromethyl)-3,4-dihydro-2H-chromen-4-yl]urea;

1-[(4R)-2,2-dimethyl-8-(trifluoromethoxy)-3,4-dihydro-2H-chromen-4-yl]-3-[(2R)-2-hydroxy-2,3-dihydro-1H-inden-4-yl]urea;

1-[(2S,4R)-7-chloro-2-(difluoromethyl)-2-methyl-3,4-dihydro-2H-chromen-4-yl]-3-[(2R)-2-hydroxy-2,3-dihydro-1H-inden-4-yl]urea;

1-[(2R)-2-hydroxy-2,3-dihydro-1H-inden-4-yl]-3-[(4R)-7-(trifluoromethyl)-3,4-dihydro-2H-chromen-4-yl]urea;

1-[(4R)-3,4-dihydrospiro[chromene-2,1'-cyclobutan]-4-yl]-3-[(2R)-2-hydroxy-2,3-dihydro-1H-inden-4-yl]urea;

1-[(4R)-2,2-dimethyl-8-(trifluoromethyl)-3,4-dihydro-2H-chromen-4-yl]-3-[(2R)-2-hydroxy-2,3-dihydro-1H-inden-4-yl]urea;

1-[(4R)-7-fluoro-2,2-dimethyl-3,4-dihydro-2H-chromen-4-yl]-3-[(2S)-2-hydroxy-2,3-dihydro-1H-inden-4-yl]urea;

1-[(4R)-2,2-dimethyl-8-(trifluoromethyl)-3,4-dihydro-2H-chromen-4-yl]-3-[(2S)-2-hydroxy-2,3-dihydro-1H-inden-4-yl]urea;

1-[(4R)-8-chloro-7-fluoro-2,2-dimethyl-3,4-dihydro-2H-chromen-4-yl]-3-[(2S)-2-hydroxy-2,3-dihydro-1H-inden-4-yl]urea;

1-[(2S)-2-hydroxy-2,3-dihydro-1H-inden-4-yl]-3-[(4R)-7-(trifluoromethoxy)-3,4-dihydro-2H-chromen-4-yl]urea;

1-[(4R)-7,8-difluoro-2,2-dimethyl-3,4-dihydro-2H-chromen-4-yl]-3-[(2S)-2-hydroxy-2,3-dihydro-1H-inden-4-yl]urea;

1-[(2R)-2-hydroxy-2,3-dihydro-1H-inden-4-yl]-3-[(4R)-7-(trifluoromethyl)-3,4-dihydrospiro[chromene-2,1'-cyclobutan]-4-yl]urea; and 1-[(4R)-7-bromo-2,2-bis(fluoromethyl)-3,4-dihydro-2H-chromen-4-yl]-3-[(2R)-2-hydroxy-2,3-dihydro-1H-inden-4-yl]urea.

15. The compound or salt according to claim 1, wherein the compound is selected from the group consisting of:

1-[(4R)-7-chloro-2,2-bis(fluoromethyl)-3,4-dihydro-2H-chromen-4-yl]-3-[(2S)-2-hydroxy-2,3-dihydro-1H-inden-4-yl]urea;

1-[(2R,4R)-7-chloro-2-(fluoromethyl)-2-methyl-3,4-dihydro-2H-chromen-4-yl]-3-(5-fluoro-2-hydroxy-2,3-dihydro-1H-inden-4-yl)urea;

1-[(2R)-2-hydroxy-2,3-dihydro-1H-inden-4-yl]-3-{[6-(trifluoromethyl)-3,4-dihydro-2H-chromen-2-yl]methyl}urea;

1-[(3S)-6-chloro-3,4-dihydro-2H-chromen-3-yl]-3-[(2R)-2-hydroxy-2,3-dihydro-1H-inden-4-yl]urea;

1-[(6-fluoro-3,4-dihydro-2H-chromen-3-yl)methyl]-3-[(2R)-2-hydroxy-2,3-dihydro-1H-inden-4-yl]urea;

1-[(4R)-2,2-dimethyl-7-(trifluoromethoxy)-3,4-dihydro-2H-chromen-4-yl]-3-[(2R)-2-hydroxy-2,3-dihydro-1H-inden-4-yl]urea;

1-[(4R)-2,2-bis(fluoromethyl)-7-(trifluoromethoxy)-3,4-dihydro-2H-chromen-4-yl]-3-[(2R)-2-hydroxy-2,3-dihydro-1H-inden-4-yl]urea;

1-[(2R,4R)-7-chloro-2-(difluoromethyl)-2-methyl-3,4-dihydro-2H-chromen-4-yl]-3-[(2R)-2-hydroxy-2,3-dihydro-1H-inden-4-yl]urea;

1-[(4R)-7-chloro-8-fluoro-2,2-dimethyl-3,4-dihydro-2H-chromen-4-yl]-3-[(2S)-2-hydroxy-2,3-dihydro-1H-inden-4-yl]urea;

1-[(2R,4R)-2-(fluoromethyl)-2-methyl-7-(trifluoromethyl)-3,4-dihydro-2H-chromen-4-yl]-3-[(2R)-2-hydroxy-2,3-dihydro-1H-inden-4-yl]urea;

1-[(2S,4R)-2-(fluoromethyl)-2-methyl-7-(trifluoromethyl)-3,4-dihydro-2H-chromen-4-yl]-3-[(2R)-2-hydroxy-2,3-dihydro-1H-inden-4-yl]urea;

1-[(4R)-8-fluoro-2,2-dimethyl-3,4-dihydro-2H-chromen-4-yl]-3-[(2R)-2-hydroxy-2,3-dihydro-1H-inden-4-yl]urea;

1-[(4R)-3,4-dihydro-2H-chromen-4-yl]-3-[(2R)-2-hydroxy-2,3-dihydro-1H-inden-4-yl]urea;

1-[(4R)-2,2-diethyl-8-fluoro-3,4-dihydro-2H-chromen-4-yl]-3-[(2R)-2-hydroxy-2,3-dihydro-1H-inden-4-yl]urea;

1-[(4R)-2,2-diethyl-3,4-dihydro-2H-chromen-4-yl]-3-[(2R)-2-hydroxy-2,3-dihydro-1H-inden-4-yl]urea;

1-[(4R)-8-tert-butyl-3,4-dihydro-2H-chromen-4-yl]-3-[(2R)-2-hydroxy-2,3-dihydro-1H-inden-4-yl]urea;

1-[(4R)-2,2-diethyl-7-fluoro-3,4-dihydro-2H-chromen-4-yl]-3-[(2R)-2-hydroxy-2,3-dihydro-1H-inden-4-yl]urea;

1-[(4R)-2,2-diethyl-7-(trifluoromethyl)-3,4-dihydro-2H-chromen-4-yl]-3-[(2R)-2-hydroxy-2,3-dihydro-1H-inden-4-yl]urea;

1-[(4R)-7-chloro-2,2-diethyl-3,4-dihydro-2H-chromen-4-yl]-3-[(2R)-2-hydroxy-2,3-dihydro-1H-inden-4-yl]urea;

1-[(4R)-7,8-dichloro-2,2-diethyl-3,4-dihydro-2H-chromen-4-yl]-3-[(2R)-2-hydroxy-2,3-dihydro-1H-inden-4-yl]urea;

1-[(4R)-6-fluoro-2,2-dipropyl-3,4-dihydro-2H-chromen-4-yl]-3-[(2R)-2-hydroxy-2,3-dihydro-1H-inden-4-yl]urea;

1-[(4R)-6-fluoro-2,2-bis(fluoromethyl)-3,4-dihydro-2H-chromen-4-yl]-3-[(2R)-2-hydroxy-2,3-dihydro-1H-inden-4-yl]urea;

1-[(4R)-2,2-diethyl-6-fluoro-3,4-dihydro-2H-chromen-4-yl]-3-[(2R)-2-hydroxy-2,3-dihydro-1H-inden-4-yl]urea;
1-[(4R)-8-fluoro-2,2-dipropyl-3,4-dihydro-2H-chromen-4-yl]-3-[(2R)-2-hydroxy-2,3-dihydro-1H-inden-4-yl]urea;
1-[(4R)-2,2-diethyl-7-(trifluoromethoxy)-3,4-dihydro-2H-chromen-4-yl]-3-[(2R)-2-hydroxy-2,3-dihydro-1H-inden-4-yl]urea;
1-[(4R)-6-chloro-2-(difluoromethyl)-2-methyl-3,4-dihydro-2H-chromen-4-yl]-3-[(2R)-2-hydroxy-2,3-dihydro-1H-inden-4-yl]urea;
1-[(4R)-7-fluoro-2,2,8-trimethyl-3,4-dihydro-2H-chromen-4-yl]-3-[(2R)-2-hydroxy-2,3-dihydro-1H-inden-4-yl]urea;
1-[(4R)-6,8-difluoro-3,4-dihydro-2H-chromen-4-yl]-3-[(2R)-2-hydroxy-2,3-dihydro-1H-inden-4-yl]urea;
1-[(4R)-7-fluoro-3,4-dihydro-2H-chromen-4-yl]-3-[(2R)-2-hydroxy-2,3-dihydro-1H-inden-4-yl]urea;
1-[(2R,4R)-8-fluoro-2-(fluoromethyl)-2-methyl-3,4-dihydro-2H-chromen-4-yl]-3-[(2R)-2-hydroxy-2,3-dihydro-1H-inden-4-yl]urea;
1-[(4R)-7-chloro-2-(fluoromethyl)-2-methyl-3,4-dihydro-2H-chromen-4-yl]-3-[(2R)-2-hydroxy-2,3-dihydro-1H-inden-4-yl]urea;
1-[(4R)-6-fluoro-2,2-bis(methoxymethyl)-3,4-dihydro-2H-chromen-4-yl]-3-[(2R)-2-hydroxy-2,3-dihydro-1H-inden-4-yl]urea;
1-[(4R)-2,2-bis(fluoromethyl)-3,4-dihydro-2H-chromen-4-yl]-3-[(2R)-2-hydroxy-2,3-dihydro-1H-inden-4-yl]urea;
1-[(4R)-8-fluoro-2,2-bis(fluoromethyl)-3,4-dihydro-2H-chromen-4-yl]-3-[(2R)-2-hydroxy-2,3-dihydro-1H-inden-4-yl]urea;
1-[(4R)-8-fluoro-2,2-dimethyl-3,4-dihydro-2H-chromen-4-yl]-3-[(2S)-2-hydroxy-2,3-dihydro-1H-inden-4-yl]urea;
1-[(4R)-2,2-dimethyl-7-(trifluoromethoxy)-3,4-dihydro-2H-chromen-4-yl]-3-[(2S)-2-hydroxy-2,3-dihydro-1H-inden-4-yl]urea;
1-[(2S)-2-hydroxy-2,3-dihydro-1H-inden-4-yl]-3-[(4R)-8-(trifluoromethoxy)-3,4-dihydro-2H-chromen-4-yl]urea;
1-[(4R)-2,2-bis(fluoromethyl)-7-(trifluoromethyl)-3,4-dihydro-2H-chromen-4-yl]-3-[(2S)-2-hydroxy-2,3-dihydro-1H-inden-4-yl]urea;
1-[(4R)-8-chloro-2,2-bis(fluoromethyl)-3,4-dihydro-2H-chromen-4-yl]-3-[(2S)-2-hydroxy-2,3-dihydro-1H-inden-4-yl]urea;
1-[(4R)-2,2-bis(fluoromethyl)-7-(trifluoromethoxy)-3,4-dihydro-2H-chromen-4-yl]-3-[(2S)-2-hydroxy-2,3-dihydro-1H-inden-4-yl]urea;
1-[(4R)-2,2-dimethyl-7-(trifluoromethyl)-3,4-dihydro-2H-chromen-4-yl]-3-[(2S)-2-hydroxy-2,3-dihydro-1H-inden-4-yl]urea;
1-[(4R)-6-fluoro-2,2-bis(fluoromethyl)-3,4-dihydro-2H-chromen-4-yl]-3-[(2S)-2-hydroxy-2,3-dihydro-1H-inden-4-yl]urea;
1-[(4R)-6,8-difluoro-2,2-bis(fluoromethyl)-3,4-dihydro-2H-chromen-4-yl]-3-[(2S)-2-hydroxy-2,3-dihydro-1H-inden-4-yl]urea;
1-[(4R)-6-fluoro-3,4-dihydrospiro[chromene-2,1'-cyclobutan]-4-yl]-3-[(2S)-2-hydroxy-2,3-dihydro-1H-inden-4-yl]urea;
1-[(4R)-7-chloro-8-fluoro-2,2-bis(fluoromethyl)-3,4-dihydro-2H-chromen-4-yl]-3-[(2S)-2-hydroxy-2,3-dihydro-1H-inden-4-yl]urea;
1-[(4R)-2,2-dimethyl-3,4-dihydro-2H-chromen-4-yl]-3-[(2S)-2-hydroxy-2,3-dihydro-1H-inden-4-yl]urea;
1-[(4R)-6-fluoro-2,2-dimethyl-3,4-dihydro-2H-chromen-4-yl]-3-[(2S)-2-hydroxy-2,3-dihydro-1H-inden-4-yl]urea;
1-[(4R)-7-chloro-2,2-dimethyl-3,4-dihydro-2H-chromen-4-yl]-3-[(2S)-2-hydroxy-2,3-dihydro-1H-inden-4-yl]urea;
1-[(4R)-2,2-bis(fluoromethyl)-3,4-dihydro-2H-chromen-4-yl]-3-[(2S)-2-hydroxy-2,3-dihydro-1H-inden-4-yl]urea;
1-[(4R)-8-fluoro-2,2-bis(fluoromethyl)-3,4-dihydro-2H-chromen-4-yl]-3-[(2S)-2-hydroxy-2,3-dihydro-1H-inden-4-yl]urea;
1-[(4R)-2,2-dimethyl-8-(trifluoromethoxy)-3,4-dihydro-2H-chromen-4-yl]-3-[(2S)-2-hydroxy-2,3-dihydro-1H-inden-4-yl]urea;
1-[(3R)-6-chloro-3,4-dihydro-2H-chromen-3-yl]-3-[(2R)-2-hydroxy-2,3-dihydro-1H-inden-4-yl]urea;
1-[(2S,4R)-7-chloro-8-fluoro-2-(fluoromethyl)-2-methyl-3,4-dihydro-2H-chromen-4-yl]-3-[(2R)-2-hydroxy-2,3-dihydro-1H-inden-4-yl]urea;
1-(6-fluoro-2,2-dimethyl-3,4-dihydro-2H-chromen-3-yl)-3-[(2R)-2-hydroxy-2,3-dihydro-1H-inden-4-yl]urea;
1-[(2R)-2-hydroxy-2,3-dihydro-1H-inden-4-yl]-3-[(4S)-7-(trifluoromethoxy)-3,4-dihydro-2H-chromen-4-yl]urea;
1-[(2S)-2-hydroxy-2,3-dihydro-1H-inden-4-yl]-3-[(4S)-7-(trifluoromethoxy)-3,4-dihydro-2H-chromen-4-yl]urea;
1-[(4R)-2,2-bis(fluoromethyl)-7-(trifluoromethyl)-3,4-dihydro-2H-chromen-4-yl]-3-[(2S)-5-fluoro-2-hydroxy-2,3-dihydro-1H-inden-4-yl]urea;
1-[(4R)-2,2-bis(fluoromethyl)-7-(trifluoromethyl)-3,4-dihydro-2H-chromen-4-yl]-3-[(2R)-5-fluoro-2-hydroxy-2,3-dihydro-1H-inden-4-yl]urea;
1-[(4S)-7-chloro-2,2-bis(fluoromethyl)-3,4-dihydro-2H-chromen-4-yl]-3-[(2R)-2-hydroxy-2,3-dihydro-1H-inden-4-yl]urea;
1-[(4S)-7-chloro-2,2-bis(fluoromethyl)-3,4-dihydro-2H-chromen-4-yl]-3-[(2S)-2-hydroxy-2,3-dihydro-1H-inden-4-yl]urea;
1-(7-chloro-3,4-dihydro-2H-chromen-3-yl)-3-[(2R)-2-hydroxy-2,3-dihydro-1H-inden-4-yl]urea;
1-[(2R,4R)-7-chloro-2-(fluoromethyl)-2-methyl-3,4-dihydro-2H-chromen-4-yl]-3-[(2S)-5-fluoro-2-hydroxy-2,3-dihydro-1H-inden-4-yl]urea;
1-[(4S)-6-fluoro-3,4-dihydrospiro[chromene-2,1'-cyclobutan]-4-yl]-3-[(2R)-2-hydroxy-2,3-dihydro-1H-inden-4-yl]urea;
1-[(4S)-6-fluoro-3,4-dihydrospiro[chromene-2,1'-cyclobutan]-4-yl]-3-[(2S)-2-hydroxy-2,3-dihydro-1H-inden-4-yl]urea;
1-[(4S)-6-fluoro-2,2-dimethyl-3,4-dihydro-2H-chromen-4-yl]-3-[(2S)-2-hydroxy-2,3-dihydro-1H-inden-4-yl]urea;
1-[(4S)-6-fluoro-2,2-dimethyl-3,4-dihydro-2H-chromen-4-yl]-3-[(2R)-2-hydroxy-2,3-dihydro-1H-inden-4-yl]urea;
1-(2-hydroxy-2,3-dihydro-1H-inden-4-yl)-3-(7-methoxy-3,4-dihydro-2H-chromen-4-yl)urea;
1-(2-hydroxy-2,3-dihydro-1H-inden-4-yl)-3-(3-phenyl-3,4-dihydro-2H-chromen-4-yl)urea;
1-[3-(3,4-dimethoxybenzyl)-3,4-dihydro-2H-chromen-4-yl]-3-(2-hydroxy-2,3-dihydro-1H-inden-4-yl)urea;
1-[2-(3-chlorophenyl)-3,4-dihydro-2H-chromen-4-yl]-3-(2-hydroxy-2,3-dihydro-1H-inden-4-yl)urea;

1-(3-benzyl-3,4-dihydro-2H-chromen-4-yl)-3-(2-hydroxy-2,3-dihydro-1H-inden-4-yl)urea;

1-[3-(3,4-dichlorobenzyl)-3,4-dihydro-2H-chromen-4-yl]-3-(2-hydroxy-2,3-dihydro-1H-inden-4-yl)urea;

1-[2-(3,4-dimethoxyphenyl)-3,4-dihydro-2H-chromen-4-yl]-3-(2-hydroxy-2,3-dihydro-1H-inden-4-yl)urea;

1-[3-(3,4-dichlorobenzyl)-7-methoxy-3,4-dihydro-2H-chromen-4-yl]-3-(2-hydroxy-2,3-dihydro-1H-inden-4-yl)urea;

1-[3-(4-chlorophenyl)-3,4-dihydro-2H-chromen-4-yl]-3-(2-hydroxy-2,3-dihydro-1H-inden-4-yl)urea;

1-(2-hydroxy-2,3-dihydro-1H-inden-4-yl)-3-[3-(4-methoxyphenyl)-3,4-dihydro-2H-chromen-4-yl]urea;

1-[2-(4-chlorophenyl)-3,4-dihydro-2H-chromen-4-yl]-3-(2-hydroxy-2,3-dihydro-1H-inden-4-yl)urea;

1-(2-hydroxy-2,3-dihydro-1H-inden-4-yl)-3-(2-phenyl-3,4-dihydro-2H-chromen-4-yl)urea;

1-[2-(4-fluorophenyl)-3,4-dihydro-2H-chromen-4-yl]-3-(2-hydroxy-2,3-dihydro-1H-inden-4-yl)urea;

1-[2-(2-chlorophenyl)-3,4-dihydro-2H-chromen-4-yl]-3-(2-hydroxy-2,3-dihydro-1H-inden-4-yl)urea;

1-(2-hydroxy-2,3-dihydro-1H-inden-4-yl)-3-{2-[4-(trifluoromethyl)phenyl]-3,4-dihydro-2H-chromen-4-yl}urea;

1-[2-(4-chlorophenyl)-7-methoxy-3,4-dihydro-2H-chromen-4-yl]-3-(2-hydroxy-2,3-dihydro-1H-inden-4-yl)urea;

1-(3,4-dihydrospiro[chromene-2,1'-cyclohexan]-4-yl)-3-(2-hydroxy-2,3-dihydro-1H-inden-4-yl)urea;

1-[(2S,4R)-2-(difluoromethyl)-2-methyl-3,4-dihydro-2H-chromen-4-yl]-3-[(2R)-2-hydroxy-2,3-dihydro-1H-inden-4-yl]urea;

1-[(2R,4R)-2-(difluoromethyl)-2-methyl-3,4-dihydro-2H-chromen-4-yl]-3-[(2R)-2-hydroxy-2,3-dihydro-1H-inden-4-yl]urea;

1-[(4R)-3,4-dihydrospiro[chromene-2,1'-cyclopentan]-4-yl]-3-[(2R)-2-hydroxy-2,3-dihydro-1H-inden-4-yl]urea;

1-[(4R)-7-fluoro-2,2-bis(fluoromethyl)-3,4-dihydro-2H-chromen-4-yl]-3-[(2R)-2-hydroxy-2,3-dihydro-1H-inden-4-yl]urea;

1-[(4R)-7-(difluoromethyl)-2,2-bis(fluoromethyl)-3,4-dihydro-2H-chromen-4-yl]-3-[(2R)-2-hydroxy-2,3-dihydro-1H-inden-4-yl]urea;

1-[(2R,4R)-7-chloro-2-(fluoromethyl)-2-methyl-3,4-dihydro-2H-chromen-4-yl]-3-(8-hydroxybicyclo[4.2.0]octa-1,3,5-then-3-yl)urea;

1-[(2R,4R)-2-(fluoromethyl)-2-methyl-3,4-dihydro-2H-chromen-4-yl]-3-(8-hydroxybicyclo[4.2.0]octa-1,3,5-then-3-yl)urea;

1-[(4R)-7-chloro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-7-chloro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-2,2-dimethyl-8-(trifluoromethyl)-3,4-dihydro-2H-chromen-4-yl]-3-[(2S)-7-fluoro-2-hydroxy-2,3-dihydro-1H-inden-4-yl]urea;

1-[(4R)-8-fluoro-2,2-dimethyl-3,4-dihydro-2H-chromen-4-yl]-3-[(2S)-7-fluoro-2-hydroxy-2,3-dihydro-1H-inden-4-yl]urea;

1-[(2S)-7-fluoro-2-hydroxy-2,3-dihydro-1H-inden-4-yl]-3-[(4R)-8-(trifluoromethoxy)-3,4-dihydro-2H-chromen-4-yl]urea;

1-[(4R)-7-fluoro-2,2-dimethyl-3,4-dihydro-2H-chromen-4-yl]-3-[(2S)-7-fluoro-2-hydroxy-2,3-dihydro-1H-inden-4-yl]urea;

1-[(4R)-2,2-bis(fluoromethyl)-7-(trifluoromethoxy)-3,4-dihydro-2H-chromen-4-yl]-3-[(2S)-7-fluoro-2-hydroxy-2,3-dihydro-1H-inden-4-yl]urea;

1-[(4R)-2,2-dimethyl-7-(trifluoromethyl)-3,4-dihydro-2H-chromen-4-yl]-3-[(2S)-7-fluoro-2-hydroxy-2,3-dihydro-1H-inden-4-yl]urea;

1-[(4R)-6-fluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-6,8-difluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-6-fluoro-3,4-dihydrospiro[chromene-2,1'-cyclobutan]-4-yl]-3-[(2S)-7-fluoro-2-hydroxy-2,3-dihydro-1H-inden-4-yl]urea;

1-[(4R)-7-chloro-8-fluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-2,2-dimethyl-3,4-dihydro-2H-chromen-4-yl]-3-[(2S)-7-fluoro-2-hydroxy-2,3-dihydro-1H-inden-4-yl]urea;

1-[(4R)-6-fluoro-2,2-dimethyl-3,4-dihydro-2H-chromen-4-yl]-3-[(2S)-7-fluoro-2-hydroxy-2,3-dihydro-1H-inden-4-yl]urea;

1-[(4R)-8-chloro-7-fluoro-2,2-dimethyl-3,4-dihydro-2H-chromen-4-yl]-3-[(2S)-7-fluoro-2-hydroxy-2,3-dihydro-1H-inden-4-yl]urea;

1-[(4R)-7-chloro-2,2-dimethyl-3,4-dihydro-2H-chromen-4-yl]-3-[(2S)-7-fluoro-2-hydroxy-2,3-dihydro-1H-inden-4-yl]urea;

1-[(2S)-7-fluoro-2-hydroxy-2,3-dihydro-1H-inden-4-yl]-3-[(4R)-7-(trifluoromethoxy)-3,4-dihydro-2H-chromen-4-yl]urea;

1-[(4R)-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-8-fluoro-2,2-bis(fluoromethyl)-3,4-dihydro-2H-chromen-4-yl]-3-[(2S)-7-fluoro-2-hydroxy-2,3-dihydro-1H-inden-4-yl]urea;

1-[(4R)-7,8-difluoro-2,2-dimethyl-3,4-dihydro-2H-chromen-4-yl]-3-[(2S)-7-fluoro-2-hydroxy-2,3-dihydro-1H-inden-4-yl]urea;

1-[(4R)-2,2-dimethyl-8-(trifluoromethoxy)-3,4-dihydro-2H-chromen-4-yl]-3-[(2S)-7-fluoro-2-hydroxy-2,3-dihydro-1H-inden-4-yl]urea;

1-[(4R)-2,2-dimethyl-8-(trifluoromethyl)-3,4-dihydro-2H-chromen-4-yl]-3-[(2R)-7-fluoro-2-hydroxy-2,3-dihydro-1H-inden-4-yl]urea;

1-[(4R)-8-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-7-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-2,2-bis(fluoromethyl)-7-(trifluoromethoxy)-3,4-dihydro-2H-chromen-4-yl]-3-[(2R)-7-fluoro-2-hydroxy-2,3-dihydro-1H-inden-4-yl]urea;

1-[(4R)-2,2-dimethyl-7-(trifluoromethyl)-3,4-dihydro-2H-chromen-4-yl]-3-[(2R)-7-fluoro-2-hydroxy-2,3-dihydro-1H-inden-4-yl]urea;

1-[(4R)-6-fluoro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-6,8-difluoro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-6-fluoro-3,4-dihydrospiro[chromene-2,1'-cyclobutan]-4-yl]-3-[(2R)-7-fluoro-2-hydroxy-2,3-dihydro-1H-inden-4-yl]urea;

1-[(4R)-2,2-dimethyl-3,4-dihydro-2H-chromen-4-yl]-3-[(2R)-7-fluoro-2-hydroxy-2,3-dihydro-1H-inden-4-yl]urea;

1-[(4R)-6-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-8-chloro-7-fluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-7-chloro-2,2-dimethyl-3,4-dihydro-2H-chromen-4-yl]-3-[(2R)-7-fluoro-2-hydroxy-2,3-dihydro-1H-inden-4-yl]urea;

1-[(2R)-7-fluoro-2-hydroxy-2,3-dihydro-1H-inden-4-yl]-3-[(4R)-7-(trifluoromethoxy)-3,4-dihydro-2H-chromen-4-yl]urea;

1-[(4R)-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-8-fluoro-2,2-bis(fluoromethyl)-3,4-dihydro-2H-chromen-4-yl]-3-[(2R)-7-fluoro-2-hydroxy-2,3-dihydro-1H-inden-4-yl]urea;

1-[(4R)-7,8-difluoro-2,2-dimethyl-3,4-dihydro-2H-chromen-4-yl]-3-[(2R)-7-fluoro-2-hydroxy-2,3-dihydro-1H-inden-4-yl]urea;

1-[(4R)-2,2-dimethyl-8-(trifluoromethoxy)-3,4-dihydro-2H-chromen-4-yl]-3-[(2R)-7-fluoro-2-hydroxy-2,3-dihydro-1H-inden-4-yl]urea;

1-[(2R)-7-fluoro-2-hydroxy-2,3-dihydro-1H-inden-4-yl]-3-[(4R)-8-(trifluoromethyl)-3,4-dihydro-2H-chromen-4-yl]urea;

1-[(4R)-7-chloro-2,2-bis(fluoromethyl)-3,4-dihydro-2H-chromen-4-yl]-3-[(2R)-5-fluoro-2-hydroxy-2,3-dihydro-1H-inden-4-yl]urea; and 1-[(4R)-7-chloro-2,2-bis(fluoromethyl)-3,4-dihydro-2H-chromen-4-yl]-3-[(2S)-5-fluoro-2-hydroxy-2,3-dihydro-1H-inden-4-yl]urea.

16. A pharmaceutical composition comprising a therapeutically effective amount of a compound of formula (I) according to claim 1, or a pharmaceutically acceptable salt thereof, in combination with a pharmaceutically acceptable carrier.

17. The pharmaceutical composition according to claim 16 further comprising an analgesic or a nonsteroidal anti-inflammatory drug, or a combination thereof.

18. A method for treating pain comprising administering a therapeutically effective amount of a compound of formula (I) according to claim 1, or a pharmaceutically acceptable salt thereof, to a subject in need thereof.

19. The method according to claim 18 further comprising the step of co-administering with an analgesic or a nonsteroidal anti-inflammatory drug, or a combination thereof.

20. The method according to claim 19 wherein the nonsteroidal anti-inflammatory drug is ibuprofen.

* * * * *